(12) United States Patent
Frisen et al.

(10) Patent No.: US 11,352,659 B2
(45) Date of Patent: *Jun. 7, 2022

(54) METHODS OF DETECTING ANALYTES

(71) Applicant: Spatial Transcriptomics AB, Stockholm (SE)

(72) Inventors: Jonas Frisen, Stockholm (SE); Patrik Stahl, Stockholm (SE); Joakim Lundeberg, Lidingö (SE)

(73) Assignee: Spatial Transcriptomics AB, Stockholm (SE)

(*) Notice: Subject to any disclaimer, the term of this patent is extended or adjusted under 35 U.S.C. 154(b) by 0 days.

This patent is subject to a terminal disclaimer.

(21) Appl. No.: 17/474,922

(22) Filed: Sep. 14, 2021

(65) Prior Publication Data

US 2022/0127659 A1    Apr. 28, 2022

Related U.S. Application Data

(63) Continuation of application No. 16/013,654, filed on Jun. 20, 2018, which is a continuation of application No. 14/111,482, filed as application No. PCT/EP2012/056823 on Apr. 13, 2012, now Pat. No. 10,030,261.

(51) Int. Cl.
*C12Q 1/682* (2018.01)
*G01N 1/30* (2006.01)
*G01N 1/42* (2006.01)

(52) U.S. Cl.
CPC .............. *C12Q 1/682* (2013.01); *G01N 1/30* (2013.01); *G01N 1/42* (2013.01)

(58) Field of Classification Search
CPC .................. C12Q 1/682; C12Q 1/6874; C12Q 2563/179; C12Q 2565/501; C12Q 2565/514; C12Q 2565/537; G01N 1/30; G01N 1/42

See application file for complete search history.

(56) References Cited

U.S. PATENT DOCUMENTS

| | | |
|---|---|---|
| 4,514,388 A | 4/1985 | Psaledakis |
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,183,053 A | 2/1993 | Yeh et al. |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,472,881 A | 12/1995 | Beebe et al. |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,559,032 A | 9/1996 | Porneroy |
| 5,582,977 A | 12/1996 | Yue |
| 5,589,173 A | 12/1996 | O'Brien |
| 5,599,675 A | 2/1997 | Brenner |
| 5,610,287 A | 3/1997 | Nikiforov et al. |
| 5,641,658 A | 6/1997 | Adams |
| 5,648,245 A | 7/1997 | Fire et al. |
| 5,658,751 A | 8/1997 | Yue |
| 5,716,825 A | 2/1998 | Hancock et al. |
| 5,750,341 A | 5/1998 | Macevicz |
| 5,763,175 A | 6/1998 | Brenner |
| 5,807,522 A | 9/1998 | Brown et al. |
| 5,830,711 A | 11/1998 | Barany et al. |
| 5,837,832 A | 11/1998 | Chee et al. |
| 5,837,860 A | 11/1998 | Anderson et al. |
| 5,854,033 A | 12/1998 | Lizardi |
| 5,863,753 A | 1/1999 | Haugland |

(Continued)

FOREIGN PATENT DOCUMENTS

| | | |
|---|---|---|
| CN | 1680604 | 10/2005 |
| CN | 1981188 | 6/2007 |

(Continued)

OTHER PUBLICATIONS

Goebl et al., "Development of a sensitive and specific in situ hybridization technique for the cellular localization of anitsense oligodeoxynucleotide drugs in tissue sections," Toxicologic Pathology, Jun. 2007, 35(4):541-548.
U.S. Appl. No. 13/080,616, filed Oct. 6, 2011, Chee.
U.S. Appl. No. 60/416,118, filed Oct. 3, 2002, Fan et al.
U.S. Appl. No. 61/839,313, filed Jun. 25, 2013, Chee et al.
U.S. Appl. No. 61/839,320, filed Jun. 25, 2013, Chee et al.
U.S. Appl. No. 61/902,105, filed Nov. 8, 2013, Kozlov et al.
U.S. Appl. No. 62/839,575, filed Apr. 26, 2019, Bent et al.

(Continued)

*Primary Examiner* — David C Thomas

(74) *Attorney, Agent, or Firm* — Fish & Richardson P.C.

(57) ABSTRACT

Localized detection of RNA in a tissue sample that includes cells is accomplished on an array. The array include a number of features on a substrate. Each feature includes a different capture probe immobilized such that the capture probe has a free 3' end. Each feature occupies a distinct position on the array and has an area of less than about 1 mm$^2$. Each capture probe is a nucleic acid molecule, which includes a positional domain including a nucleotide sequence unique to a particular feature, and a capture domain including a nucleotide sequence complementary to the RNA to be detected. The capture domain can be at a position 3' of the positional domain.

30 Claims, 28 Drawing Sheets

Specification includes a Sequence Listing.

(56) References Cited

U.S. PATENT DOCUMENTS

| | | |
|---|---|---|
| 5,866,377 A | 2/1999 | Kim et al. |
| 5,871,921 A | 2/1999 | Landegren et al. |
| 5,912,148 A | 6/1999 | Eggerding |
| 5,919,626 A | 7/1999 | Shi et al. |
| 5,925,545 A | 7/1999 | Reznikoff et al. |
| 5,958,775 A | 9/1999 | Wickstrom et al. |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,083,761 A | 7/2000 | Kedar et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,172,218 B1 | 1/2001 | Brenner |
| 6,210,891 B1 | 4/2001 | Nyren |
| 6,210,894 B1 | 4/2001 | Brennan |
| 6,214,587 B1 | 4/2001 | Dattagupta |
| 6,221,591 B1 | 4/2001 | Aerts |
| 6,258,558 B1 | 7/2001 | Szostak |
| 6,258,568 B1 | 7/2001 | Nyren |
| 6,261,804 B1 | 7/2001 | Szostak |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,281,804 B1 | 8/2001 | Haller |
| 6,291,180 B1 | 9/2001 | Chu |
| 6,300,063 B1 | 10/2001 | Lipshutz et al. |
| 6,306,597 B1 | 10/2001 | Macevicz |
| 6,309,824 B1 | 10/2001 | Drmanac |
| 6,337,472 B1 | 1/2002 | Garner et al. |
| 6,344,316 B1 | 2/2002 | Lockhart |
| 6,355,431 B1 | 3/2002 | Chee |
| 6,368,801 B1 | 4/2002 | Faruqi |
| 6,391,937 B1 | 5/2002 | Beuhler et al. |
| 6,401,267 B1 | 6/2002 | Drmanac |
| 6,404,907 B1 | 6/2002 | Gilchrist |
| 6,416,950 B1 | 7/2002 | Lohse |
| 6,432,360 B1 | 8/2002 | Church et al. |
| 6,485,982 B1 | 11/2002 | Charlton |
| 6,503,713 B1 | 1/2003 | Rana |
| 6,506,561 B1 | 1/2003 | Cheval et al. |
| 6,518,018 B1 | 2/2003 | Szostak |
| 6,544,732 B1 | 4/2003 | Chee |
| 6,565,727 B1 | 5/2003 | Shenderov |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,673,620 B1 | 1/2004 | Loeffler |
| 6,677,160 B1 | 1/2004 | Stockman et al. |
| 6,699,710 B1 | 3/2004 | Kononen |
| 6,737,236 B1 | 5/2004 | Pieken et al. |
| 6,770,441 B2 | 8/2004 | Dickinson |
| 6,773,566 B2 | 8/2004 | Shenderov |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B2 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,878,515 B1 | 4/2005 | Landegren |
| 6,890,741 B2 | 5/2005 | Fan et al. |
| 6,897,023 B2 | 5/2005 | Fu |
| 6,911,132 B2 | 6/2005 | Pamula |
| 6,911,345 B2 | 6/2005 | Quake |
| 6,913,881 B1 | 7/2005 | Aizenstein et al. |
| 6,913,921 B2 | 7/2005 | Fischer |
| 6,942,968 B1 | 9/2005 | Dickinson et al. |
| 6,969,488 B2 | 11/2005 | Bridgham |
| 6,969,589 B2 | 11/2005 | Patil |
| 6,977,033 B2 | 12/2005 | Becker |
| 7,001,792 B2 | 2/2006 | Sauer et al. |
| 7,011,944 B2 | 3/2006 | Prudent et al. |
| 7,052,244 B2 | 5/2006 | Fouillet |
| 7,057,026 B2 | 6/2006 | Barnes |
| 7,083,980 B2 | 8/2006 | Reznikoff et al. |
| 7,098,041 B2 | 8/2006 | Kaylor et al. |
| 7,115,400 B1 | 10/2006 | Adessi |
| 7,118,883 B2 | 10/2006 | Inoue |
| 7,128,893 B2 | 10/2006 | Leamon et al. |
| 7,163,612 B2 | 1/2007 | Sterling |
| 7,166,431 B2 | 1/2007 | Chee et al. |
| 7,192,735 B2 | 3/2007 | Lambalot |
| 7,211,414 B2 | 5/2007 | Hardin |
| 7,223,371 B2 | 5/2007 | Hayenga et al. |
| 7,229,769 B2 | 6/2007 | Kozlov |
| 7,244,559 B2 | 7/2007 | Rothberg |
| 7,255,994 B2 | 8/2007 | Lao |
| 7,258,976 B2 | 8/2007 | Mitsuhashi |
| 7,259,258 B2 | 8/2007 | Kozlov et al. |
| 7,264,929 B2 | 9/2007 | Rothberg |
| 7,270,950 B2 | 9/2007 | Szostak |
| 7,282,328 B2 | 10/2007 | Kong et al. |
| 7,297,518 B2 | 11/2007 | Quake |
| 7,315,019 B2 | 1/2008 | Turner |
| 7,328,979 B2 | 2/2008 | Decre |
| 7,329,492 B2 | 2/2008 | Hardin |
| 7,358,047 B2 | 4/2008 | Hafner et al. |
| 7,361,488 B2 | 4/2008 | Fan et al. |
| 7,375,234 B2 | 5/2008 | Sharpless et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,427,678 B2 | 9/2008 | Pieken et al. |
| 7,462,449 B2 | 12/2008 | Quake |
| 7,501,245 B2 | 3/2009 | Quake |
| 7,537,897 B2 | 5/2009 | Brenner |
| 7,544,473 B2 | 6/2009 | Brennan |
| 7,547,380 B2 | 6/2009 | Velev |
| 7,563,576 B2 | 7/2009 | Chee |
| 7,579,153 B2 | 8/2009 | Brenner |
| 7,582,420 B2 | 9/2009 | Oliphant et al. |
| 7,595,883 B1 | 9/2009 | El Gamal |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,641,779 B2 | 1/2010 | Becker |
| 7,666,612 B2 | 2/2010 | Johnsson |
| 7,674,589 B2 | 3/2010 | Cohen et al. |
| 7,674,752 B2 | 3/2010 | He |
| 7,700,286 B2 | 4/2010 | Stroun et al. |
| 7,709,198 B2 | 5/2010 | Luo et al. |
| 7,754,429 B2 | 7/2010 | Rigatti |
| 7,776,547 B2 | 8/2010 | Roth |
| 7,776,567 B2 | 8/2010 | Mao |
| 7,785,869 B2 | 8/2010 | Belgrader et al. |
| 7,803,943 B2 | 9/2010 | Mao |
| 7,844,940 B2 | 11/2010 | Shin et al. |
| 7,848,553 B2 | 12/2010 | Hertel et al. |
| 7,858,321 B2 | 12/2010 | Glezer |
| 7,888,009 B2 | 2/2011 | Barany et al. |
| 7,892,747 B2 | 2/2011 | Barany et al. |
| 7,914,981 B2 | 3/2011 | Barany et al. |
| 7,955,794 B2 | 6/2011 | Shen et al. |
| 7,960,119 B2 | 6/2011 | Chee |
| 7,960,120 B2 | 6/2011 | Rigatti |
| 8,003,354 B2 | 8/2011 | Shen et al. |
| 8,030,477 B2 | 10/2011 | Cerrina et al. |
| 8,076,063 B2 | 12/2011 | Fan |
| 8,092,784 B2 | 1/2012 | Mao |

(56) References Cited

U.S. PATENT DOCUMENTS

| | | |
|---|---|---|
| 8,148,068 B2 | 4/2012 | Brenner |
| 8,148,518 B2 | 4/2012 | Buchanan |
| 8,198,028 B2 | 6/2012 | Rigatti et al. |
| 8,206,917 B2 | 6/2012 | Chee |
| 8,207,093 B2 | 6/2012 | Szostak |
| 8,288,103 B2 | 10/2012 | Oliphant |
| 8,337,851 B2 | 12/2012 | Aukerman |
| 8,343,500 B2 | 1/2013 | Wraith |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| 8,481,698 B2 | 7/2013 | Lieberman et al. |
| 8,486,625 B2 | 7/2013 | Gunderson |
| 8,507,204 B2 | 8/2013 | Pierce et al. |
| 8,551,710 B2 | 10/2013 | Bernitz et al. |
| RE44,596 E | 11/2013 | Stroun et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,637,242 B2 | 1/2014 | Shen |
| 8,685,889 B2 | 4/2014 | Van Eijk |
| 8,741,564 B2 | 6/2014 | Seligmann |
| 8,741,606 B2 | 6/2014 | Casbon |
| 8,748,103 B2 | 6/2014 | Faham et al. |
| 8,778,849 B2 | 7/2014 | Bowen |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,895,249 B2 | 11/2014 | Shen |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,951,781 B2 | 2/2015 | Reed |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,121,069 B2 | 9/2015 | Lo |
| 9,163,283 B2 | 10/2015 | Chee et al. |
| 9,194,001 B2 | 11/2015 | Brenner |
| 9,217,176 B2 | 12/2015 | Faham et al. |
| 9,290,808 B2 | 3/2016 | Fodor |
| 9,290,809 B2 | 3/2016 | Fodor |
| 9,309,556 B2 | 4/2016 | Myllykangas et al. |
| 9,328,383 B2 | 5/2016 | Van Eijk |
| 9,334,536 B2 | 5/2016 | Van Eijk |
| 9,340,830 B2 | 5/2016 | Lipson |
| 9,371,598 B2 | 6/2016 | Chee |
| 9,376,716 B2 | 6/2016 | Van Eijk |
| 9,376,719 B2 | 6/2016 | Van Eijk |
| 9,404,156 B2 | 8/2016 | Hicks |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown |
| 9,512,422 B2 | 12/2016 | Barnard et al. |
| 9,512,487 B2 | 12/2016 | Faham et al. |
| 9,518,980 B2 | 12/2016 | Looger et al. |
| 9,557,330 B2 | 1/2017 | Siciliano et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,816,134 B2 | 11/2017 | Namsaraev |
| 9,834,814 B2 | 12/2017 | Peter et al. |
| 9,850,536 B2 | 12/2017 | Oliphant et al. |
| 9,868,979 B2 | 1/2018 | Chee et al. |
| 9,879,313 B2 | 1/2018 | Chee et al. |
| 9,889,422 B2 | 2/2018 | Smith et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,950 B2 | 2/2018 | Church et al. |
| 9,958,454 B2 | 5/2018 | Kozlov et al. |
| 10,002,316 B2 | 6/2018 | Fodor et al. |
| 10,023,907 B2 | 7/2018 | Van Eijk |
| 10,030,261 B2 * | 7/2018 | Frisen .................. G16B 50/20 |
| 10,072,104 B2 | 9/2018 | Winnik et al. |
| 10,095,832 B2 | 10/2018 | Van Eijk |
| 10,138,509 B2 | 11/2018 | Church et al. |
| 10,144,966 B2 | 12/2018 | Cantor |
| 10,179,932 B2 | 1/2019 | Church et al. |
| 10,196,691 B2 | 2/2019 | Harkin et al. |
| 10,221,461 B2 | 3/2019 | Robins et al. |
| 10,246,752 B2 | 4/2019 | Faham et al. |
| 10,273,541 B2 | 4/2019 | Hindson et al. |
| 10,308,982 B2 | 6/2019 | Chee |
| 10,472,669 B2 | 11/2019 | Chee |
| 10,480,022 B2 | 11/2019 | Chee |
| 10,494,667 B2 | 12/2019 | Chee |
| 10,612,079 B2 | 4/2020 | Chee |
| 10,619,196 B1 | 4/2020 | Chee |
| 10,662,467 B2 | 5/2020 | Chee |
| 10,662,468 B2 | 5/2020 | Chee |
| 10,697,013 B1 | 6/2020 | Brenner et al. |
| 10,767,223 B1 | 9/2020 | Brenner et al. |
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbrueggen et al. |
| 10,914,730 B2 | 2/2021 | Chee et al. |
| 10,927,403 B2 | 2/2021 | Chee et al. |
| 10,961,566 B2 | 3/2021 | Chee |
| 10,962,532 B2 | 3/2021 | Chee |
| 10,982,268 B2 | 4/2021 | Chee |
| 10,983,113 B2 | 4/2021 | Chee |
| 10,996,219 B2 | 5/2021 | Chee et al. |
| 11,001,878 B1 | 5/2021 | Chee et al. |
| 11,001,879 B1 | 5/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,156,603 B2 | 10/2021 | Chee |
| 11,162,132 B2 | 11/2021 | Frisen et al. |
| 11,208,684 B2 | 12/2021 | Chee |
| 2001/0039029 A1 | 11/2001 | Nemori et al. |
| 2001/0055764 A1 | 12/2001 | Empendocles et al. |
| 2002/0006477 A1 | 1/2002 | Shishido et al. |
| 2002/0040275 A1 | 4/2002 | Cravatt |
| 2002/0045169 A1 | 4/2002 | Shoemaker et al. |
| 2002/0048766 A1 | 4/2002 | Doyle et al. |
| 2002/0055100 A1 | 5/2002 | Kawashima |
| 2002/0064779 A1 | 5/2002 | Landegren |
| 2002/0086441 A1 | 7/2002 | Baranov et al. |
| 2002/0132246 A1 | 9/2002 | Kallioniemi et al. |
| 2002/0137031 A1 | 9/2002 | Wolber |
| 2002/0150909 A1 | 10/2002 | Stuelpnagel |
| 2002/0164611 A1 | 11/2002 | Bamdad |
| 2002/0168645 A1 | 11/2002 | Taylor |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0064398 A1 | 4/2003 | Barnes |
| 2003/0073086 A1 | 4/2003 | Guire et al. |
| 2003/0087232 A1 | 5/2003 | Christians |
| 2003/0096323 A1 | 5/2003 | James |
| 2003/0113713 A1 | 6/2003 | Glezer |
| 2003/0124595 A1 | 7/2003 | Lizardi |
| 2003/0138879 A1 | 7/2003 | Lambalot |

(56) References Cited

U.S. PATENT DOCUMENTS

| | | |
|---|---|---|
| 2003/0148335 A1 | 8/2003 | Shen et al. |
| 2003/0153850 A1 | 8/2003 | Davis et al. |
| 2003/0162216 A1 | 8/2003 | Gold |
| 2003/0165948 A1 | 9/2003 | Alsmadi et al. |
| 2003/0170637 A1 | 9/2003 | Pirrung et al. |
| 2003/0175947 A1 | 9/2003 | Liu et al. |
| 2003/0190744 A1 | 10/2003 | McGarry et al. |
| 2003/0205632 A1 | 11/2003 | Kim et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235535 A1 | 12/2003 | Zhou |
| 2003/0235852 A1 | 12/2003 | Roberts |
| 2004/0002090 A1 | 1/2004 | Mayer et al. |
| 2004/0019005 A1 | 1/2004 | Van Ness |
| 2004/0023320 A1 | 2/2004 | Steiner et al. |
| 2004/0033499 A1 | 2/2004 | Ilsley et al. |
| 2004/0050699 A1 | 3/2004 | Goncalves |
| 2004/0067492 A1 | 4/2004 | Peng et al. |
| 2004/0067493 A1 | 4/2004 | Matsuzaki |
| 2004/0082059 A1 | 4/2004 | Webb |
| 2004/0096853 A1 | 5/2004 | Mayer |
| 2004/0106110 A1 | 6/2004 | Balasubramanian |
| 2004/0112442 A1 | 6/2004 | Maerkl |
| 2004/0121456 A1 | 6/2004 | Fischer |
| 2004/0175822 A1 | 9/2004 | Timperman et al. |
| 2004/0219588 A1 | 11/2004 | Furuta |
| 2004/0224326 A1 | 11/2004 | Kim et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0019776 A1 | 1/2005 | Callow et al. |
| 2005/0019842 A1 | 1/2005 | Prober et al. |
| 2005/0026188 A1 | 2/2005 | Van Kessel |
| 2005/0037362 A1 | 2/2005 | Remacle et al. |
| 2005/0037393 A1 | 2/2005 | Gunderson et al. |
| 2005/0042695 A1 | 2/2005 | Meares et al. |
| 2005/0048580 A1 | 3/2005 | Labaer |
| 2005/0064460 A1 | 3/2005 | Holliger et al. |
| 2005/0079520 A1 | 4/2005 | Wu |
| 2005/0100900 A1 | 5/2005 | Kawashima et al. |
| 2005/0130173 A1 | 6/2005 | Leamon et al. |
| 2005/0130188 A1 | 6/2005 | Walt |
| 2005/0136414 A1 | 6/2005 | Gunderson et al. |
| 2005/0164292 A1 | 7/2005 | Farooqui |
| 2005/0179746 A1 | 8/2005 | Roux et al. |
| 2005/0191656 A1 | 9/2005 | Drmanac et al. |
| 2005/0191698 A1 | 9/2005 | Chee et al. |
| 2005/0196786 A1 | 9/2005 | Levy |
| 2005/0202433 A1* | 9/2005 | Van Beuningen ............... C12Q 2565/501 435/6.11 |
| 2005/0227271 A1 | 10/2005 | Kwon |
| 2005/0239192 A1 | 10/2005 | Nasarabadi et al. |
| 2005/0002572 A1 | 11/2005 | Nakajima et al. |
| 2005/0244850 A1 | 11/2005 | Huang |
| 2005/0255548 A1 | 11/2005 | Lipovsek et al. |
| 2005/0260653 A1 | 11/2005 | LaBaer |
| 2006/0003394 A1 | 1/2006 | Song |
| 2006/0039823 A1 | 2/2006 | Yamakawa et al. |
| 2006/0046313 A1 | 3/2006 | Roth |
| 2006/0063160 A1 | 3/2006 | West et al. |
| 2006/0079453 A1 | 4/2006 | Sidney et al. |
| 2006/0105352 A1 | 5/2006 | Qiao et al. |
| 2006/0110739 A1 | 5/2006 | Heyduk |
| 2006/0134669 A1 | 6/2006 | Casasanta |
| 2006/0164490 A1 | 7/2006 | Kim et al. |
| 2006/0183150 A1 | 8/2006 | Cohen et al. |
| 2006/0188875 A1 | 8/2006 | Cox et al. |
| 2006/0188901 A1 | 8/2006 | Barnes et al. |
| 2006/0194331 A1 | 8/2006 | Pamula et al. |
| 2006/0199183 A1 | 9/2006 | Valat et al. |
| 2006/0199207 A1 | 9/2006 | Matysiak |
| 2006/0211001 A1 | 9/2006 | Yu et al. |
| 2006/0216721 A1 | 9/2006 | Kozlov et al. |
| 2006/0216775 A1 | 9/2006 | Burkart et al. |
| 2006/0228758 A1 | 10/2006 | Muchhal et al. |
| 2006/0240439 A1 | 10/2006 | Smith et al. |
| 2006/0263789 A1 | 11/2006 | Kincaid |
| 2006/0275799 A1 | 12/2006 | Banerjee et al. |
| 2006/0281109 A1 | 12/2006 | Barr Ost et al. |
| 2007/0003954 A1 | 1/2007 | Kodadek et al. |
| 2007/0014810 A1 | 1/2007 | Baker et al. |
| 2007/0020625 A1 | 1/2007 | Duchaud et al. |
| 2007/0020640 A1 | 1/2007 | McCloskey et al. |
| 2007/0020669 A1 | 1/2007 | Ericsson |
| 2007/0023292 A1 | 2/2007 | Kim et al. |
| 2007/0026430 A1 | 2/2007 | Andersen et al. |
| 2007/0036511 A1 | 2/2007 | Lundquist et al. |
| 2007/0048812 A1 | 3/2007 | Moravec et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0141718 A1 | 6/2007 | Bui et al. |
| 2007/0161020 A1 | 7/2007 | Luo et al. |
| 2007/0161029 A1 | 7/2007 | Li et al. |
| 2007/0166705 A1 | 7/2007 | Milton et al. |
| 2007/0166725 A1 | 7/2007 | McBride et al. |
| 2007/0172873 A1 | 7/2007 | Brenner et al. |
| 2007/0178503 A1 | 8/2007 | Jiang |
| 2007/0207482 A1 | 9/2007 | Church et al. |
| 2007/0231823 A1 | 10/2007 | McKernan |
| 2007/0251824 A1 | 11/2007 | Patton |
| 2007/0254305 A1 | 11/2007 | Paik et al. |
| 2007/0264656 A1 | 11/2007 | Kawamura |
| 2007/0269805 A1 | 11/2007 | Hogers |
| 2007/0280517 A1 | 12/2007 | De La Torre-Bueno et al. |
| 2008/0009420 A1 | 1/2008 | Schroth et al. |
| 2008/0032301 A1 | 2/2008 | Rank et al. |
| 2008/0038734 A1 | 2/2008 | Sorge et al. |
| 2008/0047835 A1 | 2/2008 | MacConnell |
| 2008/0071071 A1 | 3/2008 | LaBaer et al. |
| 2008/0108082 A1 | 5/2008 | Rank et al. |
| 2008/0108804 A1 | 5/2008 | Hayashizaki et al. |
| 2008/0124252 A1 | 5/2008 | Marchand et al. |
| 2008/0124810 A1 | 5/2008 | Terbrueggen et al. |
| 2008/0128627 A1 | 6/2008 | Lundquist et al. |
| 2008/0132429 A1 | 6/2008 | Perov et al. |
| 2008/0153086 A1 | 6/2008 | Wong |
| 2008/0160580 A1 | 7/2008 | Adessi et al. |
| 2008/0199929 A1 | 8/2008 | Yeung et al. |
| 2008/0220434 A1 | 9/2008 | Thomas |
| 2008/0220981 A1 | 9/2008 | McGregor |
| 2008/0261204 A1 | 10/2008 | Lexow |
| 2008/0280773 A1 | 11/2008 | Fedurco et al. |
| 2008/0286795 A1 | 11/2008 | Kawashima et al. |
| 2008/0293591 A1 | 11/2008 | Taussig et al. |
| 2008/0312103 A1 | 12/2008 | Nemoto et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0062148 A1 | 3/2009 | Goldberg |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0169089 A1 | 7/2009 | Hunt et al. |
| 2009/0170713 A1 | 7/2009 | van Eijk et al. |
| 2009/0192044 A1 | 7/2009 | Fouillet |
| 2009/0197326 A1 | 8/2009 | El Gamal et al. |
| 2009/0215633 A1 | 8/2009 | van Eijk et al. |
| 2009/0233802 A1 | 9/2009 | Bignell et al. |
| 2009/0239232 A1 | 9/2009 | Kum |
| 2009/0253163 A1 | 10/2009 | Xie et al. |
| 2009/0253581 A1 | 10/2009 | van Eijk et al. |
| 2009/0253582 A1 | 10/2009 | Pena et al. |

(56) References Cited

U.S. PATENT DOCUMENTS

| | | |
|---|---|---|
| 2009/0264299 A1 | 10/2009 | Drmanac et al. |
| 2009/0280487 A1 | 11/2009 | Hung et al. |
| 2009/0283407 A1 | 11/2009 | Van Eijk |
| 2009/0289184 A1 | 11/2009 | Deininger |
| 2009/0291854 A1 | 11/2009 | Weisinger-Mayr et al. |
| 2009/0305237 A1 | 12/2009 | Cantor et al. |
| 2009/0312193 A1 | 12/2009 | Kim et al. |
| 2009/0321262 A1 | 12/2009 | Adachi et al. |
| 2010/0009871 A1 | 1/2010 | Reed et al. |
| 2010/0014537 A1 | 1/2010 | Jacquet et al. |
| 2010/0035249 A1 | 2/2010 | Hayashizaki et al. |
| 2010/0055733 A1 | 3/2010 | Lutolf et al. |
| 2010/0069263 A1 | 3/2010 | Shendure et al. |
| 2010/0096266 A1 | 4/2010 | Kim et al. |
| 2010/0099103 A1 | 4/2010 | Hsieh et al. |
| 2010/0105052 A1 | 4/2010 | Drmanac et al. |
| 2010/0105112 A1 | 4/2010 | Heltze et al. |
| 2010/0111768 A1 | 5/2010 | Banerjee et al. |
| 2010/0113302 A1 | 5/2010 | Williams |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0126862 A1 | 5/2010 | Sabin et al. |
| 2010/0129874 A1 | 5/2010 | Mitra et al. |
| 2010/0137143 A1 | 6/2010 | Rothberg et al. |
| 2010/0145037 A1 | 6/2010 | Makarov et al. |
| 2010/0151464 A1 | 6/2010 | Stuelpnagel et al. |
| 2010/0151511 A1 | 6/2010 | Gereenizer et al. |
| 2010/0159446 A1 | 6/2010 | Haff et al. |
| 2010/0173384 A1 | 7/2010 | Johnsson et al. |
| 2010/0184614 A1 | 7/2010 | Ye et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0267590 A1 | 10/2010 | Grudzien et al. |
| 2010/0273219 A1 | 10/2010 | May et al. |
| 2010/0282617 A1 | 11/2010 | Rothberg et al. |
| 2011/0024511 A1 | 2/2011 | Rietzler et al. |
| 2011/0027772 A1 | 2/2011 | Ahn et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0048951 A1 | 3/2011 | Wu |
| 2011/0059436 A1 | 3/2011 | Hardin et al. |
| 2011/0059865 A1 | 3/2011 | Smith et al. |
| 2011/0086774 A1 | 4/2011 | Dunaway |
| 2011/0111409 A1 | 5/2011 | Sinicropi et al. |
| 2011/0151451 A1 | 6/2011 | Lemaire et al. |
| 2011/0152111 A1 | 6/2011 | Fan et al. |
| 2011/0172115 A1 | 7/2011 | Thompson et al. |
| 2011/0177518 A1 | 7/2011 | Kartalov et al. |
| 2011/0201515 A1 | 8/2011 | Webster et al. |
| 2011/0223613 A1 | 9/2011 | Gut |
| 2011/0244448 A1 | 10/2011 | Shirai et al. |
| 2011/0245101 A1 | 10/2011 | Chee et al. |
| 2011/0245111 A1 | 10/2011 | Chee |
| 2011/0275077 A1 | 11/2011 | James |
| 2011/0287435 A1 | 11/2011 | Grunenwald et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0077693 A1 | 3/2012 | Cazalis et al. |
| 2012/0129248 A1 | 5/2012 | Chee et al. |
| 2012/0135871 A1 | 5/2012 | van Eijk et al. |
| 2012/0142014 A1 | 6/2012 | Cai |
| 2012/0157322 A1 | 6/2012 | Myllykangas |
| 2012/0160683 A1 | 6/2012 | Ye et al. |
| 2012/0195810 A1 | 8/2012 | Cohen et al. |
| 2012/0196297 A1 | 8/2012 | Yost et al. |
| 2012/0202698 A1 | 8/2012 | van Eijk et al. |
| 2012/0202704 A1 | 8/2012 | Fan et al. |
| 2012/0245053 A1 | 9/2012 | Shirai et al. |
| 2012/0258871 A1 | 10/2012 | Kozlov et al. |
| 2012/0270305 A1 | 10/2012 | Reed et al. |
| 2012/0270748 A1 | 10/2012 | Chee et al. |
| 2012/0289414 A1 | 11/2012 | Mitra et al. |
| 2013/0005600 A1 | 1/2013 | Olek |
| 2013/0035239 A1 | 2/2013 | Kong et al. |
| 2013/0065788 A1 | 3/2013 | Glezer et al. |
| 2013/0079232 A1 | 3/2013 | Kain et al. |
| 2013/0096033 A1 | 4/2013 | Routenberg |
| 2013/0109595 A1 | 5/2013 | Routenberg |
| 2013/0122516 A1 | 5/2013 | Hong et al. |
| 2013/0171621 A1 | 7/2013 | Luo et al. |
| 2013/0211249 A1 | 8/2013 | Barnett et al. |
| 2013/0260372 A1 | 10/2013 | Buermann et al. |
| 2013/0261019 A1 | 10/2013 | Lin et al. |
| 2013/0296174 A1 | 11/2013 | Peumans |
| 2014/0065609 A1 | 3/2014 | Hicks et al. |
| 2014/0066318 A1* | 3/2014 | Frisen .............. C12Q 1/6841 506/3 |
| 2014/0079923 A1 | 3/2014 | George et al. |
| 2014/0080715 A1 | 3/2014 | Lo et al. |
| 2014/0121118 A1 | 5/2014 | Warner |
| 2014/0155274 A1 | 6/2014 | Xie et al. |
| 2014/0155295 A1 | 6/2014 | Hindson et al. |
| 2014/0213533 A1 | 7/2014 | Suthanthiran et al. |
| 2014/0227705 A1 | 8/2014 | Vogelstein et al. |
| 2014/0243224 A1 | 8/2014 | Barnard et al. |
| 2014/0274731 A1 | 9/2014 | Raymond et al. |
| 2014/0296081 A1 | 10/2014 | Diehn et al. |
| 2014/0342921 A1 | 11/2014 | Weiner |
| 2014/0378345 A1 | 12/2014 | Hindson et al. |
| 2015/0005447 A1 | 1/2015 | Berti et al. |
| 2015/0051085 A1 | 2/2015 | Vogelstein et al. |
| 2015/0072867 A1 | 3/2015 | Soldatov |
| 2015/0087027 A1 | 3/2015 | Makarov et al. |
| 2015/0246336 A1 | 9/2015 | Somoza et al. |
| 2015/0344942 A1 | 12/2015 | Frisen et al. |
| 2015/0376609 A1 | 12/2015 | Hindson et al. |
| 2016/0003812 A1 | 1/2016 | Porreca et al. |
| 2016/0019337 A1 | 1/2016 | Roberts et al. |
| 2016/0024576 A1 | 1/2016 | Chee |
| 2016/0033496 A1 | 2/2016 | Chou et al. |
| 2016/0138091 A1 | 5/2016 | Chee et al. |
| 2016/0145677 A1 | 5/2016 | Chee et al. |
| 2016/0298180 A1 | 10/2016 | Chee |
| 2016/0304952 A1 | 10/2016 | Boyden et al. |
| 2016/0333403 A1 | 11/2016 | Chee |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |
| 2017/0166962 A1 | 6/2017 | van Eijk et al. |
| 2017/0242020 A1 | 8/2017 | Yamauchi et al. |
| 2017/0343545 A1 | 11/2017 | Hadrup et al. |
| 2018/0094316 A1 | 4/2018 | Scott et al. |
| 2018/0112209 A1 | 4/2018 | Eshoo |
| 2018/0179591 A1 | 6/2018 | van Eijk |
| 2018/0180601 A1 | 6/2018 | Pedersen et al. |
| 2018/0201980 A1 | 7/2018 | Chee et al. |
| 2018/0217094 A1 | 8/2018 | Herr et al. |
| 2018/0247017 A1 | 8/2018 | van Eijk et al. |
| 2018/0291439 A1 | 10/2018 | van Eijk et al. |
| 2019/0017106 A1 | 1/2019 | Frisen et al. |
| 2019/0024153 A1 | 1/2019 | Frisen et al. |
| 2019/0024154 A1 | 1/2019 | Frisen et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0203275 A1 | 7/2019 | Friesen et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2020/0048690 A1 | 2/2020 | Chee |
| 2020/0063195 A1 | 2/2020 | Chee |
| 2020/0063196 A1 | 2/2020 | Chee |

(56) References Cited

U.S. PATENT DOCUMENTS

| | | |
|---|---|---|
| 2020/0109443 A1 | 4/2020 | Chee |
| 2020/0140934 A1 | 5/2020 | Chee |
| 2020/0140935 A1 | 5/2020 | Chee |
| 2020/0208205 A1 | 7/2020 | Chee |
| 2020/0208206 A1 | 7/2020 | Chee |
| 2020/0224256 A1 | 7/2020 | Chee |
| 2020/0277663 A1 | 9/2020 | Ramachandran Iyer et al. |
| 2020/0277664 A1 | 9/2020 | Frenz |
| 2020/0299757 A1 | 9/2020 | Chee et al. |
| 2020/0325531 A1 | 10/2020 | Chee |
| 2020/0354774 A1 | 11/2020 | Church et al. |
| 2020/0370106 A1 | 11/2020 | Chee |
| 2020/0399687 A1 | 12/2020 | Frisen et al. |
| 2020/0407781 A1 | 12/2020 | Schnall-Levin et al. |
| 2021/0002713 A1 | 1/2021 | Chee et al. |
| 2021/0010068 A1 | 1/2021 | Chee et al. |
| 2021/0010070 A1 | 1/2021 | Schnall-Levin et al. |
| 2021/0017583 A1 | 1/2021 | Chee et al. |
| 2021/0017586 A1 | 1/2021 | Chee |
| 2021/0062249 A1 | 3/2021 | Chee |
| 2021/0123095 A1 | 4/2021 | Chee |
| 2021/0130883 A1 | 5/2021 | Chee et al. |
| 2021/0130884 A1 | 5/2021 | Chee et al. |
| 2021/0140982 A1 | 5/2021 | Uytingco |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230681 A1 | 7/2021 | Patterson et al. |
| 2021/0230692 A1 | 7/2021 | Daugharthy et al. |
| 2021/0238664 A1 | 8/2021 | Bava |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |

FOREIGN PATENT DOCUMENTS

| | | |
|---|---|---|
| CN | 101221182 | 7/2008 |
| DE | 102008025656 | 12/2009 |
| EP | 0901631 | 3/1999 |
| EP | 0961110 | 12/1999 |
| EP | 1712623 | 10/2006 |
| EP | 1782737 | 5/2007 |
| EP | 1910562 | 4/2008 |
| EP | 1923471 | 5/2008 |
| EP | 1929039 | 6/2008 |
| EP | 1966393 | 9/2008 |
| EP | 2002017 | 12/2008 |
| EP | 2292788 | 3/2011 |
| EP | 2302070 | 3/2011 |
| EP | 2350648 | 8/2011 |
| EP | 2363504 | 9/2011 |
| EP | 2580351 | 4/2013 |
| EP | 2789696 | 10/2014 |
| EP | 2881465 | 6/2015 |
| EP | 2963127 | 1/2016 |
| EP | 3045544 | 7/2016 |
| EP | 3239304 | 11/2017 |
| JP | 2007-014297 | 1/2007 |
| JP | 2007-074967 | 3/2007 |
| JP | 2009-036694 | 2/2009 |
| JP | 2011-182702 | 9/2011 |
| JP | 2013-544498 | 12/2013 |
| JP | 2014-217381 | 11/2014 |
| KR | 10-2004-0019276 | 3/2004 |
| KR | 10-2009-0000812 | 1/2009 |
| KR | 10-2009-0081260 | 7/2009 |
| RU | 2145635 | 2/2000 |
| RU | 2270254 | 2/2006 |
| RU | 2410439 C1 | 1/2011 |
| WO | WO 1989/010977 | 11/1989 |
| WO | WO 1991/006678 | 5/1991 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 1999/032654 | 7/1999 |
| WO | WO 1999/063385 | 12/1999 |
| WO | WO 1999/067641 | 12/1999 |
| WO | WO 2000/17390 | 3/2000 |
| WO | WO 2000/018957 | 4/2000 |
| WO | WO 2000/024940 | 5/2000 |
| WO | WO 2000/063437 | 10/2000 |
| WO | WO 2001/007915 | 2/2001 |
| WO | WO 2001/009363 | 2/2001 |
| WO | WO 2001/042796 | 6/2001 |
| WO | WO 2001/090415 | 11/2001 |
| WO | WO 2001/096608 | 12/2001 |
| WO | WO 2002/024952 | 3/2002 |
| WO | WO 2002/059355 | 8/2002 |
| WO | WO 2002/059364 | 8/2002 |
| WO | WO 2002/077283 | 10/2002 |
| WO | WO 2002/088396 | 11/2002 |
| WO | WO 2003/002979 | 1/2003 |
| WO | WO 2003/003810 | 1/2003 |
| WO | WO 2003/008538 | 1/2003 |
| WO | WO 2003/010176 | 2/2003 |
| WO | WO 2003/106973 | 12/2003 |
| WO | WO 2004/015080 | 2/2004 |
| WO | WO 2004/018497 | 3/2004 |
| WO | WO 2004/028955 | 4/2004 |
| WO | WO 2004/055159 | 7/2004 |
| WO | WO 2004/067759 | 8/2004 |
| WO | WO 2004/108268 | 12/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/065814 | 7/2005 |
| WO | WO 2005/067648 | 7/2005 |
| WO | WO 2005/113804 | 12/2005 |
| WO | WO 2006/020515 | 2/2006 |
| WO | WO 2006/064199 | 6/2006 |
| WO | WO 2006/065597 | 6/2006 |
| WO | WO 2006/074351 | 7/2006 |
| WO | WO 2006/084130 | 8/2006 |
| WO | WO 2006/117541 | 11/2006 |
| WO | WO 2006/124771 | 11/2006 |
| WO | WO 2006/137733 | 12/2006 |
| WO | WO 2007/000669 | 1/2007 |
| WO | WO 2007/010251 | 1/2007 |
| WO | WO 2007/030373 | 3/2007 |

(56) References Cited

FOREIGN PATENT DOCUMENTS

| | | |
|---|---|---|
| WO | WO 2007/037678 | 4/2007 |
| WO | WO 2007/041689 | 4/2007 |
| WO | WO 2007/060599 | 5/2007 |
| WO | WO 2007/073165 | 6/2007 |
| WO | WO 2007/073171 | 6/2007 |
| WO | WO 2007/073271 | 6/2007 |
| WO | WO 2007/076128 | 7/2007 |
| WO | WO 2007/076726 | 7/2007 |
| WO | WO 2007/114693 | 10/2007 |
| WO | WO 2007/120241 | 10/2007 |
| WO | WO 2007/123744 | 11/2007 |
| WO | WO 2007/139766 | 12/2007 |
| WO | WO 2007/145612 | 12/2007 |
| WO | WO 2008/022332 | 2/2008 |
| WO | WO 2008/069906 | 6/2008 |
| WO | WO 2008/093098 | 8/2008 |
| WO | WO 2009/032167 | 3/2009 |
| WO | WO 2009/036525 | 3/2009 |
| WO | WO 2009/152928 | 12/2009 |
| WO | WO 2009/156725 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/014879 | 2/2011 |
| WO | WO 2011/062933 | 5/2011 |
| WO | WO 2011/071943 | 6/2011 |
| WO | WO 2011/094669 | 8/2011 |
| WO | WO 2011/102903 | 8/2011 |
| WO | WO 2011/127006 | 10/2011 |
| WO | WO 2011/127099 | 10/2011 |
| WO | WO 2011/143583 | 11/2011 |
| WO | WO 2011/155833 | 12/2011 |
| WO | WO 2012/022975 | 2/2012 |
| WO | WO 2012/048341 | 4/2012 |
| WO | WO 2012/049316 | 4/2012 |
| WO | WO 2012/058096 | 5/2012 |
| WO | WO 2012/071428 | 5/2012 |
| WO | WO 2012/139110 | 10/2012 |
| WO | WO 2012/140224 | 10/2012 |
| WO | WO 2012/142213 | 10/2012 |
| WO | WO 2012/148477 | 11/2012 |
| WO | WO 2012/159089 | 11/2012 |
| WO | WO 2012/168003 | 12/2012 |
| WO | WO 2013/123442 | 8/2013 |
| WO | WO 2013/138510 | 9/2013 |
| WO | WO 2013/142389 | 9/2013 |
| WO | WO 2013/150083 | 10/2013 |
| WO | WO 2014/044724 | 3/2014 |
| WO | WO 2014/060483 | 4/2014 |
| WO | WO 2014/085725 | 6/2014 |
| WO | WO 2014/142841 | 9/2014 |
| WO | WO 2014/144713 | 9/2014 |
| WO | WO 2014/152397 | 9/2014 |
| WO | WO 2014/163886 | 10/2014 |
| WO | WO 2014/210223 | 12/2014 |
| WO | WO 2014/210225 | 12/2014 |
| WO | WO 2016/007837 | 1/2016 |
| WO | WO 2016/162309 | 10/2016 |
| WO | WO 2018/045181 | 3/2018 |
| WO | WO 2018/045186 | 3/2018 |
| WO | WO 2020/123305 | 6/2020 |
| WO | WO 2020/123316 | 6/2020 |
| WO | WO 2020/190509 | 9/2020 |
| WO | WO 2020/219901 | 10/2020 |
| WO | WO 2021/091611 | 5/2021 |
| WO | WO 2021/092433 | 5/2021 |
| WO | WO 2021/097255 | 5/2021 |
| WO | WO 2021/133849 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |

OTHER PUBLICATIONS

[No Author Listed], "10x Genomics Begins Shipments of Visium Spatial Gene Expression Solution," 10x Genomics, Nov. 26, 2019, 2 pages.

[No Author Listed], "FY 2020 United States Patent and Trademark Office Performance and Accountability Report," USPTO, 2021, 28 pages.

[No Author Listed], "HuSNP Mapping Assay User's Manual," Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 70 pages.

Adessi et al., "Solid phase DNA amplification: characterisation of primer attachment and amplification mechanisms," Nucl. Acids Res., Oct. 2000, 28(20):E87, 8 pages.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003.

Affymetrix, "Human Genome U95Av2," Internet Citation, retrieved from the internet: on the World Wide Web affymetrix.com, retrieved on Oct. 2, 2002.

Agasti et al., "Photocleavable DNA Barcode-Antibody Conjugates Allow Sensitive and Multiplexed Protein Analysis in Single Cells," Journal of the American Chemical Society, Oct. 23, 2012, 134(45):18499-18502.

Agbavwe et al., "Efficiency, error and yield in light-directed maskless synthesis of DNA microarrays," Journal of Nanobiotechnology, Dec. 2011, 9:57, 17 pages.

Ahern et al., "Biochemical, Reagents Kits Offer Scientists Good Return On Investment," The Scientist, 1995, 9(15):20, 7 pages.

Akeroyd, "Click chemistry for the preparation of advanced macromolecular architectures," Stellenbosch University, PhD Dissertation, Mar. 2010, 138 pages.

Albretsen et al., "Applications of magnetic beads with covalently attached oligonucleotides in hybridization: Isolation and detection of specific measles virus mRNA from a crude cell lysate", Anal. Biochem. 189: 40-50, 1990.

Allawi and SantaLucia, "Thermodynamics and NMR of Internal GaT Mismatches in DNA," Biochemistiy, 1996, 36:10581-10594.

Altaras et al., "Production and formulation of adenovirus vectors," Adv Biochem Eng Biotechnol., Nov. 2005, 99:193-260.

Anderson et al., "Microarrayed Compound Screening to Identify Activators and Inhibitors of AMP-Activated Protein Kinase," J. of Biomolecular Screening, 2004, 9:112.

Andersson et al., "Analysis of protein expression in cell microarrays: a tool for antibody-based proteomics.," J Histochem Cytochem., 4(12): 1413-1423, 2006.

Andresen et al., "Deciphering the Antibodyome—Peptide Arrays for Serum Antibody Biomarker Diagnostics," Current Proteomics, 6(1), 1-12, 2009.

Andresen et al., "Helicase-dependent amplification: use in OnChip amplification and potential for point-of-care diagnostics," Expert Rev Mol Diagn., Oct. 2009, 9(7):645-650.

(56) References Cited

OTHER PUBLICATIONS

Angenendt et al., "Cell-free Protein expression and functional assay in a nanowell chip format," Analytical Chemistry, 2004, 76(7):1844-49.
Angenendt et al., "Generation of High Density Protein Microarrays by Cell-free in Situ Expression of Unpurified PCR Products," Molecular and Cellular Proteomics, (2006) Ch. 5.9, pp. 1658-1666.
Armani et al., "2D-PCR: a method of mapping DNA in tissue sections," Lab on a Chip, 2009, 9(24):3526-34.
Asp et al., "Spatial detection of fetal marker genes expressed at low level in adult human heart tissue", Scientific Reports, 7: 12941, 10 pages, 2017.
Atkinson and Wells, "An Updated Protocol for High Throughput Plant Tissue Sectioning.", Front Plant Sci, 8: 1721, 2017.
Atkinson, Overview of Translation: Lecture Manuscript, U of Texas (2000) DD. 6.1-6.8.
Azioune et al., "Simple and rapid process for single cell micropatterning," Lab Chip, Jun. 2009, 9(11):1640-1642.
Bains et al., "A Novel Method for Nucleic Acid Sequence Determination", Journal of Theoretical Biology, 1988, 135(3), 303-7.
Baird et al., "Rapid SNP Discovery and Genetic Mapping Using Sequenced RAD markers," PLOS One, 2008, 3(10):e3376.
Barbie et al., "Systematic RNA interference reveals that oncogenic KRAS-driven cancers require TBK1," Nature, Nov. 2009, 462(7269):108-12.
Barnes, "PCR amplification of up to 35-kb DNA with high fidelity and high yield from lambda bacteriophage templates.," Proc. Natl. Acad. Sci USA, 91: 2216-2220, 1994.
Baugh et al., "Quantitative analysis of mRNA amplification by in vitro transcription," Nucleic Acids Res., 2001, 29:5:e29.
Beattie et al., "Advances in genosensor research," Clin Chem., May 1995, 41(5):700-6.
Beier et al., "Versatile derivatisation of solid support media for covalent bonding on DNA-microchips," Nucleic Acids Res., May 1999, 27(9):1970-7.
Bell, "A Simple Way to Treat PCR Products Prior to Sequencing Using ExoSAP-IT," Biotechniques, 2008, vol. 44, No. 6.
Bentley et al., "Accurate whole human genome sequencing using reversible terminator chemistry", Nature, 2008, 456:53-59.
Bielas et al., "Human cancers express a mutator phenotype," Proc. Natl. Acad. Sci. USA, 2006, 103(48): 18238-18242.
Bielas et al., "Quantification of random genomic mutations," Nat. Methods, 2005, 2(4):285-290.
Birney, et al., "Identification and analysis of functional elements in 1% of the human genome by the ENCODE pilot project," Nature, 2007, 447:799-816.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blandini et al., "Animal models of Parkinson's disease," FEBS J., Apr. 2012, 279(7):1156-66.
Blokzijl et al., "Profiling protein expression and interactions: proximity ligation as a tool for personalized medicine," J Intern. Med., 2010, 268:232-245.
Blow, "Tissue Issues," Nature, 448(23), 959-962, 2007.
Boeke et al., "Transcription and reverse transcription of retrotransposons," Annu Rev Microbiol, 1989, 43:403-34.
Bonfield et al., "The application of numerical estimates of base calling accuracy to DNA sequencing projects," Nucleic Acids Research, 1995, 23(8):1406-1410.
Bootman et al., "Loading fluorescent Ca2+ indicators into living cells," Cold Spring Harb Protoc., Feb. 2013, 2013(2):122-5.
Bos et al., "In Vitro Evaluation of DNA-DNA Hybridization as a Two-Step Approach in Radioimmunotherapy of Cancer," Cancer Res., Jul. 1, 1994, 54(13):3479-3486.
Boulgakov et al., "From Space to Sequence and Back Again: Iterative DNA Proximity Ligation and its Applications to DNA-Based Imaging", bioRxiv, 24 pages, 2018.

Boutros et al., "The art and design of genetic screens: RNA interference," Nat Rev Genet., Jul. 2008, 9(7):554-66.
Bowtell, "The genesis and evolution of high-grade serous ovarian cancer," Nat. Rev. Cancer, 2010, (11 ):803-808 Abstract.
Brandon et al., "Mitochondrial mutations in cancer," Oncogene, 2006, 25(34):4647-4662.
Brenner et al., "In vitro cloning of complex mixtures of DNA on microbeads: physical separation of differentially expressed cDNAs," Proc. Natl. Acad. Sci. USA, 2000, 97, 1665-1670.
Brenner et al., "Gene expression analysis by massively parallel signature sequencing (MPSS) on microbead arrays", Nat. Biotech. 18: 630-634, 2000.
Brockman et al., "Quality scores and SNP detection in sequencing-by-synthesis systems," Methods, 2008, 18:763-770.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Bullard et al., "Direct comparison of nick-joining activity of the nucleic acid ligases from bacteriophage T4," Biochem, J. 2006, 398:135-144.
Burgess, "A space fortranscriptomics", Nature Reviews Genetics | Published online Jul. 15, 2016; doi:10.1038/nrg.2016.94.
Burgess, "Finding structure in gene expression", Nature Reviews Genetics | Published online Apr. 13, 2018; doi:10.1038/nrg.2018.19.
Burns et al., "Well-less, gel-permeation formats for ultra-HTS," DDT, 2001, 6(12):S40-S47.
Burton et al., "Coverslip Mounted-Immersion Cycled in Situ RT-PCR for the Localization of mRNA in Tissue Sections," Biotechniques, 1998, 24; pp. 92-100.
Calvert, "Materials science. Printing cells," Science, Oct. 2007, 318(5848):208-209.
Carlson et al., "Function and Structure of a Prokaryotic Formylglycine-generating Enzyme," J. of Biological Chemistiy, 2008, 283(29):20117-125.
Carter et al., "Stabilization of an optical microscope to 0.1 nm in three dimensions," Applied Optics, 2007, 46:421-427.
Cerutti et al., "Generation of sequence-specific, high affinity anti-DNA antibodies," Journal of Biological Chemistiy, 2001, 276(16):12769-12773.
Cha et al., "Specificity, Efficiency and Fidelity of PCR," Genome Res., 1993, 3:518-29.
Chandra et al., "Cell-free synthesis-based protein microarrays and their applications," Proteomics, 2009, 5(6):717-30.
Chatterjee et al., "Protein Microarray On-Demand: A Novel Protein Microarray System," PLos One, 2008, 3(9):e3265.
Chatterjee, et al., "Mitochondrial DNA mutations in human cancer. Oncogene," 2006, 25(34):4663-4674.
Chen et al., "A Homogeneous, Ligase-mediated DNA diagnostic test," Genome research, 1998, 8(5):549-556.
Chen et al., "DNA hybridization detection in a microfluidic Channel using two fluorescently labelled nucleic acid probes," Biosensors and Bioelectronics, 2008, 23:1878-1882.
Chen et al., "Expansion Microscopy," 2015, Science. 347(6221):543-548.
Chen et al., "Geometric control of cell life and death," Science, May 1997, 276(5317):1425-1428.
Chen et al., "Spatially resolved, highly multiplexed RNA profiling in single cells", Science 348(6233), 36 pages, 2015.
Cheng et al., "Sensitive Detection of Small Molecules by Competitive Immunomagnetic-Proximity Ligation Assay," Anal Chem, 2012, 84:2129-2132.
Chial, "DNA Sequencing Technologies Key to the Human Genome Project," Nature Education, 2008, 1(1):219, 7 pages.
Chiang et al., "NFkappaB translocation in human microvessel endothelial cells using a four-compartment subcellular protein redistribution assay," J Biochem Biophys Methods, Nov. 2000, 46(1-2):53-68.
Chrisey et al., "Covalent attachment of synthetic DNA to self-assembled monolayer films," Nucleic Acids Res., Aug. 1996, 24(15):3031-9.

(56) References Cited

OTHER PUBLICATIONS

Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 16, 2013, 497:332-337.
Cockroft et al., "A single-molecule nanopore device detects DNA polymerase activity with single-nucleotide resolution," J Am Chem Soc., Jan. 2008, 130(3):818-20.
Colegio et al., "In vitro transposition system for efficient generation of random mutants of Campylobacter jejuni," J Bacteriol., Apr. 2001, 183(7):2384-8.
Condina et al., "A sensitive magnetic bead method for the detection and identification of tyrosine phosphoiylation in proteins by MALDI-TOF/TOF MS," Proteomics, 2009, 9:3047-3057.
Constantine et al., "Use of genechip high-density oligonucleotide arrays for gene expression monitoring," Life Sceience News, Amersham Life Science; 11-14, 1998.
Cook et al., "The effects of secondary structure and O2 on the formation of direct strand breaks upon UV irradiation of 5-bromodeoxyuridine-containing oligonucleotides," ChemBiol., Jul. 1999, 6(7):451-9.
Copeland et al., "Mitochondrial DNA Alterations in Cancer," Cancer Invest., 2002, 557-569.
Corces et al., "An improved ATAC-seq protocol reduces background and enables interrogation of frozen tissues", Nat. Methods. vol. 14(10):959-962, 2017.
Cornett et al., "MALDI imaging mass spectrometry: molecular snapshots of biochemical systems," Nature Methods, 2007, 4(10):828-833.
Cox et al., "Tissue subcellular fractionation and protein extraction for use in mass-spectrometry-based proteomics," Nat Protoc., 2006, 1(4):1872-8.
Craig, "Transposon Tn7," Curr Top Microbiol Immunol., 1996, 204:27-48.
Craig, "V(D)J recombination and transposition: closer than expected," Science, Mar. 1996, 271(5255):1512, 1 page.
Crosetto et al., "Spatially resolved transcriptomics and beyond," Nature Review Genetics, 2015, 57-66.
Cujec et al. "Selection of v-abl tyrosine kinase substate sequences from randomized peptide and cellular proteomic libraries using mRNA display," Chemistiy and Biology, 2002, 9:253-264.
Curtis et al., "Adhesion of cells to polystyrene surfaces," J Cell Biol., Nov. 1983, 97(5):1500-1506.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101:4548-4553.
Dandapani et al., "Selecting, Acquiring, and Using Small Molecule Libraries for High-Throughput Screening," Curr Protoc Chem Biol., Sep. 2012, 4:177-191.
Darmanis, et al., "ProteinSeq: High-Performance Proteomic Analyses by Proximity, Ligation and Next Generation Sequencing," PLos One, 2011, 6(9):e25583.
Daubendiek et al., "Rolling-Circle RNA Synthesis: Circular Oligonucleotides as Efficient Substrates for T7 RNA Polymerase," J. Am. Chem. Soc., 1995, 117:77818-7819.
Davies et al., "How best to identify chromosomal interactions: a comparison of approaches.", Nat. Methods 14, 125-134, 2017.
Dawson et al., "Genetic animal models of Parkinson's disease," Neuron, Jun. 2010, 66(5):646-661.
De Clercq, "A 40-year journey in search of selective antiviral chemotherapy," Annu Rev Pharmacol Toxicol., 2011, 51:1-24.
Deamer et al., "Characterization of nucleic acids by nanopore analysis," Acc Chem Res., Oct. 2002, 35(10):817-25.
Deamer et al., "Nanopores and nucleic acids: prospects for ultrarapid sequencing," Trends Biotechnol., Apr. 2000, 18(4):147-51.
Dean et al., "Comprehensive human genome amplification using multiple displacement amplification," Proc Natl. Acad. Sci. USA 99:5261-66, 2002.
Deibel et al., "Biochemical properties of purified human terminal deoxynucleotidyltransferase," J Biol Chem., May 1980, 255(9):4206-12.
Devine et al., "Efficient integration of artificial transposons into plasmid targets in vitro: a useful tool for DNA mapping, sequencing and genetic analysis," Nucleic Acids Res., Sep. 1994, 22(18):3765-72.
Dhindsa et al., "Virtual Electrowetting Channels: Electronic Liquid Transport with Continuous Channel Functionality," Lab Chip, 2010, 10:832-836.
Diez-Roux et al., "A high-resolution anatomical atlas of the transcriptome in the mouse embryo," PLoS Biol., Jan. 2011, 9(1):e1000582, 14 pages.
Ding et al., "On-chip manipulation of single microparticles, cells, and organisms using surface acoustic waves," PNAS, Jul. 2012, 109(28):11105-11109.
Doddridge et al., "UV-induced strand break damage in single stranded bromodeoxyuridine-containing DNA oligonucleotides," Chem Commun., 1998, p. 1997-1998.
Dressman et al., "Transforming single DNA molecules into fluorescent magnetic particles for detection and enumeration of genetic variations," Proc. Natl. Acad. Sci. USA, 2003, 100:8817-8822.
Drmanac et al., "Accurate sequencing by hybridization for DNA diagnostics and individual genomics," Nature Biotechnology, 16:54-58, 1998.
Druley et al., "Quantification of rare allelic variants from pooled genomic DNA," Nat. Methods 6:263-65, 2009.
Duhr et al., "Why molecules move along a temperature gradient," Proc Natl Acad Sci USA, Dec. 2006, 103(52):19678-19682.
Duncan et al., "Affinity chromatography of a sequence-specific DNA binding protein using teflon-linked oligonucleotides", Anal. Biochem. 169: 104-108, 1988.
Eagen, "Principles of Chromosome Architecture Revealed by Hi—C", Trends in Biochemical Sciences, vol. 43, No. 6, 10 pages, 2018.
Eberwine et al., "Analysis of gene expression in single live neurons," Proc. Natl. Acad. Sci., USA 89, 3010-3014, 1992.
Eberwine, "Amplification of mRNA Populations Using aRNA Generated from Immobilized Oligo(dT)-T7 Primed cDNA," BioTechniques 20 (4), 584, 1996.
Eguiluz et al., "Multitissue array review: A chronological description of tissue array techniques, applications and procedures," Pathology Research and Practice, 2006, 202:561-568.
Ekins et al., "Microarrays: their origins and applications," Trends in Biotechnology, Jun. 1999, 17(6):217-218.
Eldridge et al. "An in vitro selection strategy for conferring protease resistance to ligand binding peptides," Protein Eng Des Sel., 22(11): 691-698, 2009.
Ellington et al., "Antibody-based protein multiplex platforms: technical and operational challenges," Clin Chem 56(2): 186-193, 2010.
Emmert-Buck et al., "Laser capture microdissection," Science, Nov. 1996, 274(5289):998-1001.
Eng et al., "Profiling the transcriptome by RNA SPOTs", Nat Methods., 14(12): 1153-1155, 2017.
Examination Search Report issued in Australian Appln. No. 2012241730, dated Jun. 27, 2016, 3 pages.
Extended European Search Report in European Appln. No. 18208823.7, dated May 6, 2019, 12 pages.
Extended European Search Report issued in European Appln. No. 19204655.5, dated Jun. 8, 2020, 13 pages.
Fahy et al., "Design and synthesis of polyacrylamide-based oligonucleotide supports for use in nucleic acid diagnostics," Nucleic Acids Res., Apr. 1993, 21(8):1819-26.
Falconnet et al., "Surface engineering approaches to micropattern surfaces for cell-based assays," Biomaterials, Jun. 2006, 27(16):3044-3063.
Fan et al., "Highly parallel SNP genotyping," Cold Spring Symp. Quant. Biol., 68: 69-78, 2003.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Ferreira et al., "Photocrosslinkable Polymers for Biomedical Applications," Biomedical Engineering-Frontiers and Challenges, Prof. Reza, 2011, 22 pages.

(56) References Cited

OTHER PUBLICATIONS

Fire and Xu, "Rolling replication of short DNA circles," Proc. Natl. Acad. Sci., 92: 4641-4645, 1995.
Flanigon et al., "Multiplex protein detection with DNA readout via mass spectrometry," N. Biotechnol., 30(2): 153-158, 2013.
Fodor et al., "Light-Directed, Spatially Addressable Parallel Chemical Synthesis," Science, 251(4995), 767-773, 1995.
Folch et al., "Microfabricated elastomeric stencils for micropatterning cell cultures," J Biomed Mater Res, Nov. 2000, 52(2):346-353.
Forcucci et al., "All-plastic miniature fluorescence microscope for point-of-care readout of bead-based bioassays.," J. Biomed Opt. 20 (10): 105010, 15 pages, 2015.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant to pancreatic and ovarian cancer," Clin. Chem., 5(3): 582-89, 2008.
Fredriksson et al., "Protein detection using proximity-dependent DNA ligation assays," Nature Biotech., 20: 473-77, 2002.
Frese et al., "Formylglycine Aldehyde Tag-Protein Engineering through a Novel Posttranslational Modification," ChemBioChem., 10: 425-27, 2009.
Fu et al., "Counting individual DNA molecules by the stochastic attachment of diverse labels," PNAS, 108: 9026-9031, 2011.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 19: 521-532, 2009.
Galon et al., "The immune score as a new possible approach for the classification of cancer," J Transl Med., Jan. 2012, 10:1, 4 pages.
Gans et al., "Inkjet Printing of Polymers: State of the Art and Future Developments," Advanced Materials, Feb. 2004, 16(3):203-213.
Gao et al., "High density peptide microarrays. In situ synthesis and applications," Molecular Diversity, 8, 177-187, 2004.
Gao et al., "Q&A: Expansion microscopy", BMC Biology, 15: 50, 9 pages, 2017.
Geiss et al., "Direct multiplexed measurement of gene expression with color-coded probe pairs," nature biotechnology, 2008, 26(3):317-325.
Genbank Accession No. AC009495.1, "*Homo sapiens* clone NH0490I02, * Sequencing in Progress *, 12 unordered pieces," Aug. 24, 1999, 53 pages.
Genbank Accession No. AC009495.5, "*Homo sapiens* BAC clone RP11-49O12 from 2, complete sequence," Apr. 21, 2005, 32 pages.
Genbank Accession No. AC037198.2, "*Homo sapiens* chromosome 15 clone CTD-2033D15 map 15q14, * Sequencing in Progress *, 62 unordered pieces," Apr. 25, 2000, 39 pages.
Genbank Accession No. AC087379.2, "*Homo sapiens* chromosome 11 clone RP11-396O20 map 11, * Sequencing in Progress *, 5 ordered pieces," Jul. 6, 2002, 47 pages.
Genbank Accession No. AC087741.1, "*Homo sapiens* chromosome 17 clone RP11-334C17 map 17, Low-Pass Sequence Sampling," Jan. 22, 2001, 18 pages.
Genbank Accession No. AC100826.1, "*Homo sapiens* chromosome 15 clone RP11-279F6 map 15, Low-Pass Sequence Sampling," Nov. 22, 2001, 21 pages.
Genbank Accession No. AL445433.14, "Human DNA sequence from clone RP11-234N17 on chromosome 1, complete sequence," Jan. 24, 2013, 32 pages.
Genbank Accession No. AL445524.1, "*Homo sapiens* chromosome 1 clone RP11-295G20, Working Draft Sequence, 19 unordered pieces," Oct. 14, 2000, 47 pages.
Genome.ucsc.edu, [online], "Genome Browser Gateway," 2000, retrieved on Jun. 11, 2021, retrieved from URL<https://genome.ucsc.edu/cgi-bin/hgGateway>, 3 pages.
Genomeweb.com, [online], Han, "10x Genomics Describes Capabilities of Visium Spatial Genomics Product Ahead of Release," Oct. 18, 2019, retrieved on Mar. 10, 2021, retrieved from URL<https://www.genomeweb.com/sequencing/10x-genomics-describes-capabilities-visium-spatial-genomics-product-ahead-release#.YO7-Dr6SljV>, 2 pages.
Gerdtsson et al., "Evaluation of Solid Supports for Slide- and Well-Based Recombinant Antibody Microarrays", Microarrays (2016) 5:16, 2016.
Giacomello et al., "Spatially resolved transcriptome profiling in model plant species", Nature Plants 3, 17061, 11 pages, 2017.
Giam et al., "Scanning probe-enabled nanocombinatorics define the relationship between fibronectin feature size and stem cell fate," PNAS, Mar. 2012, 109(12):4377-4382.
Gibson-Corley et al., "Principles for valid histopathologic scoring in research," Vet Pathol., Nov. 2013, 50(6):1007-15.
Gill et al., "Nucleic acid isothermal amplification technologies: a review," Nucleosides Nucleotides Nucleic Acids, Mar. 2008, 27(3):224-43.
Gilles et al., "Single nucleotide polymorphic discrimination by an electronic dot blot assay on semiconductor microchips," Nat Biotechnol, Apr. 1999, 17(4):365-70.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 105, 274-278, 2009.
Goldkom and Prockop, "A simple and efficient enzymatic method for covalent attachment of DNA to cellulose. Application for hybridization-restriction analysis and for in vitro synthesis of DNA probes.", Nucleic Acids Res. 14:9171-9191, 1986.
Goryshin et al., "Tn5 in vitro transposition," J Biol Chem., Mar. 1998, 273(13):7367-74.
Gotz et al., "Animal models of Alzheimer's disease and frontotemporal dementia," Nat Rev Neurosci., Jul. 2008, 9(7):532-44.
Grant et al., "Pathways and mechanisms of endocytic recycling," Nat. Rev. Mol. Cell Biol., Sep. 2009, 10(9):597-608.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 30(2): 144-152, 2013.
Gudjonsson et al., "Myoepithelial cells: their origin and function in breast morphogenesis and neoplasia," J Mammary Gland Biol Neoplasia, Jul. 2005, 10(3):261-72.
Gunderson et al., "Decoding Randomly Ordered DNA Arrays," Genome Research 14: 870-877, 2004.
Guo et al., "Direct fluorescence analysis of genetic polymorphisms by hybridization with oligonucleotide arrays on glass supports," Nucleic Acids Res., Dec. 1994, 22(24):5456-65.
Hahnke et al., "Striptease on glass: validation of an improved stripping procedure for in situ microarrays," J Biotechnol., Jan. 2007, 128(1):1-13.
Hajduk et al., "Drug discovery: A question of library design," Nature, Feb. 2011, 470(7332):42-43.
Halova et al., "Mast cell chemotaxis—chemoattractants and signaling pathways," Front Immunol., May 2012, 3:119, 20 pages.
Hammond et al., "Profiling cellular protein complexes by proximity ligation with dual tag microarray readout," PLoS ONE, 2012, 7(7):e40405.
Han et al., "3C and 3C-based techniques: the powerful tools for spatial genome organization deciphering", Molecular Cytogenetics (2018) 11:21, 10 pages, 2018.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Harris et al., "The design and application of target-focused compound libraries," Comb Chem High Throughput Screen, Jul. 2011, 14(6):521-531.

(56) References Cited

OTHER PUBLICATIONS

Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 19:4-9, 2008.
He et al., "Printing protein arrays from DNA arrays," Nature Methods, 5:175-77, 2008.
He, "Cell-free protein synthesis: applications in proteomics and biotechnology," New Biotechnology 25: 126-132, 2008.
Healy, "Nanopore-based single-molecule DNA analysis," Nanomedicine (Lond), Aug. 2007, 2(4):459-81.
Hedskog et al., "Dynamics of HIV-1 Quasispecies during Antiviral Treatment Dissected using Ultra-Deep Pyrosequencinq," PLoS One, 5(7):e11345, 2010.
Hein et al., "Click Chemistry, A Powerful Tool for Pharmaceutical Sciences", Pharm Res., 25(10): 2216-2230, 2008.
Hejatko et al., "In Situ Hybridization Techniques for mRNA Detection in Whole Mount *Arabidopsis* Samples," Nature Protocols, 2006, 1(4):1939-1946.
Hendrickson et al., "High sensitivity multianalyte immunoassay using covalent DNA-labeled antibodies and polymerase chain reaction," Nucleic Acid Research, Feb. 11, 1995, 23(3):522-529.
Hiatt et al., "Parallel, tag-directed assembly of locally-derived short sequence reads," Nature Methods, 7(2): 119-25, 2010.
Hlubek et al., "Heterogeneous expression of Wnt/beta-catenin target genes within colorectal cancer," Int J Cancer., Nov. 2007, 121(9):1941-8.
Ho et al., "Bacteriophage T4 RNA ligase 2 (gp24.1) exemplifies a family of RNA ligases found in all phylogenetic domains," PNAS, Oct. 2002, 99(20):12709-14.
Hober et al., "Human protein atlas and the use of microarray technologies," Curr Opin Biotechnol., Feb. 2008, 19(1):30-35.
Holmstrøm et al., "A highly sensitive and fast nonradioactive method for detection of polymerase chain reaction products," Anal Biochem, Mar. 1993, 209(2):278-83.
Hoyer et al., "Electrostatic spraying: a novel technique for preparation of polymer coatings on electrodes," Anal Chem, Nov. 1996, 68(21):3840-4.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Hytönen et al., "Design and construction of highly stable, protease-resistant chimeric avidins," J Biol Chem., Mar. 2005, 280(11):10228-33.
Ichikawa et al., "In vitro transposition of transposon Tn3," J Biol. Chem., Nov. 1990, 265(31):18829-32, Abstract.
Illumina.com [online], "Array-Based Gene Expression Analysis," 2011, retrieved on Dec. 13, 2021, retrieved from URL<https://www.illumina.com/documents/products/datasheets/datasheet_gene_exp_analysis.pdf>, 5 pages.
Inoue and Wittbrodt, "One for All—A Highly Efficient and Versatile Method for Fluorescent Immunostaining in Fish Embiyos," PLoS One 6, e19713, 2011.
Invitrogen, Immune Response Biomarker Profiling Service Report, Invitrogen, 2009, 1-33.
Jabara et al., Accurate sampling and deep sequencing of the HIV-1 protease gene using a PrimerID. PNAS 108(50); 20166-20171, 2011.
Jain, "Transport of molecules, particles, and cells in solid tumors," Annu. Rev. Biomed. Eng., 1999, 1:241-263.
Jamur and Oliver, "Permeabilization of cell membranes.," Method Mal. Biol., 588: 63-66, 2010.
Jawhar et al., "Tissue Microarray: A rapidly evolving diagnostic and research tool," Annals of Saudi Medicine, Mar. 2009, 29(2):123-7.

Jemt et al., "An automated approach to prepare tissue-derived spatially barcoded RNA-sequencing libraries", Scientific Reports, 6: 37137, 10 pages, 2016.
Jones et al., Comparative lesion sequencing provides insights into tumor evolution. Proc. Natl. Acad. Sci. USA 105(11): 4283-4288, 2008.
Joos et al., "Covalent attachment of hybridizable oligonucleotides to glass supports," Anal Biochem., Apr. 1997, 247(1):96-101.
Kainkaryam et al., "Pooling in high-throughput drug screening" Curr Opin Drug Discov Devel., May 2009, 12(3):339-50.
Kanehisa, "Use of statistical criteria for screening potential homologies in nucleic acid sequences ", Nucleic Acids Res. 12: 203-213, 1984.
Kap et al., "Histological Assessment of PAXgene Tissue Fixation and Stabilization Reagents," PLoS One 6, e27704, 10 pages, 2011.
Kapteyn et al., "Incorporation of Non-Natural Nucleotides Into Template-Switching Oligonucleotides Reduces Background and Improves cDNA Synthesis From Very Small RNA Samples," BMC Genomics, 2010, 11(413): 1-9.
Kirby et al., "Cryptic plasmids of Mycobacterium avium: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Koch et al., "Photochemical immobilization of anthraquinone conjugated oligonucleotides and PCR amplicons on solid surfaces," Bioconjugate Chem., Jul. 2000, 11(4):474-483.
Kolb et al., "Click Chemistry: Diverse Chemical Function from a Few Good Reactions," Angew. Chem. Int. Ed., 40(11): 2004-2021, 2001.
Kolbert et al., "Ribosomal DNA sequencing as a tool for identification of bacterial pathogens," Curr Opin Microbiol, Jun. 1999, 2(3):299-305.
Kolovos et al., "Investigation of the spatial structure and interactions of the genome at sub-kilobasepair resolution using T2C," Nat. Protoc. 13, 459-477, 2018.
Korbel et al., "Paired-End Mapping Reveals Extensive Structural Variation in the Human Genome," Science, 318(5849): 420-426, 2007.
Korlach et al., "Selective aluminum passivation for targeted immobilization of single DNA polymerase molecules in zero-mode waveguide nanostructures," Proc. Natl. Acad. Sci. USA 105, 1176-1181, 2008.
Kozlov et al., "A High-Complexity Multiplexed Solution-Phase Assay for Profiling Protease Activity on Microarrays," Comb Chem High Throughput Screen, 11: 24-35, 2008.
Kozlov et al., "A Highly Scalable Peptide-Based Assay System for Proteomics," PLoS ONE, 7(6): e37441, 2012.
Kozlov et al., "A Method for Rapid Protease Substrate Evaluation and Optimization," Comb Chem High Throughput Screen, 9: 481-87, 2006.
Kristensen et al., "High-Throughput Methods for Detection of Genetic Variation," BioTechniques, Feb. 2001, 30(2):318-332.
Kuijpers et al. "Specific recognition of antibody-oligonucleotide conjugates by radiolabeled antisense nucleotides: a novel approach for two-step radioimmunotherapy of cancer," Bioconjugate Chem., Jan. 1, 1993, 4(1):94-102.
Kurz et al., "cDNA-Protein Fusions: Covalent Protein-Gene Conjugates for the In Vitro Selection of Peptides and Proteins," ChemBioChem., 2: 666-72, 2001.
Kwok, "High-throughput genotyping assay approaches," Pharmocogenomics, Feb. 2000, 1(1):95-100.
LaFerla et al., "Animal models of Alzheimer disease," Cold Spring Harb Perspect Med., Nov. 2012, 2(11):a006320, 14 pages.
Lage et al., "Whole Genome Analysis of Genetic Alterations in Small DNA Samples Using Hyperbranched Strand Displacement Amplification and Array-CGH," Genome Research 13: 294-307, 2003.
Lampe et al., "A purified mariner transposase is sufficient to mediate transposition in vitro," EMBO J., Oct. 1996, 15(19):5470-9.
Lamture et al., "Direct detection of nucleic acid hybridization on the surface of a charge coupled device," Nucleic Acid Res., Jun. 1994, 22(11):2121-5.

(56) References Cited

OTHER PUBLICATIONS

Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl", Gene 36: 201-210, 1985.
Larman et al., "Autoantigen discovery with a synthetic human peptidome," Nature Biotechnology, doi:1 0.1038/nbt.1856, vol. 29, No. 6, pp. 535-541, 2011.
Lassmann et al., A Novel Approach For Reliable Microarray Analysis of Microdissected Tumor Cells From Formalin-Fixed and Paraffin-Embedded Colorectal Cancer Resection Specimens, J Mol Med, 87, 211-224, 2009.
Laurell et al., "Chip integrated strategies for acoustic separation and manipulation of cells and particles," Chem. Soc. Rev., Mar. 2007, 36(3):492-506.
Lee et al., "A novel COL3A1 gene mutation in patient with aortic dissected aneurysm and cervical artery dissections," Heart Vessels, Mar. 2008, 23(2):144-8.
Lee et al., "Cytokines in cancer immunotherapy," Cancers (Basel), Oct. 2011, 3(4):3856-3893.
Lee et al., "Fluorescent in situ sequencing (FISSEQ) of RNA for gene expression profiling in intact cells and tissues", Nature Protec, 10(3): 442-458, 2015.
Lee et al., "Highly multiplexed subcellular RNA sequencing in situ", Science, 343(6177): 1360-1363, 2014.
Lee et al., "Improving the efficiency of genomic loci capture using oligonucleotide arrays for high throughput resequencing," BMC Genomics, Dec. 2009, 10:646, 12 pages.
Lee et al., "Protein nanoarrays generated by dip-pen nanolithography," Science, Mar. 2002, 295(5560):1702-1705.
Lein et al., "The promise of spatial transcriptomics for neuroscience in the era of molecular cell typing", Science 358, 64-69, 2017.
Lenard, "Viral Membranes," Encyclopedia of Virology, Jul. 2008, pp. 308-314.
Leriche et al., "Cleavable linkers in chemical biology.", Bioorganic & Medicinal Chemistry, 20: 571-582, 2012.
Levene et al., "Zero-Mode Waveguides for Single-Molecule Analysis at High Concentrations," Science 299, 682-686, 2003.
Li et al., "A photocleavable fluorescent nucleotide for DNA sequencing and analysis," Proc. Natl. Acad. Sci., 100: 414-419, 2003.
Li et al., "DNA molecules and configurations in a solid-state nanopore microscope," Nat Mater., Sep. 2003, 2(9):611-5.
Li et al., "RASL-seq for Massively Parallel and Quantitative Analysis of Gene Expression," Curr Protoc Mol Biol., Apr. 2012, 4(13):1-10.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 316: 1339-1343, 2010.
Liu et al., "Method for Quantitative Proteomics Research by Using Metal Element Chelated Tags Coupled with Mass Spectrometry," Analytical Chemistry, 2006, 78:6614-6621.
Liu et al., "Surface and interface control on photochemically initiated immobilization," J Am Chem Soc., Nov. 2006, 128(43):14067-72.
Liu et al., An integrated and sensitive detection platform for biosensing application based on Fe@Au magnetic nanoparticles as bead array carries Biosensors and Bioelectronics, 2010, 26(4):1442-1448.
Lizardi et al., "Mutation detection and single-molecule counting using isothermal rolling-circle amplification," Nat. Genet. 19: 225-232, 1998.
Lovatt et al., "Transcriptome in vivo analysis (TIVA) of spatially defined single cells in live tissue.", Nature Methods 11, 190-196, 2014.
Lu et al., "A microfluidic electroporation device for cell lysis," Lab Chip., Jan. 2005, 5(1):23-29.
Lund et al., "Assessment of methods for covalent binding of nucleic acids to magnetic beads, Dynabeads, and the characteristics of the bound nucleic acids in hybridization reactions.", Nucleic Acids Res., 16: 10861-80, 1988.
Lundberg et al., "High-fidelity amplification using a thermostable DNA polymerase isolated from Pyrococcus furiosus.," Gene., 108(1): 1-6, 1991.
Lundberg et al., "Homogeneous antibody-based proximity extension assays provide sensitive and specific detection of low-abundant proteins in human blood," Nucleic Acids Res., 39(15): e102, 2011.
Lundberg et al., "Multiplexed homogeneous proximity ligation assays for high-throughput protein biomarker research in serological material," Mol Cell Proteomics, 10(4): M110.004978, 2011.
Lundin et al., "Increased throughput by parallelization of library preparation for massive sequencing," PLoS One, Apr. 2010, 5(4):e10029, 7 pages.
Lundquist et al., "Parallel confocal detection of single molecules in real time," Opt. Lett. 33, 1026-1028, 2008.
Lyck, et al., "Immunohistochemical Markers for Quantitative Studies of Neurons and Glia in Human Neocortex," J Histochem Cytochem 56, 201-21, 2008.
MacBeath et al., "Printing proteins as microarrays for high-throughput function determination," Science, Sep. 2000, 289(5485):1760-1763.
MacIntyre, "Unmasking antigens for immunohistochemistiy.," Br J Biomed Sci. 58, 190-6, 2001.
Macosko et al., "Highly Parallel Genome-wide Expression Profiling of Individual Cells Using Nanoliter Droplets," Cell 161, 1202-1214, May 2015.
Malkov et al., "Multiplexed measurements of gene signatures in different analytes using the Nanostring nCounter™ Assay System," BMC research notes., 2009, 2:80.
Maniatis et al., "Spatiotemporal Dynamics of Molecular Pathology in Amyotrophic Lateral Sclerosis", 54 pages, 2018.
Marx, "Method of the Year 2020: spatially resolved transcriptomics," Jan. 2021, 18(1):1 pages.
Marx, "Method of the Year: spatially resolved transcriptomics," Nat Methods, Jan. 2021, 18(1):9-14.
Materna et al., "High accuracy, high-resolution prevalence measurement for the majority of locally expressed regulatory genes in early sea urchin development," Gene Expr Patterns., 2010, 10(4-5):177-184.
Mauleon et al., "Precise Spatial and Temporal Control of Oxygen within In Vitro Brain Slices via Microfluidic Gas Channels," PLoS One, Aug. 2012, 7(8):e43309, 9 pages.
McCloskey et al., "Encoding PCR Products with Batch-stamps and Barcodes," Biochem. Genet. 45: 761-767, 2007.
Mcgee, "Structure and Analysis of Affymetrix Arrays," UTSW Microarray Analysis Course, Oct. 28, 2005, 68 pages.
McKernan et al., "Sequence and structural variation in a human genome uncovered by short-read, massively parallel ligation sequencing using two-base encoding," Genome Res., 19: 1527-41, 2009.
Metzker "Sequencing technologies—the next generation," Nature Reviews Genetics, 11: 31-46, 2010.
Miele et al., "Mapping cis- and trans- chromatin interaction networks using chromosome conformation capture (3C)," Methods Mol Biol., 2009, 464:105-21.
Miller et al., "Basic Concepts of Microarrays and Potential Applications in Clinical Microbiology," Clinical Microbiology Reviews, vol. 22, No. 4, pp. 611-633, 2009.
Mir et al., "Sequencing by cyclic ligation and cleavage (CycliC) directly on a microarray captured template," Nucleic Acids Research, 37(1):e5, 8 pages, 2009.
Mishra, "Three-dimensional genome architecture and emerging technologies: looping in disease", Genome Medicine, 9: 87, 14 pages, 2017.
Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.

(56) References Cited

OTHER PUBLICATIONS

Mitra et al., "In situ localized amplification and contact replication of many individual DNA molecules," Nucleic Acids Res., Dec. 1999, 27(24):e34, 6 pages.
Mitsuhashi et al., "Gene manipulation on plastic plates," Nature 357: 519-520, 1992.
Mizusawa et al., "A bacteriophage lambda vector for cloning with BamHI and Sau3A," Gene, 20: 317-322, 1982.
Mlecinik et al., "Histopathologic-based prognostic factors of colorectal cancers are associated with the state of the local immune reaction," J Clin Oncol., Feb. 2011, 29(6):610-8.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes by RNA-Seq," Nature Methods, 5(7): 621-8, 2008.
Moshrefzadeh et al., "Nonuniform photobleaching of dyed polymers for optical waveguides," Applied Physics Letters, 1993, 62:16-18.
Motea et al., "Terminal deoxynucleotidyl transferase: the story of a misguided DNA polymerase," Biochim Biophys Acta., May 2010, 1804(5): 1151-66.
Nagahara et al., "Neuroprotective effects of brain-derived neurotrophic factor in rodent and primate models of Alzheimer's disease," Nat Med., Mar. 2009, 15(3):331-337.
Nagai et al., "Site-specific DNA cleavage by antisense oligonucleotides covalently linked to phenazine di-N-oxide," J Biol. Chem., Dec. 1991, 266(35):23994-4002.
Nakamura et al., "Biocompatible inkjet printing technique for designed seeding of individual living cells," Tissue Eng, Nov. 2005, 11(11-12):1658-1666.
Nakao et al., "Myosin heavy chain gene expression in human heart failure," J Clin Invest., Nov. 1997, 100(9):2362-70.
Nam et al., "Nanoparticle-Based Bio-Bar Codes for the Ultrasensitive Detection of Proteins," Science, Sep. 26, 2003, 301(5641):1884-1886.
Nandakumar et al., "How an RNA Ligase Discriminates RNA versus DNA Damage," Molecular Cell, 2004, 16(2):211-221.
Nawy, "Spatial transcriptomics", Nature Methods, vol. 15, No. 1, 2018.
Ng et al., "Gene identification signature (GIS) analysis for transcriptome characterization and genome annotation," Nature Methods, 2(2): 105-111, 2005.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nichols et al., "RNA Ligases," Curr Protoc Mol Biol., Oct. 2008, 84(1):3.15.1-3.15.4.
Nicholson, "Diffusion and related transport mechanisms in brain tissue," Rep. Prog. Phys., Jun. 2001, 64(7):815-884.
Niemeyer, "The developments of semisynthetic DNA-protein conjugates," Trends Biotechnol, Sep. 2002, 20(9): 395-401.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nuovo, "In situ PCR: protocols and applications.," Genome Res, Feb. 1995, 4 (4):151-167.
Ohtsubo et al., "Bacterial insertion sequences," Curr Top Microbiol Immunol., 1996, 204:1-26.
Oleinikov et al., "Self-assembling protein arrays using electronic semiconductor microchips and in vitro translation," J Proteome Res, May-Jun. 2003, 2(3): 313-319.
Olink Proteomics AB, Proseek® Multiplex 96×96 User Manual, 2016, 12 pages.
Oren et al., "Selective lysis of bacteria but not mammalian cells by diastereomers of melittin: structure-function study," Biochemistiy, Feb. 1997, 36(7):1826-35.
Osada et al., "Epitope mapping using ribosome display in a resconstituted cell-free protein synthesis system," J Biochem, May 2009, 145(5): 693-700.
O-Shannessy et al., "Detection and quantitation of hexa-histidine-tagged recombinant proteins on western blots and by a surface plasmon resonance biosensor technique," Anal Biochem, 229(1): 119-124, 1995.
Ostuni et al., "Patterning Mammalian Cells Using Elastomeric Membranes," Langmuir, Aug. 2000, 16(20):7811-7819.
Palamanda et al., "Evaluation of CYP1A1 and CYP2B1/2 m-RNA Induction in Rat Liver Slices Using the NanoString® Technology: A Novel Tool for Drug Discovery Lead Optimization," Drug metabolism letters, Nov. 3, 2009, 3(3):171-175.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Cancer gene therapy using adeno-associated virus vectors," Front Biosci., Jan. 2008, 13:2653-59.
Park et al., "The Estimation of Breast Cancer Disease-Probability by Difference of Individual Susceptibility," Cancer Res. Treat., Feb. 2003, 35(1):35-51, Abstract.
Patil et al., "DNA-based therapeutics and DNA delivery systems: a comprehensive review," AAPS J, Apr. 2005, 7(1):E61-77.
Patton et al., "Rainbow's end: the quest for multiplexed fluorescence quantitative analysis in proteomics." Current Opinion in Chemical Biology, Feb. 1, 2002, 6(1):63-69.
PCT International Preliminary Report on Patentability in International Appln. No. PCT/EP2012/056823, dated Oct. 15, 2013, 7 pages.
PCT International Preliminary Report on Patentability in International Appln. No. PCT/EP2013/071645, dated Apr. 21, 2015, 6 pages.
PCT International Search Report and Written Opinion in International Appln. No. PCT/EP2012/056823, dated Jun. 29, 2012, 12 pages.
PCT International Search Report and Written Opinion issued in International Appln. No. PCT/EP2013/071645, dated Nov. 28, 2013, 10 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gene," PNAS USA, Jun. 1992, 89(12): 5577-5581.
Petterson et al., "Generations of sequencing technologies," Genomics, 2009, 105-111.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Plasterk, "The Tc1/mariner transposon family," Curr Top Microbiol Immunol., 1996, 204:125-43.
Pluen et al., "Diffusion of macromolecules in agarose gels: comparison of linear and globular configurations," Biophys J., Jul. 1999, 77(1):542-552.
Polsky-Cynkin et al., "Use of DNA Immobilizedon Plastic and Agarose Supports to Detect DNA by Sandwich Hybridization," Clin. Chem. 31: 1438-1443, 1985.

(56) References Cited

OTHER PUBLICATIONS

U.S. Appl. No. 61/267,363, filed Dec. 7, 2009 (Year: 2009).
Punwaney et al., "Human papillomavirus may be common within nasopharyngeal carcinoma of Caucasian Americans: investigation of Epstein-Barr virus and human papillomavirus in eastern and western nasopharyngeal carcinoma using ligation-dependent polymerase chain reaction," Head & Neck, Jan. 1999, 21(1):21-29.
Raab et al., "Human tRNA genes function as chromatin insulators," EMBO J., Jan. 2012, 31(2):330-50.
Rajeswari et al., "Multiple pathogen biomarker detection using an encoded bead array in droplet PCR," J. Microbial Methods, Aug. 2017, 139:22-28.
Ramachandran et al., "Next-generation high-density self-assembling functional protein arrays," Nature Methods, Jun. 2008, 5(6):535-538.
Ramanujan et al., "Diffusion and convection in collagen gels: implications for transport in the tumor interstitium," Biophys. J., Sep. 2002, 83(3):1650-1660.
Ranki et al., "Sandwich hybridization as a convenient method for the detection of nucleic acids in crude samples", Gene 21: 77-85, cellulose, 1983.
Raouane et al., "Lipid conjugated oligonucleotides: a useful strategy for delivery," Bioconjug Chem., Jun. 2012, 23(6):1091-104.
Razonable, "Antiviral drugs for viruses other than human immunodeficiency virus," Mayo Clinic Proceedings, Oct. 2011, 86(10):1009-26.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rettig et al., "Large-scale single-cell trapping and imaging using microwell arrays," Anal Chem, Sep. 2005, 77(17):5628-5634.
Reznikoff, "Tn5 as a model for understanding DNA transposition," Mol Microbiol., Mar. 2003, 47(5):1199-206.
Roberts et al., "RNA-peptide fusions for the in vitro selection of peptides and proteins," PNAS USA, Nov. 1997, 94: 12297-122302.
Robinson et al., "Small-sample estimation of negative binomial dispersion, with applications to SAGE data," Biostatistics, Apr. 2008, 9(2):321-332.
Rogers et al., "Immobilization of oligonucleotides onto a glass support via disulfide bonds: A method for preparation of DNA microarrays," Anal Biochem., Jan. 1999, 266(1):23-30.
Rogers et al., "Use of a novel cross-linking method to modify adenovirus tropism," Gene Ther., Dec. 1997, 4(12):1387-92.
Ronaghi et al., "A sequencing method based on real-time pyrophosphate," Science, Jul. 1998, 281(5375): 363-365.
Ronaghi et al., "Real-time DNA sequencing using detection of pyrophosphate release," Analytical Biochemistiy, Nov. 1996, 242(1): 84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Rouillard et al., "OligoArray 2.0: design of oligonucleotide probes forDNA microarrays using a thermodynamic approach," Nuc. Acid Research, Jun. 2003, 31(12): 3057-3062.
Rountenberg et al., "Microfluidic probe: a new tool for integrating microfluidic environments and electronic wafer-probing," Lab Chip, Oct. 2009, 10(1):123-127.
Rubin et al., "Whole-genome resequencing reveals loci under selection during chicken domestication.," Nature, Mar. 2010, 464: 587-591.
Rubina et al., "Hydrogel-based protein microchips: manufacturing, properties, and applications," Biotechniques, May 2003, 34(5):1008-14.
Running et al., "A procedure for productive coupling of synthetic oligonucleotides to polystyrene microtiter wells for hybridization capture," Biotechniques, Mar. 1990, 8(3):276-279.

Rush et al., "New Aldehyde Tag Sequences Identified by Screening Formylglycine Generating Enzymes in Vitro and in Vivo," J. of American Chemical Society, Aug. 2008, 130(37): 12240-12241.
Rusk, "Spatial transcriptomics", Nature Methods, vol. 13, No. 9, 2016.
Russell et al., "Molecular mechanisms of late endosome morphology, identity and sorting," Curr. Opin. Cell Bio., Aug. 2006, 18(4):422-428.
Salem et al., "Multidimensional transcriptomics provides detailed information about immune cell distribution and identity in HER2+ breast tumors", bioRxiv, 41 pages, 2018.
Sano et al., "Immuno-PCR: Very Sensitive Antigen Detection by Means of Specific Antibody-DNA Conjugates," Science, Oct. 2, 1992, 258(5079):120-122.
Saxonov, "Mastering Biology to Advance Human Health," 10x Genomics, Sep. 2020, 41 pages.
Schaus et al., "A DNA nanoscope via auto-cycling proximity recording," Nat. Commun. 8, 696, 10 pages, 2017.
Schellings et al., "Absence of SPARC results in increased cardiac rupture and dysfunction after acute myocardial infarction," J Exp Med., Jan. 2009, 206(1):113-23.
Schena et al., "Quantitative monitoring of gene expression patterns with a complementary DNA microarray," Science, Oct. 1995, 270(5235):467-470.
Schena et al., "Entering the Postgenome Era," Science, 1995, 270:368-9, 371.
Schlapak et al., "Glass surfaces grafted with high-density poly (ethylene glycol) as substrates for DNA oligonucleotide microarrays," Langinuir, Jan. 2006, 22: 277-285.
Schmitt et al., "Detection of ultra-rare mutations by next-generation sequencing," PNAS (2012) 109:14508-14523.
Scholz et al., "The Molecular Chaperone Hsp90 Is Required for Signal Transduction by Wild-Type Hck and Maintenance of Its Constitutively Active Counterpart1," Cell Growth Differ., Aug. 2001, 12(8):409-417.
Schwartz et al., "Capturing native long-range contiguity by in situ library construction and optical sequencing," PNAS, Nov. 13, 2012, 109(46):18749-18754.
Schweitzer et al., "Multiplexed protein profiling on microarrays by rolling-circle amplification," Nature Biotechnology, Apr. 2002, 20(4):359-365.
Sergeeva et al., "Display technologies: Application for the discovery of drug and gene delivery aaents," Advanced Drug Delivery Reviews (2006) 58(15):1622-1654.
Seurynck-Servoss et al., "Evaluation of Surface Chemistries for Antibody Microarrays", Anal Biochem., 371(1): 105-115, 2007.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction,", Chem. Commun., 47: 6257-6259, 2011.
Shendure et al., "Accurate Multiplex Polony Sequencing of an Evolved Bacterial Genome," Science, 2005, 309:1728-1732.
Shi et al., "The Micro Array Quality Control (MAQC) project shows inter- and intraplatform reproducibility of gene expression measurements," Nature Biotechnology, 2006, 24(9):1151-61.
Shi, "Enabling large-scale pharmacogenetic studies by high-throughput mutation detection and genotyping technologies," Clin. Chem., Feb. 2001, 47(2):164-172.
Shirai et al., "Novel Tools for Analyzing Gene Expressions in Single Cells," The 5th International Workshop on Approaches to Single-Cell Analysis, The University of Tokyo, Mar. 3 -4, 2011, 1 page.
Shoemaker et al., "Quantitative phenotypic analysis of yeast deletion mutants using a highly parallel molecular bar-coding strategy," Nature genetics (1996) 14:450-456.
Shults et al., "A multiplexed protein kinase assay," Chem Bio Chem (2007) 8:933-942.
Sievertzon et al., "Transcriptome analysis in primary neural stem cells using a tag cDNA amplification method," BMC Neuroscience, Dec. 2005, 6: 28.

(56) References Cited

OTHER PUBLICATIONS

Simonis et al., "Nuclear organization of active and inactive chromatin domains uncovered by chromosome conformation capture-on-chip (4C)," Nat Genet., Nov. 2006, 38(11) 1348-54.
Slonim and Yanai, "Getting started in gene expression microarray analysis," Plos Computational Biology, 2009, 5(10):e1000543.
Smolock et al., "Ribosomal Protein L17, RpL17, is an Inhibitor of Vascular Smooth Muscle Growth and Carotid Intima Formation," Circulation, Nov. 2012, 126(20):2418-2427.
Soderberg et al. "Characterizing proteins and their interactions in cells and tissues using the in situ proximity ligation assay," Methods, Jul. 2008, 45(3):227-232.
Soderberg et al., "Direct observation of individual endogenous protein complexes in situ by proximity ligation," Nature Methods, 2006, 3:995-1000.
Son et al., "A platform for ultrasensitive and selective multiplexed marker protein assay toward early-stage cancer diagnosis," Nanomedicine, Feb. 7, 2007, 2(1):79-82.
Soni and Meller, "Progress toward ultrafast DNA sequencing using solid-state nanopores," Clin Chem., 2007, 53: 1996-2001.
Spitale et al., "Structural imprints in vivo decode RNA regulatory mechanisms", Nature, 519(7544): 486-90, 2015.
Spurgeon et al., "High Throughput Gene Expression Measurement with Real Time PCR in a Microfluidic Dynamic Array," Plos ONE, 2008, 3(2):e1662.
Stahl et al., "Supplementary Materials for Visualization and analysis of gene expression in tissue sections by spatial transcriptomics," Science, Jun. 2016, 353(6294):78-82, 40 pages.
Stahl et al., "Visualization and analysis of gene expression in tissue sections by spatial transcriptomics," Science, Jul. 2016, 353(6294):78-82.
Stevens Jr. et al., "Enhancement of phosphoprotein analysis using a fluorescent affinity tag and mass spectrometry," Rapid Commun Mass Spectrom, 2005, 19(15):2157-62.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS U S A., May 2009, 106(19):7702-7707.
Strell et al., "Placing RNA in context and space—methods for spatially resolved transcriptomics", The FEBS Journal, 14 pages, 2017.
Stroh et al., "Quantum dots spectrally distinguish multiple species within the tumor milieu in vivo," Nat Med., Jun. 2005, 11(6):678-82.
Subramanian et al., "Gene set enrichment analysis: a knowledge-based approach for interpreting genome-wide expression profiles," PNAS, Oct. 2005, 102(43):15545-15550.
Suh et al., "A simple soft lithographic route to fabrication of poly(ethylene glycol) microstructures for protein and cell patterning," Biomaterials, Feb. 2004, 25(3):557-563.
Sumitomo et al., "Ca2+ ion transport through channels formed by -hemolysin analyzed using a microwell array on a Si substrate," Biosensors and Bioelectronics, 2012, 31(1):445-450.
Summersgill et al., "Fluorescence In Situ Hybridization Analysis of Formalin Fixed Paraffin Embedded Tissues, Including Tissue Microarrays," Chapter 4, Bridger, J. Ed., Methods in Molecular Biology 659, 2010, 51-70, 2010.
Sun et al., "Direct immobilization of DNA probes on non-modified plastics by UV irradiation and integration in microfluidic devices for rapid bioassay," Anal. Bio. Cherm., 402: 741-748, 2012.
Surzhik et al., "Template-dependent biosynthesis of poly(G) x poly (C) and its antiviral activity in vitro and in vivo," Antiviral Res., May 1988, 38(2):131-40.
Swartz et al., "Interstitial flow and its effects in soft tissues," Annu Rev Biomed Eng., 2007, 9:229-56.
Syková et al., "Diffusion in brain extracellular space," Physiol Rev., Oct. 2008, 88(4):1277-340.

Tai et al., "Replication-competent retrovirus vectors for cancer gene therapy," Front Biosci., Jan. 2008, 13:3083-95.
Takahashi et al., "In Vitro Selection of Protein and Peptide Libraries Using mRNA Display," Nucleic Acid and Peptide Aptamers: Methods and Protocols (2009) 535:293-314 (Ch. 17).
Tan et al., "Parylene peel-off arrays to probe the role of cell-cell interactions in tumour angiogenesis," Integr Biol (Camb), Oct. 2009, 1(10):587-594.
Tang et al., "RNA—Seq analysis to capture the transcriptome landscape of a single cell.," Nat Protoc., 5: 516-35, 2010.
Taniguchi et al., "Quantitative analysis of gene expression in a single cell by qPCR," Nature Methods, 6, pp. 503-506, 2009.
Taylor et al., "Mitochondrial DNA mutations in human disease." Nature Reviews Genetics. May 2005, 6(5):389-402.
Tedpella.com, [online], "Glass Microscope Slides," 2021, retrieved on Jun. 9, 2021, retrieved from URL<https://www.tedpella.com/histo_html/slides.htm>, 7 pages.
Tegtmeyer et al., "Alternative Interactions of the SV40 A Protein with DNA," Virology, 1981, 115:75-87.
Tentori et al., "Detection of Isoforms Differing by a Single Charge Unit in Individual Cells.", Chem. Int. Ed., 55, 12431, 2016.
Thiery et al., "Multiplex target protein imaging in tissue sections by mass spectrometry—TAMSIM," Rapid Commun. Mass Spectrom., 2007, 21:823-829.
Thorne et al., "In vivo diffusion analysis with quantum dots and dextrans predicts the width of brain extracellular space," Proc Natl Acad Sci USA, Apr. 2006, 103(14):5567-5572.
Thornton, "High rate thick film growth." Annual review of materials science, Aug. 1977, 7(1):239-60.
Tian et al., "Antigen peptide-based immunosensors for rapid detection of antibodies and antigens," Anal Chem May 26, 2009, 81 (13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Timofeev et al., "Regioselective immobilization of short oligonucleotides to acrylic copolymer gels," Nucleic Acids Res., Aug. 1996, 24(16):3142-8.
Tolbert et al., "New Methods for Proteomic Research: Preparation of Proteins with N-Terminal Cysteines for Labeling and Conjugation," Angewandte Chemie International Edition, Jun. 17, 2002, 41(12):2171-4.
Tseng et al., "Magnetic nanoparticle-mediated massively parallel mechanical modulation of single-cell behavior," Nat Methods, Nov. 2012, 9(11):1113-1119.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Valencia et al., "mRNA-Display-Based Selections for Proteins with Desired Functions: A Protease-Substrate Case Study." Biotechnology progress, May 2008, 24(3):561-9.
Van Gelder et al., "Amplified RNA synthesized from limited quantities of heterogeneous cDNA," Proc. Natl. Acad. Sci. USA 87, 1663-1667, 1990.
Van Ness et al., "A versatile solid support system for oligodeoxynucleotide probe-based hybridization assays", Nucleic Acids Res. 19: 3345-3350, 1991.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 20, 1995, 270(5235):484-7.
Vermesh et al., "High-density, multiplexed patterning of cells at single-cell resolution for tissue engineering and other applications," Angew Chem Int Ed Engl, Aug. 2011, 50(32):7378-7380.
Vickovic et al., "High-definition spatial transcriptomics for in situ tissue profiling," Nat Methods, Oct. 2019, 16(10):987-990.

(56) References Cited

OTHER PUBLICATIONS

Vickovic et al., "Massive and parallel expression profiling using microarrayed single-cell sequencing," Nature Communications, 2016, 7(13182):1-9.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 3, 1999, 96:9236-9241.
Wade et al., "Genome sequence, comparative analysis, and population genetics of the domestic horse.," Science., 326: 865-7, 2009.
Waichman et al., "Functional immobilization and patterning of proteins by an enzymatic transfer reaction," Analytical chemistry, Jan. 21, 2010, 82(4):1478-85.
Walker et al., "Strand displacement amplification—an isothermal, in vitro DNA amplification technique." Nucleic acids research, Apr. 11, 1992, 1992, 20(7):1691-1696.
Wang et al., "Mutations in NEXN, a Z-disc gene, are associated with hypertrophic cardiomyopathy," Am J Hum Genet., Nov. 2010, 87(5):687-93.
Wang et al., "Single cell analysis: the new frontier in 'omics'," Trends Biotechnol., 28: 281-90, 2010.
Wang et al., "Three-dimensional intact-tissue sequencing of single-cell transcriptional states", Science, 361(6400), 22 pages, 2018.
Wang et al., "High-fidelity mRNA amplification for gene profiling." Nature biotechnology. Apr. 2000, 18(4):457-459.
Wang, "RNA amplification for successful gene profiling analysis," J Transl Med., Jul. 2005, 3:28, 11 pages.
Watanabe et al., "Cellular networks involved in the influenza virus life cycle," Cell Host & Microbe, Jun. 2010, 7(6):427-39.
Waxman et al., "De-regulation of common housekeeping genes in hepatocellular carcinoma," BMC Genomics, 2007, 1-9.
Weichhart et al., "Functional selection of vaccine candidate peptides from *Staphylococcus aureus* whole-genome expression libraries in vitro," Infection and Immunity, 2003, 71 (8):4333-4641.
Weinreich et al., "Evidence that the cis Preference of the Tn5 Transposase is Caused by Nonproductive Multimerization," Genes and Development, Oct. 1994, 8(19):2363-2374.
Weinstein et al., "DNA microscopy: Optics-free spatio-genetic imaging by a stand-alone chemical reaction", bioRxiv, 41 pages, 2018.
Wheeler et al., "Microfluidic device for single-cell analysis," Analytical Chemistry, Jul. 2003, 75(14):3581-3586.
Wiedmann et al., "Ligase chain reaction (LCR)—overview and applications," PCR Methods Appl., Feb. 1994, 3(4):S51-64.
Williams, "RAC reviews serious adverse event associated with AAV therapy trial," Mol Ther., Dec. 2007, 15(12):2053-54.
Willi-Monnerat et al., "Comprehensive spatiotemporal transcriptomic analyses of the ganglionic eminences demonstrate the uniqueness of its caudal subdivision," Molecular and Cellular Nueorsciences 37(4):845-856, 2008.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles", Nucleic Acids Res. 15: 2911-2926, 1987.
Wong et al., "Direct Site-Selective Covalent Protein Immobilization Catalyzed by a Phosphopantetheinyl Transferase," J. Am. Chem Soc., 2008, 130:12456-64.
Woo et al., "A Comparison of cDNA, Oligonucleotide, and Affymetrix GeneChip Gene Expression Microarray Platforms," Journal of Biomolecular Techniques, 2004, 15(4), 276-284.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Analyt. Biochem, 2001, 294:169-175.
Wright et al., "Reusable, reversibly sealable parylene membranes for cell and protein patterning," J Biomed Mater Res A., May 2008, 85(2):530-538.
Wu et al., "Detection DNA Point Mutation with Rolling-Circle Amplification Chip," Bioinformatics and Biomedical Engineering (ICBBE), 2010 4th International Conference on IEEE, Piscatway, NJ, USA, Jun. 18, 2010, 1-4 pages.
Xiao et al., "Direct determination of haplotypes from single DNA molecules," Nature Methods, 2009, 6(3):199-201.
Xie et al., "CryoFISH: Fluorescence In Situ Hybridization on Ultrathin Cryosections," Fluorescence in situ Hybridization (FISH), Jul. 2010, pp. 221-230.
Yan et al., "Decorin gene delivery inhibits cardiac fibrosis in spontaneously hypertensive rats by modulation of transforming growth factor-beta/Smad and p38 mitogen-activated protein kinase signaling pathways," Hum Gene Ther., Oct. 2009, 20(10):1190-200.
Yeakley et al., "Profiling alternative splicing on fiber-optic arrays," Nature Biotechnology, Apr. 2002, 20(4):353-358.
Yershov et al., "DNA analysis and diagnostics on oligonucleotide microchips," Proc. Natl. Acad. Sci. USA, May 1996, 93(10):4913-4918.
Yet et al., "Cardiac-specific expression of heme oxygenase-1 protects against ischemia and reperfusion injury in transgenic mice," Circ Res., Jul. 2001, 89(2):168-73.
Yin et al., "Genetically encoded short peptide tag for versatile protein labeling by Sfp phosphopantetheinyl transferase," PNAS, 2005, 102(44):15815-20.
Yonezawa et al., "DNA display for in vitro selection of diverse peptide libraries," Nucleic Acids Research, 2003, 31 (19):e118.
Yusof et al., "Inkjet-like printing of single-cells," Lab Chip, Jul. 2011, 11(14):2447-2454.
Zhang et al., "A novel mechanism of transposon-mediated gene activation," PLoS Genet., Oct. 2009, 5(10):e1000689, 10 pages.
Zhang et al., "Assembling DNA through Affinity Binding to Achieve Ultrasensitive Protein Detection," Angew Chem Int Ed (2013) 52:2-10.
Zhang et al., "Binding-induced DNA assembly and its application to yoctomole detection of proteins," Anal Chem (2012) 84(2):877-884.
Zhang et al., "Single-base mutational analysis of cancer and genetic diseases using membrane bound modified oligonucleotides," Nucleic Acids Res., Jul. 1991, 19(14):3929-33.
Zhang et al., "Stripping custom microRNA microarrays and the lessons learned about probe-slide interactions," Anal Biochem., Mar. 2009, 386(2):222-7.
Zheng et al., Origins of human mitochondrial point mutations as DNA polymerase mediated errors. Mutat. Res. 599(1-2): 11-20, 2006.
Zhou et al., "Genetically encoded short peptide tags for orthogonal protein labeling by Sfp and AcpS phosphopantetheinyl transferases," ACS Chemical Biol., 2007 25:337-346.
Zhu et al., "Reverse Transcriptase Template Switching: A SMART Approach for Full-Length cDNA Library Construction," BioTechniques, 2001, 30(4): 892-897.
Zieba et al., "Bright-field microscopy visualization of proteins and protein complexes by in situ proximity ligation with peroxidase detection," Clin Chem, Jan. 2010, 56(1):99-110.
Zilberman et al., "Genome-wide analysis of DNA methylation patterns," Development (2007) 134: 3959-3965.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine, 2013 11(104):1-7.
Espina et al., "Laser-capture microdissection," Nat Protoc, 2006. 1(2):586-603.
Extended European Search Report in European Appln. No. 21163827.5, dated Sep. 24, 2021, 12 pages.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
König et al., "iCLIP reveals the function of hnRNP particles in splicing at individual nucleotide resolution," Nat Struct Mol Biol., Jul. 2010, 17(7):909-915.

(56) References Cited

OTHER PUBLICATIONS

Larsson et al., "In situ detection and genotyping of individual mRNA molecules," Nat Methods, May 2010, 7(5):395-7.

Larsson et al., "In situ genotyping individual DNA molecules by target-primed rolling-circle amplification of padlock probes," Nat Methods, Dec. 2004, 1(3):227-32.

Lyamichev et al., "Polymorphism identification and quantitative detection of genomic DNA by invasive cleavage of oligonucleotide probes," Nat Biotechnol., Mar. 1999, 17(3):292-6.

Martin, "Cutadapt removes adapter sequences front high-throughput sequencing reads," EMBnet Journal, 2011, 17(1):10-12.

Miner et al., "Molecular barcodes detect redundancy and contamination in hairpin-bisulfite PCR," Nucleic Acids Res., Sep. 2004, 32(17):e135, 4 pages.

Nilsson et al., "RNA-templated DNA ligation for transcript analysis," Nucleic Acids Res., Jan. 2001, 29(2):578-81.

Olivier, "The Invader assay for SNP genotyping" Mutat. Res., Jun. 2005, 573(1-2):103-110.

Wikipedia.org [online], "Random hexamer," Jan. 2012, Retrieved on Jan. 21, 2022, retrieved from URL<https://en.wikipedia.org/w/index.php?title=Random_hexamer&oldid=473042236>, 1 page.

Ciaccio et al., "Systems analysis of EGF receptor signaling dynamics with microwestern arrays," Nat Methods, Feb. 2010, 7(2):148-55.

Hughes et al., "Microfluidic Western blotting," PNAS, Dec. 2012, 109(52):21450-21455.

Berger et al., "Universal bases for hybridization, replication and chain termination," Nucleic Acid Res., Aug. 2000, 28(15):2911-2914.

Biol.wwu.edu [online], "Principles of Di-Base Sequencing and the Advantages of Color Space Analysis in the SOLiD System," 2008, retrieved on Mar. 11, 2022, retrieved from URL<https://biol.wwu.edu//young/470/stuff/abi-solid.pdf>, 4 pages.

\* cited by examiner

Overall Results for sample 3 : R6 3/1 2011
Number of peaks found:    1
Peak table  for sample 3 : R6 3/1 2011

| Peak | Size [bp] | Conc. [ng/µl] | Molarity [nmol/l] | Observations |
|---|---|---|---|---|
| 1 | ◂50 | 8.30 | 251.5 | Lower Marker |
| 2 | 386 | 22.87 | 89.8 | |
| 3 | ▸10,380 | 4.20 | 0.6 | Upper Marker |

Overall Results for sample 4 : R8 3/1 2011
Number of peaks found:    1
Peak table  for sample 4 : R8 3/1 2011

| Peak | Size [bp] | Conc. [ng/µl] | Molarity [nmol/l] | Observations |
|---|---|---|---|---|
| 1 | ◂50 | 8.30 | 251.5 | Lower Marker |
| 2 | 676 | 21.53 | 48.2 | |
| 3 | ▸10,380 | 4.20 | 0.6 | Upper Marker |

SEQUENCE LISTING

<160> NUMBER OF SEQ ID NOS: 121

<210> SEQ ID NO 1
<211> LENGTH: 72
<212> TYPE: DNA
<213> ORGANISM: Artificial Sequence
<220> FEATURE:
<223> OTHER INFORMATION: TAP-ID1
<220> FEATURE:
<221> NAME/KEY: misc_feature
<222> LOCATION: (1)..(1)
<223> OTHER INFORMATION: 5'-terminus amino linker with a C6 spacer
<220> FEATURE:
<221> NAME/KEY: misc_feature
<222> LOCATION: (72)..(72)
<223> OTHER INFORMATION: n is a, c, g, t or u

<400> SEQUENCE: 1
uuaagtacaa atctcgactg ccactctgaa ccttctcctt ctccttcacc tttttttttt    60
tttttttttt vn                                                        72

<210> SEQ ID NO 2
<211> LENGTH: 10
<212> TYPE: DNA
<213> ORGANISM: Artificial Sequence
<220> FEATURE:
<223> OTHER INFORMATION: Enzymatic recognition sequence

<400> SEQUENCE: 2
uuaagtacaa                                                           10

<210> SEQ ID NO 3
<211> LENGTH: 20
<212> TYPE: DNA
<213> ORGANISM: Artificial Sequence
<220> FEATURE:
<223> OTHER INFORMATION: Universal amplification handle P

<400> SEQUENCE: 3
atctcgactg ccactctgaa                                                20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
ccttctcctt ctccttcacc                                                20

<210> SEQ ID NO 5
<211> LENGTH: 22
<212> TYPE: DNA
<213> ORGANISM: Artificial sequence
<220> FEATURE:
<223> OTHER INFORMATION: Capture sequence
<220> FEATURE:
<221> NAME/KEY: misc_feature
<222> LOCATION: (22)..(22)
<223> OTHER INFORMATION: n is a, c, g, or t

<400> SEQUENCE: 5
tttttttttt tttttttttt vn                                             22

<210> SEQ ID NO 6
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 6
ccttctcctt ctccttcacc                                               20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
ccttgctgct tctcctcctc                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
acctcctccg cctcctcctc                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
gagacatacc accaagagac                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gtcctctatt ccgtcaccat                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
gactgagctc gaacatatgg                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
```
tggaggattg acacagaacg                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ccagcctctc cattacatcg                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
aagatctacc agccagccag                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
cgaacttcca ctgtctcctc                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ttgcgccttc tccaatacac                                              20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ctcttcttag catgccacct                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
accacttctg cattacctcc                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
acagcctcct cttcttcctt                                           20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
aatcctctcc ttgccagttc                                           20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gatgcctcca cctgtagaac                                           20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gaaggaatgg aggatatcgc                                           20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gatccaagga ccatcgactg                                           20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ccactggaac ctgacaaccg                                           20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ctgcttcttc ctggaactca                                           20

```
<210> SEQ ID NO 26
<211> LENGTH: 66
<212> TYPE: DNA
<213> ORGANISM: Artificial sequence
<220> FEATURE:
<223> OTHER INFORMATION: Free 5' surface probe - A
<220> FEATURE:
<221> NAME/KEY: misc_feature
<222> LOCATION: (66)..(66)
<223> OTHER INFORMATION: 3'-terminus amino linker with a C7 spacer

<400> SEQUENCE: 26
gcgttcagag tggcagtcga gatcacgcgg caatcatatc ggacagatcg gaagagcgta      60
gtgtag                                                                 66

<210> SEQ ID NO 27
<211> LENGTH: 66
<212> TYPE: DNA
<213> ORGANISM: Artificial sequence
<220> FEATURE:
<223> OTHER INFORMATION: Free 5' surface probe - U
<220> FEATURE:
<221> NAME/KEY: misc_feature
<222> LOCATION: (66)..(66)
<223> OTHER INFORMATION: 3'-terminus amino linker with a C7 spacer

<400> SEQUENCE: 27
gcgttcagag tggcagtcga gatcacgcgg caatcatatc ggacggctgc tggtaaatag      60
agatca                                                                 66

<210> SEQ ID NO 28
<211> LENGTH: 23
<212> TYPE: DNA
<213> ORGANISM: Artificial sequence
<220> FEATURE:
<223> OTHER INFORMATION: LP'

<400> SEQUENCE: 28
ttcagagtgg cagtcgagat cac                                              23

<210> SEQ ID NO 29
<211> LENGTH: 18
<212> TYPE: DNA
<213> ORGANISM: Artificial sequence
<220> FEATURE:
<223> OTHER INFORMATION: ID'

<400> SEQUENCE: 29
gcggcaatca tatcggac                                                    18

<210> SEQ ID NO 30
<211> LENGTH: 22
<212> TYPE: DNA
<213> ORGANISM: Artificial sequence
<220> FEATURE:
<223> OTHER INFORMATION: A' 22bp MutY mismatch

<400> SEQUENCE: 30
agatcggaag agcgtagtgt ag                                               22

<210> SEQ ID NO 31
<211> LENGTH: 22
<212> TYPE: DNA
<213> ORGANISM: Artificial sequence
<220> FEATURE:
<223> OTHER INFORMATION: U' 22bp MutY mismatch
```

<400> SEQUENCE: 31
ggctgctggt aaatagagat ca                                              22

<210> SEQ ID NO 32
<211> LENGTH: 33
<212> TYPE: DNA
<213> ORGANISM: Artificial sequence
<220> FEATURE:
<223> OTHER INFORMATION: Illumina amplification handle A

<400> SEQUENCE: 32
acactctttc cctacacgac gctcttccga tct                                  33

<210> SEQ ID NO 33
<211> LENGTH: 35
<212> TYPE: DNA
<213> ORGANISM: Artificial sequence
<220> FEATURE:
<223> OTHER INFORMATION: Universal amplification handle U

<400> SEQUENCE: 33
aagtgtggaa agttgatcgc tatttaccag cagcc                                35

<210> SEQ ID NO 34
<211> LENGTH: 45
<212> TYPE: DNA
<213> ORGANISM: Artificial sequence
<220> FEATURE:
<223> OTHER INFORMATION: Capture LP Poly-dTVN
<220> FEATURE:
<221> NAME/KEY: misc_feature
<222> LOCATION: (1)..(1)
<223> OTHER INFORMATION: Phosphorylated
<220> FEATURE:
<221> NAME/KEY: misc_feature
<222> LOCATION: (45)..(45)
<223> OTHER INFORMATION: n is a, c, g, or t

<400> SEQUENCE: 34
gtgatctcga ctgccactct gaattttttt tttttttttt tttvn                     45

<210> SEQ ID NO 35
<211> LENGTH: 47
<212> TYPE: DNA
<213> ORGANISM: Artificial sequence
<220> FEATURE:
<223> OTHER INFORMATION: Capture LP Poly-d24T
<220> FEATURE:
<221> NAME/KEY: misc_feature
<222> LOCATION: (1)..(1)
<223> OTHER INFORMATION: Phosphorylated

<400> SEQUENCE: 35
gtgatctcga ctgccactct gaattttttt tttttttttt ttttttt                   47

<210> SEQ ID NO 36
<211> LENGTH: 21
<212> TYPE: DNA
<213> ORGANISM: Artificial sequence
<220> FEATURE:
<223> OTHER INFORMATION: Illumina amplification handle B

<400> SEQUENCE: 36
agacgtgtgc tcttccgatc t                                               21

<210> SEQ ID NO 37

```
<211> LENGTH: 20
<212> TYPE: DNA
<213> ORGANISM: Artificial sequence
<220> FEATURE:
<223> OTHER INFORMATION: Universal amplification handle X

<400> SEQUENCE: 37
acgtctgtga atagccgcat                                              20

<210> SEQ ID NO 38
<211> LENGTH: 29
<212> TYPE: DNA
<213> ORGANISM: Artificial sequence
<220> FEATURE:
<223> OTHER INFORMATION: B R6 handle (or X)
<220> FEATURE:
<221> NAME/KEY: misc_feature
<222> LOCATION: (22)..(29)
<223> OTHER INFORMATION: n is a, c, g, or t

<400> SEQUENCE: 38
agacgtgtgc tcttccgatc tnnnnnnnn                                    29

<210> SEQ ID NO 39
<211> LENGTH: 31
<212> TYPE: DNA
<213> ORGANISM: Artificial sequence
<220> FEATURE:
<223> OTHER INFORMATION: B R8 handle (or X)
<220> FEATURE:
<221> NAME/KEY: misc_feature
<222> LOCATION: (22)..(31)
<223> OTHER INFORMATION: n is a, c, g, or t

<400> SEQUENCE: 39
agacgtgtgc tcttccgatc tnnnnnnnnn n                                 31

<210> SEQ ID NO 40
<211> LENGTH: 43
<212> TYPE: DNA
<213> ORGANISM: Artificial sequence
<220> FEATURE:
<223> OTHER INFORMATION: B polyTVN (or X)
<220> FEATURE:
<221> NAME/KEY: misc_feature
<222> LOCATION: (43)..(43)
<223> OTHER INFORMATION: n is a, c, g, or t

<400> SEQUENCE: 40
agacgtgtgc tcttccgatc tttttttttt tttttttttt tvn                    43

<210> SEQ ID NO 41
<211> LENGTH: 45
<212> TYPE: DNA
<213> ORGANISM: Artificial sequence
<220> FEATURE:
<223> OTHER INFORMATION: B poly24T (or X)

<400> SEQUENCE: 41
agacgtgtgc tcttccgatc tttttttttt tttttttttt ttttt                  45

<210> SEQ ID NO 42
<211> LENGTH: 53
<212> TYPE: DNA
<213> ORGANISM: Artificial sequence
<220> FEATURE:
<223> OTHER INFORMATION: A P handle

<400> SEQUENCE: 42
```

```
acactctttc cctacacgac gctcttccga tctatctcga ctgccactct gaa    53
```

<210> SEQ ID NO 43
<211> LENGTH: 20
<212> TYPE: DNA
<213> ORGANISM: Artificial sequence
<220> FEATURE:
<223> OTHER INFORMATION: Beta-2 microglobulin (B2M) primer

<400> SEQUENCE: 43

```
tgggggtgag aattgctaag                                         20
```

<210> SEQ ID NO 44
<211> LENGTH: 20
<212> TYPE: DNA
<213> ORGANISM: Artificial sequence
<220> FEATURE:
<223> OTHER INFORMATION: ID-1 primer

<400> SEQUENCE: 44

```
ccttctcctt ctccttcacc                                         20
```

<210> SEQ ID NO 45
<211> LENGTH: 20
<212> TYPE: DNA
<213> ORGANISM: Artificial sequence
<220> FEATURE:
<223> OTHER INFORMATION: ID-5 primer

<400> SEQUENCE: 45

```
gtcctctatt ccgtcaccat                                         20
```

<210> SEQ ID NO 46
<211> LENGTH: 20
<212> TYPE: DNA
<213> ORGANISM: Artificial sequence
<220> FEATURE:
<223> OTHER INFORMATION: ID-20 primer

<400> SEQUENCE: 46

```
ctgcttcttc ctggaactca                                         20
```

<210> SEQ ID NO 47
<211> LENGTH: 20
<212> TYPE: DNA
<213> ORGANISM: Artificial sequence
<220> FEATURE:
<223> OTHER INFORMATION: Forward - Genomic DNA Human primer

<400> SEQUENCE: 47

```
gactgctctt ttcacccatc                                         20
```

<210> SEQ ID NO 48
<211> LENGTH: 18
<212> TYPE: DNA
<213> ORGANISM: Artificial sequence
<220> FEATURE:
<223> OTHER INFORMATION: Reverse - Genomic DNA Human primer

<400> SEQUENCE: 48

```
ggagctgctg gtgcaggg                                           18
```

<210> SEQ ID NO 49
<211> LENGTH: 20
<212> TYPE: DNA

```
<213> ORGANISM: Artificial sequence
<220> FEATURE:
<223> OTHER INFORMATION: P - label specific primer

<400> SEQUENCE: 49
atctcgactg ccactctgaa                                              20

<210> SEQ ID NO 50
<211> LENGTH: 78
<212> TYPE: DNA
<213> ORGANISM: Artificial sequence
<220> FEATURE:
<223> OTHER INFORMATION: Probe 1
<220> FEATURE:
<221> NAME/KEY: misc_feature
<222> LOCATION: (78)..(78)
<223> OTHER INFORMATION: n is a, c, g, t or u

<400> SEQUENCE: 50
uuuuuacact ctttccctac acgacgctct tccgatctgt ccgatatgat tgccgctttt    60
tttttttttt tttttvn                                                  78

<210> SEQ ID NO 51
<211> LENGTH: 78
<212> TYPE: DNA
<213> ORGANISM: Artificial sequence
<220> FEATURE:
<223> OTHER INFORMATION: Probe 2
<220> FEATURE:
<221> NAME/KEY: misc_feature
<222> LOCATION: (78)..(78)
<223> OTHER INFORMATION: n is a, c, g, t or u

<400> SEQUENCE: 51
uuuuuacact ctttccctac acgacgctct tccgatctat gagccgggtt catctttttt    60
tttttttttt tttttvn                                                  78

<210> SEQ ID NO 52
<211> LENGTH: 78
<212> TYPE: DNA
<213> ORGANISM: Artificial sequence
<220> FEATURE:
<223> OTHER INFORMATION: Probe 3
<220> FEATURE:
<221> NAME/KEY: misc_feature
<222> LOCATION: (78)..(78)
<223> OTHER INFORMATION: n is a, c, g, t or u

<400> SEQUENCE: 52
uuuuuacact ctttccctac acgacgctct tccgatcttg aggcactctg ttgggatttt    60
tttttttttt tttttvn                                                  78

<210> SEQ ID NO 53
<211> LENGTH: 78
<212> TYPE: DNA
<213> ORGANISM: Artificial sequence
<220> FEATURE:
<223> OTHER INFORMATION: Probe 4
<220> FEATURE:
<221> NAME/KEY: misc_feature
<222> LOCATION: (78)..(78)
<223> OTHER INFORMATION: n is a, c, g, t or u

<400> SEQUENCE: 53
uuuuuacact ctttccctac acgacgctct tccgatctat gattagtcgc cattcgtttt    60
tttttttttt tttttvn                                                  78
```

<210> SEQ ID NO 54
<211> LENGTH: 78
<212> TYPE: DNA
<213> ORGANISM: Artificial sequence
<220> FEATURE:
<223> OTHER INFORMATION: Probe 5
<220> FEATURE:
<221> NAME/KEY: misc_feature
<222> LOCATION: (78)..(78)
<223> OTHER INFORMATION: n is a, c, g, t or u

<400> SEQUENCE: 54
uuuuuacact ctttccctac acgacgctct tccgatctac ttgagggtag atgttttttt    60
tttttttttt tttttvn                                                  78

<210> SEQ ID NO 55
<211> LENGTH: 78
<212> TYPE: DNA
<213> ORGANISM: Artificial sequence
<220> FEATURE:
<223> OTHER INFORMATION: Probe 6
<220> FEATURE:
<221> NAME/KEY: misc_feature
<222> LOCATION: (78)..(78)
<223> OTHER INFORMATION: n is a, c, g, t or u

<400> SEQUENCE: 55
uuuuuacact ctttccctac acgacgctct tccgatctat ggccaatact gttatctttt    60
tttttttttt tttttvn                                                  78

<210> SEQ ID NO 56
<211> LENGTH: 78
<212> TYPE: DNA
<213> ORGANISM: Artificial sequence
<220> FEATURE:
<223> OTHER INFORMATION: Probe 7
<220> FEATURE:
<221> NAME/KEY: misc_feature
<222> LOCATION: (78)..(78)
<223> OTHER INFORMATION: n is a, c, g, t or u

<400> SEQUENCE: 56
uuuuuacact ctttccctac acgacgctct tccgatctcg ctaccctgat tcgaccttttt   60 tttttttttt tttttvn                                                  78

<210> SEQ ID NO 57
<211> LENGTH: 78
<212> TYPE: DNA
<213> ORGANISM: Artificial sequence
<220> FEATURE:
<223> OTHER INFORMATION: Probe 8
<220> FEATURE:
<221> NAME/KEY: misc_feature
<222> LOCATION: (78)..(78)
<223> OTHER INFORMATION: n is a, c, g, t or u

<400> SEQUENCE: 57
uuuuuacact ctttccctac acgacgctct tccgatctgc ccactttcgc cgtagttttt    60
tttttttttt tttttvn                                                  78

<210> SEQ ID NO 58
<211> LENGTH: 78
<212> TYPE: DNA
<213> ORGANISM: Artificial sequence
<220> FEATURE:

```
<223> OTHER INFORMATION: Probe 9
<220> FEATURE:
<221> NAME/KEY: misc_feature
<222> LOCATION: (78)..(78)
<223> OTHER INFORMATION: n is a, c, g, t or u

<400> SEQUENCE: 58
uuuuuacact ctttccctac acgacgctct tccgatctag caactttgag caagatttt      60 tttttttttt tttttvn                                                    78

<210> SEQ ID NO 59
<211> LENGTH: 78
<212> TYPE: DNA
<213> ORGANISM: Artificial sequence
<220> FEATURE:
<223> OTHER INFORMATION: Probe 10
<220> FEATURE:
<221> NAME/KEY: misc_feature
<222> LOCATION: (78)..(78)
<223> OTHER INFORMATION: n is a, c, g, t or u

<400> SEQUENCE: 59
uuuuuacact ctttccctac acgacgctct tccgatctgc caattcggaa ttccggtttt     60
tttttttttt tttttvn                                                    78

<210> SEQ ID NO 60
<211> LENGTH: 78
<212> TYPE: DNA
<213> ORGANISM: Artificial sequence
<220> FEATURE:
<223> OTHER INFORMATION: Probe 11
<220> FEATURE:
<221> NAME/KEY: misc_feature
<222> LOCATION: (78)..(78)
<223> OTHER INFORMATION: n is a, c, g, t or u

<400> SEQUENCE: 60
uuuuuacact ctttccctac acgacgctct tccgatcttc gcccaaggta atacatttt      60 tttttttttt tttttvn                                                    78

<210> SEQ ID NO 61
<211> LENGTH: 78
<212> TYPE: DNA
<213> ORGANISM: Artificial sequence
<220> FEATURE:
<223> OTHER INFORMATION: Probe 12
<220> FEATURE:
<221> NAME/KEY: misc_feature
<222> LOCATION: (78)..(78)
<223> OTHER INFORMATION: n is a, c, g, t or u

<400> SEQUENCE: 61
uuuuuacact ctttccctac acgacgctct tccgatcttc gcatttccta ttcgagtttt     60
tttttttttt tttttvn                                                    78

<210> SEQ ID NO 62
<211> LENGTH: 78
<212> TYPE: DNA
<213> ORGANISM: Artificial sequence
<220> FEATURE:
<223> OTHER INFORMATION: Probe 13
<220> FEATURE:
<221> NAME/KEY: misc_feature
<222> LOCATION: (78)..(78)
<223> OTHER INFORMATION: n is a, c, g, t or u

<400> SEQUENCE: 62
```
uuuuuacact ctttccctac acgacgctct tccgatcttt gctaaatcta accgccttt   60 tttttttttt tttttvn                                                  78

<210> SEQ ID NO 63
<211> LENGTH: 78
<212> TYPE: DNA
<213> ORGANISM: Artificial sequence
<220> FEATURE:
<223> OTHER INFORMATION: Probe 14
<220> FEATURE:
<221> NAME/KEY: misc_feature
<222> LOCATION: (78)..(78)
<223> OTHER INFORMATION: n is a, c, g, t or u

<400> SEQUENCE: 63
uuuuuacact ctttccctac acgacgctct tccgatctgg aattaaattc tgatggtttt   60
tttttttttt tttttvn                                                  78

<210> SEQ ID NO 64
<211> LENGTH: 78
<212> TYPE: DNA
<213> ORGANISM: Artificial sequence
<220> FEATURE:
<223> OTHER INFORMATION: Probe 15
<220> FEATURE:
<221> NAME/KEY: misc_feature
<222> LOCATION: (78)..(78)
<223> OTHER INFORMATION: n is a, c, g, t or u

<400> SEQUENCE: 64
uuuuuacact ctttccctac acgacgctct tccgatctca ttacataggt gctaagtttt   60
tttttttttt tttttvn                                                  78

<210> SEQ ID NO 65
<211> LENGTH: 78
<212> TYPE: DNA
<213> ORGANISM: Artificial sequence
<220> FEATURE:
<223> OTHER INFORMATION: Probe 16
<220> FEATURE:
<221> NAME/KEY: misc_feature
<222> LOCATION: (78)..(78)
<223> OTHER INFORMATION: n is a, c, g, t or u

<400> SEQUENCE: 65
uuuuuacact ctttccctac acgacgctct tccgatctat tgacttgcgc tcgcactttt   60
tttttttttt tttttvn                                                  78

<210> SEQ ID NO 66
<211> LENGTH: 78
<212> TYPE: DNA
<213> ORGANISM: Artificial sequence
<220> FEATURE:
<223> OTHER INFORMATION: Probe 17
<220> FEATURE:
<221> NAME/KEY: misc_feature
<222> LOCATION: (78)..(78)
<223> OTHER INFORMATION: n is a, c, g, t or u

<400> SEQUENCE: 66
uuuuuacact ctttccctac acgacgctct tccgatctat agtatctccc aagttctttt   60
tttttttttt tttttvn                                                  78

<210> SEQ ID NO 67

```
<211> LENGTH: 78
<212> TYPE: DNA
<213> ORGANISM: Artificial sequence
<220> FEATURE:
<223> OTHER INFORMATION: Probe 18
<220> FEATURE:
<221> NAME/KEY: misc_feature
<222> LOCATION: (78)..(78)
<223> OTHER INFORMATION: n is a, c, g, t or u

<400> SEQUENCE: 67
uuuuuacact ctttccctac acgacgctct tccgatctgt gcgcctgtaa tccgcatttt      60
tttttttttt tttttvn                                                    78

<210> SEQ ID NO 68
<211> LENGTH: 78
<212> TYPE: DNA
<213> ORGANISM: Artificial sequence
<220> FEATURE:
<223> OTHER INFORMATION: Probe 19
<220> FEATURE:
<221> NAME/KEY: misc_feature
<222> LOCATION: (78)..(78)
<223> OTHER INFORMATION: n is a, c, g, t or u

<400> SEQUENCE: 68
uuuuuacact ctttccctac acgacgctct tccgatctgc gccactcttt aggtagtttt      60
tttttttttt tttttvn                                                    78

<210> SEQ ID NO 69
<211> LENGTH: 78
<212> TYPE: DNA
<213> ORGANISM: Artificial sequence
<220> FEATURE:
<223> OTHER INFORMATION: Probe 20
<220> FEATURE:
<221> NAME/KEY: misc_feature
<222> LOCATION: (78)..(78)
<223> OTHER INFORMATION: n is a, c, g, t or u

<400> SEQUENCE: 69
uuuuuacact ctttccctac acgacgctct tccgatctta tgcaagtgat tggcttttt      60 tttttttttt tttttvn                                                    78

<210> SEQ ID NO 70
<211> LENGTH: 78
<212> TYPE: DNA
<213> ORGANISM: Artificial sequence
<220> FEATURE:
<223> OTHER INFORMATION: Probe 21
<220> FEATURE:
<221> NAME/KEY: misc_feature
<222> LOCATION: (78)..(78)
<223> OTHER INFORMATION: n is a, c, g, t or u

<400> SEQUENCE: 70
uuuuuacact ctttccctac acgacgctct tccgatctcc aagccacgtt tatacgtttt      60
tttttttttt tttttvn                                                    78

<210> SEQ ID NO 71
<211> LENGTH: 78
<212> TYPE: DNA
<213> ORGANISM: Artificial sequence
<220> FEATURE:
<223> OTHER INFORMATION: Probe 22
<220> FEATURE:
<221> NAME/KEY: misc_feature
```

```
<222> LOCATION: (78)..(78)
<223> OTHER INFORMATION: n is a, c, g, t or u

<400> SEQUENCE: 71
uuuuuacact ctttccctac acgacgctct tccgatctac ctgattgctg tataactttt    60
tttttttttt tttttttvn                                                 78

<210> SEQ ID NO 72
<211> LENGTH: 78
<212> TYPE: DNA
<213> ORGANISM: Artificial sequence
<220> FEATURE:
<223> OTHER INFORMATION: Probe 23
<220> FEATURE:
<221> NAME/KEY: misc_feature
<222> LOCATION: (78)..(78)
<223> OTHER INFORMATION: n is a, c, g, t or u

<400> SEQUENCE: 72
uuuuuacact ctttccctac acgacgctct tccgatctca gcgcatctat cctctatttt    60
tttttttttt tttttttvn                                                 78

<210> SEQ ID NO 73
<211> LENGTH: 78
<212> TYPE: DNA
<213> ORGANISM: Artificial sequence
<220> FEATURE:
<223> OTHER INFORMATION: Probe 24
<220> FEATURE:
<221> NAME/KEY: misc_feature
<222> LOCATION: (78)..(78)
<223> OTHER INFORMATION: n is a, c, g, t or u

<400> SEQUENCE: 73
uuuuuacact ctttccctac acgacgctct tccgatcttc cacgcgtagg actagttttt    60
tttttttttt tttttttvn                                                 78

<210> SEQ ID NO 74
<211> LENGTH: 78
<212> TYPE: DNA
<213> ORGANISM: Artificial sequence
<220> FEATURE:
<223> OTHER INFORMATION: Probe 25
<220> FEATURE:
<221> NAME/KEY: misc_feature
<222> LOCATION: (78)..(78)
<223> OTHER INFORMATION: n is a, c, g, t or u

<400> SEQUENCE: 74
uuuuuacact ctttccctac acgacgctct tccgatctcg actaagtatg tagcgctttt    60
tttttttttt tttttttvn                                                 78

<210> SEQ ID NO 75
<211> LENGTH: 30
<212> TYPE: DNA
<213> ORGANISM: Artificial sequence
<220> FEATURE:
<223> OTHER INFORMATION: Frame probe - Layout 1

<400> SEQUENCE: 75
aaatttcgtc tgctatcgcg cttctgtacc                                     30

<210> SEQ ID NO 76
<211> LENGTH: 21
<212> TYPE: DNA
```

<213> ORGANISM: Artificial sequence
<220> FEATURE:
<223> OTHER INFORMATION: Fluorescent marker probe PS 1
<220> FEATURE:
<221> NAME/KEY: misc_feature
<222> LOCATION: (21)..(21)
<223> OTHER INFORMATION: Coupled to cyanine 3 fluorescent dye

<400> SEQUENCE: 76
ggtacagaag cgcgatagca g                                              21

<210> SEQ ID NO 77
<211> LENGTH: 33
<212> TYPE: DNA
<213> ORGANISM: Artificial sequence
<220> FEATURE:
<223> OTHER INFORMATION: Second strand synthesis and first PCR
      amplification handle - A primer

<400> SEQUENCE: 77
acactctttc cctacacgac gctcttccga tct                                 33

<210> SEQ ID NO 78
<211> LENGTH: 43
<212> TYPE: DNA
<213> ORGANISM: Artificial sequence
<220> FEATURE:
<223> OTHER INFORMATION: Second strand synthesis and first PCR
      amplification handle - B dt20VN primer
<220> FEATURE:
<221> NAME/KEY: misc_feature
<222> LOCATION: (43)..(43)
<223> OTHER INFORMATION: n is a, c, g, or t

<400> SEQUENCE: 78
agacgtgtgc tcttccgatc tttttttttt tttttttttt tvn                      43

<210> SEQ ID NO 79
<211> LENGTH: 43
<212> TYPE: DNA
<213> ORGANISM: Artificial sequence
<220> FEATURE:
<223> OTHER INFORMATION: Custom sequencing primer B r2

<400> SEQUENCE: 79
tcagacgtgt gctcttccga tcttttttttt tttttttttt ttt                     43

<210> SEQ ID NO 80
<211> LENGTH: 66
<212> TYPE: DNA
<213> ORGANISM: Artificial sequence
<220> FEATURE:
<223> OTHER INFORMATION: Probe 1

<400> SEQUENCE: 80
gcgttcagag tggcagtcga gatcacgcgg caatcatatc ggacagatcg aagagcgta     60 gtgtag                                                               66

<210> SEQ ID NO 81
<211> LENGTH: 66
<212> TYPE: DNA
<213> ORGANISM: Artificial sequence
<220> FEATURE:
<223> OTHER INFORMATION: Probe 2

<400> SEQUENCE: 81
gcgttcagag tggcagtcga gatcacaaga tgaacccggc tcatagatcg aagagcgta     60

-continued

```
gtgtag                                                            66

<210> SEQ ID NO 82
<211> LENGTH: 66
<212> TYPE: DNA
<213> ORGANISM: Artificial sequence
<220> FEATURE:
<223> OTHER INFORMATION: Probe 3

<400> SEQUENCE: 82
gcgttcagag tggcagtcga gatcactccc aacagagtgc ctcaagatcg gaagagcgta    60
gtgtag                                                            66

<210> SEQ ID NO 83
<211> LENGTH: 66
<212> TYPE: DNA
<213> ORGANISM: Artificial sequence
<220> FEATURE:
<223> OTHER INFORMATION: Probe 4

<400> SEQUENCE: 83
gcgttcagag tggcagtcga gatcaccgaa tggcgactaa tcatagatcg gaagagcgta    60
gtgtag                                                            66

<210> SEQ ID NO 84
<211> LENGTH: 66
<212> TYPE: DNA
<213> ORGANISM: Artificial sequence
<220> FEATURE:
<223> OTHER INFORMATION: Probe 5

<400> SEQUENCE: 84
gcgttcagag tggcagtcga gatcacaaac atctaccctc aagtagatcg gaagagcgta    60
gtgtag                                                            66

<210> SEQ ID NO 85
<211> LENGTH: 66
<212> TYPE: DNA
<213> ORGANISM: Artificial sequence
<220> FEATURE:
<223> OTHER INFORMATION: Probe 6

<400> SEQUENCE: 85
gcgttcagag tggcagtcga gatcacgata acagtattgg ccatagatcg gaagagcgta    60
gtgtag                                                            66

<210> SEQ ID NO 86
<211> LENGTH: 66
<212> TYPE: DNA
<213> ORGANISM: Artificial sequence
<220> FEATURE:
<223> OTHER INFORMATION: Probe 7

<400> SEQUENCE: 86
gcgttcagag tggcagtcga gatcacggtc gaatcagggt agcgagatcg gaagagcgta    60
gtgtag                                                            66

<210> SEQ ID NO 87
<211> LENGTH: 66
<212> TYPE: DNA
<213> ORGANISM: Artificial sequence
<220> FEATURE:
```

```
<223> OTHER INFORMATION: Probe 8

<400> SEQUENCE: 87
gcgttcagag tggcagtcga gatcacacta cggcgaaagt gggcagatcg gaagagcgta    60
gtgtag                                                               66

<210> SEQ ID NO 88
<211> LENGTH: 66
<212> TYPE: DNA
<213> ORGANISM: Artificial sequence
<220> FEATURE:
<223> OTHER INFORMATION: Probe 9

<400> SEQUENCE: 88
gcgttcagag tggcagtcga gatcacatct tgctcaaagt tgctagatcg gaagagcgta    60
gtgtag                                                               66

<210> SEQ ID NO 89
<211> LENGTH: 66
<212> TYPE: DNA
<213> ORGANISM: Artificial sequence
<220> FEATURE:
<223> OTHER INFORMATION: Probe 10

<400> SEQUENCE: 89
gcgttcagag tggcagtcga gatcacccgg aattccgaat tggcagatcg gaagagcgta    60
gtgtag                                                               66

<210> SEQ ID NO 90
<211> LENGTH: 66
<212> TYPE: DNA
<213> ORGANISM: Artificial sequence
<220> FEATURE:
<223> OTHER INFORMATION: Probe 11

<400> SEQUENCE: 90
gcgttcagag tggcagtcga gatcacatgt attaccttgg gcgaagatcg gaagagcgta    60
gtgtag                                                               66

<210> SEQ ID NO 91
<211> LENGTH: 66
<212> TYPE: DNA
<213> ORGANISM: Artificial sequence
<220> FEATURE:
<223> OTHER INFORMATION: Probe 12

<400> SEQUENCE: 91
gcgttcagag tggcagtcga gatcacctcg aataggaaat gcgaagatcg gaagagcgta    60
gtgtag                                                               66

<210> SEQ ID NO 92
<211> LENGTH: 66
<212> TYPE: DNA
<213> ORGANISM: Artificial sequence
<220> FEATURE:
<223> OTHER INFORMATION: Probe 13

<400> SEQUENCE: 92
gcgttcagag tggcagtcga gatcacggcg gttagattta gcaaagatcg gaagagcgta    60
gtgtag                                                               66
```

-continued

```
<210> SEQ ID NO 93
<211> LENGTH: 66
<212> TYPE: DNA
<213> ORGANISM: Artificial sequence
<220> FEATURE:
<223> OTHER INFORMATION: Probe 14

<400> SEQUENCE: 93
gcgttcagag tggcagtcga gatcacccat cagaatttaa ttccagatcg gaagagcgta    60
gtgtag                                                                66

<210> SEQ ID NO 94
<211> LENGTH: 66
<212> TYPE: DNA
<213> ORGANISM: Artificial sequence
<220> FEATURE:
<223> OTHER INFORMATION: Probe 15

<400> SEQUENCE: 94
gcgttcagag tggcagtcga gatcacctta gcacctatgt aatgagatcg gaagagcgta    60
gtgtag                                                                66

<210> SEQ ID NO 95
<211> LENGTH: 66
<212> TYPE: DNA
<213> ORGANISM: Artificial sequence
<220> FEATURE:
<223> OTHER INFORMATION: Probe 16

<400> SEQUENCE: 95
gcgttcagag tggcagtcga gatcacgtgc gagcgcaagt caatagatcg gaagagcgta    60
gtgtag                                                                66

<210> SEQ ID NO 96
<211> LENGTH: 66
<212> TYPE: DNA
<213> ORGANISM: Artificial sequence
<220> FEATURE:
<223> OTHER INFORMATION: Probe 17

<400> SEQUENCE: 96
gcgttcagag tggcagtcga gatcacgaac ttgggagata ctatagatcg gaagagcgta    60
gtgtag                                                                66

<210> SEQ ID NO 97
<211> LENGTH: 66
<212> TYPE: DNA
<213> ORGANISM: Artificial sequence
<220> FEATURE:
<223> OTHER INFORMATION: Probe 18

<400> SEQUENCE: 97
gcgttcagag tggcagtcga gatcactgcg gattacaggc gcacagatcg gaagagcgta    60
gtgtag                                                                66

<210> SEQ ID NO 98
<211> LENGTH: 66
<212> TYPE: DNA
<213> ORGANISM: Artificial sequence
<220> FEATURE:
<223> OTHER INFORMATION: Probe 19

<400> SEQUENCE: 98
```

```
gcgttcagag tggcagtcga gatcacctac ctaaagagtg gcgcagatcg aagagcgta      60 gtgtag                                                                66

<210> SEQ ID NO 99
<211> LENGTH: 66
<212> TYPE: DNA
<213> ORGANISM: Artificial sequence
<220> FEATURE:
<223> OTHER INFORMATION: Probe 20

<400> SEQUENCE: 99
gcgttcagag tggcagtcga gatcacaagc caatcacttg cataagatcg gaagagcgta     60
gtgtag                                                                66

<210> SEQ ID NO 100
<211> LENGTH: 66
<212> TYPE: DNA
<213> ORGANISM: Artificial sequence
<220> FEATURE:
<223> OTHER INFORMATION: Probe 21

<400> SEQUENCE: 100
gcgttcagag tggcagtcga gatcaccgta taaacgtggc ttggagatcg gaagagcgta     60
gtgtag                                                                66

<210> SEQ ID NO 101
<211> LENGTH: 66
<212> TYPE: DNA
<213> ORGANISM: Artificial sequence
<220> FEATURE:
<223> OTHER INFORMATION: Probe 22

<400> SEQUENCE: 101
gcgttcagag tggcagtcga gatcacgtta tacagcaatc aggtagatcg gaagagcgta     60
gtgtag                                                                66

<210> SEQ ID NO 102
<211> LENGTH: 66
<212> TYPE: DNA
<213> ORGANISM: Artificial sequence
<220> FEATURE:
<223> OTHER INFORMATION: Probe 23

<400> SEQUENCE: 102
gcgttcagag tggcagtcga gatcactaga ggatagatgc gctgagatcg gaagagcgta     60
gtgtag                                                                66

<210> SEQ ID NO 103
<211> LENGTH: 66
<212> TYPE: DNA
<213> ORGANISM: Artificial sequence
<220> FEATURE:
<223> OTHER INFORMATION: Probe 24

<400> SEQUENCE: 103
gcgttcagag tggcagtcga gatcacacta gtcctacgcg tggaagatcg gaagagcgta     60
gtgtag                                                                66

<210> SEQ ID NO 104
<211> LENGTH: 66
<212> TYPE: DNA
<213> ORGANISM: Artificial sequence
```

```
<220> FEATURE:
<223> OTHER INFORMATION: Probe 25

<400> SEQUENCE: 104
gcgttcagag tggcagtcga gatcacgcgc tacatactta gtcgagatcg gaagagcgta      60
gtgtag                                                                 66

<210> SEQ ID NO 105
<211> LENGTH: 30
<212> TYPE: DNA
<213> ORGANISM: Artificial sequence
<220> FEATURE:
<223> OTHER INFORMATION: Frame probe - layout 1

<400> SEQUENCE: 105
aaatttcgtc tgctatcgcg cttctgtacc                                       30

<210> SEQ ID NO 106
<211> LENGTH: 45
<212> TYPE: DNA
<213> ORGANISM: Artificial sequence
<220> FEATURE:
<223> OTHER INFORMATION: Capture probe - LP poly-dTVN
<220> FEATURE:
<221> NAME/KEY: misc_feature
<222> LOCATION: (45)..(45)
<223> OTHER INFORMATION: n is a, c, g, or t

<400> SEQUENCE: 106
gtgatctcga ctgccactct gaatttttt tttttttttt tttvn                       45

<210> SEQ ID NO 107
<211> LENGTH: 33
<212> TYPE: DNA
<213> ORGANISM: Artificial sequence
<220> FEATURE:
<223> OTHER INFORMATION: Amplification handle probe A-handle

<400> SEQUENCE: 107
acactctttc cctacacgac gctcttccga tct                                   33

<210> SEQ ID NO 108
<211> LENGTH: 33
<212> TYPE: DNA
<213> ORGANISM: Artificial sequence
<220> FEATURE:
<223> OTHER INFORMATION: Second strand synthesis and first PCR
      amplification handle - A primer

<400> SEQUENCE: 108
acactctttc cctacacgac gctcttccga tct                                   33

<210> SEQ ID NO 109
<211> LENGTH: 43
<212> TYPE: DNA
<213> ORGANISM: Artificial sequence
<220> FEATURE:
<223> OTHER INFORMATION: Second strand synthesis and first PCR
      amplification handle - B dt20VN primer
<220> FEATURE:
<221> NAME/KEY: misc_feature
<222> LOCATION: (43)..(43)
<223> OTHER INFORMATION: n is a, c, g, or t

<400> SEQUENCE: 109
agacgtgtgc tcttccgatc tttttttttt tttttttttt tvn                        43
```

```
<210> SEQ ID NO 110
<211> LENGTH: 33
<212> TYPE: DNA
<213> ORGANISM: Artificial sequence
<220> FEATURE:
<223> OTHER INFORMATION: Second PCR - A primer

<400> SEQUENCE: 110
acactctttc cctacacgac gctcttccga tct                              33

<210> SEQ ID NO 111
<211> LENGTH: 34
<212> TYPE: DNA
<213> ORGANISM: Artificial sequence
<220> FEATURE:
<223> OTHER INFORMATION: Second PCR - B primer

<400> SEQUENCE: 111
gtgactggag ttcagacgtg tgctcttccg atct                             34

<210> SEQ ID NO 112
<211> LENGTH: 39
<212> TYPE: DNA
<213> ORGANISM: Artificial sequence
<220> FEATURE:
<223> OTHER INFORMATION: Template Switching primer - longB
<220> FEATURE:
<221> NAME/KEY: misc_feature
<222> LOCATION: (37)..(39)
<223> OTHER INFORMATION: Ribonucleotides

<400> SEQUENCE: 112
gtgactggag ttcagacgtg tgctcttccg atctatggg                        39

<210> SEQ ID NO 113
<211> LENGTH: 33
<212> TYPE: DNA
<213> ORGANISM: Artificial sequence
<220> FEATURE:
<223> OTHER INFORMATION: Spatial genomics - A primer

<400> SEQUENCE: 113
acactctttc cctacacgac gctcttccga tct                              33

<210> SEQ ID NO 114
<211> LENGTH: 39
<212> TYPE: DNA
<213> ORGANISM: Artificial sequence
<220> FEATURE:
<223> OTHER INFORMATION: Spatial genomics - B A431 Chr2+2 FW A

<400> SEQUENCE: 114
agacgtgtgc tcttccgatc ttggctgcct gaggcaatg                        39

<210> SEQ ID NO 115
<211> LENGTH: 43
<212> TYPE: DNA
<213> ORGANISM: Artificial sequence
<220> FEATURE:
<223> OTHER INFORMATION: Spatial genomics - B A431 Chr2+2 RE A

<400> SEQUENCE: 115
agacgtgtgc tcttccgatc tctcgctaac aagcagagag aac                   43

<210> SEQ ID NO 116
<211> LENGTH: 40
```

```
<212> TYPE: DNA
<213> ORGANISM: Artificial sequence
<220> FEATURE:
<223> OTHER INFORMATION: Spatial genomics - B A431 Chr3+7 FW B

<400> SEQUENCE: 116
agacgtgtgc tcttccgatc ttgagaacaa gggggaagag                              40

<210> SEQ ID NO 117
<211> LENGTH: 41
<212> TYPE: DNA
<213> ORGANISM: Artificial sequence
<220> FEATURE:
<223> OTHER INFORMATION: Spatial genomics - B A431 Chr3+7 RE B

<400> SEQUENCE: 117
agacgtgtgc tcttccgatc tcggtgaaac aagcaggtaa c                            41

<210> SEQ ID NO 118
<211> LENGTH: 41
<212> TYPE: DNA
<213> ORGANISM: Artificial sequence
<220> FEATURE:
<223> OTHER INFORMATION: Spatial genomics - B NT 1 FW

<400> SEQUENCE: 118
agacgtgtgc tcttccgatc tcattcccac actcatcaca c                            41

<210> SEQ ID NO 119
<211> LENGTH: 40
<212> TYPE: DNA
<213> ORGANISM: Artificial sequence
<220> FEATURE:
<223> OTHER INFORMATION: Spatial genomics - B NT 1 RE

<400> SEQUENCE: 119
agacgtgtgc tcttccgatc ttcacactgg agaaagaccc                              40

<210> SEQ ID NO 120
<211> LENGTH: 43
<212> TYPE: DNA
<213> ORGANISM: Artificial sequence
<220> FEATURE:
<223> OTHER INFORMATION: Spatial genomics - B NT 2 FW

<400> SEQUENCE: 120
agacgtgtgc tcttccgatc tgggggttcag agtgattttt cag                         43

<210> SEQ ID NO 121
<211> LENGTH: 40
<212> TYPE: DNA
<213> ORGANISM: Artificial sequence
<220> FEATURE:
<223> OTHER INFORMATION: Spatial genomics - B NT 2 RE

<400> SEQUENCE: 121
agacgtgtgc tcttccgatc ttccgttttc tttcagtgcc                              40
```

METHODS OF DETECTING ANALYTES

CROSS-REFERENCE TO RELATED APPLICATIONS

The application is a continuation of U.S. patent application Ser. No. 16/013,654, filed on Jun. 20, 2018, which is a continuation of U.S. patent application Ser. No. 14/111,482, filed on Oct. 11, 2013 (issued as U.S. Pat. No. 10,030,261), which is a U.S. National Phase Application under 35 U.S.C. § 371 of International Patent Application No. PCT/EP2012/056823, filed Apr. 13, 2012, which claims benefit to U.K. Patent Application No. 1106254.4, filed on Apr. 13, 2011, the entire contents of the foregoing applications are incorporated herein by reference.

SEQUENCE LISTING IN ELECTRONIC FORMAT

The application contains a Sequence Listing that has been submitted electronically as an ASCII text filed named 47706-0011007_SeqListing.TXT. The ASCII text file, created on Sep. 14, 2021, is 32 kilobytes in size. The material in the ASCII text file is hereby incorporated by reference in its entirety.

The present invention relates generally to the localized or spatial detection of nucleic acid in a tissue sample. The nucleic acid may be RNA or DNA. Thus, the present invention provides methods for detecting and/or analysing RNA, e.g. RNA transcripts or genomic DNA, so as to obtain spatial information about the localisation, distribution or expression of genes, or indeed about the localisation or distribution of any genomic variation (not necessarily in a gene) in a tissue sample, for example in an individual cell. The present invention thus enables spatial genomics and spatial transcriptomics.

More particularly, the present invention relates to a method for determining and/or analysing a transcriptome or genome and especially the global transcriptome or genome, of a tissue sample. In particular the method relates to a quantitative and/or qualitative method for analysing the distribution, location or expression of genomic sequences in a tissue sample wherein the spatial expression or distribution or location pattern within the tissue sample is retained. Thus, the new method provides a process for performing "spatial transcriptomics" or "spatial genomics", which enables the user to determine simultaneously the expression pattern, or the location/distribution pattern of the genes expressed or genes or genomic loci present in a tissue sample.

The invention is particularly based on array technology coupled with high throughput DNA sequencing technologies, which allows the nucleic acid molecule (e.g. RNA or DNA molecules) in the tissue sample, particularly mRNA or DNA, to be captured and labelled with a positional tag. This step is followed by synthesis of DNA molecules which are sequenced and analysed to determine which genes are expressed in any and all parts of the tissue sample. Advantageously, the individual, separate and specific transcriptome of each cell in the tissue sample may be obtained at the same time. Hence, the methods of the invention may be said to provide highly parallel comprehensive transcriptome signatures from individual cells within a tissue sample without losing spatial information within said investigated tissue sample. The invention also provides an array for performing the method of the invention and methods for making the arrays of the invention.

The human body comprises over 100 trillion cells and is organized into more than 250 different organs and tissues. The development and organization of complex organs, such as the brain, are far from understood and there is a need to dissect the expression of genes expressed in such tissues using quantitative methods to investigate and determine the genes that control the development and function of such tissues. The organs are in themselves a mixture of differentiated cells that enable all bodily functions, such as nutrient transport, defence etc. to be coordinated and maintained. Consequently, cell function is dependent on the position of the cell within a particular tissue structure and the interactions it shares with other cells within that tissue, both directly and indirectly. Hence, there is a need to disentangle how these interactions influence each cell within a tissue at the transcriptional level.

Recent findings by deep RNA sequencing have demonstrated that a majority of the transcripts can be detected in a human cell line and that a large fraction (75%) of the human protein-coding genes are expressed in most tissues. Similarly, a detailed study of 1% of the human genome showed that chromosomes are ubiquitously transcribed and that the majority of all bases are included in primary transcripts. The transcription machinery can therefore be described as promiscuous at a global level.

It is well-known that transcripts are merely a proxy for protein abundance, because the rates of RNA translation, degradation etc will influence the amount of protein produced from any one transcript. In this respect, a recent antibody-based analysis of human organs and tissues suggests that tissue specificity is achieved by precise regulation of protein levels in space and time, and that different tissues in the body acquire their unique characteristics by controlling not which proteins are expressed but how much of each is produced.

However, in subsequent global studies transcriptome and proteome correlations have been compared demonstrating that the majority of all genes were shown to be expressed. Interestingly, there was shown to be a high correlation between changes in RNA and protein levels for individual gene products which is indicative of the biological usefulness of studying the transcriptome in individual cells in the context of the functional role of proteins.

Indeed, analysis of the histology and expression pattern in tissues is a cornerstone in biomedical research and diagnostics. Histology, utilizing different staining techniques, first established the basic structural organization of healthy organs and the changes that take place in common pathologies more than a century ago. Developments in this field resulted in the possibility of studying protein distribution by immunohistochemistry and gene expression by in situ hybridization.

However, the parallel development of increasingly advanced histological and gene expression techniques has resulted in the separation of imaging and transcriptome analysis and, until the methods of the present invention, there has not been any feasible method available for global transcriptome analysis with spatial resolution.

As an alternative, or in addition, to in situ techniques, methods have developed for the in vitro analysis of proteins and nucleic acids, i.e. by extracting molecules from whole tissue samples, single cell types, or even single cells, and quantifying specific molecules in said extracts, e.g. by ELISA, qPCR etc.

Recent developments in the analysis of gene expression have resulted in the possibility of assessing the complete transcriptome of tissues using microarrays or RNA sequencing, and such developments have been instrumental in our understanding of biological processes and for diagnostics. However, transcriptome analysis typically is performed on mRNA extracted from whole tissues (or even whole organisms), and methods for collecting smaller tissue areas or individual cells for transcriptome analysis are typically labour intensive, costly and have low precision.

Hence, the majority of gene expression studies based on microarrays or next generation sequencing of RNA use a representative sample containing many cells. Thus the results represent the average expression levels of the investigated genes. The separation of cells that are phenotypically different has been used in some cases together with the global gene expression platforms (Tang F et al, Nat Protoc. 2010; 5: 516-35; Wang D & Bodovitz S, Trends Biotechnol. 2010; 28:281-90) and resulted in very precise information about cell-to-cell variations. However, high throughput methods to study transcriptional activity with high resolution in intact tissues have not, until now, been available.

Thus, existing techniques for the analysis of gene expression patterns provide spatial transcriptional information only for one or a handful of genes at a time or offer transcriptional information for all of the genes in a sample at the cost of losing positional information. Hence, it is evident that methods to determine simultaneously, separately and specifically the transcriptome of each cell in a sample are required, i.e. to enable global gene expression analysis in tissue samples that yields transcriptomic information with spatial resolution, and the present invention addresses this need.

The novel approach of the methods and products of the present invention utilizes now well established array and sequencing technology to yield transcriptional information for all of the genes in a sample, whilst retaining the positional information for each transcript. It will be evident to the person of skill in the art that this represents a milestone in the life sciences. The new technology opens a new field of so-called "spatial transcriptomics", which is likely to have profound consequences for our understanding of tissue development and tissue and cellular function in all multicellular organisms. It will be apparent that such techniques will be particularly useful in our understanding of the cause and progress of disease states and in developing effective treatments for such diseases, e.g. cancer. The methods of the invention will also find uses in the diagnosis of numerous medical conditions.

Whilst initially conceived with the aim of transcriptome analysis in mind, as described in detail below, the principles and methods of the present invention may be applied also to the analysis of DNA and hence for genomic analyses also ("spatial genomics"). Accordingly, at its broadest the invention pertains to the detection and/or analysis of nucleic acid in general.

Array technology, particularly microarrays, arose from research at Stanford University where small amounts of DNA oligonucleotides were successfully attached to a glass surface in an ordered arrangement, a so-called "array", and used it to monitor the transcription of 45 genes (Schena M et al, Science. 1995; 270: 368-9, 371).

Since then, researchers around the world have published more than 30,000 papers using microarray technology. Multiple types of microarray have been developed for various applications, e.g. to detect single nucleotide polymorphisms (SNPs) or to genotype or re-sequence mutant genomes, and an important use of microarray technology has been for the investigation of gene expression. Indeed, the gene expression microarray was created as a means to analyze the level of expressed genetic material in a particular sample, with the real gain being the possibility to compare expression levels of many genes simultaneously. Several commercial microarray platforms are available for these types of experiments but it has also been possible to create custom made gene expression arrays.

Whilst the use of microarrays in gene expression studies is now commonplace, it is evident that new and more comprehensive so-called "next-generation DNA sequencing" (NGS) technologies are starting to replace DNA microarrays for many applications, e.g. in-depth transcriptome analysis.

The development of NGS technologies for ultra-fast genome sequencing represents a milestone in the life sciences (Petterson E et al, *Genomics*. 2009; 93: 105-11). These new technologies have dramatically decreased the cost of DNA sequencing and enabled the determination of the genome of higher organisms at an unprecedented rate, including those of specific individuals (Wade C M et al Science. 2009; 326: 865-7; Rubin J et al, *Nature* 2010; 464: 587-91). The new advances in high-throughput genomics have reshaped the biological research landscape and in addition to complete characterization of genomes it is possible also to study the full transcriptome in a digital and quantitative fashion. The bioinformatics tools to visualize and integrate these comprehensive sets of data have also been significantly improved during recent years.

However, it has surprisingly been found that a unique combination of histological, microarray and NGS techniques can yield comprehensive transcriptional or genomic information from multiple cells in a tissue sample which information is characterised by a two-dimensional spatial resolution. Thus, at one extreme the methods of the present invention can be used to analyse the expression of a single gene in a single cell in a sample, whilst retaining the cell within its context in the tissue sample. At the other extreme, and in a preferred aspect of the invention, the methods can be used to determine the expression of every gene in each and every cell, or substantially all cells, in a sample simultaneously, i.e. the global spatial expression pattern of a tissue sample. It will be apparent that the methods of the invention also enable intermediate analyses to be performed.

In its simplest form, the invention may be illustrated by the following summary. The invention requires reverse transcription (RT) primers, which comprise also unique positional tags (domains), to be arrayed on an object substrate, e.g. a glass slide, to generate an "array". The unique positional tags correspond to the location of the RT primers on the array (the features of the array). Thin tissue sections are placed onto the array and a reverse transcription reaction is performed in the tissue section on the object slide. The RT primers, to which the RNA in the tissue sample binds (or hybridizes), are extended using the bound RNA as a template to obtain cDNA, which is therefore bound to the surface of the array. As consequence of the unique positional tags in the RT primers, each cDNA strand carries information about the position of the template RNA in the tissue section. The tissue section may be visualised or imaged, e.g. stained and photographed, before or after the cDNA synthesis step to enable the positional tag in the cDNA molecule to be correlated with a position within the tissue sample. The cDNA is sequenced, which results in a transcriptome with exact positional information. A schematic of the process is shown in FIG. 1. The sequence data can then be matched to a position in the tissue sample, which enables the visualization, e.g. using a computer, of the sequence data together with the tissue section, for instance to display the expression pattern of any gene of interest across the tissue (FIG. 2). Similarly, it would be possible to mark different areas of the tissue section on the computer screen and obtain information on differentially expressed genes between any selected areas of interest. It will be evident that the methods of the invention result in data that is in stark contrast to the data obtained using current methods to study mRNA populations. For example, methods based on in situ hybridization provide only relative information of single mRNA transcripts. Thus, the methods of the present invention have clear advantages over current in situ technologies. The global gene expression information obtainable from the methods of the invention also allows co-expression information and quantitative estimates of transcript abundance. It will be evident that this is a generally applicable strategy available for the analysis of any tissue in any species, e.g. animal, plant, fungus.

As noted above, and described in more detail below, it will be evident that this basic methodology could readily be extended to the analysis of genomic DNA, e.g. to identify cells within a tissue sample that comprise one or more specific mutations. For instance, the genomic DNA may be fragmented and allowed to hybridise to primers (equivalent to the RT primers described above), which are capable of capturing the fragmented DNA (e.g. an adapter with a sequence that is complementary to the primer may be ligated to the fragmented DNA or the fragmented DNA may be extended e.g. using an enzyme to incorporate additional nucleotides at the end of the sequence, e.g. a poly-A tail, to generate a sequence that is complementary to the primer) and priming the synthesis of complementary strands to the capture molecules. The remaining steps of the analysis may be as described above. Hence, the specific embodiments of the invention described below in the context of transcriptome analysis may also be employed in methods of analysing genomic DNA, where appropriate.

It will be seen from the above explanation that there is an immense value in coupling positional information to transcriptome or genome information. For instance, it enables global gene expression mapping at high resolution, which will find utility in numerous applications, including e.g. cancer research and diagnostics.

Furthermore, it is evident that the methods described herein differ significantly from the previously described methods for analysis of the global transcriptome of a tissue sample and these differences result in numerous advantages. The present invention is predicated on the surprising discovery that the use of tissue sections does not interfere with synthesis of DNA (e.g. cDNA) primed by primers (e.g. reverse transcription primers) that are coupled to the surface of an array.

Thus, in its first and broadest aspect, the present invention provides a method for localized detection of nucleic acid in a tissue sample comprising:

(a) providing an array comprising a substrate on which multiple species of capture probes are directly or indirectly immobilized such that each species occupies a distinct position on the array and is oriented to have a free 3' end to enable said probe to function as a primer for a primer extension or ligation reaction, wherein each species of said capture probe comprises a nucleic acid molecule with 5' to 3':
  (i) a positional domain that corresponds to the position of the capture probe on the array, and
  (ii) a capture domain;
(b) contacting said array with a tissue sample such that the position of a capture probe on the array may be correlated with a position in the tissue sample and allowing nucleic acid of the tissue sample to hybridise to the capture domain in said capture probes;
(c) generating DNA molecules from the captured nucleic acid molecules using said capture probes as extension or ligation primers, wherein said extended or ligated DNA molecules are tagged by virtue of the positional domain;
(d) optionally generating a complementary strand of said tagged DNA and/or optionally amplifying said tagged DNA;
(e) releasing at least part of the tagged DNA molecules and/or their complements or amplicons from the surface of the array, wherein said part includes the positional domain or a complement thereof;
(f) directly or indirectly analysing the sequence of the released DNA molecules.

The methods of the invention represent a significant advance over other methods for spatial transcriptomics known in the art. For example the methods described herein result in a global and spatial profile of all transcripts in the tissue sample. Moreover, the expression of every gene can be quantified for each position or feature on the array, which enables a multiplicity of analyses to be performed based on data from a single assay. Thus, the methods of the present invention make it possible to detect and/or quantify the spatial expression of all genes in single tissue sample. Moreover, as the abundance of the transcripts is not visualised directly, e.g. by fluorescence, akin to a standard microarray, it is possible to measure the expression of genes in a single sample simultaneously even wherein said transcripts are present at vastly different concentrations in the same sample.

Accordingly, in a second and more particular aspect, the present invention can be seen to provide a method for determining and/or analysing a transcriptome of a tissue sample comprising:

(a) providing an array comprising a substrate on which multiple species of capture probes are directly or indirectly immobilized such that each species occupies a distinct position on the array and is oriented to have a free 3' end to enable said probe to function as a reverse transcriptase (RT) primer, wherein each species of said capture probe comprises a nucleic acid molecule with 5' to 3':
  (i) a positional domain that corresponds to the position of the capture probe on the array, and
  (ii) a capture domain;
(b) contacting said array with a tissue sample such that the position of a capture probe on the array may be correlated with a position in the tissue sample and allowing RNA of the tissue sample to hybridise to the capture domain in said capture probes;
(c) generating cDNA molecules from the captured RNA molecules using said capture probes as RT primers, and optionally amplifying said cDNA molecules;
(d) releasing at least part of the cDNA molecules and/or optionally their amplicons from the surface of the array, wherein said released molecule may be a first strand and/or second strand cDNA molecule or an amplicon thereof and wherein said part includes the positional domain or a complement thereof;
(e) directly or indirectly analysing the sequence of the released molecules.

As described in more detail below, any method of nucleic acid analysis may be used in the analysis step. Typically this may involve sequencing, but it is not necessary to perform an actual sequence determination. For example sequence-specific methods of analysis may be used. For example a sequence-specific amplification reaction may be performed, for example using primers which are specific for the positional domain and/or for a specific target sequence, e.g. a particular target DNA to be detected (i.e. corresponding to a particular cDNA/RNA or gene etc.). An exemplary analysis method is a sequence-specific PCR reaction.

The sequence analysis information obtained in step (e) may be used to obtain spatial information as to the RNA in the sample. In other words the sequence analysis information may provide information as to the location of the RNA in the sample. This spatial information may be derived from the nature of the sequence analysis information determined, for example it may reveal the presence of a particular RNA which may itself be spatially informative in the context of the tissue sample used, and/or the spatial information (e.g. spatial localisation) may be derived from the position of the tissue sample on the array, coupled with the sequencing information. Thus, the method may involve simply correlating the sequence analysis information to a position in the tissue sample e.g. by virtue of the positional tag and its correlation to a position in the tissue sample. However, as described above, spatial information may conveniently be obtained by correlating the sequence analysis data to an image of the tissue sample and this represents one preferred embodiment of the invention. Accordingly, in a preferred embodiment the method also includes a step of:

(f) correlating said sequence analysis information with an image of said tissue sample, wherein the tissue sample is imaged before or after step (c).

In its broadest sense, the method of the invention may be used for localized detection of a nucleic acid in a tissue sample. Thus, in one embodiment, the method of the invention may be used for determining and/or analysing all of the transcriptome or genome of a tissue sample e.g. the global transcriptome of a tissue sample. However, the method is not limited to this and encompasses determining and/or analysing all or part of the transcriptome or genome. Thus, the method may involve determining and/or analysing a part or subset of the transcriptome or genome, e.g. a transcriptome corresponding to a subset of genes, e.g. a set of particular genes, for example related to a particular disease or condition, tissue type etc.

Viewed from another aspect, the method steps set out above can be seen as providing a method of obtaining a spatially defined transcriptome or genome, and in particular the spatially defined global transcriptome or genome, of a tissue sample.

Alternatively viewed, the method of the invention may be seen as a method for localized or spatial detection of nucleic acid, whether DNA or RNA in a tissue sample, or for localized or spatial determination and/or analysis of nucleic acid (DNA or RNA) in a tissue sample. In particular, the method may be used for the localized or spatial detection or determination and/or analysis of gene expression or genomic variation in a tissue sample. The localized/spatial detection/determination/analysis means that the RNA or DNA may be localized to its native position or location within a cell or tissue in the tissue sample. Thus for example, the RNA or DNA may be localized to a cell or group of cells, or type of cells in the sample, or to particular regions of areas within a tissue sample. The native location or position of the RNA or DNA (or in other words, the location or position of the RNA or DNA in the tissue sample), e.g. an expressed gene or genomic locus, may be determined.

The invention can also be seen to provide an array for use in the methods of the invention comprising a substrate on which multiple species of capture probes are directly or indirectly immobilized such that each species occupies a distinct position on the array and is oriented to have a free 3' end to enable said probe to function as a reverse transcriptase (RT) primer, wherein each species of said capture probe comprises a nucleic acid molecule with 5' to 3':

(i) a positional domain that corresponds to the position of the capture probe on the array, and (ii) a capture domain to capture RNA of a tissue sample that is contacted with said array.

In a related aspect, the present invention also provides use of an array, comprising a substrate on which multiple species of capture probe are directly or indirectly immobilized such that each species occupies a distinct position on the array and is oriented to have a free 3' end to enable said probe to function as a reverse transcriptase (RT) primer, wherein each species of said capture probe comprises a nucleic acid molecule with 5' to 3':

(i) a positional domain that corresponds to the position of the capture probe on the array; and (ii) a capture domain;

to capture RNA of a tissue sample that is contacted with said array.

Preferably, said use is for determining and/or analysing a transcriptome and in particular the global transcriptome, of a tissue sample and further comprises steps of:

(a) generating cDNA molecules from the captured RNA molecules using said capture probes as RT primers and optionally amplifying said cDNA molecules;

(b) releasing at least part of the cDNA molecules and/or optionally their amplicons from the surface of the array, wherein said released molecule may be a first strand and/or second strand cDNA molecule or an amplicon thereof and wherein said part includes the positional domain or a complement thereof;

(c) directly or indirectly analysing the sequence of the released molecules; and optionally (d) correlating said sequence analysis information with an image of said tissue sample, wherein the tissue sample is imaged before or after step (a).

It will be seen therefore that the array of the present invention may be used to capture RNA, e.g. mRNA of a tissue sample that is contacted with said array. The array may also be used for determining and/or analysing a partial or global transcriptome of a tissue sample or for obtaining a spatially defined partial or global transcriptome of a tissue sample. The methods of the invention may thus be considered as methods of quantifying the spatial expression of one or more genes in a tissue sample. Expressed another way, the methods of the present invention may be used to detect the spatial expression of one or more genes in a tissue sample. In yet another way, the methods of the present invention may be used to determine simultaneously the expression of one or more genes at one or more positions within a tissue sample. Still further, the methods may be seen as methods for partial or global transcriptome analysis of a tissue sample with two-dimensional spatial resolution.

The RNA may be any RNA molecule which may occur in a cell. Thus it may be mRNA, tRNA, rRNA, viral RNA, small nuclear RNA (snRNA), small nucleolar RNA (snoRNA), microRNA (miRNA), small interfering RNA (siRNA), piwi-interacting RNA (piRNA), ribozymal RNA, antisense RNA or non-coding RNA. Preferably however it is mRNA.

Step (c) in the method above (corresponding to step (a) in the preferred statement of use set out above) of generating cDNA from the captured RNA will be seen as relating to the synthesis of the cDNA. This will involve a step of reverse transcription of the captured RNA, extending the capture probe, which functions as the RT primer, using the captured RNA as template. Such a step generates so-called first strand cDNA. As will be described in more detail below, second strand cDNA synthesis may optionally take place on the array, or it may take place in a separate step, after release of first strand cDNA from the array. As also described in more detail below, in certain embodiments second strand synthesis may occur in the first step of amplification of a released first strand cDNA molecule.

Arrays for use in the context of nucleic acid analysis in general, and DNA analysis in particular, are discussed and described below. Specific details and embodiments described herein in relation to arrays and capture probes for use in the context of RNA, apply equally (where appropriate) to all such arrays, including those for use with DNA.

As used herein the term "multiple" means two or more, or at least two, e.g. 3, 5, 10, 15, 20, 30, 40, 50, 60, 70, 80, 90, 100, 150, 200, 400, 500, 1000, 2000, 5000, 10,000, or more etc. Thus for example, the number of capture probes may be any integer in any range between any two of the aforementioned numbers. It will be appreciated however that it is envisaged that conventional-type arrays with many hundreds, thousands, tens of thousands, hundreds of thousands or even millions of capture probes may be used.

Thus, the methods outlined herein utilise high density nucleic acid arrays comprising "capture probes" for capturing and labelling transcripts from all of the single cells within a tissue sample e.g. a thin tissue sample slice, or "section". The tissue samples or sections for analysis are produced in a highly parallelized fashion, such that the spatial information in the section is retained. The captured RNA (preferably mRNA) molecules for each cell, or "transcriptomes", are transcribed into cDNA and the resultant cDNA molecules are analyzed, for example by high throughput sequencing. The resultant data may be correlated to images of the original tissue samples e.g. sections through so-called barcode sequences (or ID tags, defined herein as positional domains) incorporated into the arrayed nucleic acid probes.

High density nucleic acid arrays or microarrays are a core component of the spatial transcriptome labelling method described herein. A microarray is a multiplex technology used in molecular biology. A typical microarray consists of an arrayed series of microscopic spots of oligonucleotides (hundreds of thousands of spots, generally tens of thousands, can be incorporated on a single array). The distinct position of each nucleic acid (oligonucleotide) spot (each species of oligonucleotide/nucleic acid molecule) is known as a "feature" (and hence in the methods set out above each species of capture probe may be viewed as a specific feature of the array; each feature occupies a distinct position on the array), and typically each separate feature contains in the region of picomoles ($10^{-12}$ moles) of a specific DNA sequence (a "species"), which are known as "probes" (or "reporters"). Typically, these can be a short section of a gene or other nucleic acid element to which a cDNA or cRNA sample (or "target") can hybridize under high-stringency hybridization conditions. However, as described below, the probes of the present invention differ from the probes of standard microarrays.

In gene expression microarrays, probe-target hybridization is usually detected and quantified by detection of visual signal, e.g. a fluorophore, silver ion, or chemiluminescence-label, which has been incorporated into all of the targets. The intensity of the visual signal correlates to the relative abundance of each target nucleic acid in the sample. Since an array can contain tens of thousands of probes, a microarray experiment can accomplish many genetic tests in parallel.

In standard microarrays, the probes are attached to a solid surface or substrate by a covalent bond to a chemical matrix, e.g. epoxy-silane, amino-silane, lysine, polyacrylamide etc. The substrate typically is a glass, plastic or silicon chip or slide, although other microarray platforms are known, e.g. microscopic beads.

The probes may be attached to the array of the invention by any suitable means. In a preferred embodiment the probes are immobilized to the substrate of the array by chemical immobilization. This may be an interaction between the substrate (support material) and the probe based on a chemical reaction. Such a chemical reaction typically does not rely on the input of energy via heat or light, but can be enhanced by either applying heat, e.g. a certain optimal temperature for a chemical reaction, or light of certain wavelength. For example, a chemical immobilization may take place between functional groups on the substrate and corresponding functional elements on the probes. Such corresponding functional elements in the probes may either be an inherent chemical group of the probe, e.g. a hydroxyl group or be additionally introduced. An example of such a functional group is an amine group. Typically, the probe to be immobilized comprises a functional amine group or is chemically modified in order to comprise a functional amine group. Means and methods for such a chemical modification are well known.

The localization of said functional group within the probe to be immobilized may be used in order to control and shape the binding behaviour and/or orientation of the probe, e.g. the functional group may be placed at the 5' or 3' end of the probe or within sequence of the probe. A typical substrate for a probe to be immobilized comprises moieties which are capable of binding to such probes, e.g. to amine-functionalized nucleic acids. Examples of such substrates are carboxy, aldehyde or epoxy substrates. Such materials are known to the person skilled in the art. Functional groups, which impart a connecting reaction between probes which are chemically reactive by the introduction of an amine group, and array substrates are known to the person skilled in the art.

Alternative substrates on which probes may be immobilized may have to be chemically activated, e.g. by the activation of functional groups, available on the array substrate. The term "activated substrate" relates to a material in which interacting or reactive chemical functional groups were established or enabled by chemical modification procedures as known to the person skilled in the art. For example, a substrate comprising carboxyl groups has to be activated before use. Furthermore, there are substrates available that contain functional groups that can react with specific moieties already present in the nucleic acid probes.

Alternatively, the probes may be synthesized directly on the substrate. Suitable methods for such an approach are known to the person skilled in the art. Examples are manufacture techniques developed by Agilent Inc., Affymetrix Inc., Roche Nimblegen Inc. or Flexgen BV. Typically, lasers and a set of mirrors that specifically activate the spots where nucleotide additions are to take place are used. Such an approach may provide, for example, spot sizes (i.e. features) of around 30 µm or larger.

The substrate therefore may be any suitable substrate known to the person skilled in the art. The substrate may have any suitable form or format, e.g. it may be flat, curved, e.g. convexly or concavely curved towards the area where the interaction between the tissue sample and the substrate takes place. Particularly preferred is the where the substrate is a flat, i.e. planar, chip or slide.

Typically, the substrate is a solid support and thereby allows for an accurate and traceable positioning of the probes on the substrate. An example of a substrate is a solid material or a substrate comprising functional chemical groups, e.g. amine groups or amine-functionalized groups. A substrate envisaged by the present invention is a non-porous substrate. Preferred non-porous substrates are glass, silicon, poly-L-lysine coated material, nitrocellulose, polystyrene, cyclic olefin copolymers (COCs), cyclic olefin polymers (COPs), polypropylene, polyethylene and polycarbonate.

Any suitable material known to the person skilled in the art may be used. Typically, glass or polystyrene is used. Polystyrene is a hydrophobic material suitable for binding negatively charged macromolecules because it normally contains few hydrophilic groups. For nucleic acids immobilized on glass slides, it is furthermore known that by increasing the hydrophobicity of the glass surface the nucleic acid immobilization may be increased. Such an enhancement may permit a relatively more densely packed formation. In addition to a coating or surface treatment with poly-L-lysine, the substrate, in particular glass, may be treated by silanation, e.g. with epoxy-silane or amino-silane or by silynation or by a treatment with polyacrylamide.

A number of standard arrays are commercially available and both the number and size of the features may be varied. In the present invention, the arrangement of the features may be altered to correspond to the size and/or density of the cells present in different tissues or organisms. For instance, animal cells typically have a cross-section in the region of 1-100 μm, whereas the cross-section of plant cells typically may range from 1-10000 μm. Hence, Nimblegen® arrays, which are available with up to 2.1 million features, or 4.2 million features, and feature sizes of 13 micrometers, may be preferred for tissue samples from an animal or fungus, whereas other formats, e.g. with 8×130k features, may be sufficient for plant tissue samples. Commercial arrays are also available or known for use in the context of sequence analysis and in particular in the context of NGS technologies. Such arrays may also be used as the array surface in the context of the present invention e.g. an Illumina bead array. In addition to commercially available arrays, which can themselves be customized, it is possible to make custom or non-standard "in-house" arrays and methods for generating arrays are well-established. The methods of the invention may utilise both standard and non-standard arrays that comprise probes as defined below.

The probes on a microarray may be immobilized, i.e. attached or bound, to the array preferably via the 5' or 3' end, depending on the chemical matrix of the array. Typically, for commercially available arrays, the probes are attached via a 3' linkage, thereby leaving a free 5' end. However, arrays comprising probes attached to the substrate via a 5' linkage, thereby leaving a free 3' end, are available and may be synthesized using standard techniques that are well known in the art and are described elsewhere herein.

The covalent linkage used to couple a nucleic acid probe to an array substrate may be viewed as both a direct and indirect linkage, in that the although the probe is attached by a "direct" covalent bond, there may be a chemical moiety or linker separating the "first" nucleotide of the nucleic acid probe from the, e.g. glass or silicon, substrate i.e. an indirect linkage. For the purposes of the present invention probes that are immobilized to the substrate by a covalent bond and/or chemical linker are generally seen to be immobilized or attached directly to the substrate.

As will be described in more detail below, the capture probes of the invention may be immobilized on, or interact with, the array directly or indirectly. Thus the capture probes need not bind directly to the array, but may interact indirectly, for example by binding to a molecule which itself binds directly or indirectly to the array (e.g. the capture probe may interact with (e.g. bind or hybridize to) a binding partner for the capture probe, i.e. a surface probe, which is itself bound to the array directly or indirectly). Generally speaking, however, the capture probe will be, directly or indirectly (by one or more intermediaries), bound to, or immobilized on, the array.

The use, method and array of the invention may comprise probes that are immobilized via their 5' or 3' end. However, when the capture probe is immobilized directly to the array substrate, it may be immobilized only such that the 3' end of the capture probe is free to be extended, e.g. it is immobilized by its 5' end. The capture probe may be immobilized indirectly, such that it has a free, i.e. extendible, 3' end.

By extended or extendible 3' end, it is meant that further nucleotides may be added to the most 3' nucleotide of the nucleic acid molecule, e.g. capture probe, to extend the length of the nucleic acid molecule, i.e. the standard polymerization reaction utilized to extend nucleic acid molecules, e.g. templated polymerization catalyzed by a polymerase.

Thus, in one embodiment, the array comprises probes that are immobilized directly via their 3' end, so-called surface probes, which are defined below. Each species of surface probe comprises a region of complementarity to each species of capture probe, such that the capture probe may hybridize to the surface probe, resulting in the capture probe comprising a free extendible 3' end. In a preferred aspect of the invention, when the array comprises surface probes, the capture probes are synthesized in situ on the array.

The array probes may be made up of ribonucleotides and/or deoxyribonucleotides as well as synthetic nucleotide residues that are capable of participating in Watson-Crick type or analogous base pair interactions. Thus, the nucleic acid domain may be DNA or RNA or any modification thereof e.g. PNA or other derivatives containing non-nucleotide backbones. However, in the context of transcriptome analysis the capture domain of the capture probe must capable of priming a reverse transcription reaction to generate cDNA that is complementary to the captured RNA molecules. As described below in more detail, in the context of genome analysis, the capture domain of the capture probe must be capable of binding to the DNA fragments, which may comprise binding to a binding domain that has been added to the fragmented DNA. In some embodiments, the capture domain of the capture probe may prime a DNA extension (polymerase) reaction to generate DNA that is complementary to the captured DNA molecules. In other embodiments, the capture domain may template a ligation reaction between the captured DNA molecules and a surface probe that is directly or indirectly immobilised on the substrate. In yet other embodiments, the capture domain may be ligated to one strand of the captured DNA molecules.

In a preferred embodiment of the invention at least the capture domain of the capture probe comprises or consists of deoxyribonucleotides (dNTPs). In a particularly preferred embodiment the whole of the capture probe comprises or consists of deoxyribonucleotides.

In a preferred embodiment of the invention the capture probes are immobilized on the substrate of the array directly, i.e. by their 5' end, resulting in a free extendible 3' end.

The capture probes of the invention comprise at least two domains, a capture domain and a positional domain (or a feature identification tag or domain; the positional domain may alternatively be defined as an identification (ID) domain or tag, or as a positional tag). The capture probe may further comprise a universal domain as defined further below. Where the capture probe is indirectly attached to the array surface via hybridization to a surface probe, the capture probe requires a sequence (e.g. a portion or domain) which is complementary to the surface probe. Such a complementary sequence may be complementary to a positional/identification domain and/or a universal domain on the surface probe. In other words the positional domain and/or universal domain may constitute the region or portion of the probe which is complementary to the surface probe. However, the capture probe may also comprise an additional domain (or region, portion or sequence) which is complementary to the surface probe. For ease of synthesis, as described in more detail below, such a surface probe-complementary region may be provided as part, or as an extension of the capture domain (such a part or extension not itself being used for, or capable of, binding to the target nucleic acid, e.g. RNA).

The capture domain is typically located at the 3' end of the capture probe and comprises a free 3' end that can be extended, e.g. by template dependent polymerization. The capture domain comprises a nucleotide sequence that is capable of hybridizing to nucleic acid, e.g. RNA (preferably mRNA) present in the cells of the tissue sample contact with the array.

Advantageously, the capture domain may be selected or designed to bind (or put more generally may be capable of binding) selectively or specifically to the particular nucleic acid, e.g. RNA it is desired to detect or analyse. For example the capture domain may be selected or designed for the selective capture of mRNA. As is well known in the art, this may be on the basis of hybridisation to the poly-A tail of mRNA. Thus, in a preferred embodiment the capture domain comprises a poly-T DNA oligonucleotide, i.e. a series of consecutive deoxythymidine residues linked by phosphodiester bonds, which is capable of hybridizing to the poly-A tail of mRNA. Alternatively, the capture domain may comprise nucleotides which are functionally or structurally analogous to poly-T i.e., are capable of binding selectively to poly-A, for example a poly-U oligonucleotide or an oligonucleotide comprised of deoxythymidine analogues, wherein said oligonucleotide retains the functional property of binding to poly-A. In a particularly preferred embodiment the capture domain, or more particularly the poly-T element of the capture domain, comprises at least 10 nucleotides, preferably at least 11, 12, 13, 14, 15, 16, 17, 18, 19 or 20 nucleotides. In a further embodiment, the capture domain, or more particularly the poly-T element of the capture domain comprises at least 25, 30 or 35 nucleotides.

Random sequences may also be used in the capture of nucleic acid, as is known in the art, e.g. random hexamers or similar sequences, and hence such random sequences may be used to form all or a part of the capture domain. For example, random sequences may be used in conjunction with poly-T (or poly-T analogue etc.) sequences. Thus where a capture domain comprises a poly-T (or a "poly-T-like") oligonucleotide, it may also comprise a random oligonucleotide sequence. This may for example be located 5' or 3' of the poly-T sequence, e.g. at the 3' end of the capture probe, but the positioning of such a random sequence is not critical. Such a construct may facilitate the capturing of the initial part of the poly-A of mRNA. Alternatively, the capture domain may be an entirely random sequence. Degenerate capture domains may also be used, according to principles known in the art.

The capture domain may be capable of binding selectively to a desired sub-type or subset of nucleic acid, e.g. RNA, for example a particular type of RNA such mRNA or rRNA etc. as listed above, or to a particular subset of a given type of RNA, for example, a particular mRNA species e.g. corresponding to a particular gene or group of genes. Such a capture probe may be selected or designed based on sequence of the RNA it is desired to capture. Thus it may be a sequence-specific capture probe, specific for a particular RNA target or group of targets (target group etc). Thus, it may be based on a particular gene sequence or particular motif sequence or common/conserved sequence etc., according to principles well known in the art.

In embodiments where the capture probe is immobilized on the substrate of the array indirectly, e.g. via hybridization to a surface probe, the capture domain may further comprise an upstream sequence (5' to the sequence that hybridizes to the nucleic acid, e.g. RNA of the tissue sample) that is capable of hybridizing to 5' end of the surface probe. Alone, the capture domain of the capture probe may be seen as a capture domain oligonucleotide, which may be used in the synthesis of the capture probe in embodiments where the capture probe is immobilized on the array indirectly.

The positional domain (feature identification domain or tag) of the capture probe is located directly or indirectly upstream, i.e. closer to the 5' end of the capture probe nucleic acid molecule, of the capture domain. Preferably the positional domain is directly adjacent to the capture domain, i.e. there is no intermediate sequence between the capture domain and the positional domain. In some embodiments the positional domain forms the 5' end of the capture probe, which may be immobilized directly or indirectly on the substrate of the array.

As discussed above, each feature (distinct position) of the array comprises a spot of a species of nucleic acid probe, wherein the positional domain at each feature is unique. Thus, a "species" of capture probe is defined with reference to its positional domain; a single species of capture probe will have the same positional domain. However, it is not required that each member of a species of capture probe has the same sequence in its entirety. In particular, since the capture domain may be or may comprise a random or degenerate sequence, the capture domains of individual probes within a species may vary. Accordingly, in some embodiments where the capture domains of the capture probes are the same, each feature comprises a single probe sequence. However in other embodiments where the capture probe varies, members of a species of probe will not have the exact same sequence, although the sequence of the positional domain of each member in the species will be the same. What is required is that each feature or position of the array carries a capture probe of a single species (specifically each feature or position carries a capture probe which has an identical positional tag, i.e. there is a single positional domain at each feature or position). Each species has a different positional domain which identifies the species. However, each member of a species, may in some cases, as described in more detail herein, have a different capture domain, as the capture domain may be random or degenerate or may have a random or degenerate component. This means that within a given feature, or position, the capture domain of the probes may differ.

Thus in some, but not necessarily in all embodiments, the nucleotide sequence of any one probe molecule immobilized at a particular feature is the same as the other probe molecules immobilized at the same feature, but the nucleotide sequence of the probes at each feature is different, distinct or distinguishable from the probes immobilized at every other feature. Preferably each feature comprises a different species of probe. However, in some embodiments it may be advantageous for a group of features to comprise the same species of probe, i.e. effectively to produce a feature covering an area of the array that is greater than a single feature, e.g. to lower the resolution of the array. In other embodiments of the array, the nucleotide sequence of the positional domain of any one probe molecule immobilized at a particular feature may be the same as the other probe molecules immobilized at the same feature but the capture domain may vary. The capture domain may nonetheless be designed to capture the same type of molecule, e.g. mRNA in general.

The positional domain (or tag) of the capture probe comprises the sequence which is unique to each feature and acts as a positional or spatial marker (the identification tag). In this way each region or domain of the tissue sample, e.g. each cell in the tissue, will be identifiable by spatial resolution across the array linking the nucleic acid, e.g. RNA (e.g. the transcripts) from a certain cell to a unique positional domain sequence in the capture probe. By virtue of the positional domain a capture probe in the array may be correlated to a position in the tissue sample, for example it may be correlated to a cell in the sample. Thus, the positional domain of the capture domain may be seen as a nucleic acid tag (identification tag).

Any suitable sequence may be used as the positional domain in the capture probes of the invention. By a suitable sequence, it is meant that the positional domain should not interfere with (i.e. inhibit or distort) the interaction between the RNA of the tissue sample and the capture domain of the capture probe. For example, the positional domain should be designed such that nucleic acid molecules in the tissue sample do not hybridize specifically to the positional domain. Preferably, the nucleic acid sequence of the positional domain of the capture probes has less than 80% sequence identity to the nucleic acid sequences in the tissue sample. Preferably, the positional domain of the capture probe has less than 70%, 60%, 50% or less than 40% sequence identity across a substantial part of the nucleic acids molecules in the tissue sample. Sequence identity may be determined by any appropriate method known in the art, e.g. the using BLAST alignment algorithm.

In a preferred embodiment the positional domain of each species of capture probe contains a unique barcode sequence. The barcode sequences may be generated using random sequence generation. The randomly generated sequences may be followed by stringent filtering by mapping to the genomes of all common reference species and with pre-set Tm intervals, GC content and a defined distance of difference to the other barcode sequences to ensure that the barcode sequences will not interfere with the capture of the nucleic acid, e.g. RNA from the tissue sample and will be distinguishable from each other without difficulty.

As mentioned above, and in a preferred embodiment, the capture probe comprises also a universal domain (or linker domain or tag). The universal domain of the capture probe is located directly or indirectly upstream, i.e. closer to the 5' end of the capture probe nucleic acid molecule, of the positional domain. Preferably the universal domain is directly adjacent to the positional domain, i.e. there is no intermediate sequence between the positional domain and the universal domain. In embodiments where the capture probe comprises a universal domain, the domain will form the 5' end of the capture probe, which may be immobilized directly or indirectly on the substrate of the array.

The universal domain may be utilized in a number of ways in the methods and uses of the invention. For example, the methods of the invention comprise a step of releasing (e.g. removing) at least part of the synthesised (i.e. extended or ligated) nucleic acid, e.g. cDNA molecules from the surface of the array. As described elsewhere herein, this may be achieved in a number of ways, of which one comprises cleaving the nucleic acid, e.g. cDNA molecule from the surface of the array. Thus, the universal domain may itself comprise a cleavage domain, i.e. a sequence that can be cleaved specifically, either chemically or preferably enzymatically.

Thus, the cleavage domain may comprise a sequence that is recognised by one or more enzymes capable of cleaving a nucleic acid molecule, i.e. capable of breaking the phosphodiester linkage between two or more nucleotides. For instance, the cleavage domain may comprise a restriction endonuclease (restriction enzyme) recognition sequence. Restriction enzymes cut double-stranded or single stranded DNA at specific recognition nucleotide sequences known as restriction sites and suitable enzymes are well known in the art. For example, it is particularly advantageous to use rare-cutting restriction enzymes, i.e. enzymes with a long recognition site (at least 8 base pairs in length), to reduce the possibility of cleaving elsewhere in the nucleic acid, e.g. cDNA molecule. In this respect, it will be seen that removing or releasing at least part of the nucleic acid, e.g. cDNA molecule requires releasing a part comprising the positional domain of the nucleic acid, e.g. cDNA and all of the sequence downstream of the domain, i.e. all of the sequence that is 3' to the positional domain. Hence, cleavage of the nucleic acid, e.g. cDNA molecule should take place 5' to the positional domain.

By way of example, the cleavage domain may comprise a poly-U sequence which may be cleaved by a mixture of Uracil DNA glycosylase (UDG) and the DNA glycosylase-lyase Endonuclease VIII, commercially known as the USER™ enzyme.

A further example of a cleavage domain can be utilised in embodiments where the capture probe is immobilized to the array substrate indirectly, i.e. via a surface probe. The cleavage domain may comprise one or more mismatch nucleotides, i.e. when the complementary parts of the surface probe and the capture probe are not 100% complementary. Such a mismatch is recognised, e.g. by the MutY and T7 endonuclease I enzymes, which results in cleavage of the nucleic acid molecule at the position of the mismatch.

In some embodiments of the invention, the positional domain of the capture probe comprises a cleavage domain, wherein the said cleavage domain is located at the 5' end of the positional domain.

The universal domain may comprise also an amplification domain. This may be in addition to, or instead of, a cleavage domain. In some embodiments of the invention, as described elsewhere herein, it may be advantageous to amplify the nucleic acid, e.g. cDNA molecules, for example after they have been released (e.g. removed or cleaved) from the array substrate. It will be appreciated however, that the initial cycle of amplification, or indeed any or all further cycles of amplification may also take place in situ on the array. The amplification domain comprises a distinct sequence to which an amplification primer may hybridize. The amplification domain of the universal domain of the capture probe is preferably identical for each species of capture probe. Hence a single amplification reaction will be sufficient to amplify all of the nucleic acid, e.g. cDNA molecules (which may or may not be released from the array substrate prior to amplification).

Any suitable sequence may be used as the amplification domain in the capture probes of the invention. By a suitable sequence, it is meant that the amplification domain should not interfere with (i.e. inhibit or distort) the interaction between the nucleic acid, e.g. RNA of the tissue sample and the capture domain of the capture probe. Furthermore, the amplification domain should comprise a sequence that is not the same or substantially the same as any sequence in the nucleic acid, e.g. RNA of the tissue sample, such that the primer used in the amplification reaction can hybridized only to the amplification domain under the amplification conditions of the reaction.

For example, the amplification domain should be designed such that nucleic acid molecules in the tissue sample do not hybridize specifically to the amplification domain or the complementary sequence of the amplification domain. Preferably, the nucleic acid sequence of the amplification domain of the capture probes and the complement thereof has less than 80% sequence identity to the nucleic acid sequences in the tissue sample. Preferably, the positional domain of the capture probe has less than 70%, 60%, 50% or less than 40% sequence identity across a substantial part of the nucleic acid molecules in the tissue sample. Sequence identity may be determined by any appropriate method known in the art, e.g. the using BLAST alignment algorithm.

Thus, alone, the universal domain of the capture probe may be seen as a universal domain oligonucleotide, which may be used in the synthesis of the capture probe in embodiments where the capture probe is immobilized on the array indirectly.

In one representative embodiment of the invention only the positional domain of each species of capture probe is unique. Hence, the capture domains and universal domains (if present) are in one embodiment the same for every species of capture probe for any particular array to ensure that the capture of the nucleic acid, e.g. RNA from the tissue sample is uniform across the array. However, as discussed above, in some embodiments the capture domains may differ by virtue of including random or degenerate sequences.

In embodiments where the capture probe is immobilized on the substrate of the array indirectly, e.g. via hybridisation to a surface probe, the capture probe may be synthesised on the array as described below.

The surface probes are immobilized on the substrate of the array directly by or at, e.g. their 3' end. Each species of surface probe is unique to each feature (distinct position) of the array and is partly complementary to the capture probe, defined above.

Hence the surface probe comprises at its 5' end a domain (complementary capture domain) that is complementary to a part of the capture domain that does not bind to the nucleic acid, e.g. RNA of the tissue sample. In other words, it comprises a domain that can hybridize to at least part of a capture domain oligonucleotide. The surface probe further comprises a domain (complementary positional domain or complementary feature identification domain) that is complementary to the positional domain of the capture probe. The complementary positional domain is located directly or indirectly downstream (i.e. at the 3' end) of the complementary capture domain, i.e. there may be an intermediary or linker sequence separating the complementary positional domain and the complementary capture domain. In embodiments where the capture probe is synthesized on the array surface, the surface probes of the array always comprise a domain (complementary universal domain) at the 3' end of the surface probe, i.e. directly or indirectly downstream of the positional domain, which is complementary to the universal domain of the capture probe. In other words, it comprises a domain that can hybridize to at least part of the universal domain oligonucleotide.

In some embodiments of the invention the sequence of the surface probe shows 100% complementarity or sequence identity to the positional and universal domains and to the part of the capture domain that does not bind to the nucleic acid, e.g. RNA of the tissue sample. In other embodiments the sequence of the surface probe may show less than 100% sequence identity to the domains of the capture probe, e.g. less than 99%, 98%, 97%, 96%, 95%, 94%, 93%, 92%, 91% or 90%. In a particularly preferred embodiment of the invention, the complementary universal domain shares less than 100% sequence identity to the universal domain of the capture probe.

In one embodiment of the invention, the capture probe is synthesized or generated on the substrate of the array. In a representative embodiment (see FIG. 3), the array comprises surface probes as defined above. Oligonucleotides that correspond to the capture domain and universal domain of the capture probe are contacted with the array and allowed to hybridize to the complementary domains of the surface probes. Excess oligonucleotides may be removed by washing the array under standard hybridization conditions. The resultant array comprises partially single stranded probes, wherein both the 5' and 3' ends of the surface probe are double stranded and the complementary positional domain is single stranded. The array may be treated with a polymerase enzyme to extend the 3' end of the universal domain oligonucleotide, in a template dependent manner, so as to synthesize the positional domain of the capture probe. The 3' end of the synthesized positional domain is then ligated, e.g. using a ligase enzyme, to the 5' end of the capture domain oligonucleotide to generate the capture probe. It will be understood in this regard that the 5' end of the capture domain oligonucleotide is phosphorylated to enable ligation to take place. As each species of surface probe comprises a unique complementary positional domain, each species of capture probe will comprise a unique positional domain.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 90% (preferably at least about 95%) of the nucleotides share base pair organization over a defined length of the molecule. The domains of the capture and surface probes thus contain a region of complementarity. Furthermore the capture domain of the capture probe contains a region of complementarity for the nucleic acid, e.g. RNA (preferably mRNA) of the tissue sample.

The capture probe may also be synthesised on the array substrate using polymerase extension (similarly to as described above) and a terminal transferase enzyme to add a "tail" which may constitute the capture domain. This is described further in Example 7 below. The use of terminal transferases to add nucleotide sequences to the end of an oligonucleotide is known in the art, e.g. to introduce a homopolymeric tail e.g. a poly-T tail. Accordingly, in such a synthesis an oligonucleotide that corresponds to the universal domain of the capture probe may be contacted with the array and allowed to hybridize to the complementary domain of the surface probes. Excess oligonucleotides may be removed by washing the array under standard hybridization conditions. The resultant array comprises partially single stranded probes, wherein the 5' ends of the surface probes are double stranded and the complementary positional domain is single stranded. The array may be treated with a polymerase enzyme to extend the 3' end of the universal domain oligonucleotide, in a template dependent manner, so as to synthesize the positional domain of the capture probe. The capture domain, e.g. comprising a poly-T sequence may then be introduced using a terminal transferase to add a poly-T tail to generate the capture probe.

The typical array of, and for use in the methods of, the invention may contain multiple spots, or "features". A feature may be defined as an area or distinct position on the array substrate at which a single species of capture probe is immobilized. Hence each feature will comprise a multiplicity of probe molecules, of the same species. It will be understood in this context that whilst it is encompassed that each capture probe of the same species may have the same sequence, this need not necessarily be the case. Each species of capture probe will have the same positional domain (i.e. each member of a species and hence each probe in a feature will be identically "tagged"), but the sequence of each member of the feature (species) may differ, because the sequence of a capture domain may differ. As described above, random or degenerate capture domains may be used. Thus the capture probes within a feature may comprise different random or degenerate sequences. The number and density of the features on the array will determine the resolution of the array, i.e. the level of detail at which the transcriptome or genome of the tissue sample can be analysed. Hence, a higher density of features will typically increase the resolution of the array.

As discussed above, the size and number of the features on the array of the invention will depend on the nature of the tissue sample and required resolution. Thus, if it is desirable to determine a transcriptome or genome only for regions of cells within a tissue sample (or the sample contains large cells) then the number and/or density of features on the array may be reduced (i.e. lower than the possible maximum number of features) and/or the size of the features may be increased (i.e. the area of each feature may be greater than the smallest possible feature), e.g. an array comprising few large features. Alternatively, if it is desirable to determine a transcriptome or genome of individual cells within a sample, it may be necessary to use the maximum number of features possible, which would necessitate using the smallest possible feature size, e.g. an array comprising many small features.

Whilst single cell resolution may be a preferred and advantageous feature of the present invention, it is not essential to achieve this, and resolution at the cell group level is also of interest, for example to detect or distinguish a particular cell type or tissue region, e.g. normal vs tumour cells.

In representative embodiments of the invention, an array may contain at least 2, 5, 10, 50, 100, 500, 750, 1000, 1500, 3000, 5000, 10000, 20000, 40000, 50000, 75000, 100000, 150000, 200000, 300000, 400000, 500000, 750000, 800000, 1000000, 1200000, 1500000, 1750000, 2000000, 2100000. 3000000, 3500000, 4000000 or 4200000 features. Whilst 4200000 represents the maximum number of features presently available on a commercial array, it is envisaged that arrays with features in excess of this may be prepared and such arrays are of interest in the present invention. As noted above, feature size may be decreased and this may allow greater numbers of features to be accommodated within the same or a similar area. By way of example. these features may be comprised in an area of less than about 20 $cm^2$, 10 $cm^2$, 5 $cm^2$, 1 $cm^2$, 1 $mm^2$, or 100 $\mu m^2$.

Thus, in some embodiments of the invention the area of each feature may be from about 1 $\mu m^2$, 2 $\mu m^2$, 3 $\mu m^2$, 4 $\mu m^2$, 5 $\mu m^2$, 10 $\mu m^2$, 12 $\mu m^2$, 15 $\mu m^2$, 20 $\mu m^2$, 50 $\mu m^2$, 75 $\mu m^2$, 100 $\mu m^2$, 150 $\mu m^2$, 200 $\mu m^2$, 250 $\mu m^2$, 300 $\mu m^2$, 400 $\mu m^2$, or 500 $\mu m^2$.

It will be evident that a tissue sample from any organism could be used in the methods of the invention, e.g. plant, animal or fungal. The array of the invention allows the capture of any nucleic acid, e.g. mRNA molecules, which are present in cells that are capable of transcription and/or translation. The arrays and methods of the invention are particularly suitable for isolating and analysing the transcriptome or genome of cells within a sample, wherein spatial resolution of the transcriptomes or genomes is desirable, e.g. where the cells are interconnected or in contact directly with adjacent cells. However, it will be apparent to a person of skill in the art that the methods of the invention may also be useful for the analysis of the transcriptome or genome of different cells or cell types within a sample even if said cells do not interact directly, e.g. a blood sample. In other words, the cells do not need to present in the context of a tissue and can be applied to the array as single cells (e.g. cells isolated from a non-fixed tissue). Such single cells, whilst not necessarily fixed to a certain position in a tissue, are nonetheless applied to a certain position on the array and can be individually identified. Thus, in the context of analysing cells that do not interact directly, or are not present in a tissue context, the spatial properties of the described methods may be applied to obtaining or retrieving unique or independent transcriptome or genome information from individual cells.

The sample may thus be a harvested or biopsied tissue sample, or possibly a cultured sample. Representative samples include clinical samples e.g. whole blood or blood-derived products, blood cells, tissues, biopsies, or cultured tissues or cells etc. including cell suspensions. Artificial tissues may for example be prepared from cell suspension (including for example blood cells). Cells may be captured in a matrix (for example a gel matrix e.g. agar, agarose, etc) and may then be sectioned in a conventional way. Such procedures are known in the art in the context of immuno-histochemistry (see e.g. Andersson et al 2006, J. Histochem. Cytochem. 54(12): 1413-23. Epub 2006 Sep. 6).

The mode of tissue preparation and how the resulting sample is handled may effect the transcriptomic or genomic analysis of the methods of the invention. Moreover, various tissue samples will have different physical characteristics and it is well within the skill of a person in the art to perform the necessary manipulations to yield a tissue sample for use with the methods of the invention. However, it is evident from the disclosures herein that any method of sample preparation may be used to obtain a tissue sample that is suitable for use in the methods of the invention. For instance any layer of cells with a thickness of approximately 1 cell or less may be used in the methods of the invention. In one embodiment, the thickness of the tissue sample may be less than 0.9, 0.8, 0.7, 0.6, 0.5, 0.4, 0.3, 0.2 or 0.1 of the cross-section of a cell. However, since as noted above, the present invention is not limited to single cell resolution and hence it is not a requirement that the tissue sample has a thickness of one cell diameter or less; thicker tissue samples may if desired be used. For example cryostat sections may be used, which may be e.g. 10-20 μm thick.

The tissue sample may be prepared in any convenient or desired way and the invention is not restricted to any particular type of tissue preparation. Fresh, frozen, fixed or unfixed tissues may be used. Any desired convenient procedure may be used for fixing or embedding the tissue sample, as described and known in the art. Thus any known fixatives or embedding materials may be used.

As a first representative example of a tissue sample for use in the invention, the tissue may prepared by deep freezing at temperature suitable to maintain or preserve the integrity (i.e. the physical characteristics) of the tissue structure, e.g. less than −20° C. and preferably less than −25, −30, −40, −50, −60, −70 or −80° C. The frozen tissue sample may be sectioned, i.e. thinly sliced, onto the array surface by any suitable means. For example, the tissue sample may be prepared using a chilled microtome, a cryostat, set at a temperature suitable to maintain both the structural integrity of the tissue sample and the chemical properties of the nucleic acids in the sample, e.g. to less than −15° C. and preferably less than −20 or −25° C. Thus, the sample should be treated so as to minimize the degeneration or degradation of the nucleic acid, e.g. RNA in the tissue. Such conditions are well-established in the art and the extent of any degradation may be monitored through nucleic acid extraction, e.g. total RNA extraction and subsequent quality analysis at various stages of the preparation of the tissue sample.

In a second representative example, the tissue may be prepared using standard methods of formalin-fixation and paraffin-embedding (FFPE), which are well-established in the art. Following fixation of the tissue sample and embedding in a paraffin or resin block, the tissue samples may sectioned, i.e. thinly sliced, onto the array. As noted above, other fixatives and/or embedding materials can be used.

It will be apparent that the tissue sample section will need to be treated to remove the embedding material e.g. to deparaffinize, i.e. to remove the paraffin or resin, from the sample prior to carrying out the methods of the invention. This may be achieved by any suitable method and the removal of paraffin or resin or other material from tissue samples is well established in the art, e.g. by incubating the sample (on the surface of the array) in an appropriate solvent e.g. xylene, e.g. twice for 10 minutes, followed by an ethanol rinse, e.g. 99.5% ethanol for 2 minutes, 96% ethanol for 2 minutes, and 70% ethanol for 2 minutes.

It will be evident to the skilled person that the RNA in tissue sections prepared using methods of FFPE or other methods of fixing and embedding is more likely to be partially degraded than in the case of frozen tissue. However, without wishing to be bound by any particular theory, it is believed that this may be advantageous in the methods of the invention. For instance, if the RNA in the sample is partially degraded the average length of the RNA polynucleotides will be less and more randomized than a non-degraded sample. It is postulated therefore that partially degraded RNA would result in less bias in the various processing steps, described elsewhere herein, e.g. ligation of adaptors (amplification domains), amplification of the cDNA molecules and sequencing thereof.

Hence, in one embodiment of the invention the tissue sample, i.e. the section of the tissue sample contacted with the array, is prepared using FFPE or other methods of fixing and embedding. In other words the sample may be fixed, e.g. fixed and embedded. In an alternative embodiment of the invention the tissue sample is prepared by deep-freezing. In another embodiment a touch imprint of a tissue may be used, according to procedures known in the art. In other embodiments an unfixed sample may be used.

The thickness of the tissue sample section for use in the methods of the invention may be dependent on the method used to prepare the sample and the physical characteristics of the tissue. Thus, any suitable section thickness may be used in the methods of the invention. In representative embodiments of the invention the thickness of the tissue sample section will be at least 0.1 μm, further preferably at least 0.2, 0.3, 0.4, 0.5, 0.7, 1.0, 1.5, 2, 3, 4, 5, 6, 7, 8, 9 or 10 μm. In other embodiments the thickness of the tissue sample section is at least 10, 12, 13, 14, 15, 20, 30, 40 or 50 μm. However, the thickness is not critical and these are representative values only. Thicker samples may be used if desired or convenient e.g. 70 or 100 μm or more. Typically, the thickness of the tissue sample section is between 1-100 μm, 1-50 μm, 1-30 μm, 1-25 μm, 1-20 μm, 1-15 μm, 1-10 μm, 2-8 μm, 3-7 μm or 4-6 μm, but as mentioned above thicker samples may be used.

On contact of the tissue sample section with the array, e.g. following removal of the embedding material e.g. deparafinization, the nucleic acid, e.g. RNA molecules in the tissue sample will bind to the immobilized capture probes on the array. In some embodiments it may be advantageous to facilitate the hybridization of the nucleic acid, e.g. RNA molecules to the capture probes. Typically, facilitating the hybridization comprises modifying the conditions under which hybridization occurs. The primary conditions that can be modified are the time and temperature of the incubation of the tissue section on the array prior to the reverse transcription step, which is described elsewhere herein.

For instance, on contacting the tissue sample section with the array, the array may be incubated for at least 1 hour to allow the nucleic acid, e.g. RNA to hybridize to the capture probes. Preferably the array may be incubated for at least 2, 3, 5, 10, 12, 15, 20, 22 or 24 hours or until the tissue sample section has dried. The array incubation time is not critical and any convenient or desired time may be used. Typical array incubations may be up to 72 hours. Thus, the incubation may occur at any suitable temperature, for instance at room temperature, although in a preferred embodiment the tissue sample section is incubated on the array at a temperature of at least 25, 26, 27, 28, 29, 30, 31, 32, 33, 34, 35, 36 or 37° C. Incubation temperatures of up to 55° C. are commonplace in the art. In a particularly preferred embodiment the tissue sample section is allowed to dry on the array at 37° C. for 24 hours. Once the tissue sample section has dried the array may be stored at room temperature before performing the reverse transcription step. It will be understood that the if the tissue sample section is allowed to dry on the surface of the array, it will need to be rehydrated before further manipulation of the captured nucleic acid can be achieved, e.g. the step of reverse transcribing the captured RNA.

Hence, the method of the invention may comprise a further step of rehydrating the tissue sample after contacting the sample with the array.

In some embodiments it may be advantageous to block (e.g. mask or modify) the capture probes prior to contacting the tissue sample with the array, particularly when the nucleic acid in the tissue sample is subject to a process of modification prior to its capture on the array. Specifically, it may be advantageous to block or modify the free 3' end of the capture probe. In a particular embodiment, the nucleic acid in the tissue sample, e.g. fragmented genomic DNA, may be modified such that it can be captured by the capture probe. For instance, and as described in more detail below, an adaptor sequence (comprising a binding domain capable of binding to the capture domain of the capture probe) may be added to the end of the nucleic acid, e.g. fragmented genomic DNA. This may be achieved by, e.g. ligation of an adaptor or extension of the nucleic acid, e.g. using an enzyme to incorporate additional nucleotides at the end of the sequence, e.g. a poly-A tail. It is necessary to block or modify the capture probes, particularly the free 3' end of the capture probe, prior to contacting the tissue sample with the array to avoid modification of the capture probes, e.g. to avoid the addition of a poly-A tail to the free 3' end of the capture probes. Preferably the incorporation of a blocking domain may be incorporated into the capture probe when it is synthesised. However, the blocking domain may be incorporated to the capture probe after its synthesis.

In some embodiments the capture probes may be blocked by any suitable and reversible means that would prevent modification of the capture domains during the process of modifying the nucleic acid of the tissue sample, which occurs after the tissue sample has been contacted with the array. In other words, the capture probes may be reversibly masked or modified such that the capture domain of the capture probe does not comprise a free 3' end, i.e. such that the 3' end is removed or modified, or made inaccessible so that the capture probe is not susceptible to the process which is used to modify the nucleic acid of the tissue sample, e.g. ligation or extension, or the additional nucleotides may be removed to reveal and/or restore the 3' end of the capture domain of the capture probe.

For example, blocking probes may be hybridised to the capture probes to mask the free 3' end of the capture domain, e.g. hairpin probes or partially double stranded probes, suitable examples of which are known in the art. The free 3' end of the capture domain may be blocked by chemical modification, e.g. addition of an azidomethyl group as a chemically reversible capping moiety such that the capture probes do not comprise a free 3' end. Suitable alternative capping moieties are well known in the art, e.g. the terminal nucleotide of the capture domain could be a reversible terminator nucleotide, which could be included in the capture probe during or after probe synthesis.

Alternatively or additionally, the capture domain of the capture probe could be modified so as to allow the removal of any modifications of the capture probe, e.g. additional nucleotides, that occur when the nucleic acid molecules of the tissue sample are modified. For instance, the capture probes may comprise an additional sequence downstream of the capture domain, i.e. 3' to capture domain, namely a blocking domain. This could be in the form of, e.g. a restriction endonuclease recognition sequence or a sequence of nucleotides cleavable by specific enzyme activities, e.g. uracil. Following the modification of the nucleic acid of the tissue sample, the capture probes could be subjected to an enzymatic cleavage, which would allow the removal of the blocking domain and any of the additional nucleotides that are added to the 3' end of the capture probe during the modification process. The removal of the blocking domain would reveal and/or restore the free 3' end of the capture domain of the capture probe. The blocking domain could be synthesised as part of the capture probe or could be added to the capture probe in situ (i.e. as a modification of an existing array), e.g. by ligation of the blocking domain.

The capture probes may be blocked using any combination of the blocking mechanisms described above.

Once the nucleic acid of the tissue sample, e.g. fragmented genomic DNA, has been modified to enable it to hybridise to the capture domain of the capture probe, the capture probe must be unblocked, e.g. by dissociation of the blocking oligonucleotide, removal of the capping moiety and/or blocking domain.

In order to correlate the sequence analysis or transcriptome or genome information obtained from each feature of the array with the region (i.e. an area or cell) of the tissue sample the tissue sample is oriented in relation to the features on the array. In other words, the tissue sample is placed on the array such that the position of a capture probe on the array may be correlated with a position in the tissue sample. Thus it may be identified where in the tissue sample the position of each species of capture probe (or each feature of the array) corresponds. In other words, it may be identified to which location in the tissue sample the position of each species of capture probe corresponds. This may be done by virtue of positional markers present on the array, as described below. Conveniently, but not necessarily, the tissue sample may be imaged following its contact with the array. This may be performed before or after the nucleic acid of the tissue sample is processed, e.g. before or after the cDNA generation step of the method, in particular the step of generating the first strand cDNA by reverse transcription. In a preferred embodiment the tissue sample is imaged prior to the release of the captured and synthesised (i.e. extended or ligated) DNA, e.g. cDNA, from the array. In a particularly preferred embodiment the tissue is imaged after the nucleic acid of the tissue sample has been processed, e.g. after the reverse transcription step, and any residual tissue is removed (e.g. washed) from the array prior to the release of molecules, e.g. of the cDNA from the array. In some embodiments, the step of processing the captured nucleic acid, e.g. the reverse transcription step, may act to remove residual tissue from the array surface, e.g. when using tissue preparing by deep-freezing. In such a case, imaging of the tissue sample may take place prior to the processing step, e.g. the cDNA synthesis step. Generally speaking, imaging may take place at any time after contacting the tissue sample with the area, but before any step which degrades or removes the tissue sample. As noted above, this may depend on the tissue sample.

Advantageously, the array may comprise markers to facilitate the orientation of the tissue sample or the image thereof in relation to the features of the array. Any suitable means for marking the array may be used such that they are detectable when the tissue sample is imaged. For instance, a molecule, e.g. a fluorescent molecule, that generates a signal, preferably a visible signal, may be immobilized directly or indirectly on the surface of the array. Preferably, the array comprises at least two markers in distinct positions on the surface of the array, further preferably at least 3, 4, 5, 6, 7, 8, 9, 10, 12, 15, 20, 30, 40, 50, 60, 70, 80, 90 or 100 markers. Conveniently, several hundred or even several thousand markers may be used. The markers may be provided in a pattern, for example make up an outer edge of the array, e.g. an entire outer row of the features of an array. Other informative patterns may be used, e.g. lines sectioning the array. This may facilitate aligning an image of the tissue sample to an array, or indeed generally in correlating the features of the array to the tissue sample. Thus, the marker may be an immobilized molecule to which a signal giving molecule may interact to generate a signal. In a representative example, the array may comprise a marker feature, e.g. a nucleic acid probe immobilized on the substrate of array, to which a labelled nucleic acid may hybridize. For instance, the labelled nucleic acid molecule, or marker nucleic acid, may be linked or coupled to a chemical moiety capable of fluorescing when subjected to light of a specific wavelength (or range of wavelengths), i.e. excited. Such a marker nucleic acid molecule may be contacted with the array before, contemporaneously with or after the tissue sample is stained in order to visualize or image the tissue sample. However, the marker must be detectable when the tissue sample is imaged. Thus, in a preferred embodiment the marker may be detected using the same imaging conditions used to visualize the tissue sample.

In a particularly preferred embodiment of the invention, the array comprises marker features to which a labelled, preferably fluorescently labelled, marker nucleic acid molecule, e.g. oligonucleotide, is hybridized.

The step of imaging the tissue may use any convenient histological means known in the art, e.g. light, bright field, dark field, phase contrast, fluorescence, reflection, interference, confocal microscopy or a combination thereof. Typically the tissue sample is stained prior to visualization to provide contrast between the different regions, e.g. cells, of the tissue sample. The type of stain used will be dependent on the type of tissue and the region of the cells to be stained. Such staining protocols are known in the art. In some embodiments more than one stain may be used to visualize (image) different aspects of the tissue sample, e.g. different regions of the tissue sample, specific cell structures (e.g. organelles) or different cell types. In other embodiments, the tissue sample may be visualized or imaged without staining the sample, e.g. if the tissue sample contains already pigments that provide sufficient contrast or if particular forms of microscopy are used.

In a preferred embodiment, the tissue sample is visualized or imaged using fluorescence microscopy.

The tissue sample, i.e. any residual tissue that remains in contact with the array substrate following the reverse transcription step and optionally imaging, if imaging is desired and was not carried out before reverse transcription, preferably is removed prior to the step of releasing the cDNA molecules from the array. Thus, the methods of the invention may comprise a step of washing the array. Removal of the residual tissue sample may be performed using any suitable means and will be dependent on the tissue sample. In the simplest embodiment, the array may be washed with water. The water may contain various additives, e.g. surfactants (e.g. detergents), enzymes etc to facilitate to removal of the tissue. In some embodiments, the array is washed with a solution comprising a proteinase enzyme (and suitable buffer) e.g. proteinase K. In other embodiments, the solution may comprise also or alternatively cellulase, hemicelluase or chitinase enzymes, e.g. if the tissue sample is from a plant or fungal source. In further embodiments, the temperature of the solution used to wash the array may be, e.g. at least 30° C., preferably at least 35, 40, 45, 50 or 55° C. It will be evident that the wash solution should minimize the disruption of the immobilized nucleic acid molecules. For instance, in some embodiments the nucleic acid molecules may be immobilized on the substrate of the array indirectly, e.g. via hybridization of the capture probe and the RNA and/or the capture probe and the surface probe, thus the wash step should not interfere with the interaction between the molecules immobilized on the array, i.e. should not cause the nucleic acid molecules to be denatured.

Following the step of contacting the array with a tissue sample, under conditions sufficient to allow hybridization to occur between the nucleic acid, e.g. RNA (preferably mRNA), of the tissue sample to the capture probes, the step of securing (acquiring) the hybridized nucleic acid takes place. Securing or acquiring the captured nucleic acid involves a covalent attachment of a complementary strand of the hybridized nucleic acid to the capture probe (i.e. via a nucleotide bond, a phosphodiester bond between juxtaposed 3'-hydroxyl and 5'-phosphate termini of two immediately adjacent nucleotides), thereby tagging or marking the captured nucleic acid with the positional domain specific to the feature on which the nucleic acid is captured.

In some embodiments, securing the hybridized nucleic acid, e.g. a single stranded nucleic acid, may involve extending the capture probe to produce a copy of the captured nucleic acid, e.g. generating cDNA from the captured (hybridized) RNA. It will be understood that this refers to the synthesis of a complementary strand of the hybridized nucleic acid, e.g. generating cDNA based on the captured RNA template (the RNA hybridized to the capture domain of the capture probe). Thus, in an initial step of extending the capture probe, e.g. the cDNA generation, the captured (hybridized) nucleic acid, e.g. RNA acts as a template for the extension, e.g. reverse transcription, step. In other embodiments, as described below, securing the hybridized nucleic acid, e.g. partially double stranded DNA, may involve covalently coupling the hybridized nucleic acid, e.g. fragmented DNA, to the capture probe, e.g. ligating to the capture probe the complementary strand of the nucleic acid hybridized to the capture probe, in a ligation reaction.

Reverse transcription concerns the step of synthesizing cDNA (complementary or copy DNA) from RNA, preferably mRNA (messenger RNA), by reverse transcriptase. Thus cDNA can be considered to be a copy of the RNA present in a cell at the time at which the tissue sample was taken, i.e. it represents all or some of the genes that were expressed in said cell at the time of isolation.

The capture probe, specifically the capture domain of the capture probe, acts as a primer for producing the complementary strand of the nucleic acid hybridized to the capture probe, e.g. a primer for reverse transcription. Hence, the nucleic acid, e.g. cDNA, molecules generated by the extension reaction, e.g. reverse transcription reaction, incorporate the sequence of the capture probe, i.e. the extension reaction, e.g. reverse transcription reaction, may be seen as a way of labelling indirectly the nucleic acid, e.g. transcripts, of the tissue sample that are in contact with each feature of the array. As mentioned above, each species of capture probe comprises a positional domain (feature identification tag) that represents a unique sequence for each feature of the array. Thus, all of the nucleic acid, e.g. cDNA, molecules synthesized at a specific feature will comprise the same nucleic acid "tag".

The nucleic acid, e.g. cDNA, molecules synthesized at each feature of the array may represent the genome of, or genes expressed from, the region or area of the tissue sample in contact with that feature, e.g. a tissue or cell type or group or sub-group thereof, and may further represent genes expressed under specific conditions, e.g. at a particular time, in a specific environment, at a stage of development or in response to stimulus etc. Hence, the cDNA at any single feature may represent the genes expressed in a single cell, or if the feature is in contact with the sample at a cell junction, the cDNA may represent the genes expressed in more than one cell. Similarly, if a single cell is in contact with multiple features, then each feature may represent a proportion of the genes expressed in said cell. Similarly, in embodiments in which the captured nucleic acid is DNA, any single feature may be representative of the genome of a single cell or more than one cell. Alternatively, the genome of a single cell may be represented by multiple features.

The step of extending the capture probe, e.g. reverse transcription, may be performed using any suitable enzymes and protocol of which many exist in the art, as described in detail below. However, it will be evident that it is not necessary to provide a primer for the synthesis of the first nucleic acid, e.g. cDNA, strand because the capture domain of the capture probe acts as the primer, e.g. reverse transcription primer.

Preferably, in the context of the present invention the secured nucleic acid (i.e. the nucleic acid covalently attached to the capture probe), e.g. cDNA is treated to comprise double stranded DNA. However, in some embodiments, the captured DNA may already comprise double stranded DNA, e.g. where partially double stranded fragmented DNA is ligated to the capture probe. Treatment of the captured nucleic acid to produce double stranded DNA may be achieved in a single reaction to generate only a second DNA, e.g. cDNA, strand, i.e. to produce double stranded DNA molecules without increasing the number of double stranded DNA molecules, or in an amplification reaction to generate multiple copies of the second strand, which may be in the form of single stranded DNA (e.g. linear amplification) or double stranded DNA, e.g. cDNA (e.g. exponential amplification).

The step of second strand DNA, e.g. cDNA, synthesis may take place in situ on the array, either as a discrete step of second strand synthesis, for example using random primers as described in more detail below, or in the initial step of an amplification reaction. Alternatively, the first strand DNA, e.g. cDNA (the strand comprising, i.e. incorporating, the capture probe) may be released from the array and second strand synthesis, whether as a discrete step or in an amplification reaction may occur subsequently, e.g. in a reaction carried out in solution.

Where second strand synthesis takes place on the array (i.e. in situ) the method may include an optional step of removing the captured nucleic acid, e.g. RNA before the second strand synthesis, for example using an RNA digesting enzyme (RNase) e.g. RNase H. Procedures for this are well known and described in the art. However, this is generally not necessary, and in most cases the RNA degrades naturally. Removal of the tissue sample from the array will generally remove the RNA from the array. RNase H can be used if desired to increase the robustness of RNA removal.

For instance, in tissue samples that comprise large amounts of RNA, the step of generating the double stranded cDNA may yield a sufficient amount of cDNA that it may be sequenced directly (following release from the array). In this case, second strand cDNA synthesis may be achieved by any means known in the art and as described below. The second strand synthesis reaction may be performed on the array directly, i.e. whilst the cDNA is immobilized on the array, or preferably after the cDNA has been released from the array substrate, as described below.

In other embodiments it will be necessary to enhance, i.e. amplify, the amount of secured nucleic acid, e.g. synthesized cDNA to yield quantities that are sufficient for DNA sequencing. In this embodiment, the first strand of the secured nucleic acid, e.g. cDNA molecules, which comprise also the capture probe of the features of the array, acts as a template for the amplification reaction, e.g. a polymerase chain reaction. The first reaction product of the amplification will be a second strand of DNA, e.g. cDNA, which itself will act as a template for further cycles of the amplification reaction.

In either of the above described embodiments, the second strand of DNA, e.g. cDNA, will comprise a complement of the capture probe. If the capture probe comprises a universal domain, and particularly an amplification domain within the universal domain, then this may be used for the subsequent amplification of the DNA, e.g. cDNA, e.g. the amplification reaction may comprise a primer with the same sequence as the amplification domain, i.e. a primer that is complementary (i.e. hybridizes) to the complement of the amplification domain. In view of the fact that the amplification domain is upstream of the positional domain of the capture probe (in the secured nucleic acid, e.g. the first cDNA strand), the complement of the positional domain will be incorporated in the second strand of the DNA, e.g. cDNA molecules.

In embodiments where the second strand of DNA, e.g. cDNA is generated in a single reaction, the second strand synthesis may be achieved by any suitable means. For instance, the first strand cDNA, preferably, but not necessarily, released from the array substrate, may be incubated with random primers, e.g. hexamer primers, and a DNA polymerase, preferably a strand displacement polymerase, e.g. klenow (exo), under conditions sufficient for templated DNA synthesis to occur. This process will yield double stranded cDNA molecules of varying lengths and is unlikely to yield full-length cDNA molecules, i.e. cDNA molecules that correspond to entire mRNA from which they were synthesized. The random primers will hybridise to the first strand cDNA molecules at a random position, i.e. within the sequence rather than at the end of the sequence.

If it is desirable to generate full-length DNA, e.g. cDNA, molecules, i.e. molecules that correspond to the whole of the captured nucleic acid, e.g. RNA molecule (if the nucleic acid, e.g. RNA, was partially degraded in the tissue sample then the captured nucleic acid, e.g. RNA, molecules will not be "full-length" transcripts or the same length as the initial fragments of genomic DNA), then the 3' end of the secured nucleic acid, e.g. first stand cDNA, molecules may be modified. For example, a linker or adaptor may be ligated to the 3' end of the cDNA molecules. This may be achieved using single stranded ligation enzymes such as T4 RNA ligase or Circligase™ (Epicentre Biotechnologies).

Alternatively, a helper probe (a partially double stranded DNA molecule capable of hybridising to the 3' end of the first strand cDNA molecule), may be ligated to the 3' end of the secured nucleic acid, e.g. first strand cDNA, molecule using a double stranded ligation enzyme such as T4 DNA ligase. Other enzymes appropriate for the ligation step are known in the art and include, e.g. Tth DNA ligase, Taq DNA ligase, *Thermococcus* sp. (strain 9° N) DNA ligase (9° N™ DNA ligase, New England Biolabs), and Ampligase™ (Epicentre Biotechnologies). The helper probe comprises also a specific sequence from which the second strand DNA, e.g. cDNA, synthesis may be primed using a primer that is complementary to the part of the helper probe that is ligated to the secured nucleic acid, e.g. first cDNA strand. A further alternative comprises the use of a terminal transferase active enzyme to incorporate a polynucleotide tail, e.g. a poly-A tail, at the 3' end of the secured nucleic acid, e.g. first strand of cDNA, molecules. The second strand synthesis may be primed using a poly-T primer, which may also comprise a specific amplification domain for further amplification. Other methods for generating "full-length" double stranded DNA, e.g. cDNA, molecules (or maximal length second strand synthesis) are well-established in the art.

In some embodiments, second strand synthesis may use a method of template switching, e.g. using the SMARTT™ technology from Clontech®. SMART (Switching Mechanism at 5' End of RNA Template) technology is well established in the art and is based that the discovery that reverse transcriptase enzymes, e.g. Superscript® II (Invitrogen), are capable of adding a few nucleotides at the 3' end of an extended cDNA molecule, i.e. to produce a DNA/RNA hybrid with a single stranded DNA overhang at the 3' end. The DNA overhang may provide a target sequence to which an oligonucleotide probe can hybridise to provide an additional template for further extension of the cDNA molecule. Advantageously, the oligonucleotide probe that hybridises to the cDNA overhang contains an amplification domain sequence, the complement of which is incorporated into the synthesised first strand cDNA product. Primers containing the amplification domain sequence, which will hybridise to the complementary amplification domain sequence incorporated into the cDNA first strand, can be added to the reaction mix to prime second strand synthesis using a suitable polymerase enzyme and the cDNA first strand as a template. This method avoids the need to ligate adaptors to the 3' end of the cDNA first strand. Whilst template switching was originally developed for full-length mRNAs, which have a 5' cap structure, it has since been demonstrated to work equally well with truncated mRNAs without the cap structure. Thus, template switching may be used in the methods of the invention to generate full length and/or partial or truncated cDNA molecules. Thus, in a preferred embodiment of the invention, the second strand synthesis may utilise, or be achieved by, template switching. In a particularly preferred embodiment, the template switching reaction, i.e. the further extension of the cDNA first strand to incorporate the complementary amplification domain, is performed in situ (whilst the capture probe is still attached, directly or indirectly, to the array). Preferably, the second strand synthesis reaction is also performed in situ.

In embodiments where it may be necessary or advantageous to enhance, enrich or amplify the DNA, e.g. cDNA molecules, amplification domains may be incorporated in the DNA, e.g. cDNA molecules. As discussed above, a first amplification domain may be incorporated into the secured nucleic acid molecules, e.g. the first strand of the cDNA molecules, when the capture probe comprises a universal domain comprising an amplification domain. In these embodiments, the second strand synthesis may incorporate a second amplification domain. For example, the primers used to generate the second strand cDNA, e.g. random hexamer primers, poly-T primer, the primer that is complementary to the helper probe, may comprise at their 5' end an amplification domain, i.e. a nucleotide sequence to which an amplification primer may hybridize. Thus, the resultant double stranded DNA may comprise an amplification domain at or towards each 5' end of the double stranded DNA, e.g. cDNA molecules. These amplification domains may be used as targets for primers used in an amplification reaction, e.g. PCR. Alternatively, the linker or adaptor which is ligated to the 3' end of the secured nucleic acid molecules, e.g. first strand cDNA molecules, may comprise a second universal domain comprising a second amplification domain. Similarly, a second amplification domain may be incorporated into the first strand cDNA molecules by template switching.

In embodiments where the capture probe does not comprise a universal domain, particularly comprising an amplification domain, the second strand of the cDNA molecules may be synthesised in accordance with the above description. The resultant double stranded DNA molecules may be modified to incorporate an amplification domain at the 5' end of the first DNA, e.g. cDNA strand (a first amplification domain) and, if not incorporated in the second strand DNA, e.g. cDNA synthesis step, at the 5' end of the second DNA, e.g. cDNA strand (a second amplification domain). Such amplification domains may be incorporated, e.g. by ligating double stranded adaptors to the ends of the DNA, e.g. cDNA molecules. Enzymes appropriate for the ligation step are known in the art and include, e.g. Tth DNA ligase, Taq DNA ligase, *Thermococcus* sp. (strain 9° N) DNA ligase (9° N™ DNA ligase, New England Biolabs), Ampligase™ (Epicentre Biotechnologies) and T4 DNA ligase. In a preferred embodiment the first and second amplification domains comprise different sequences.

From the above, it is therefore apparent that universal domains, which may comprise an amplification domain, may be added to the secured (i.e. extended or ligated) DNA molecules, for example to the cDNA molecules, or their complements (e.g. second strand) by various methods and techniques and combinations of such techniques known in the art e.g. by use of primers which include such a domain, ligation of adaptors, use of terminal transferase enzymes and/or by template switching methods. As is clear from the discussion herein, such domains may be added before or after release of the DNA molecules from the array.

It will be apparent from the above description that all of the DNA, e.g. cDNA molecules from a single array that have been synthesized by the methods of the invention may all comprise the same first and second amplification domains. Consequently, a single amplification reaction, e.g. PCR, may be sufficient to amplify all of the DNA, e.g. cDNA molecules. Thus in a preferred embodiment, the method of the invention may comprise a step of amplifying the DNA, e.g. cDNA molecules. In one embodiment the amplification step is performed after the release of the DNA, e.g. cDNA molecules from the substrate of the array. In other embodiments amplification may be performed on the array (i.e. in situ on the array). It is known in the art that amplification reactions may be carried out on arrays and on-chip thermocyclers exist for carrying out such reactions. Thus, in one embodiment arrays which are known in the art as sequencing platforms or for use in any form of sequence analysis (e.g. in or by next generation sequencing technologies) may be used as the basis of the arrays of the present invention (e.g. Illumina bead arrays etc.)

For the synthesis of the second strand of DNA, e.g. cDNA it is preferable to use a strand displacement polymerase (e.g. φ29 DNA polymerase, Bst (exo⁻) DNA polymerase, klenow (exo⁻) DNA polymerase) if the cDNA released from the substrate of the array comprises a partially double stranded nucleic acid molecule. For instance, the released nucleic acids will be at least partially double stranded (e.g. DNA:DNA, DNA:RNA or DNA:DNA/RNA hybrid) in embodiments where the capture probe is immobilized indirectly on the substrate of the array via a surface probe and the step of releasing the DNA, e.g. cDNA molecules comprises a cleavage step. The strand displacement polymerase is necessary to ensure that the second cDNA strand synthesis incorporates the complement of the positional domain (feature identification domain) into the second DNA, e.g. cDNA strand.

It will be evident that the step of releasing at least part of the DNA, e.g. cDNA molecules or their amplicons from the surface or substrate of the array may be achieved using a number of methods. The primary aim of the release step is to yield molecules into which the positional domain of the capture probe (or its complement) is incorporated (or included), such that the DNA, e.g. cDNA molecules or their amplicons are "tagged" according to their feature (or position) on the array. The release step thus removes DNA, e.g. cDNA molecules or amplicons thereof from the array, which DNA, e.g. cDNA molecules or amplicons include the positional domain or its complement (by virtue of it having been incorporated into the secured nucleic acid, e.g. the first strand cDNA by, e.g. extension of the capture probe, and optionally copied in the second strand DNA if second strand synthesis takes place on the array, or copied into amplicons if amplification takes place on the array). Hence, in order to yield sequence analysis data that can be correlated with the various regions in the tissue sample it is essential that the released molecules comprise the positional domain of the capture probe (or its complement).

Since the released molecule may be a first and/or second strand DNA, e.g. cDNA molecule or amplicon, and since the capture probe may be immobilised indirectly on the array, it will be understood that whilst the release step may comprise a step of cleaving a DNA, e.g. cDNA molecule from the array, the release step does not require a step of nucleic acid cleavage; a DNA, e.g. cDNA molecule or an amplicon may simply be released by denaturing a double-stranded molecule, for example releasing the second cDNA strand from the first cDNA strand, or releasing an amplicon from its template or releasing the first strand cDNA molecule (i.e. the extended capture probe) from a surface probe. Accordingly, a DNA, e.g. cDNA molecule may be released from the array by nucleic acid cleavage and/or by denaturation (e.g. by heating to denature a double-stranded molecule). Where amplification is carried out in situ on the array, this will of course encompass releasing amplicons by denaturation in the cycling reaction.

In some embodiments, the DNA, e.g. cDNA molecules are released by enzymatic cleavage of a cleavage domain, which may be located in the universal domain or positional domain of the capture probe. As mentioned above, the cleavage domain must be located upstream (at the 5' end) of the positional domain, such that the released DNA, e.g. cDNA molecules comprise the positional (identification) domain. Suitable enzymes for nucleic acid cleavage include restriction endonucleases, e.g. RsaI. Other enzymes, e.g. a mixture of Uracil DNA glycosylase (UDG) and the DNA glycosylase-lyase Endonuclease VIII (USER™ enzyme) or a combination of the MutY and T7 endonuclease I enzymes, are preferred embodiments of the methods of the invention.

In an alternative embodiment, the DNA, e.g. cDNA molecules may be released from the surface or substrate of the array by physical means. For instance, in embodiments where the capture probe is indirectly immobilized on the substrate of the array, e.g. via hybridization to the surface probe, it may be sufficient to disrupt the interaction between the nucleic acid molecules. Methods for disrupting the interaction between nucleic acid molecules, e.g. denaturing double stranded nucleic acid molecules, are well known in the art. A straightforward method for releasing the DNA, e.g. cDNA molecules (i.e. of stripping the array of the synthesized DNA, e.g. cDNA molecules) is to use a solution that interferes with the hydrogen bonds of the double stranded molecules. In a preferred embodiment of the invention, the DNA, e.g. cDNA molecules may be released by applying heated water, e.g. water or buffer of at least 85° C., preferably at least 90, 91, 92, 93, 94, 95, 96, 97, 98, 99° C. As an alternative or addition to the use of a temperature sufficient to disrupt the hydrogen bonding, the solution may comprise salts, surfactants etc. that may further destabilize the interaction between the nucleic acid molecules, resulting in the release of the DNA, e.g. cDNA molecules.

It will be understood that the application of a high temperature solution, e.g. 90-99° C. water may be sufficient to disrupt a covalent bond used to immobilize the capture probe or surface probe to the array substrate. Hence, in a preferred embodiment, the DNA, e.g. cDNA molecules may be released by applying hot water to the array to disrupt covalently immobilized capture or surface probes.

It is implicit that the released DNA, e.g. cDNA molecules (the solution comprising the released DNA, e.g. cDNA molecules) are collected for further manipulation, e.g. second strand synthesis and/or amplification. Nevertheless, the method of the invention may be seen to comprise a step of collecting or recovering the released DNA, e.g. cDNA molecules. As noted above, in the context of in situ amplification the released molecules may include amplicons of the secured nucleic acid, e.g. cDNA.

In embodiments of methods of the invention, it may be desirable to remove any unextended or unligated capture probes. This may be, for example, after the step of releasing DNA molecules from the array. Any desired or convenient method may be used for such removal including, for example, use of an enzyme to degrade the unextended or unligated probes, e.g. exonuclease.

The DNA, e.g. cDNA molecules, or amplicons, that have been released from the array, which may have been modified as discussed above, are analysed to investigate (e.g. determine their sequence, although as noted above actual sequence determination is not required—any method of analysing the sequence may be used). Thus, any method of nucleic acid analysis may be used. The step of sequence analysis may identify the positional domain and hence allow the analysed molecule to be localized to a position in the tissue sample. Similarly, the nature or identity of the analysed molecule may be determined. In this way the nucleic acid, e.g. RNA at given position in the array, and hence in the tissue sample may be determined. Hence the analysis step may include or use any method which identifies the analysed molecule (and hence the "target" molecule) and its positional domain. Generally such a method will be a sequence-specific method. For example, the method may use sequence-specific primers or probes, particularly primers or probes specific for the positional domain and/or for a specific nucleic acid molecule to be detected or analysed e.g. a DNA molecule corresponding to a nucleic acid, e.g. RNA or cDNA molecule to be detected. Typically in such a method sequence-specific amplification primers e.g. PCR primers may be used.

In some embodiments it may be desirable to analyse a subset or family of target related molecules, e.g. all of the sequences that encode a particular group of proteins which share sequence similarity and/or conserved domains, e.g. a family of receptors. Hence, the amplification and/or analysis methods described herein may use degenerate or gene family specific primers or probes that hybridise to a subset of the captured nucleic acids or nucleic acids derived therefrom, e.g. amplicons. In a particularly preferred embodiment, the amplification and/or analysis methods may utilise a universal primer (i.e. a primer common to all of the captured sequences) in combination with a degenerate or gene family specific primer specific for a subset of target molecules.

Thus in one embodiment, amplification-based, especially PCR-based methods of sequence analysis are used.

However, the steps of modifying and/or amplifying the released DNA, e.g. cDNA molecules may introduce additional components into the sample, e.g. enzymes, primers, nucleotides etc. Hence, the methods of the invention may further comprise a step of purifying the sample comprising the released DNA, e.g. cDNA molecules or amplicons prior to the sequence analysis, e.g. to remove oligonucleotide primers, nucleotides, salts etc that may interfere with the sequencing reactions. Any suitable method of purifying the DNA, e.g. cDNA molecules may be used.

As noted above, sequence analysis of the released DNA molecules may be direct or indirect. Thus the sequence analysis substrate (which may be viewed as the molecule which is subjected to the sequence analysis step or process) may directly be the molecule which is released from the array or it may be a molecule which is derived therefrom. Thus, for example in the context of sequence analysis step which involves a sequencing reaction, the sequencing template may be the molecule which is released from the array or it may be a molecule derived therefrom. For example, a first and/or second strand DNA, e.g. cDNA molecule released from the array may be directly subjected to sequence analysis (e.g. sequencing), i.e. may directly take part in the sequence analysis reaction or process (e.g. the sequencing reaction or sequencing process, or be the molecule which is sequenced or otherwise identified). In the context of in situ amplification the released molecule may be an amplicon. Alternatively, the released molecule may be subjected to a step of second strand synthesis or amplification before sequence analysis (e.g. sequencing or identification by other means). The sequence analysis substrate (e.g. template) may thus be an amplicon or a second strand of a molecule which is directly released from the array.

Both strands of a double stranded molecule may be subjected to sequence analysis (e.g. sequenced) but the invention is not limited to this and single stranded molecules (e.g. cDNA) may be analysed (e.g. sequenced). For example various sequencing technologies may be used for single molecule sequencing, e.g. the Helicos or Pacbio technologies, or nanopore sequencing technologies which are being developed. Thus, in one embodiment the first strand of DNA, e.g. cDNA may be subjected to sequencing. The first strand DNA, e.g. cDNA may need to be modified at the 3' end to enable single molecule sequencing. This may be done by procedures analogous to those for handling the second DNA, e.g. cDNA strand. Such procedures are known in the art.

In a preferred aspect of the invention the sequence analysis will identify or reveal a portion of captured nucleic acid, e.g. RNA sequence and the sequence of the positional domain. The sequence of the positional domain (or tag) will identify the feature to which the nucleic acid, e.g. mRNA molecule was captured. The sequence of the captured nucleic acid, e.g. RNA molecule may be compared with a sequence database of the organism from which the sample originated to determine the gene to which it corresponds. By determining which region (e.g. cell) of the tissue sample was in contact with the feature, it is possible to determine which region of the tissue sample was expressing said gene (or contained the gene, in the case of spatial genomics). This analysis may be achieved for all of the DNA, e.g. cDNA molecules generated by the methods of the invention, yielding a spatial transcriptome or genome of the tissue sample.

By way of a representative example, sequencing data may be analysed to sort the sequences into specific species of capture probe, i.e. according to the sequence of the positional domain. This may be achieved by, e.g. using the FastX toolkit FASTQ Barcode splitter tool to sort the sequences into individual files for the respective capture probe positional domain (tag) sequences. The sequences of each species, i.e. from each feature, may be analyzed to determine the identity of the transcripts. For instance, the sequences may be identified using e.g. Blastn software, to compare the sequences to one or more genome databases, preferably the database for the organism from which the tissue sample was obtained. The identity of the database sequence with the greatest similarity to the sequence generated by the methods of the invention will be assigned to said sequence. In general, only hits with a certainty of at least $1e^{-6}$, preferably $1e^{-7}$, $1e^{-8}$, or $1e^{-9}$ will be considered to have been successfully identified.

It will be apparent that any nucleic acid sequencing method may be utilised in the methods of the invention. However, the so-called "next generation sequencing" techniques will find particular utility in the present invention. High-throughput sequencing is particularly useful in the methods of the invention because it enables a large number of nucleic acids to be partially sequenced in a very short period of time. In view of the recent explosion in the number of fully or partially sequenced genomes, it is not essential to sequence the full length of the generated DNA, e.g. cDNA molecules to determine the gene to which each molecule corresponds. For example, the first 100 nucleotides from each end of the DNA, e.g. cDNA molecules should be sufficient to identify both the feature to which the nucleic acid, e.g. mRNA was captured (i.e. its location on the array) and the gene expressed. The sequence reaction from the "capture probe end" of the DNA, e.g. cDNA molecules yields the sequence of the positional domain and at least about 20 bases, preferably 30 or 40 bases of transcript specific sequence data. The sequence reaction from the "non-capture probe end" may yield at least about 70 bases, preferably 80, 90, or 100 bases of transcript specific sequence data.

As a representative example, the sequencing reaction may be based on reversible dye-terminators, such as used in the Illumina™ technology. For example, DNA molecules are first attached to primers on, e.g. a glass or silicon slide and amplified so that local clonal colonies are formed (bridge amplification). Four types of ddNTPs are added, and non-incorporated nucleotides are washed away. Unlike pyrosequencing, the DNA can only be extended one nucleotide at a time. A camera takes images of the fluorescently labelled nucleotides then the dye along with the terminal 3' blocker is chemically removed from the DNA, allowing a next cycle. This may be repeated until the required sequence data is obtained. Using this technology, thousands of nucleic acids may be sequenced simultaneously on a single slide.

Other high-throughput sequencing techniques may be equally suitable for the methods of the invention, e.g. pyrosequencing. In this method the DNA is amplified inside water droplets in an oil solution (emulsion PCR), with each droplet containing a single DNA template attached to a single primer-coated bead that then forms a clonal colony. The sequencing machine contains many picolitre-volume wells each containing a single bead and sequencing enzymes. Pyrosequencing uses luciferase to generate light for detection of the individual nucleotides added to the nascent DNA and the combined data are used to generate sequence read-outs.

An example of a technology in development is based on the detection of hydrogen ions that are released during the polymerisation of DNA. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogen ions and a proportionally higher electronic signal.

Thus, it is clear that future sequencing formats are slowly being made available, and with shorter run times as one of the main features of those platforms it will be evident that other sequencing technologies will be useful in the methods of the invention.

An essential feature of the present invention, as described above, is a step of securing a complementary strand of the captured nucleic acid molecules to the capture probe, e.g. reverse transcribing the captured RNA molecules. The reverse transcription reaction is well known in the art and in representative reverse transcription reactions, the reaction mixture includes a reverse transcriptase, dNTPs and a suitable buffer. The reaction mixture may comprise other components, e.g. RNase inhibitor(s). The primers and template are the capture domain of the capture probe and the captured RNA molecules are described above. In the subject methods, each dNTP will typically be present in an amount ranging from about 10 to 5000 µM, usually from about 20 to 1000 µM. It will be evident that an equivalent reaction may be performed to generate a complementary strand of a captured DNA molecule, using an enzyme with DNA polymerase activity. Reactions of this type are well known in the art and are described in more detail below.

The desired reverse transcriptase activity may be provided by one or more distinct enzymes, wherein suitable examples are: M-MLV, MuLV, AMV, HIV, ArrayScript™' Multi-Scribe™, ThermoScript™, and SuperScript® I, II, and III enzymes.

The reverse transcriptase reaction may be carried out at any suitable temperature, which will be dependent on the properties of the enzyme. Typically, reverse transcriptase reactions are performed between 37-55° C., although temperatures outside of this range may also be appropriate. The reaction time may be as little as 1, 2, 3, 4 or 5 minutes or as much as 48 hours. Typically the reaction will be carried out for between 5-120 minutes, preferably 5-60, 5-45 or 5-30 minutes or 1-10 or 1-5 minutes according to choice. The reaction time is not critical and any desired reaction time may be used.

As indicated above, certain embodiments of the methods include an amplification step, where the copy number of generated DNA, e.g. cDNA molecules is increased, e.g., in order to enrich the sample to obtain a better representation of the nucleic acids, e.g. transcripts captured from the tissue sample. The amplification may be linear or exponential, as desired, where representative amplification protocols of interest include, but are not limited to: polymerase chain reaction (PCR); isothermal amplification, etc.

The polymerase chain reaction (PCR) is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above released DNA, e.g. cDNA molecules from the array, which are combined with one or more primers that are employed in the primer extension reaction, e.g., the PCR primers that hybridize to the first and/or second amplification domains (such as forward and reverse primers employed in geometric (or exponential) amplification or a single primer employed in a linear amplification). The oligonucleotide primers with which the released DNA, e.g. cDNA molecules (hereinafter referred to as template DNA for convenience) is contacted will be of sufficient length to provide for hybridization to complementary template DNA under annealing conditions (described in greater detail below). The length of the primers will depend on the length of the amplification domains, but will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired.

In addition to the above components, the reaction mixture produced in the subject methods typically includes a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Barnes et al, Proc. Natl. Acad. Sci USA (1994) 91:2216-2220); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) as described in Perler et al., Proc. Natl. Acad. Sci. USA (1992) 89:5577-5581; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases present, i.e. dATP, dTTP, dCTP and dGTP. In the subject methods, each dNTP will typically be present in an amount ranging from about 10 to 5000 µM, usually from about 20 to 1000 µM.

The reaction mixtures prepared in the reverse transcriptase and/or amplification steps of the subject methods may further include an aqueous buffer medium that includes a source of monovalent ions, a source of divalent cations and a buffering agent. Any convenient source of monovalent ions, such as KCl, K-acetate, NH$_4$-acetate, K-glutamate, NH₄Cl, ammonium sulphate, and the like may be employed. The divalent cation may be magnesium, manganese, zinc and the like, where the cation will typically be magnesium. Any convenient source of magnesium cation may be employed, including MgCl$_2$, Mg-acetate, and the like. The amount of Mg$^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reverse transcriptase, DNA extension or amplification reaction mixture of the steps of the subject methods, the various constituent components may be combined in any convenient order. For example, in the amplification reaction the buffer may be combined with primer, polymerase and then template DNA, or all of the various constituent components may be combined at the same time to produce the reaction mixture.

As discussed above, a preferred embodiment of the invention the DNA, e.g. cDNA molecules may be modified by the addition of amplification domains to the ends of the nucleic acid molecules, which may involve a ligation reaction. A ligation reaction is also required for the in situ synthesis of the capture probe on the array, when the capture probe is immobilized indirectly on the array surface.

As is known in the art, ligases catalyze the formation of a phosphodiester bond between juxtaposed 3'-hydroxyl and 5'-phosphate termini of two immediately adjacent nucleic acids. Any convenient ligase may be employed, where representative ligases of interest include, but are not limited to: Temperature sensitive and thermostable ligases. Temperature sensitive ligases include, but are not limited to, bacteriophage T4 DNA ligase, bacteriophage T7 ligase, and *E. coli* ligase. Thermostable ligases include, but are not limited to, Taq ligase, Tth ligase, and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

In this ligation step, a suitable ligase and any reagents that are necessary and/or desirable are combined with the reaction mixture and maintained under conditions sufficient for ligation of the relevant oligonucleotides to occur. Ligation reaction conditions are well known to those of skill in the art. During ligation, the reaction mixture in certain embodiments may be maintained at a temperature ranging from about 4° C. to about 50° C., such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM MgCl$_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed. The amount of adaptor in the reaction will be dependent on the concentration of the DNA, e.g. cDNA in the sample and will generally be present at between 10-100 times the molar amount of DNA, e.g. cDNA.

By way of a representative example the method of the invention may comprise the following steps:

(a) contacting an array with a tissue sample, wherein the array comprises a substrate on which multiple species of capture probes are directly or indirectly immobilized such that each species occupies a distinct position on the array and is oriented to have a free 3' end to enable said probe to function as a reverse transcriptase (RT) primer, wherein each species of said capture probe comprises a nucleic acid molecule with 5' to 3':

(i) a positional domain that corresponds to the position of the capture probe on the array, and (ii) a capture domain;

such that RNA of the tissue sample hybridises to said capture probes;

(b) imaging the tissue sample on the array;

(c) reverse transcribing the captured mRNA molecules to generate cDNA molecules;

(d) washing the array to remove residual tissue;

(e) releasing at least part of the cDNA molecules from the surface of the array;

(f) performing second strand cDNA synthesis on the released cDNA molecules;

and (g) analysing the sequence of (e.g. sequencing) the cDNA molecules.

By way of an alternative representative example the method of the invention may comprise the following steps:

(a) contacting an array with a tissue sample, wherein the array comprises a substrate on which at least two species of capture probes are directly or indirectly immobilized such that each species occupies a distinct position on the array and is oriented to have a free 3' end to enable said probe to function as a reverse transcriptase (RT) primer, wherein each species of said capture probe comprises a nucleic acid molecule with 5' to 3':

(i) a positional domain that corresponds to the position of the capture probe on the array, and (ii) a capture domain;

such that RNA of the tissue sample hybridises to said capture probes;

(b) optionally rehydrating the tissue sample;

(c) reverse transcribing the captured mRNA molecules to generate first strand cDNA molecules and optionally synthesising second strand cDNA molecules;

(d) imaging the tissue sample on the array;

(e) washing the array to remove residual tissue;

(f) releasing at least part of the cDNA molecules from the surface of the array;

(g) amplifying the released cDNA molecules;

and (h) analysing the sequence of (e.g. sequencing) the amplified cDNA molecules.

By way of yet a further representative example the method of the invention may comprise the following steps:

(a) contacting an array with a tissue sample, wherein the array comprises a substrate on which multiple species of capture probes are directly or indirectly immobilized such that each species occupies a distinct position on the array and is oriented to have a free 3' end to enable said probe to function as a reverse transcriptase (RT) primer, wherein each species of said capture probe comprises a nucleic acid molecule with 5' to 3':
- (i) a positional domain that corresponds to the position of the capture probe on the array, and
- (ii) a capture domain;

such that RNA of the tissue sample hybridises to said capture probes;
- (b) optionally imaging the tissue sample on the array;
- (c) reverse transcribing the captured mRNA molecules to generate cDNA molecules;
- (d) optionally imaging the tissue sample on the array if not already performed as step (b):
- (e) washing the array to remove residual tissue;
- (f) releasing at least part of the cDNA molecules from the surface of the array;
- (g) performing second strand cDNA synthesis on the released cDNA molecules;
- (h) amplifying the double stranded cDNA molecules;
- (i) optionally purifying the cDNA molecules to remove components that may interfere with the sequencing reaction; and
- (j) analysing the sequence of (e.g. sequencing) the amplified cDNA molecules.

The present invention includes any suitable combination of the steps in the above described methods. It will be understood that the invention also encompasses variations of these methods, for example where amplification is performed in situ on the array. Also encompassed are methods which omit the imaging step.

The invention may also be seen to include a method for making or producing an array (i) for use in capturing mRNA from a tissue sample that is contacted with said array; or (ii) for use in determining and/or analysing a (e.g. the partial or global) transcriptome of a tissue sample, said method comprising immobilizing, directly or indirectly, multiple species of capture probe to an array substrate, wherein each species of said capture probe comprises a nucleic acid molecule with 5' to 3':
- (i) a positional domain that corresponds to the position of the capture probe on the array; and
- (ii) a capture domain.

The method of producing an array of the invention may be further defined such that each species of capture probe is immobilized as a feature on the array.

The method of immobilizing the capture probes on the array may be achieved using any suitable means as described herein. Where the capture probes are immobilized on the array indirectly the capture probe may be synthesized on the array. Said method may comprise any one or more of the following steps:
- (a) immobilizing directly or indirectly multiple surface probes to an array substrate, wherein the surface probes comprise:
  - (i) a domain capable of hybridizing to part of the capture domain oligonucleotide (a part not involved in capturing the nucleic acid, e.g. RNA);
  - (ii) a complementary positional domain; and
  - (iii) a complementary universal domain;
- (b) hybridizing to the surface probes immobilized on the array capture domain oligonucleotides and universal domain oligonucleotides;
- (c) extending the universal domain oligonucleotides, by templated polymerisation, to generate the positional domain of the capture probe; and
- (d) ligating the positional domain to the capture domain oligonucleotide to produce the capture oligonucleotide.

Ligation in step (d) may occur simultaneously with extension in step (c). Thus it need not be carried out in a separate step, although this is course encompassed if desired.

The features of the array produced by the above method of producing the array of the invention, may be further defined in accordance with the above description.

Although the invention is described above with reference to detection or analysis of RNA, and transcriptome analysis or detection, it will be appreciated that the principles described can be applied analogously to the detection or analysis of DNA in cells and to genomic studies. Thus, more broadly viewed, the invention can be seen as being generally applicable to the detection of nucleic acids in general and in a further more particular aspect, as providing methods for the analysis or detection of DNA. Spatial information may be valuable also in a genomics context i.e. detection and/or analysis of a DNA molecule with spatial resolution. This may be achieved by genomic tagging according to the present invention. Such localized or spatial detection methods may be useful for example in the context of studying genomic variations in different cells or regions of a tissue, for example comparing normal and diseased cells or tissues (e.g. normal vs tumour cells or tissues) or in studying genomic changes in disease progression etc. For example, tumour tissues may comprise a heterogeneous population of cells which may differ in the genomic variants they contain (e.g. mutations and/or other genetic aberrations, for example chromosomal rearrangements, chromosomal amplifications/deletions/insertions etc.). The detection of genomic variations, or different genomic loci, in different cells in a localized way may be useful in such a context, e.g. to study the spatial distribution of genomic variations. A principal utility of such a method would be in tumour analysis. In the context of the present invention, an array may be prepared which is designed, for example, to capture the genome of an entire cell on one feature. Different cells in the tissue sample may thus be compared. Of course the invention is not limited to such a design and other variations may be possible, wherein the DNA is detected in a localized way and the position of the DNA captured on the array is correlated to a position or location in the tissue sample.

Accordingly, in a more general aspect, the present invention can be seen to provide a method for localized detection of nucleic acid in a tissue sample comprising:
- (a) providing an array comprising a substrate on which multiple species of capture probes are directly or indirectly immobilized such that each species occupies a distinct position on the array and is oriented to have a free 3' end to enable said probe to function as a primer for a primer extension or ligation reaction, wherein each species of said capture probe comprises a nucleic acid molecule with 5' to 3':
  - (i) a positional domain that corresponds to the position of the capture probe on the array, and
  - (ii) a capture domain;
- (b) contacting said array with a tissue sample such that the position of a capture probe on the array may be correlated with a position in the tissue sample and allowing nucleic acid of the tissue sample to hybridise to the capture domain in said capture probes;
- (c) generating DNA molecules from the captured nucleic acid molecules using said capture probes as extension or ligation primers, wherein said extended or ligated DNA molecules are tagged by virtue of the positional domain;

(d) optionally generating a complementary strand of said tagged DNA and/or optionally amplifying said tagged DNA;

(e) releasing at least part of the tagged DNA molecules and/or their complements or amplicons from the surface of the array, wherein said part includes the positional domain or a complement thereof;

(f) directly or indirectly analysing the sequence of (e.g. sequencing) the released DNA molecules.

As described in more detail above, any method of nucleic acid analysis may be used in the analysis step. Typically this may involve sequencing, but it is not necessary to perform an actual sequence determination. For example sequence-specific methods of analysis may be used. For example a sequence-specific amplification reaction may be performed, for example using primers which are specific for the positional domain and/or for a specific target sequence, e.g. a particular target DNA to be detected (i.e. corresponding to a particular cDNA/RNA or gene or gene variant or genomic locus or genomic variant etc.). An exemplary analysis method is a sequence-specific PCR reaction.

The sequence analysis (e.g. sequencing) information obtained in step (f) may be used to obtain spatial information as to the nucleic acid in the sample. In other words the sequence analysis information may provide information as to the location of the nucleic acid in the sample. This spatial information may be derived from the nature of the sequence analysis information obtained e.g. from a sequence determined or identified, for example it may reveal the presence of a particular nucleic acid molecule which may itself be spatially informative in the context of the tissue sample used, and/or the spatial information (e.g. spatial localisation) may be derived from the position of the tissue sample on the array, coupled with the sequence analysis information. However, as described above, spatial information may conveniently be obtained by correlating the sequence analysis data to an image of the tissue sample and this represents one preferred embodiment of the invention.

Accordingly, in a preferred embodiment the method also includes a step of:

(g) correlating said sequence analysis information with an image of said tissue sample, wherein the tissue sample is imaged before or after step (c).

The primer extension reaction referred to in step (a) may be defined as a polymerase-catalysed extension reaction and acts to acquire a complementary strand of the captured nucleic acid molecule that is covalently attached to the capture probe, i.e. by synthesising the complementary strand utilising the capture probe as a primer and the captured nucleic acid as a template. In other words it may be any primer extension reaction carried out by any polymerase enzyme. The nucleic acid may be RNA or it may be DNA. Accordingly the polymerase may be any polymerase. It may be a reverse transcriptase or it may be a DNA polymerase. The ligation reaction may be carried out by any ligase and acts to secure the complementary strand of the captured nucleic acid molecule to the capture probe, i.e. wherein the captured nucleic acid molecule (hybridised to the capture probe) is partially double stranded and the complementary strand is ligated to the capture probe.

One preferred embodiment of such a method is the method described above for the determination and/or analysis of a transcriptome, or for the detection of RNA. In alternative preferred embodiment the detected nucleic acid molecule is DNA. In such an embodiment the invention provides a method for localized detection of DNA in a tissue sample comprising:

(a) providing an array comprising a substrate on which multiple species of capture probes are directly or indirectly immobilized such that each species occupies a distinct position on the array and is oriented to have a free 3' end to enable said probe to function as a primer for a primer extension or ligation reaction, wherein each species of said capture probe comprises a nucleic acid molecule with 5' to 3':

(i) a positional domain that corresponds to the position of the capture probe on the array, and (ii) a capture domain;

(b) contacting said array with a tissue sample such that the position of a capture probe on the array may be correlated with a position in the tissue sample and allowing DNA of the tissue sample to hybridise to the capture domain in said capture probes;

(c) fragmenting DNA in said tissue sample, wherein said fragmentation is carried out before, during or after contacting the array with the tissue sample in step (b);

(d) extending said capture probes in a primer extension reaction using the captured DNA fragments as templates to generate extended DNA molecules, or ligating the captured DNA fragments to the capture probes in a ligation reaction to generate ligated DNA molecules, wherein said extended or ligated DNA molecules are tagged by virtue of the positional domain;

(e) optionally generating a complementary strand of said tagged DNA and/or optionally amplifying said tagged DNA;

(f) releasing at least part of the tagged DNA molecules and/or their complements and/or amplicons from the surface of the array, wherein said part includes the positional domain or a complement thereof;

(g) directly or indirectly analysing the sequence of the released DNA molecules.

The method may further include a step of:

(h) correlating said sequence analysis information with an image of said tissue sample, wherein the tissue sample is imaged before or after step (d).

In the context of spatial genomics, where the target nucleic acid is DNA the inclusion of imaging and image correlation steps may in some circumstances be preferred.

In embodiments in which DNA is captured, the DNA may be any DNA molecule which may occur in a cell. Thus it may be genomic, i.e. nuclear, DNA, mitochondrial DNA or plastid DNA, e.g. chloroplast DNA. In a preferred embodiment, the DNA is genomic DNA.

It will be understood that where fragmentation is carried out after the contacting in step (b), i.e. after the tissue sample is placed on the array, fragmentation occurs before the DNA is hybridised to the capture domain. In other words the DNA fragments are hybridised (or more particularly, allowed to hybridise) to the capture domain in said capture probes.

Advantageously, but not necessarily, in a particular embodiment of this aspect of the invention, the DNA fragments of the tissue sample may be provided with a binding domain to enable or facilitate their capture by the capture probes on the array. Accordingly, the binding domain is capable of hybridising to the capture domain of the capture probe. Such a binding domain may thus be regarded as a complement of the capture domain (i.e. it may be viewed as a complementary capture domain), although absolute complementarity between the capture and binding domains is not required, merely that the binding domain is sufficiently complementary to allow a productive hybridisation to take place, i.e. that the DNA fragments in the tissue sample are able to hybridise to the capture domain of the capture probes. Provision of such a binding domain may ensure that DNA in the sample does not bind to the capture probes until after the fragmentation step. The binding domain may be provided to the DNA fragments by procedures well known in the art, for example by ligation of adaptor or linker sequences which may contain the binding domain. For example a linker sequence with a protruding end may be used. The binding domain may be present in the single-stranded portion of such a linker, such that following ligation of the linker to the DNA fragments, the single-stranded portion containing the binding domain is available for hybridisation to the capture domain of the capture probes. Alternatively and in a preferred embodiment, the binding domain may be introduced by using a terminal transferase enzyme to introduce a polynucleotide tail e.g. a homopolymeric tail such as a poly-A domain. This may be carried out using a procedure analogous to that described above for introducing a universal domain in the context of the RNA methods. Thus, in advantageous embodiments a common binding domain may be introduced. In other words, a binding domain which is common to all the DNA fragments and which may be used to achieve the capture of the fragments on the array.

Where a tailing reaction is carried out to introduce a (common) binding domain, the capture probes on the array may be protected from the tailing reaction, i.e. the capture probes may be blocked or masked as described above. This may be achieved for example by hybridising a blocking oligonucleotide to the capture probe e.g. to the protruding end (e.g. single stranded portion) of the capture probe. Where the capture domain comprises a poly-T sequence for example, such a blocking oligonucleotide may be a poly-A oligonucleotide. The blocking oligonucleotide may have a blocked 3' end (i.e. an end incapable of being extended, or tailed). The capture probes may also be protected, i.e. blocked, by chemical and/or enzymatic modifications, as described in detail above.

Where the binding domain is provided by ligation of a linker as described above, it will be understood that rather than extending the capture probe to generate a complementary copy of the captured DNA fragment which comprises the positional tag of the capture probe primer, the DNA fragment may be ligated to the 3' end of the capture probe. As noted above ligation requires that the 5' end to be ligated is phosphorylated. Accordingly, in one embodiment, the 5' end of the added linker, namely the end which is to be ligated to the capture probe (i.e. the non-protruding end of the linker added to the DNA fragments) will be phosphorylated. In such a ligation embodiment, it will accordingly be seen that a linker may be ligated to double stranded DNA fragments, said linker having a single stranded protruding 3' end which contains the binding domain. Upon contact with the array, the protruding end hybridises to the capture domain of the capture probes. This hybridisation brings the 3' end of the capture probe into juxtaposition for ligation to the 5' (non-protruding) end of the added linker. The capture probe, and hence the positional domain, is thus incorporated into the captured DNA fragment by this ligation. Such an embodiment is shown schematically in FIG. 21.

Thus, the method of this aspect of the invention may in a more particular embodiment comprise:

(a) providing an array comprising a substrate on which multiple species of capture probes are directly or indirectly immobilized such that each species occupies a distinct position on the array and is oriented to have a free 3' end to enable said probe to function as a primer for a primer extension or ligation reaction, wherein each species of said capture probe comprises a nucleic acid molecule with 5' to 3':

(i) a positional domain that corresponds to the position of the capture probe on the array, and
(ii) a capture domain;

(b) contacting said array with a tissue sample such that the position of a capture probe on the array may be correlated with a position in the tissue sample;

(c) fragmenting DNA in said tissue sample, wherein said fragmentation is carried out before, during or after contacting the array with the tissue sample in step (b);

(d) providing said DNA fragments with a binding domain which is capable of hybridising to said capture domain;

(e) allowing said DNA fragments to hybridise to the capture domain in said capture probes;

(f) extending said capture probes in a primer extension reaction using the captured DNA fragments as templates to generate extended DNA molecules, or ligating the captured DNA fragments to the capture probes in a ligation reaction to generate ligated DNA molecules, wherein said extended or ligated DNA molecules are tagged by virtue of the positional domain;

(g) optionally generating a complementary strand of said tagged DNA and/or optionally amplifying the tagged DNA;

(h) releasing at least part of the tagged DNA molecules and/or their complements and/or amplicons from the surface of the array, wherein said part includes the positional domain or a complement thereof;

(i) directly or indirectly analysing the sequence of the released DNA molecules.

The method may optionally include a further step of (j) correlating said sequence analysis information with an image of said tissue sample, wherein the tissue sample is imaged before or after step (f).

In the methods of nucleic acid or DNA detection set out above, the optional step of generating a complementary copy of the tagged nucleic acid/DNA or of amplifying the tagged DNA, may involve the use of a strand displacing polymerase enzyme, according to the principles explained above in the context of the RNA/transcriptome analysis/detection methods. Suitable strand displacing polymerases are discussed above. This is to ensure that the positional domain is copied into the complementary copy or amplicon. This will particularly be the case where the capture probe is immobilized on the array by hybridisation to a surface probe.

However, the use of a strand displacing polymerase in this step is not essential. For example a non-strand displacing polymerase may be used together with ligation of an oligonucleotide which hybridises to the positional domain. Such a procedure is analogous to that described above for the synthesis of capture probes on the array.

In one embodiment, the method of the invention may be used for determining and/or analysing all of the genome of a tissue sample e.g. the global genome of a tissue sample. However, the method is not limited to this and encompasses determining and/or analysing all or part of the genome. Thus, the method may involve determining and/or analysing a part or subset of the genome, e.g. a partial genome corresponding to a subset or group of genes or of chromosomes, e.g. a set of particular genes or chromosomes or a particular region or part of the genome, for example related to a particular disease or condition, tissue type etc. Thus, the method may be used to detect or analyse genomic sequences or genomic loci from tumour tissue as compared to normal tissue, or even within different types of cell in a tissue sample. The presence or absence, or the distribution or location of different genomic variants or loci in different cells, groups of cells, tissues or parts or types of tissue may be examined.

Viewed from another aspect, the method steps set out above can be seen as providing a method of obtaining spatial information regarding the nucleic acids, e.g. genomic sequences, variants or loci of a tissue sample. Put another way, the methods of the invention may be used for the labelling (or tagging) of genomes, particularly individual or spatially distributed genomes.

Alternatively viewed, the method of the invention may be seen as a method for spatial detection of DNA in a tissue sample, or a method for detecting DNA with spatial resolution, or for localized or spatial determination and/or analysis of DNA in a tissue sample. In particular, the method may be used for the localized or spatial detection or determination and/or analysis of genes or genomic sequences or genomic variants or loci (e.g. distribution of genomic variants or loci) in a tissue sample. The localized/spatial detection/determination/analysis means that the DNA may be localized to its native position or location within a cell or tissue in the tissue sample. Thus for example, the DNA may be localized to a cell or group of cells, or type of cells in the sample, or to particular regions of areas within a tissue sample. The native location or position of the DNA (or in other words, the location or position of the DNA in the tissue sample), e.g. a genomic variant or locus, may be determined.

It will be seen therefore that the array of the present invention may be used to capture nucleic acid, e.g. DNA of a tissue sample that is contacted with said array. The array may also be used for determining and/or analysing a partial or global genome of a tissue sample or for obtaining a spatially defined partial or global genome of a tissue sample. The methods of the invention may thus be considered as methods of quantifying the spatial distribution of one or more genomic sequences (or variants or loci) in a tissue sample. Expressed another way, the methods of the present invention may be used to detect the spatial distribution of one or more genomic sequences or genomic variants or genomic loci in a tissue sample. In yet another way, the methods of the present invention may be used to determine simultaneously the location or distribution of one or more genomic sequences or genomic variants or genomic loci at one or more positions within a tissue sample. Still further, the methods may be seen as methods for partial or global analysis of the nucleic acid e.g. DNA of a tissue sample with spatial resolution e.g. two-dimensional spatial resolution.

The invention can also be seen to provide an array for use in the methods of the invention comprising a substrate on which multiple species of capture probes are directly or indirectly immobilized such that each species occupies a distinct position on the array and is oriented to have a free 3' end to enable said probe to function as an extension or ligation primer, wherein each species of said capture probe comprises a nucleic acid molecule with 5' to 3':

(i) a positional domain that corresponds to the position of the capture probe on the array, and (ii) a capture domain to capture nucleic acid of a tissue sample that is contacted with said array.

In one aspect the nucleic acid molecule to be captured is DNA. The capture domain may be specific to a particular DNA to be detected, or to a particular class or group of DNAs, e.g. by virtue of specific hybridisation to a specific sequence of motif in the target DNA e.g. a conserved sequence, by analogy to the methods described in the context of RNA detection above. Alternatively the DNA to be captured may be provided with a binding domain, e.g. a common binding domain as described above, which binding domain may be recognised by the capture domain of the capture probes. Thus, as noted above, the binding domain may for example be a homopolymeric sequence e.g. poly-A. Again such a binding domain may be provided according to or analogously to the principles and methods described above in relation to the methods for RNA/transcriptome analysis or detection. In such a case, the capture domain may be complementary to the binding domain introduced into the DNA molecules of the tissue sample.

As also described in the RNA context above, the capture domain may be a random or degenerate sequence. Thus, DNA may be captured non-specifically by binding to a random or degenerate capture domain or to a capture domain which comprises at least partially a random or degenerate sequence.

In a related aspect, the present invention also provides use of an array, comprising a substrate on which multiple species of capture probe are directly or indirectly immobilized such that each species occupies a distinct position on the array and is oriented to have a free 3' end to enable said probe to function as a primer for a primer extension or ligation reaction, wherein each species of said capture probe comprises a nucleic acid molecule with 5' to 3':

(i) a positional domain that corresponds to the position of the capture probe on the array; and (ii) a capture domain;

to capture nucleic acid, e.g. DNA or RNA, of a tissue sample that is contacted with said array.

Preferably, said use is for localized detection of nucleic acid in a tissue sample and further comprises steps of:

(a) generating DNA molecules from the captured nucleic acid molecules using said capture probes as extension or ligation primers, wherein said extended or ligated molecules are tagged by virtue of the positional domain;

(b) optionally generating a complementary strand of said tagged nucleic acid and/or amplifying said tagged nucleic acid;

(c) releasing at least part of the tagged DNA molecules and/or their complements or amplicons from the surface of the array, wherein said part includes the positional domain or a complement thereof;

(d) directly or indirectly analysing the sequence of the released DNA molecules; and optionally (e) correlating said sequence analysis information with an image of said tissue sample, wherein the tissue sample is imaged before or after step (a).

The step of fragmenting DNA in a tissue sample may be carried out using any desired procedure known in the art. Thus physical methods of fragmentation may be used e.g. sonication or ultrasound treatment. Chemical methods are also known. Enzymatic methods of fragmentation may also be used, e.g. with endonucleases, for example restriction enzymes. Again methods and enzymes for this are well known in the art. Fragmentation may be done before during or after preparing the tissue sample for placing on an array, e.g. preparing a tissue section. Conveniently, fragmentation may be achieved in the step of fixing tissue. Thus for example, formalin fixation will result in fragmentation of DNA. Other fixatives may produce similar results.

In terms of the detail of preparing and using the arrays in these aspects of the invention, it will understood that the description and detail given above in the context of RNA methods applies analogously to the more general nucleic acid detection and DNA detection methods set out herein. Thus, all aspects and details discussed above apply analogously. For example, the discussion of reverse transcriptase primers and reactions etc may be applied analogously to any aspect of the extension primers, polymerase reactions etc. referred to above. Likewise, references and to first and second strand cDNA synthesis may be applied analogously to the tagged DNA molecule and its complement. Methods of sequence analysis as discussed above may be used.

By way of example, the capture domain may be as described for the capture probes above. A poly-T or poly-T-containing capture domain may be used for example where the DNA fragments are provided with a binding domain comprising a poly-A sequence.

The capture probes/tagged DNA molecules (i.e. the tagged extended or ligated molecules) may be provided with universal domains as described above, e.g. for amplification and/or cleavage.

The invention will be further described with reference to the following non-limiting Examples with reference to the following drawings in which.

Figure 5:

FIG. 5 shows a fluorescent image captured after 99° C. water mediated release of DNA surface probes from commercial arrays manufactured by Agilent. A fluorescent detection probe was hybridized after hot water treatment. Top array is an untreated control.

Figure 6:
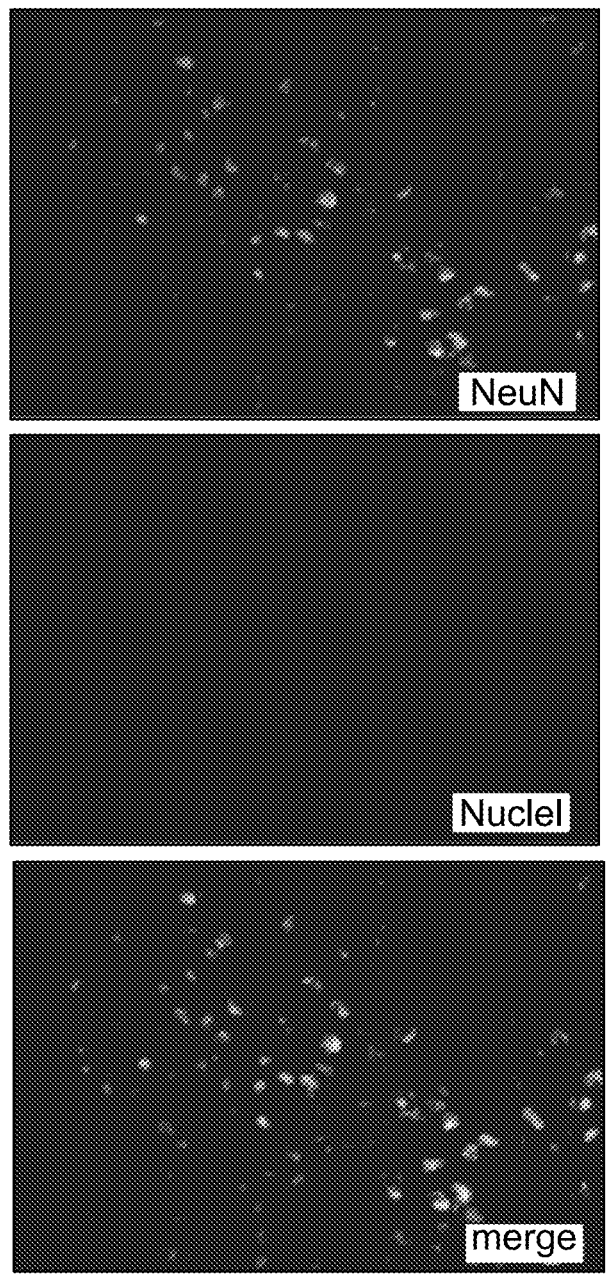

FIG. 6 shows a fixated mouse brain tissue section on top of the transcriptome capture array post cDNA synthesis and treated with cytoplasmic (top) and nucleic stains (middle), respectively, and merged image showing both stains (bottom).

Figure 7:
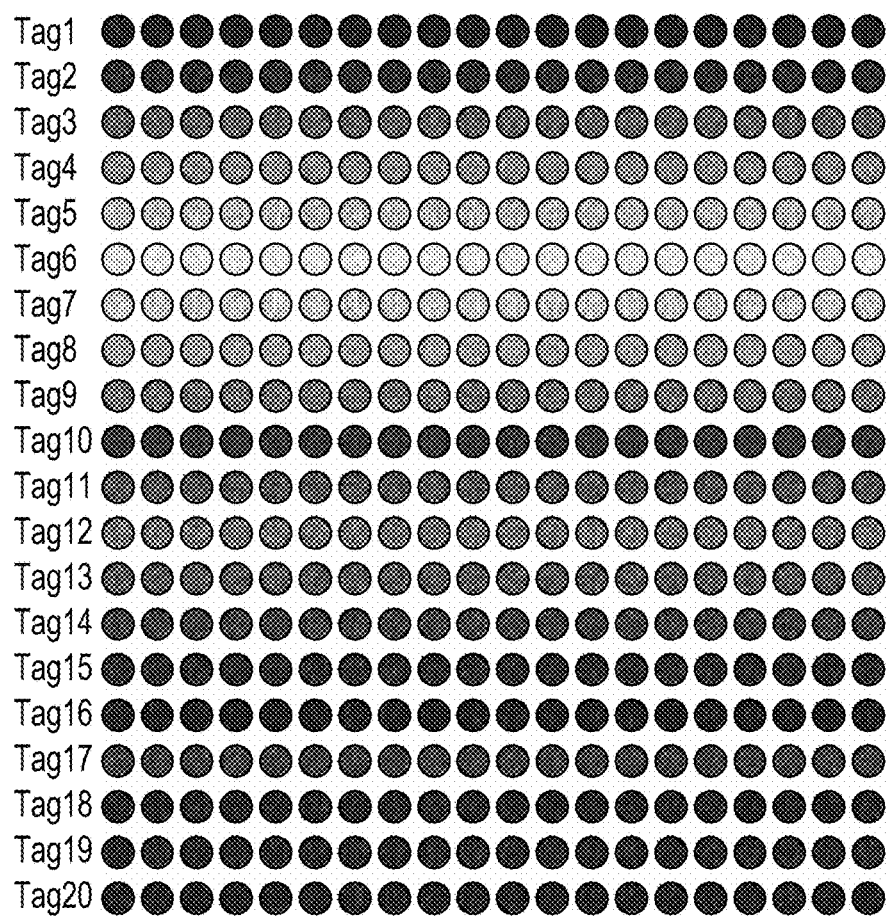

FIG. 7 shows a table that lists the reads sorted for their origin across the low density in-house manufactured DNA-capture array as seen in the schematic representation.

Figure 8:
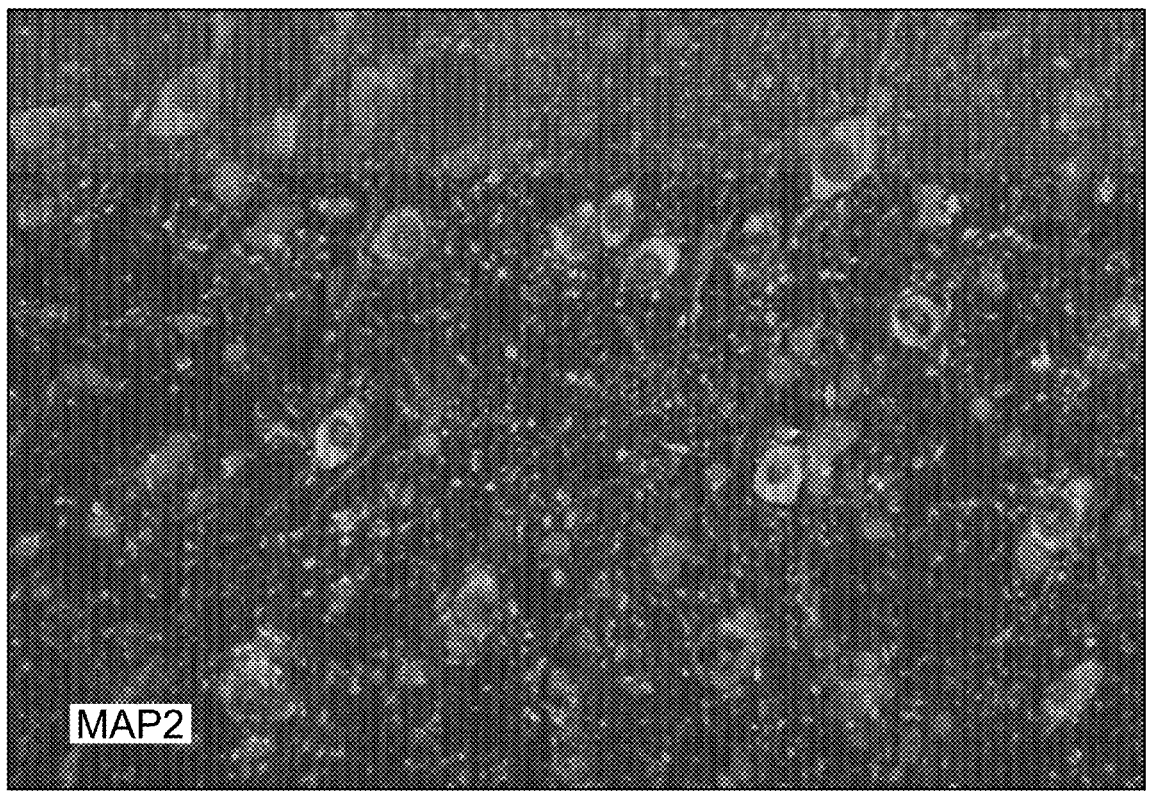

FIG. 8 shows a FFPE mouse brain tissue with nucleic and Map2 specific stains using a barcoded microarray.

Figure 9:
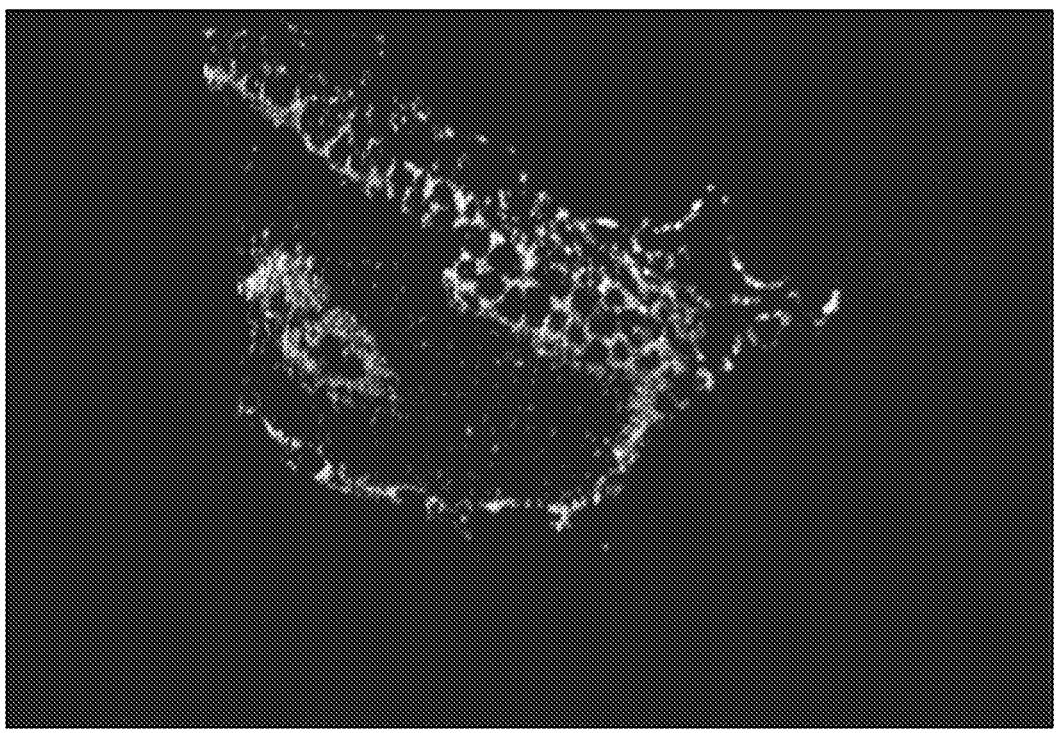

FIG. 9 shows FFPE mouse brain olfactory bulb with nucleic stain (white) and visible morphology.

Figure 10:
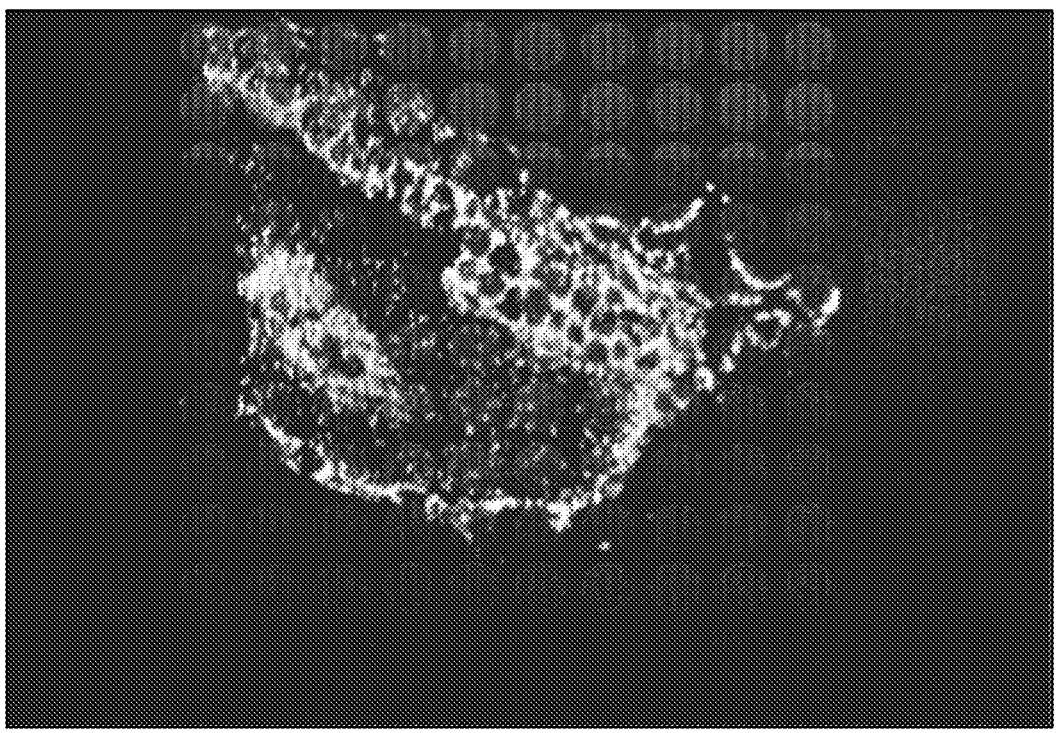

FIG. 10 shows FFPE mouse brain olfactory bulb (approx 2×2 mm) with nucleic stain (white), overlaid with theoretical spotting pattern for low resolution array.

Figure 11:
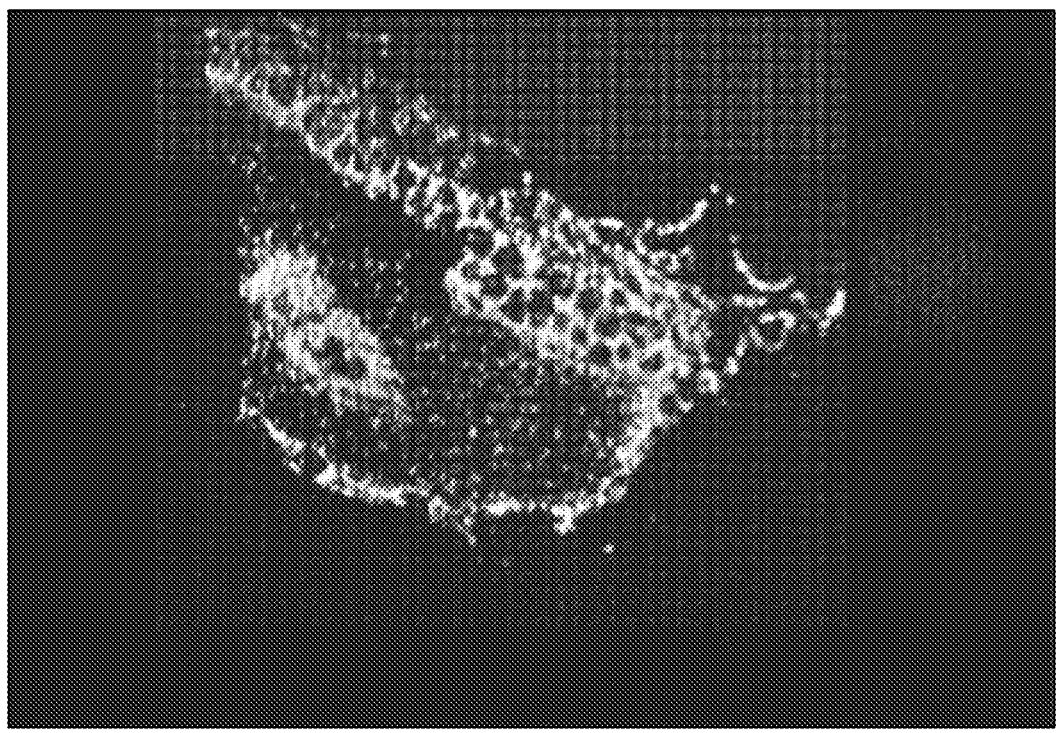

FIG. 11 shows FFPE mouse brain olfactory bulb (approx 2×2 mm) with nucleic stain (white), overlaid with theoretical spotting pattern for medium-high resolution array.

Figure 12:
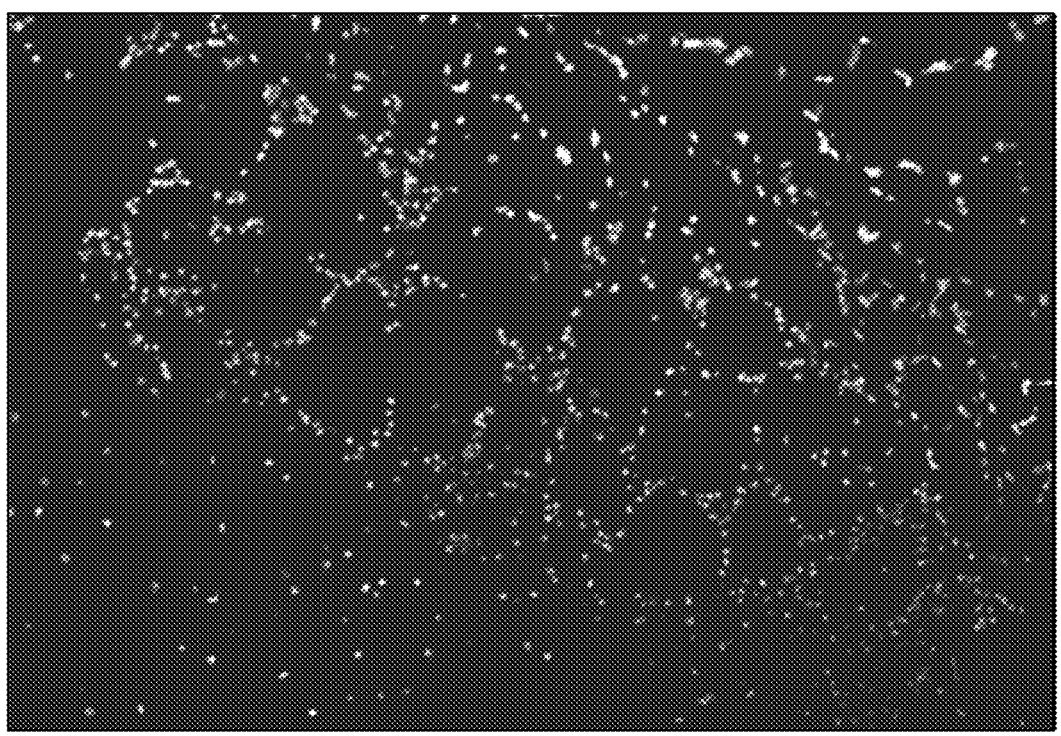

FIG. 12 shows FFPE mouse brain olfactory bulb zoomed in on glomerular area (top right of FIG. 9).

Figure 13:
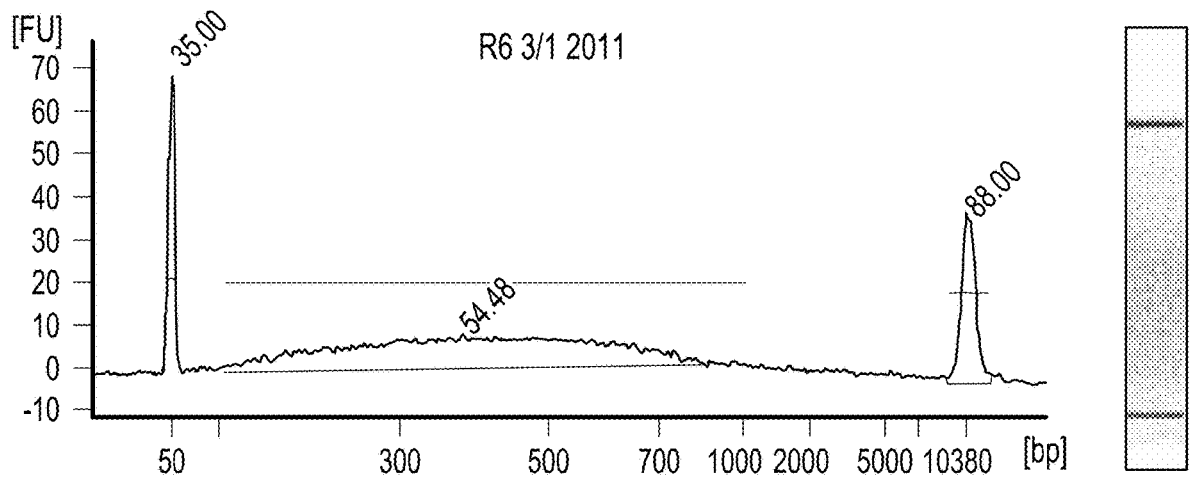

FIG. 13 shows the resulting product from a USER release using a random hexamer primer (R6) coupled to the B_handle (B_R6) during amplification; product as depicted on a bioanalyzer.

Figure 14:
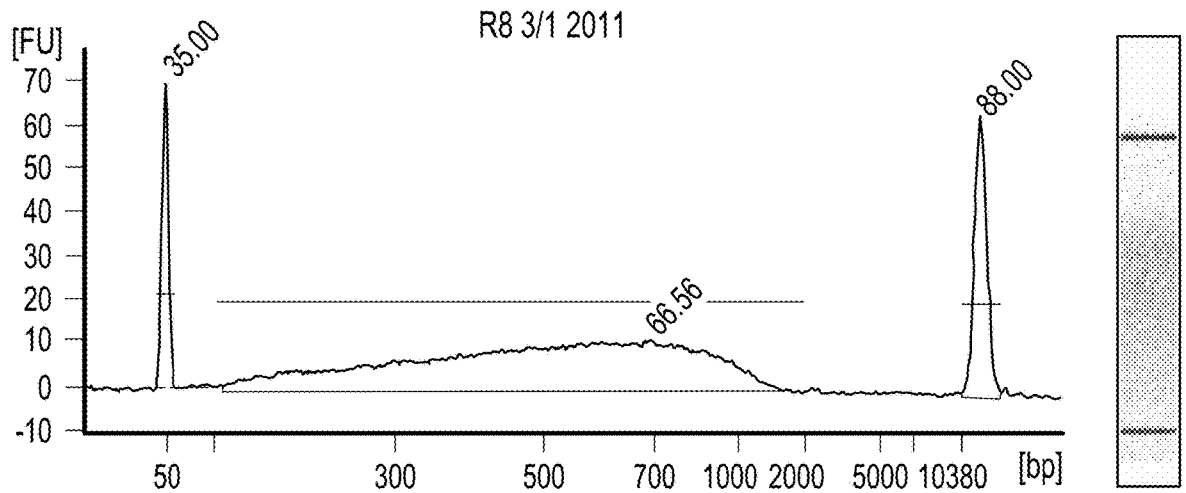

FIG. 14 shows the resulting product from a USER release using a random octamer primer (R8) coupled to the B_handle (B_R8) during amplification; product as depicted on a bioanalyzer.

Figure 15:
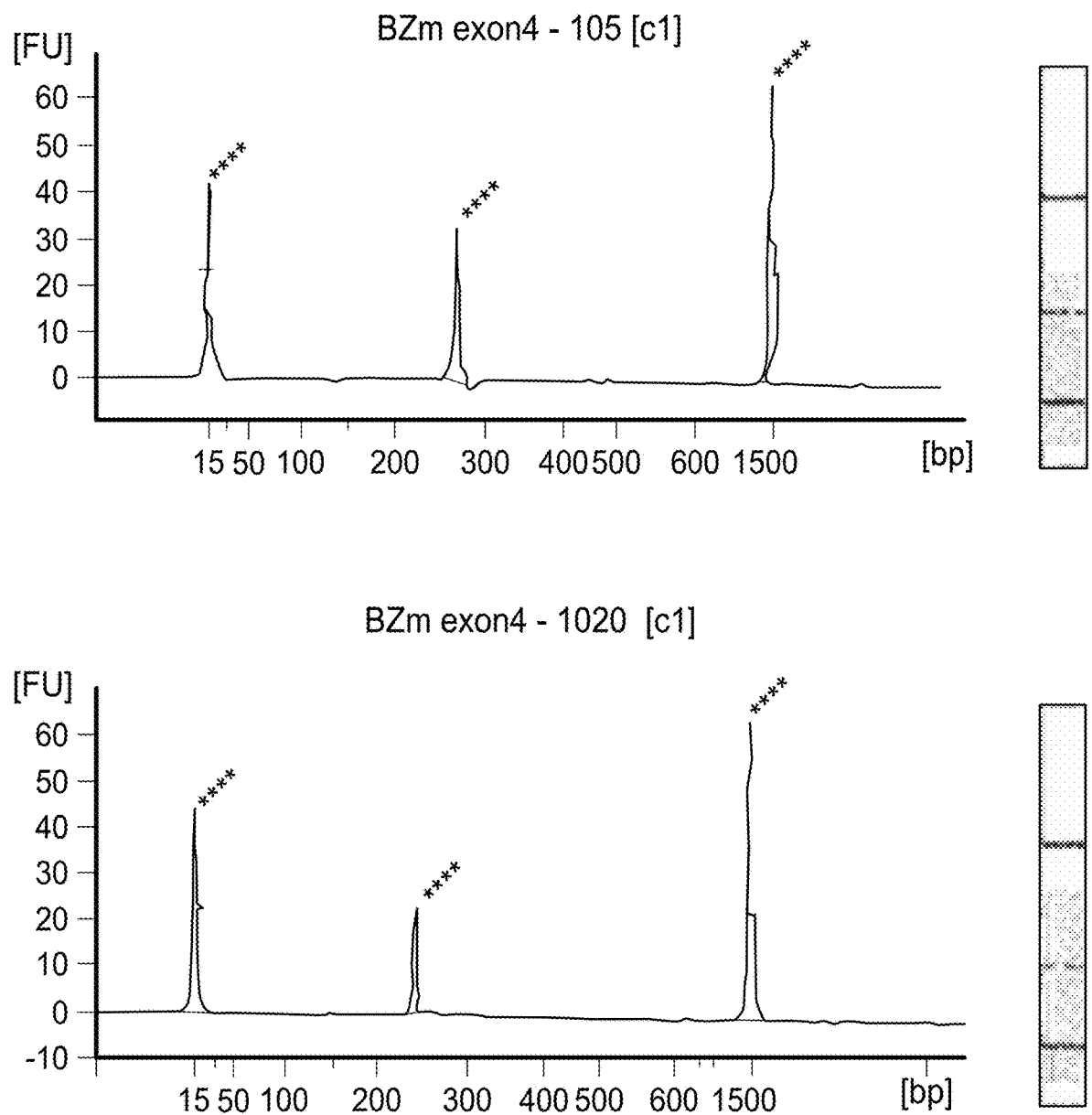

FIG. 15 shows the results of an experiment performed on FFPE brain tissue covering the whole array. ID5 (left) and ID20 (right) amplified with ID specific and gene specific primers (B2M exon 4) after synthesis and release of cDNA from surface; ID5 and ID20 amplified.

Figure 16:
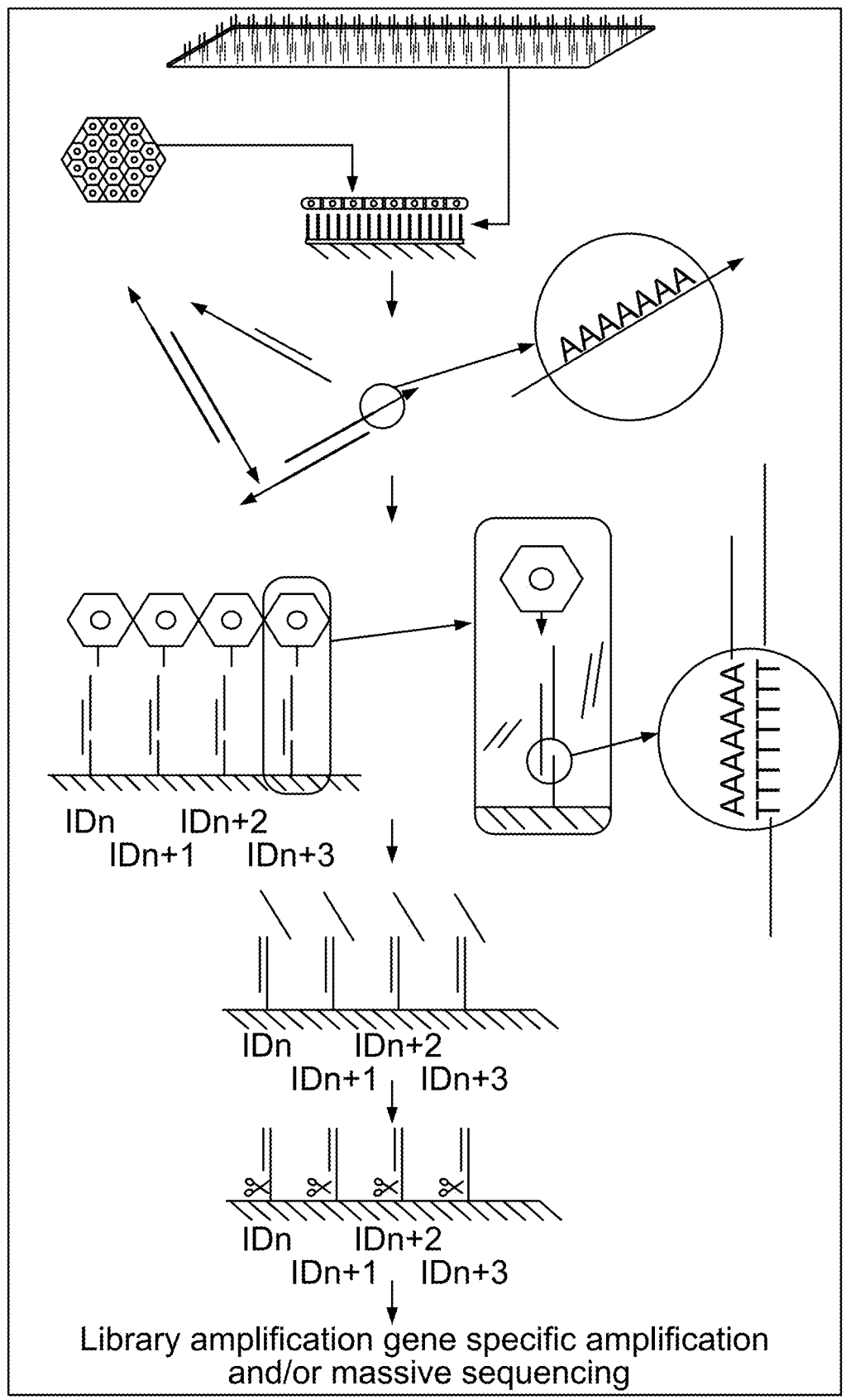

FIG. 16 shows a schematic illustration of the principle of the method described in Example 4, i.e. use of microarrays with immobilized DNA oligos (capture probes) carrying spatial labeling tag sequences (positional domains). Each feature of oligos of the microarray carries a 1) a unique labeling tag (positional domain) and 2) a capture sequence (capture domain).

Figure 17:
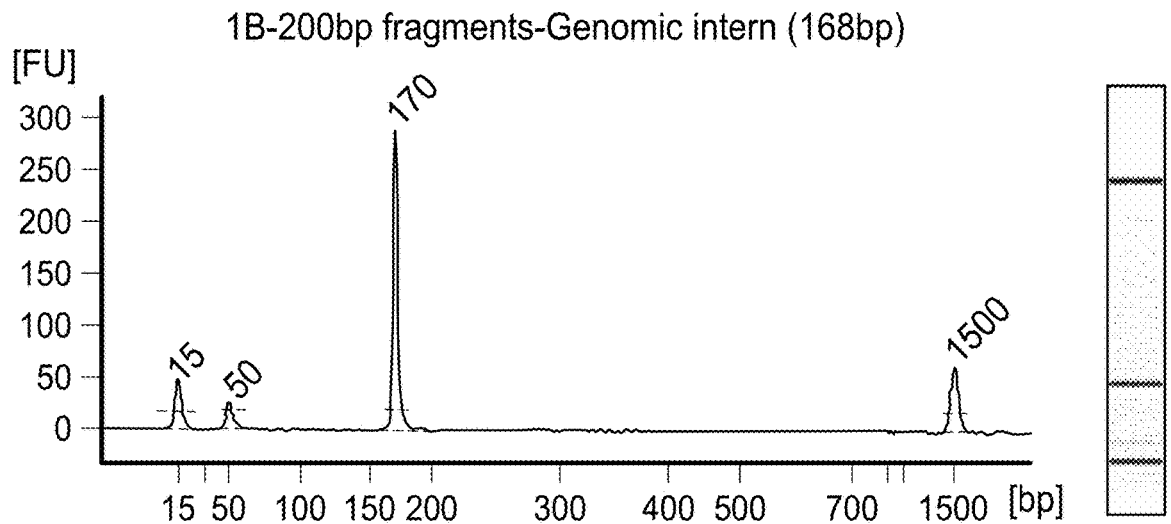

FIG. 17 shows the results of the spatial genomics protocol described in Example 5 carried out with genomic DNA prefragmented to mean size of 200 bp. Internal products amplified on array labeled and synthesized DNA. The detected peak is of expected size.

Figure 18:
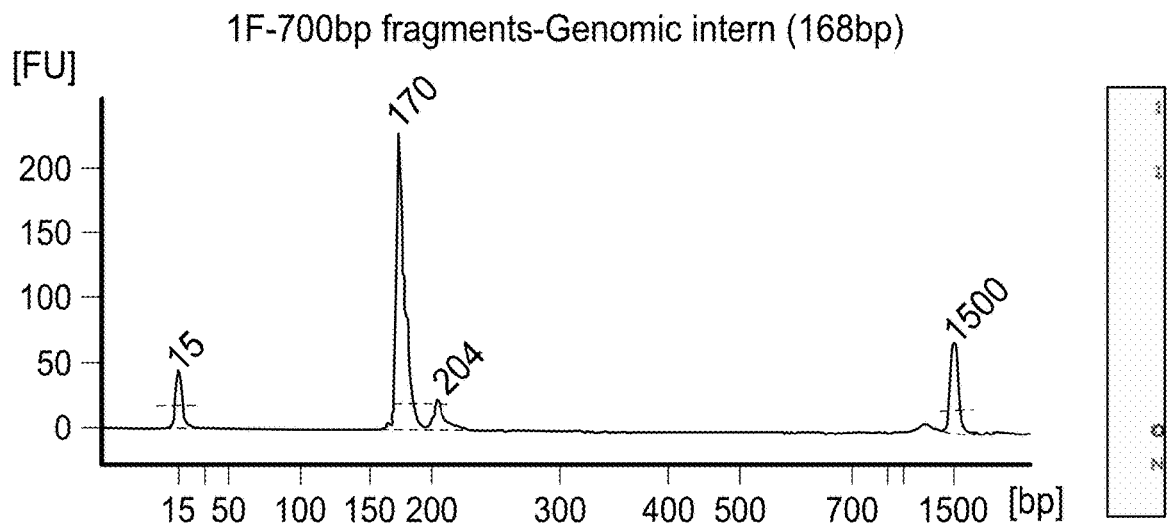

FIG. 18 shows the results of the spatial genomics protocol described in Example 5 carried out with genomic DNA prefragmented to mean size of 700 bp. Internal products amplified on array labeled and synthesized DNA. The detected peak is of expected size.

Figure 19:
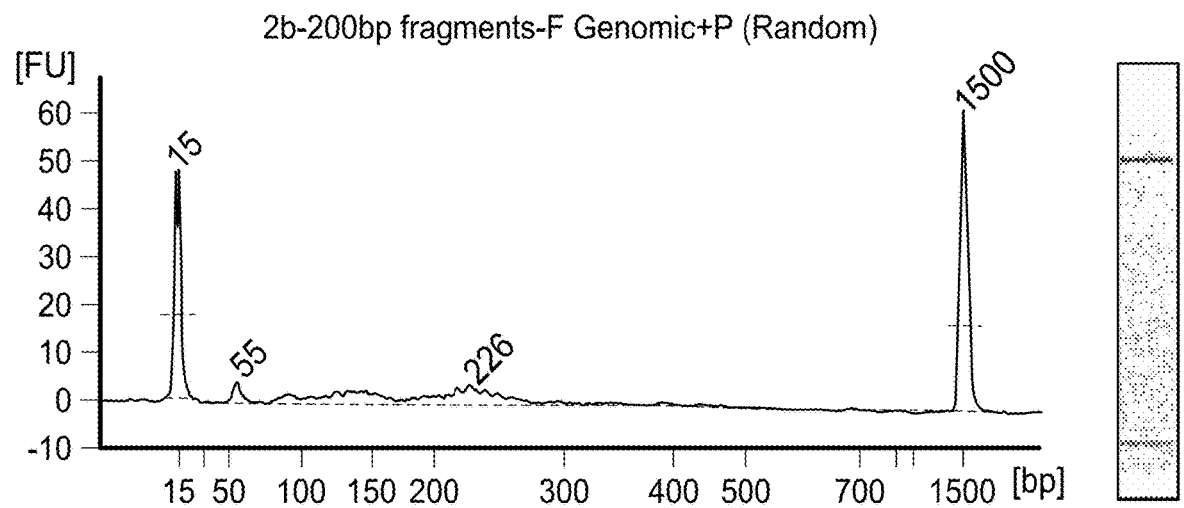

FIG. 19 shows the results of the spatial genomics protocol described in Example 5 carried out with genomic DNA prefragmented to mean size of 200 bp. Products amplified with one internal primer and one universal sequence contained in the surface oligo. Amplification carried out on array labeled and synthesized DNA. The expected product is a smear given that the random fragmentation and terminal transferase labeling of genomic DNA will generate a very diverse sample pool.

Figure 20:
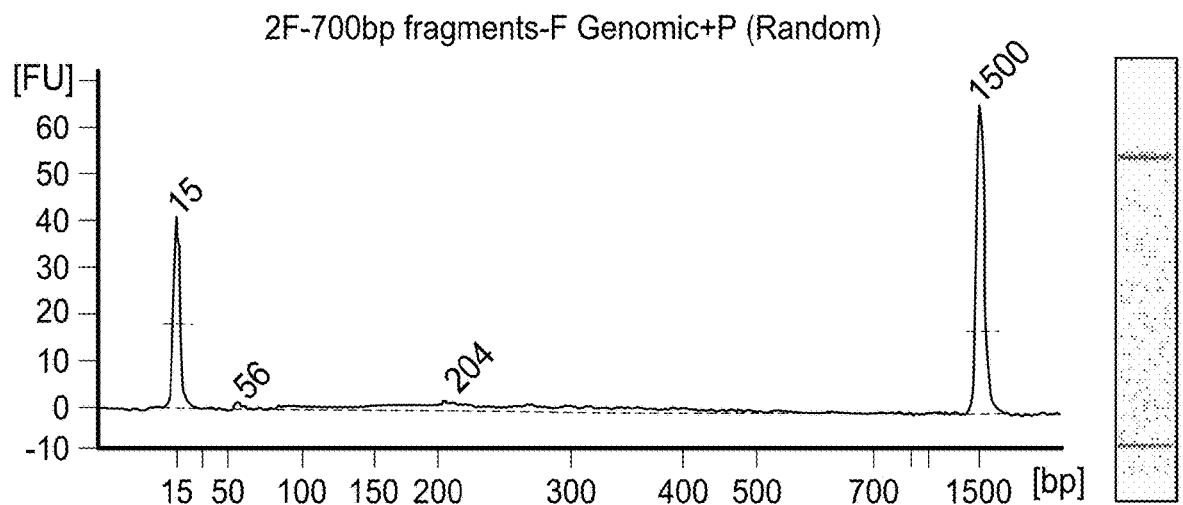

FIG. 20 shows the results of the spatial genomics protocol described in Example 5 carried out with genomic DNA prefragmented to mean size of 700 bp. Products amplified with one internal primer and one universal sequence contained in the surface oligo. Amplification carried out on array labeled and synthesized DNA. The expected product is a smear given that the random fragmentation and terminal transferase labeling of genomic DNA will generate a very diverse sample pool.

Figure 21:
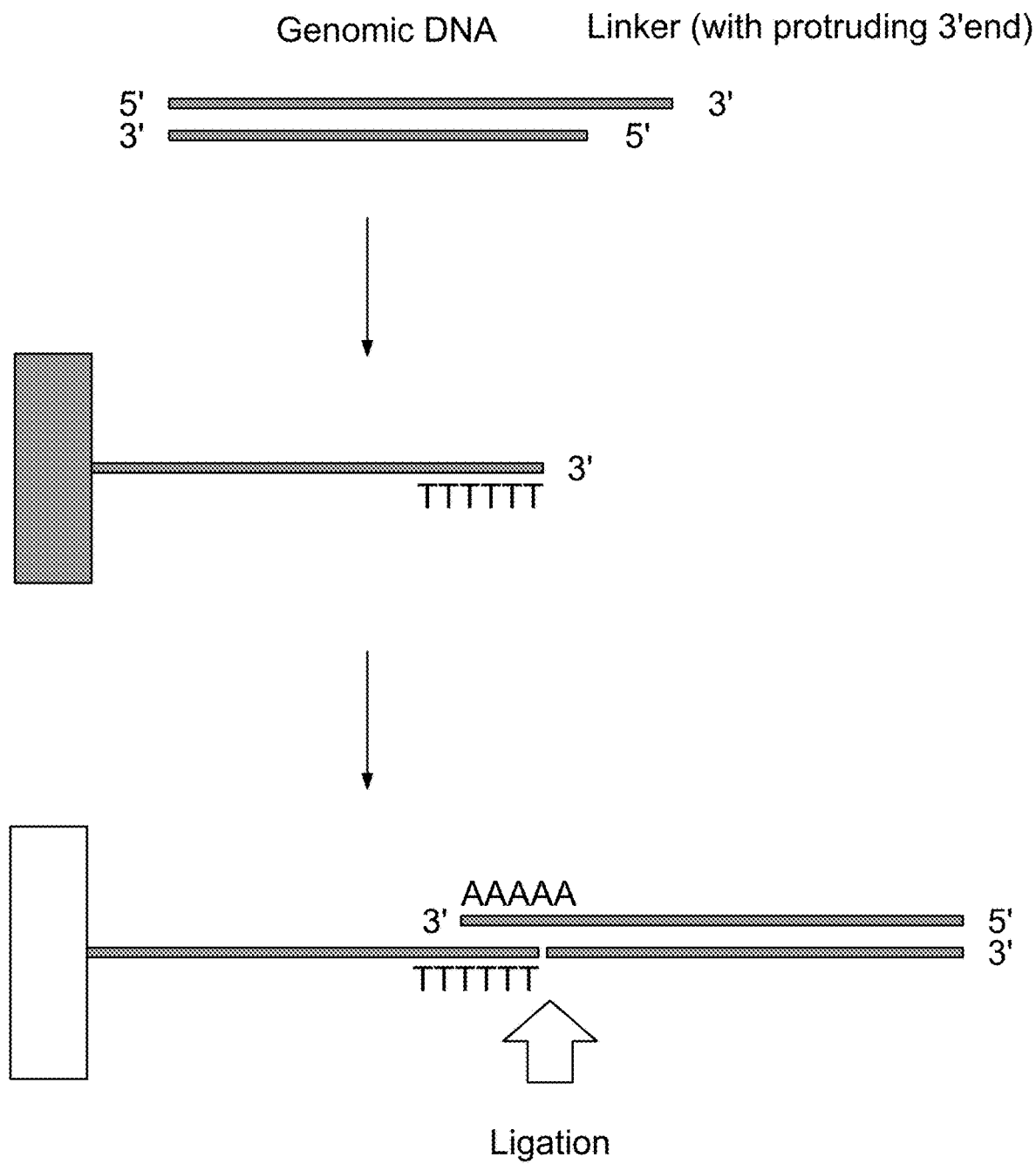

FIG. 21 shows a schematic illustration of the ligation of a linker to a DNA fragment to introduce a binding domain for hybridisation to a poly-T capture domain, and subsequent ligation to the capture probe.

Figure 22:
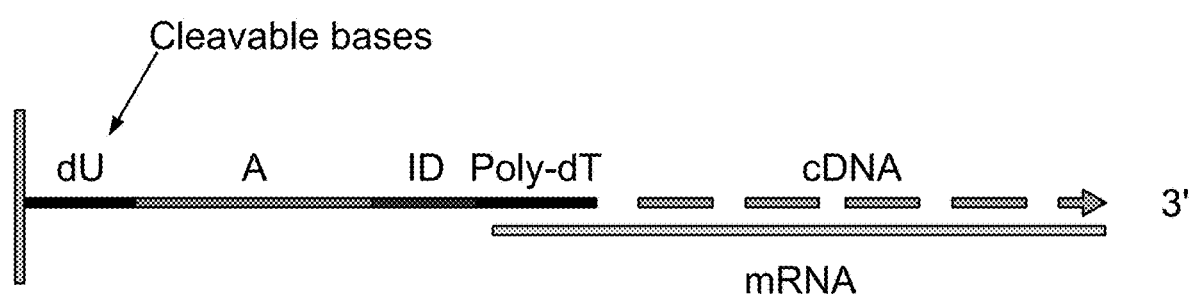

FIG. 22 shows the composition of 5' to 3' oriented capture probes used on high-density capture arrays.

Figure 23:
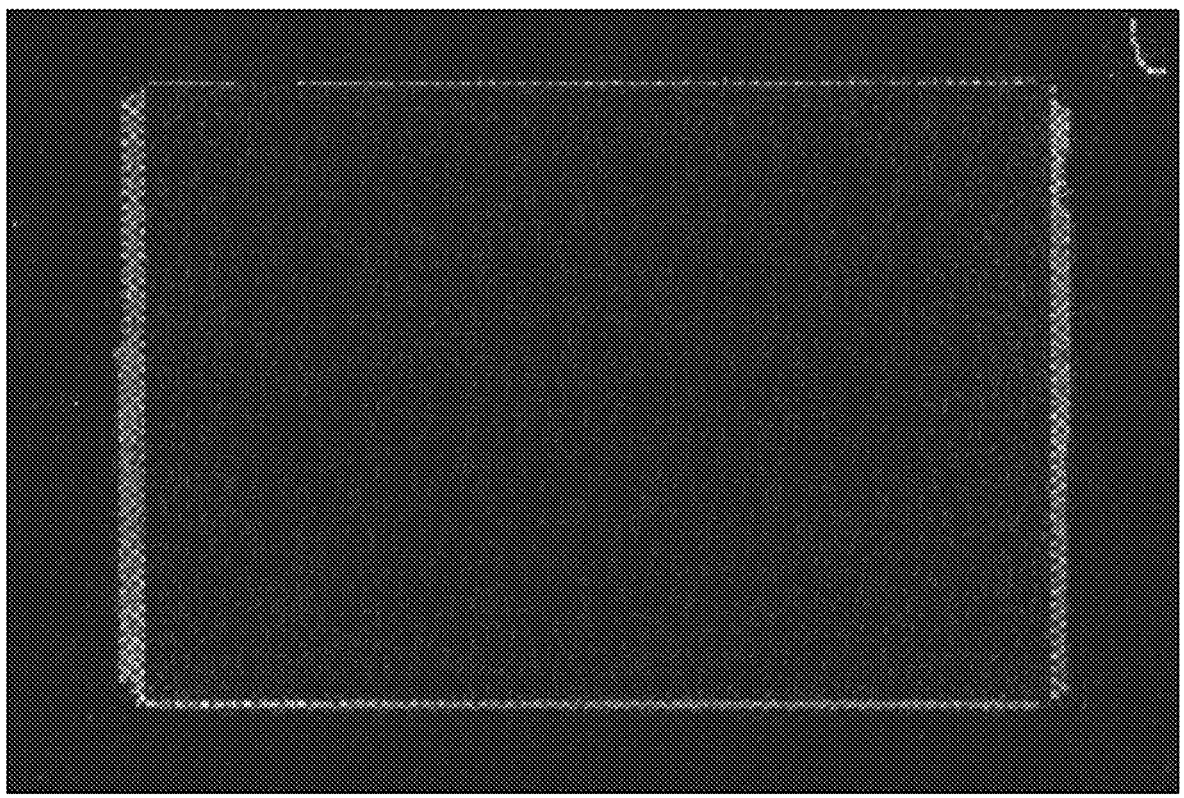

FIG. 23 shows the frame of the high-density arrays, which is used to orientate the tissue sample, visualized by hybridization of fluorescent marker probes.

Figure 24:
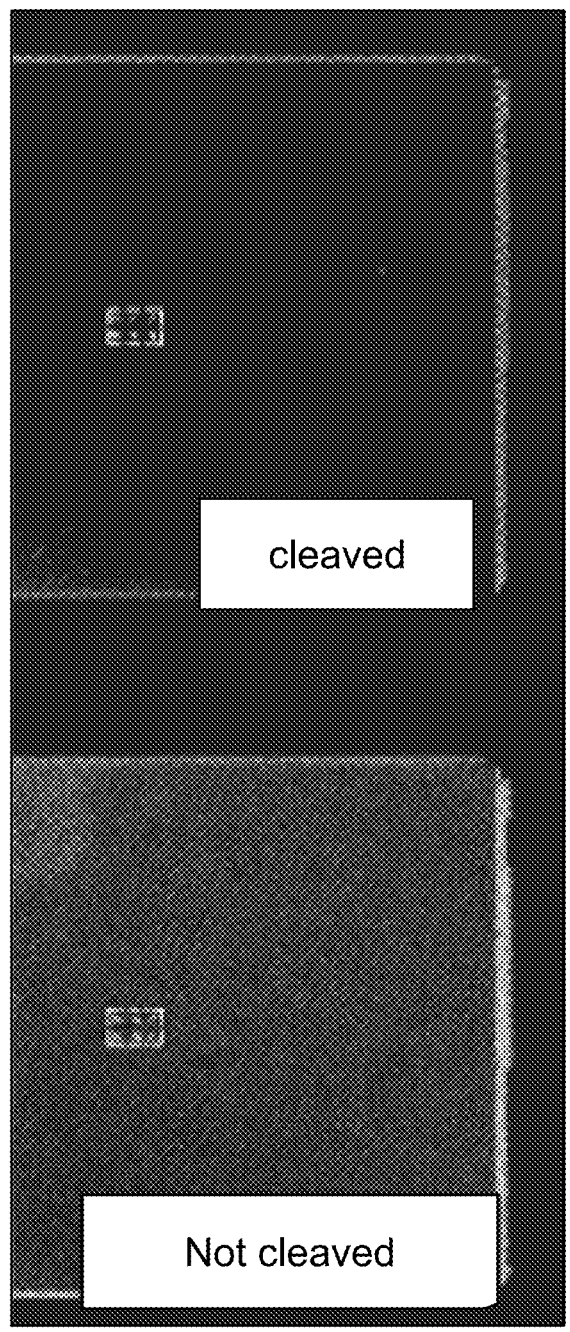

FIG. 24 shows capture probes cleaved and non-cleaved from high-density array, wherein the frame probes are not cleaved since they do not contain uracil bases. Capture probes were labelled with fluorophores coupled to poly-A oligonucleotides.

Figure 25:
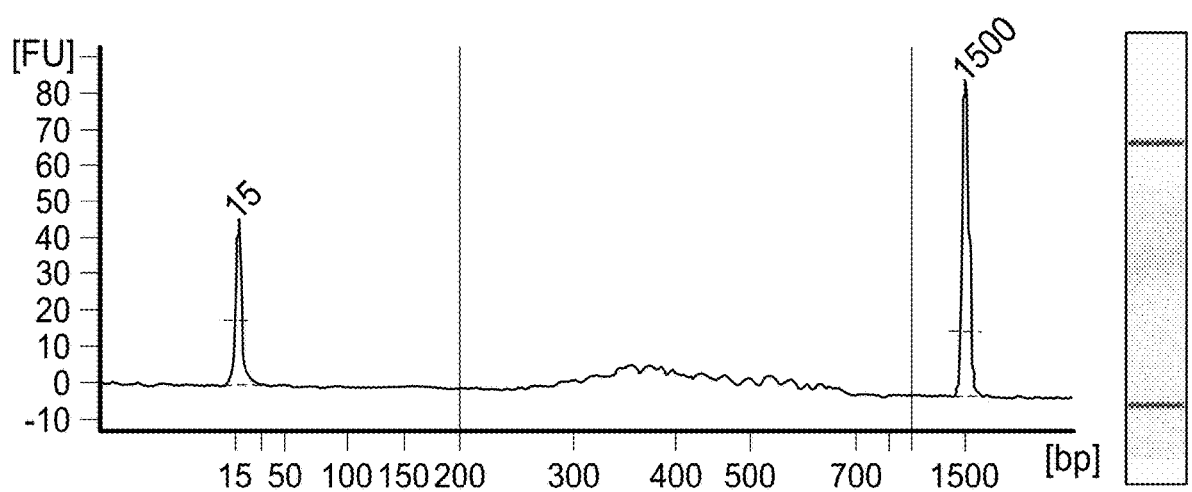

FIG. 25 shows a bioanalyzer image of a prepared sequencing library with transcripts captured from mouse olfactory bulb.

Figure 26:
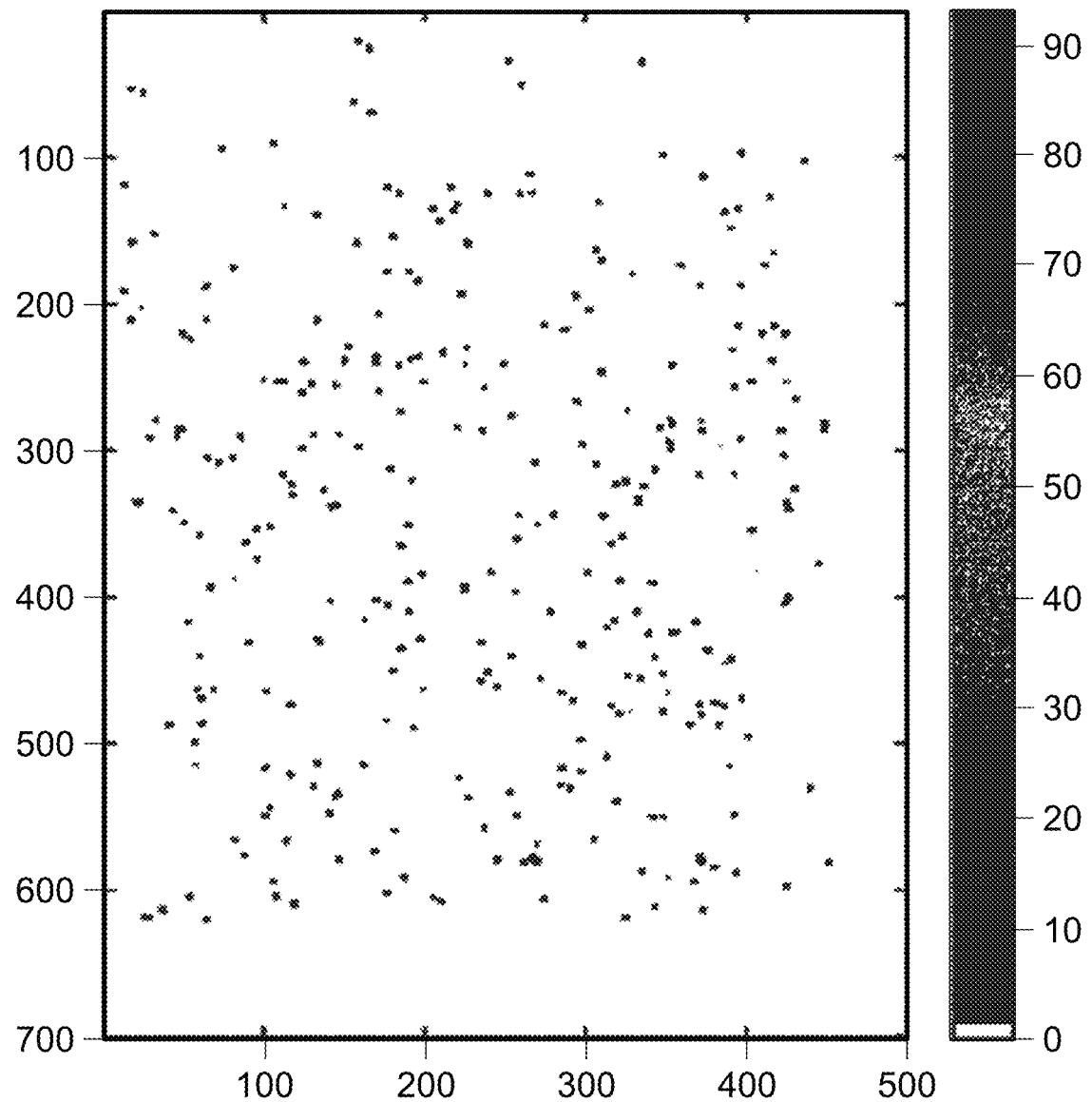

FIG. 26 shows a Matlab visualization of captured transcripts from total RNA extracted from mouse olfactory bulb.

Figure 27:
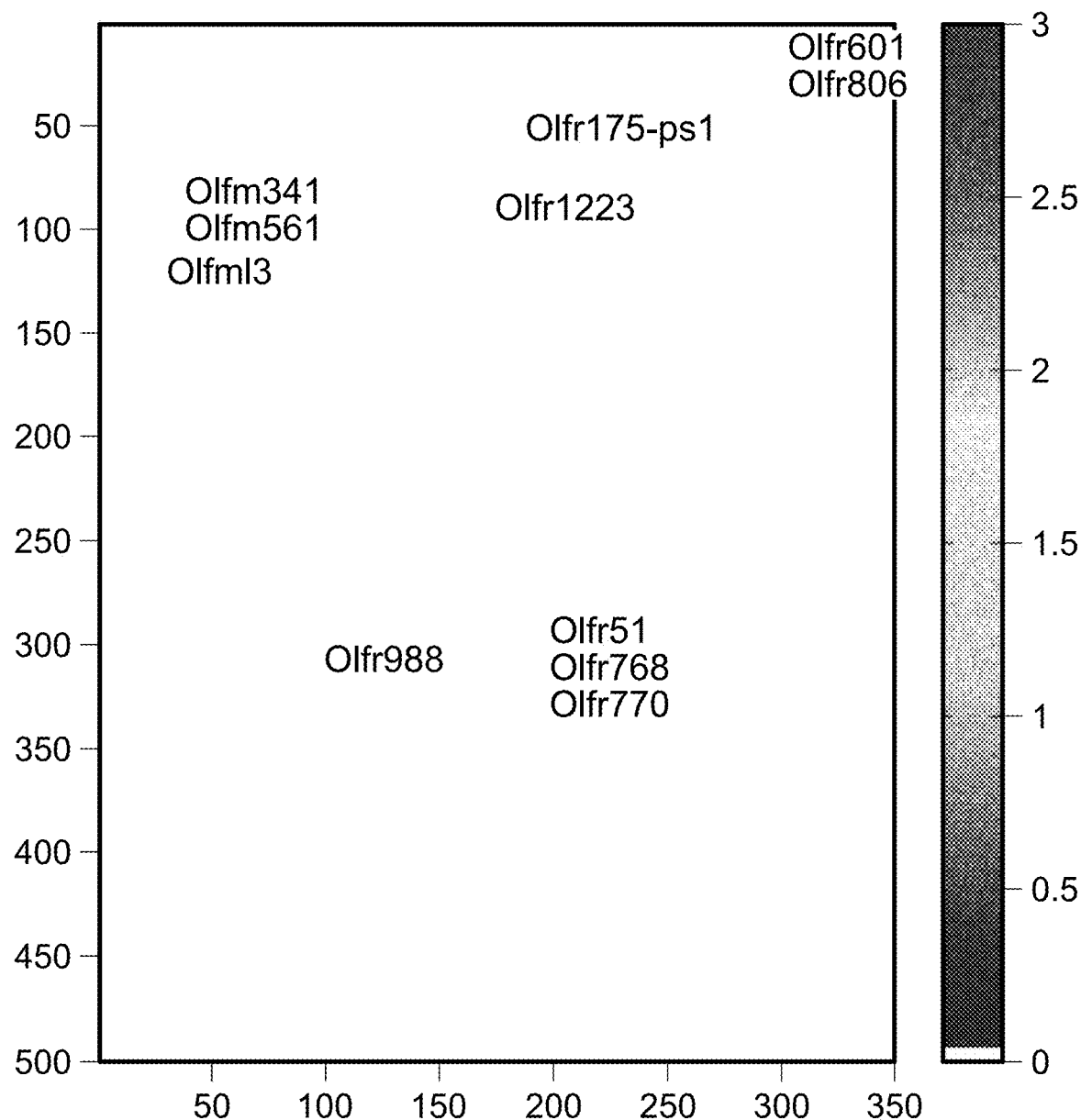

FIG. 27 shows Olfr (olfactory receptor) transcripts as visualized across the capture array using Matlab visualization after capture from mouse olfactory bulb tissue.

Figure 28:
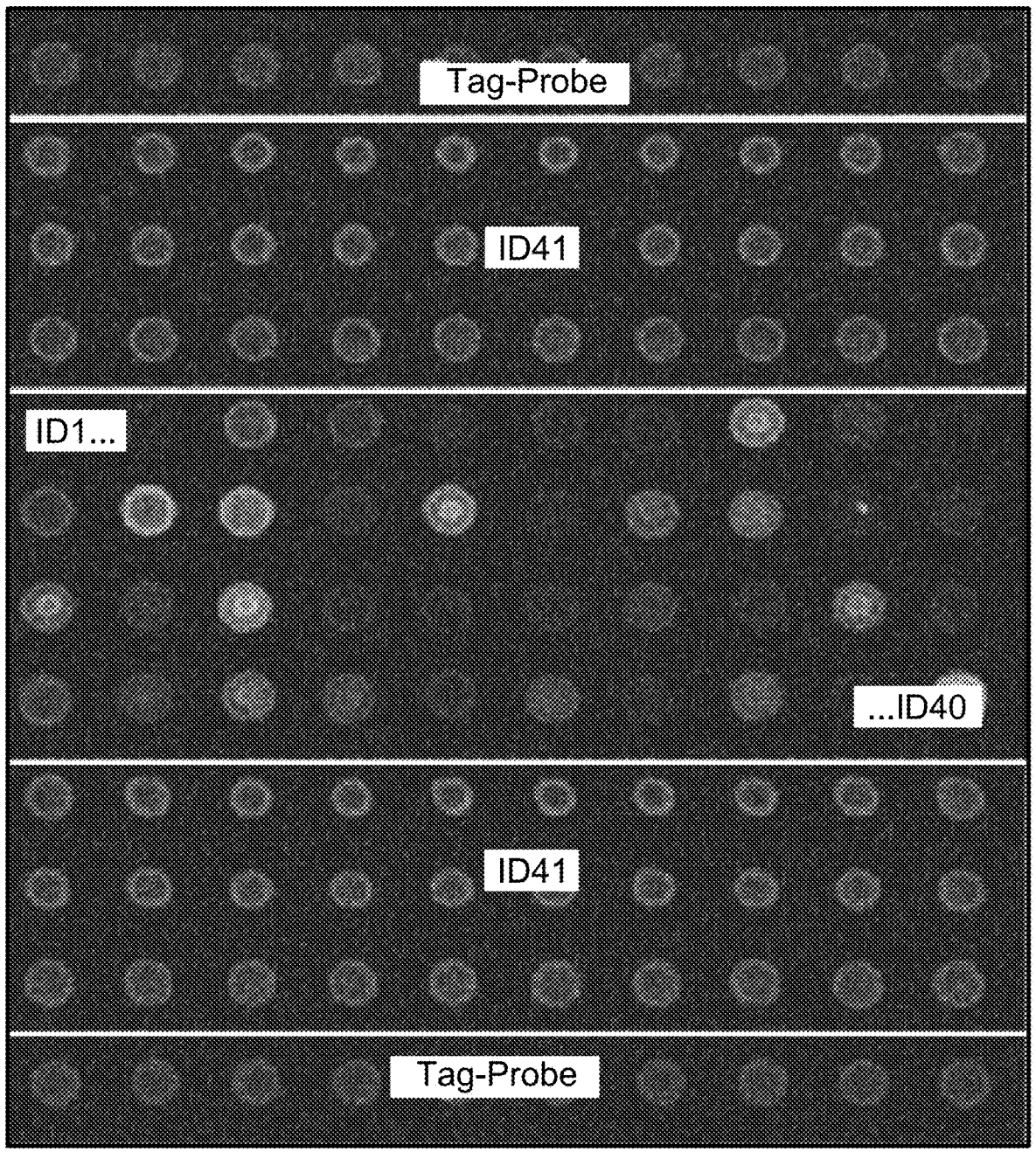

FIG. 28 shows a pattern of printing for in-house 41-ID-tag microarrays.

Figure 29:
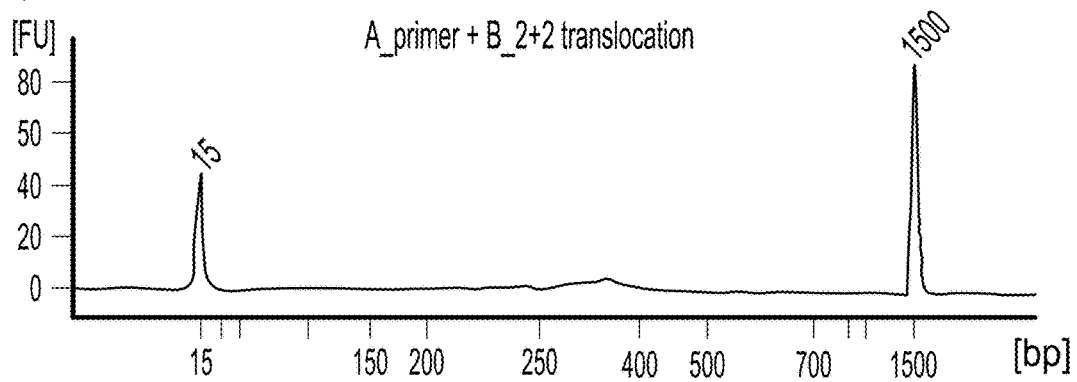
Figure 29:
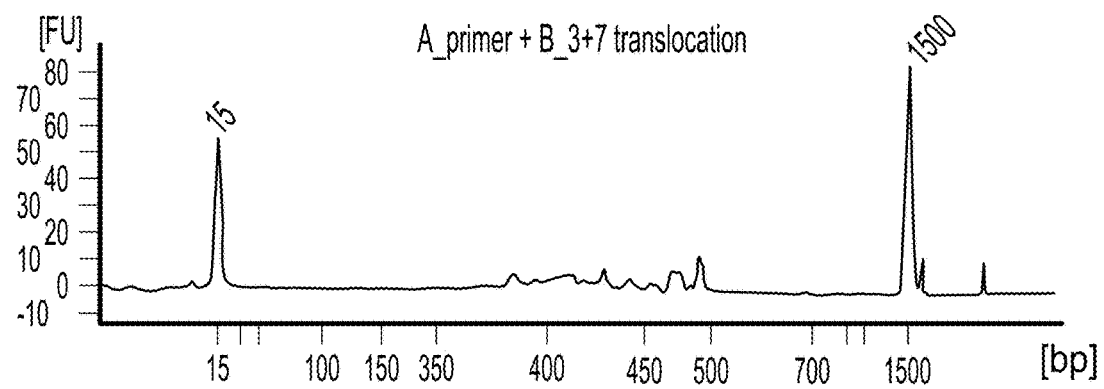
Figure 29:
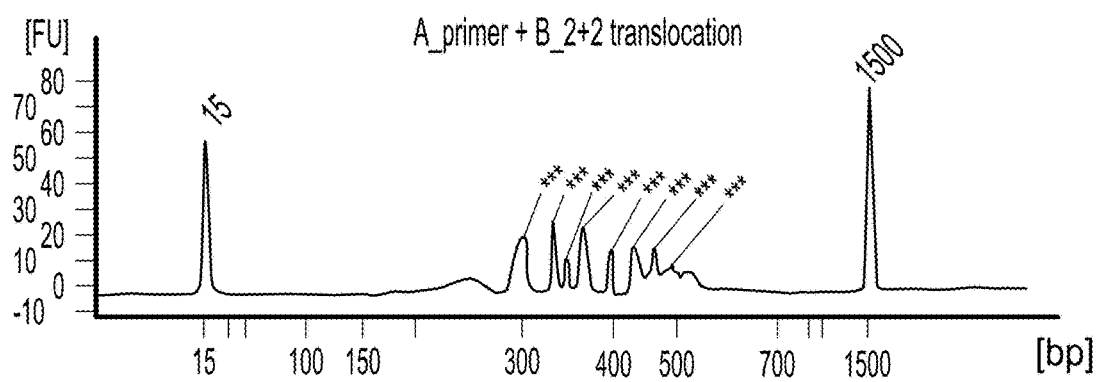
Figure 29:
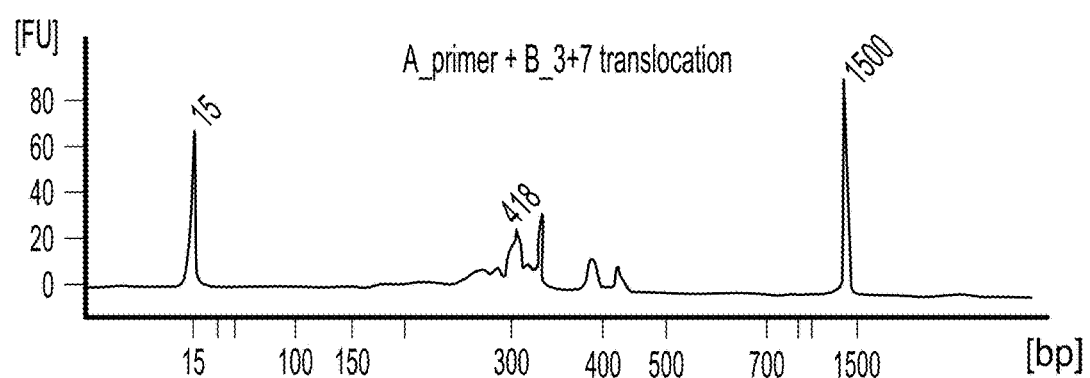

FIG. 29 shows a spatial genomics library generated from a A431 specific translocation after capture of poly-A tailed genomic fragments on capture array.

Figure 30:
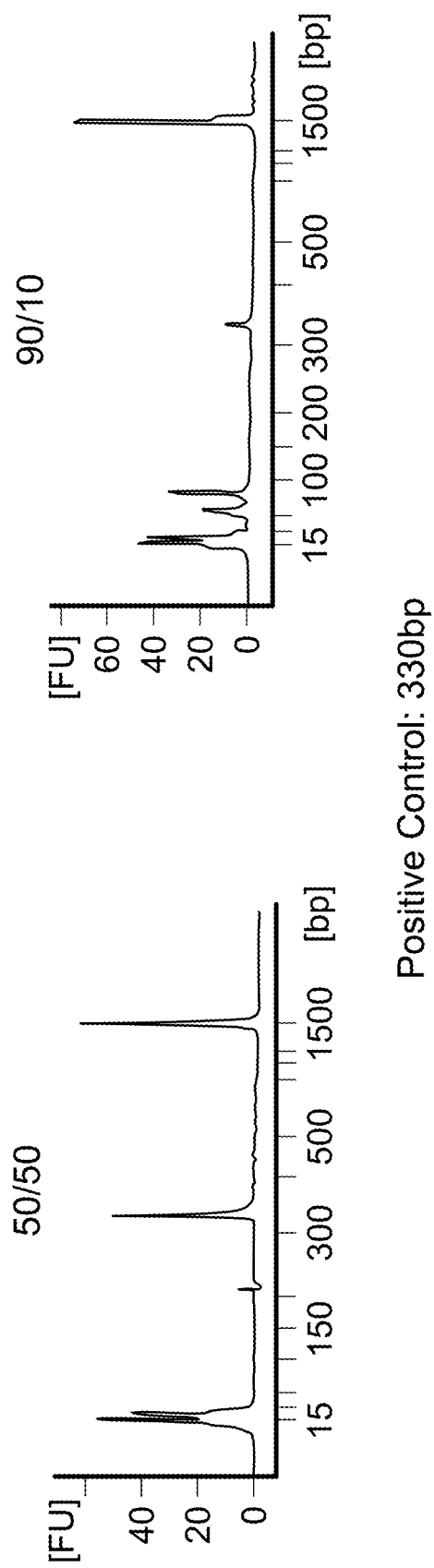

FIG. 30 shows the detection of A431 specific translocation after capture of spiked 10% and 50% poly-A tailed A431 genomic fragments into poly-A tailed U2OS genomic fragments on capture array.

Figure 31:
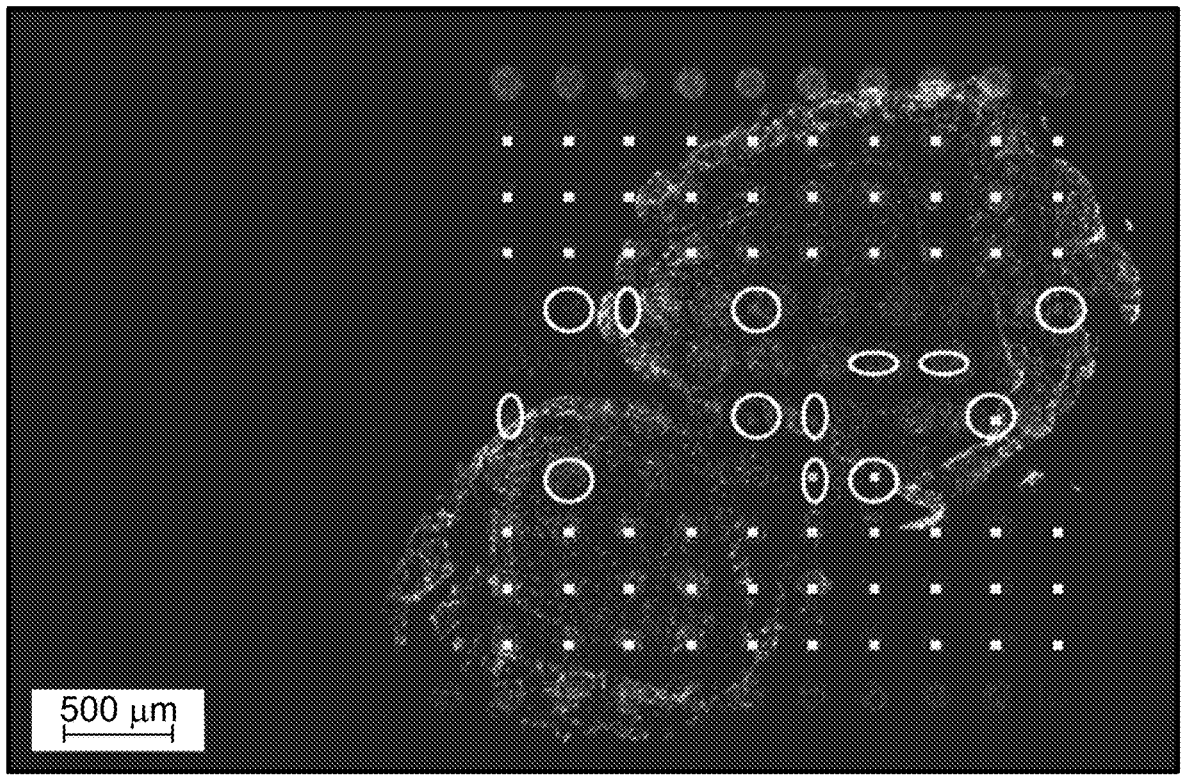

FIG. 31 shows a Matlab visualization of captured ID-tagged transcripts from mouse olfactory bulb tissue on 41-ID-tag in-house arrays overlaid with the tissue image. For clarity, the specific features on which particular genes were identified have been circled.

EXAMPLE 1

Preparation of the Array

The following experiments demonstrate how oligonucleotide probes may be attached to an array substrate by either the 5' or 3' end to yield an array with capture probes capable of hybridizing to mRNA.

Preparation of In-House Printed Microarray with 5' to 3' Oriented Probes

20 RNA-capture oligonucleotides with individual tag sequences (Tag 1-20, Table 1 were spotted on glass slides to function as capture probes. The probes were synthesized with a 5'-terminus amino linker with a C6 spacer. All probes where synthesized by Sigma-Aldrich (St. Louis, Mo., USA). The RNA-capture probes were suspended at a concentration of 20 µM in 150 mM sodium phosphate, pH 8.5 and were spotted using a Nanoplotter NP2.1/E (Gesim, Grosserkmannsdorf, Germany) onto CodeLink™ Activated microarray slides (7.5 cm×2.5 cm; Surmodics, Eden Prairie, Minn., USA). After printing, surface blocking was performed according to the manufacturer's instructions. The probes were printed in 16 identical arrays on the slide, and each array contained a pre-defined printing pattern. The 16 subarrays were separated during hybridization by a 16-pad mask (ChipClip™ Schleicher & Schuell BioScience, Keene, N.H., USA).

TABLE 1

| Name | Sequence | 5' mod | 3' mod | Length |
|---|---|---|---|---|
| Sequences for free 3' capture probes | | | | |
| TAP-ID1 | UUAAGTACAAATCTCGACTGCCACTCTGAACCTTCTCCTTCTCCTTC ACCTTTTTTTTTTTTTTTTTTTVN (SEQ ID NO: 1) | Amino-C6 | | 72 |
| Enzymatic recog | UUAAGTACAA (SEQ ID NO: 2) | | | 10 |
| Universal amp handle P | ATCTCGACTGCCACTCTGAA (SEQ ID NO: 3) | | | 20 |
| ID1 | CCTTCTCCTTCTCCTTCACC (SEQ ID NO: 4) | | | 20 |
| Capture sequence | TTTTTTTTTTTTTTTTTTTVN (SEQ ID NO: 5) | | | 22 |
| ID1 | CCTTCTCCTTCTCCTTCACC (SEQ ID NO: 6) | | | 20 |
| ID2 | CCTTGCTGCTTCTCCTCCTC (SEQ ID NO: 7) | | | 20 |
| ID3 | ACCTCCTCCGCCTCCTCCTC (SEQ ID NO: 8) | | | 20 |
| ID4 | GAGACATACCACCAAGAGAC (SEQ ID NO: 9) | | | 20 |
| ID5 | GTCCTCTATTCCGTCACCAT (SEQ ID NO: 10) | | | 20 |
| ID6 | GACTGAGCTCGAACATATGG (SEQ ID NO: 11) | | | 20 |
| ID7 | TGGAGGATTGACACAGAACG (SEQ ID NO: 12) | | | 20 |
| ID8 | CCAGCCTCTCCATTACATCG (SEQ ID NO: 13) | | | 20 |
| ID9 | AAGATCTACCAGCCAGCCAG (SEQ ID NO: 14) | | | 20 |
| ID10 | CGAACTTCCACTGTCTCCTC (SEQ ID NO: 15) | | | 20 |
| ID11 | TTGCGCCTTCTCCAATACAC (SEQ ID NO: 16) | | | 20 |
| ID12 | CTCTTCTTAGCATGCCACCT (SEQ ID NO: 17) | | | 20 |
| ID13 | ACCACTTCTGCATTACCTCC (SEQ ID NO: 18) | | | 20 |
| ID14 | ACAGCCTCCTCTTCTTCCTT (SEQ ID NO: 19) | | | 20 |
| ID15 | AATCCTCTCCTTGCCAGTTC (SEQ ID NO: 20) | | | 20 |
| ID16 | GATGCCTCCACCTGTAGAAC (SEQ ID NO: 21) | | | 20 |
| ID17 | GAAGGAATGGAGGATATCGC (SEQ ID NO: 22) | | | 20 |
| ID18 | GATCCAAGGACCATCGACTG (SEQ ID NO: 23) | | | 20 |

TABLE 1-continued

| Name | Sequence | 5' mod | 3' mod | Length |
|---|---|---|---|---|
| ID19 | CCACTGGAACCTGACAACCG (SEQ ID NO: 24) | | | 20 |
| ID20 | CTGCTTCTTCCTGGAACTCA (SEQ ID NO: 25) | | | 20 |
| Sequences for free 5' surface probes and on-chip free 3' capture probe synthesis | | | | |
| Free 5' surface probe-A | GCGTTCAGAGTGGCAGTCGAGATCACGCGGCAATCATATCGGACAGATCGGAAGAGCGTAGTGTAG (SEQ ID NO: 26) | Amino C7 | | 66 |
| Free 5' surface probe-U | GCGTTCAGAGTGGCAGTCGAGATCACGCGGCAATCATATCGGACGGCTGCTGGTAAATAGAGATCA (SEQ ID NO: 27) | Amino C7 | | 66 |
| Nick | GCG | | | 3 |
| LP' | TTCAGAGTGGCAGTCGAGATCAC (SEQ ID NO: 28) | | | 23 |
| ID' | GCGGCAATCATATCGGAC (SEQ ID NO: 29) | | | 18 |
| A' 22 bp MutY mismatch | AGATCGGAAGAGCGTAGTGTAG (SEQ ID NO: 30) | | | 22 |
| U' 22 bp MutY mismatch | GGCTGCTGGTAAATAGAGATCA (SEQ ID NO: 31) | | | 22 |
| Hybridized sequences for capture probe synthesis | | | | |
| Illumina amp handle A | ACACTCTTTCCCTACACGACGCTCTTCCGATCT (SEQ ID NO: 32) | | | 33 |
| Universal ampl handle U | AAGTGTGGAAAGTTGATCGCTATTTACCAGCAGCC (SEQ ID NO: 33) | | | 35 |
| Capture_LP_Poly-dTVN | GTGATCTCGACTGCCACTCTGAATTTTTTTTTTTTTTTTTTTTTVN (SEQ ID NO: 34) | | Phosphorylated | 45 |
| Capture_LP_Poly-d24T | GTGATCTCGACTGCCACTCTGAATTTTTTTTTTTTTTTTTTTTTTTT (SEQ ID NO: 35) | | Phosphorylated | 47 |
| Additional secondary universal amplification handles | | | | |
| Illumina amp handle B | AGACGTGTGCTCTTCCGATCT (SEQ ID NO: 36) | | | 21 |
| Universal amp handle X | ACGTCTGTGAATAGCCGCAT (SEQ ID NO: 37) | | | 20 |
| B_R6 handle (or X) | AGACGTGTGCTCTTCCGATCTNNNNNN (SEQ ID NO: 38) | | | 27(26) |
| B_R8 handle (or X) | AGACGTGTGCTCTTCCGATCTNNNNNNNN (SEQ ID NO: 39) | | | 29(28) |
| B_polyTVN (or X) | AGACGTGTGCTCTTCCGATCTTTTTTTTTTTTTTTTTTTTVN (SEQ ID NO: 40) | | | 43(42) |
| B_poly24T (or X) | AGACGTGTGCTCTTCCGATCTTTTTTTTTTTTTTTTTTTTTTTT (SEQ ID NO: 41) | | | 45(44) |
| Amplification handle to incorporate A handle into P handle products | | | | |
| A_P handle | ACACTCTTTCCCTACACGACGCTCTTCCGATCTATCTCGACTGCCACTCTGAA (SEQ ID NO: 42) | | | 53 |

Preparation of In-House Printed Microarray with 3' to 5' Oriented Probes and Synthesis of 5' to 3' Oriented Capture Probes Printing of surface probe oligonucleotides was performed as in the case with 5' to 3' oriented probes above, with an amino-C7 linker at the 3' end, as shown in Table 1.

To hybridize primers for capture probe synthesis, hybridization solution containing 4×SSC and 0.1% SDS, 2 µM extension primer (the universal domain oligonucleotide) and 2 µM thread joining primer (the capture domain oligonucleotide) was incubated for 4 min at 50° C. Meanwhile the in-house array was attached to a ChipClip (Whatman). The array was subsequently incubated at 50° C. for 30 min at 300 rpm shake with 50 µL of hybridization solution per well.

After incubation, the array was removed from the ChipClip and washed with the 3 following steps: 1) 50° C. 2×SSC solution with 0.1% SDS for 6 min at 300 rpm shake; 2) 0.2×SSC for 1 min at 300 rpm shake; and 3) 0.1×SSC for 1 min at 300 rpm shake. The array was then spun dry and placed back in the ChipClip.

For extension and ligation reaction (to generate the positional domain of the capture probe) 50 µL of enzyme mix containing 10×Ampligase buffer, 2.5 U AmpliTaq DNA Polymerase Stoffel Fragment (Applied Biosystems), 10 U Ampligase (Epicentre Biotechnologies), dNTPs 2 mM each (Fermentas) and water, was pipetted to each well. The array was subsequently incubated at 55° C. for 30 min. After incubation the array was washed according to the previously described array washing method but the first step has the duration of 10 min instead of 6 min.

Figure 1:
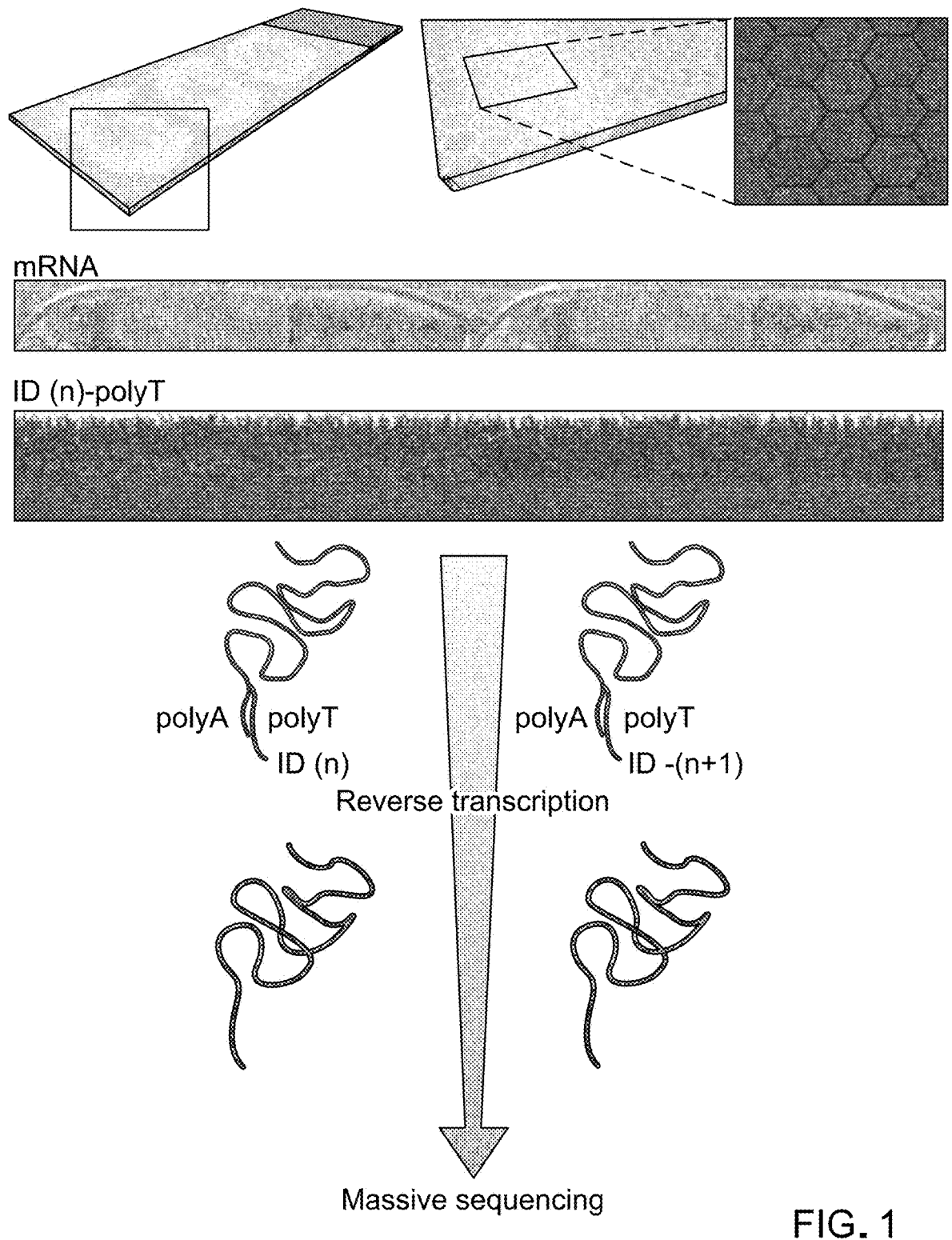
FIG. 1 shows the overall concept using arrayed "barcoded" oligo-dT probes to capture mRNA from tissue sections for transcriptome analysis.
Figure 2:
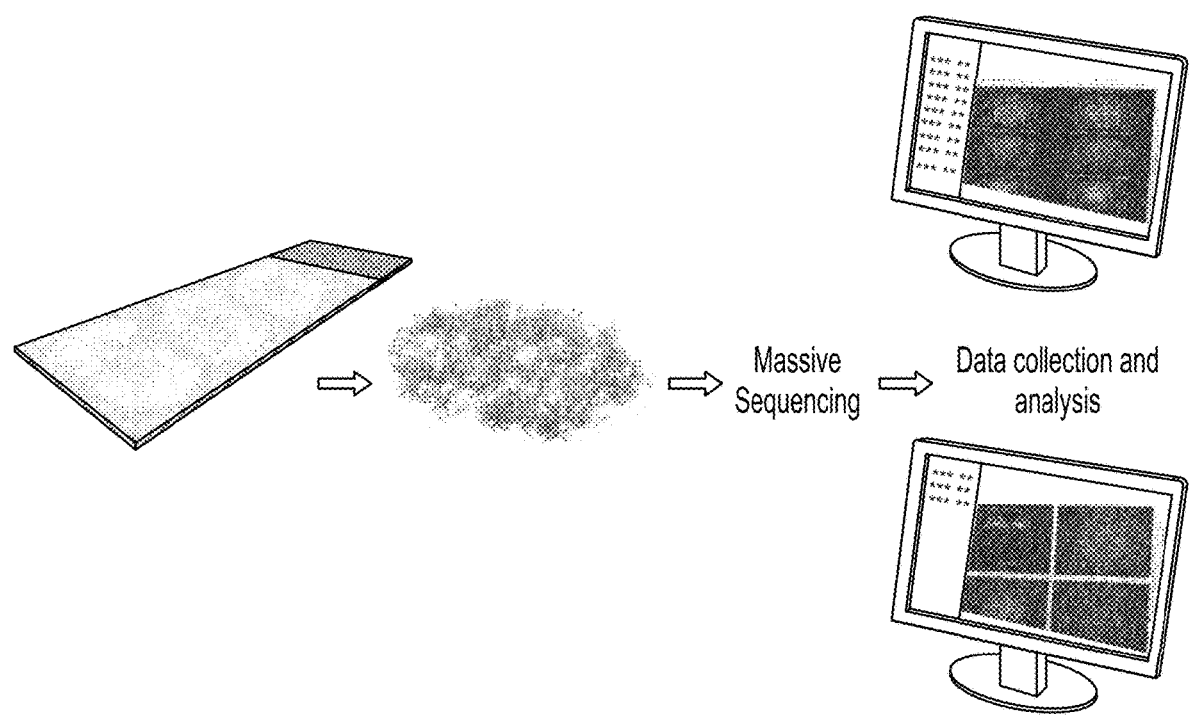
FIG. 2 shows the a schematic for the visualization of transcript abundance for corresponding tissue sections.
Figure 3:
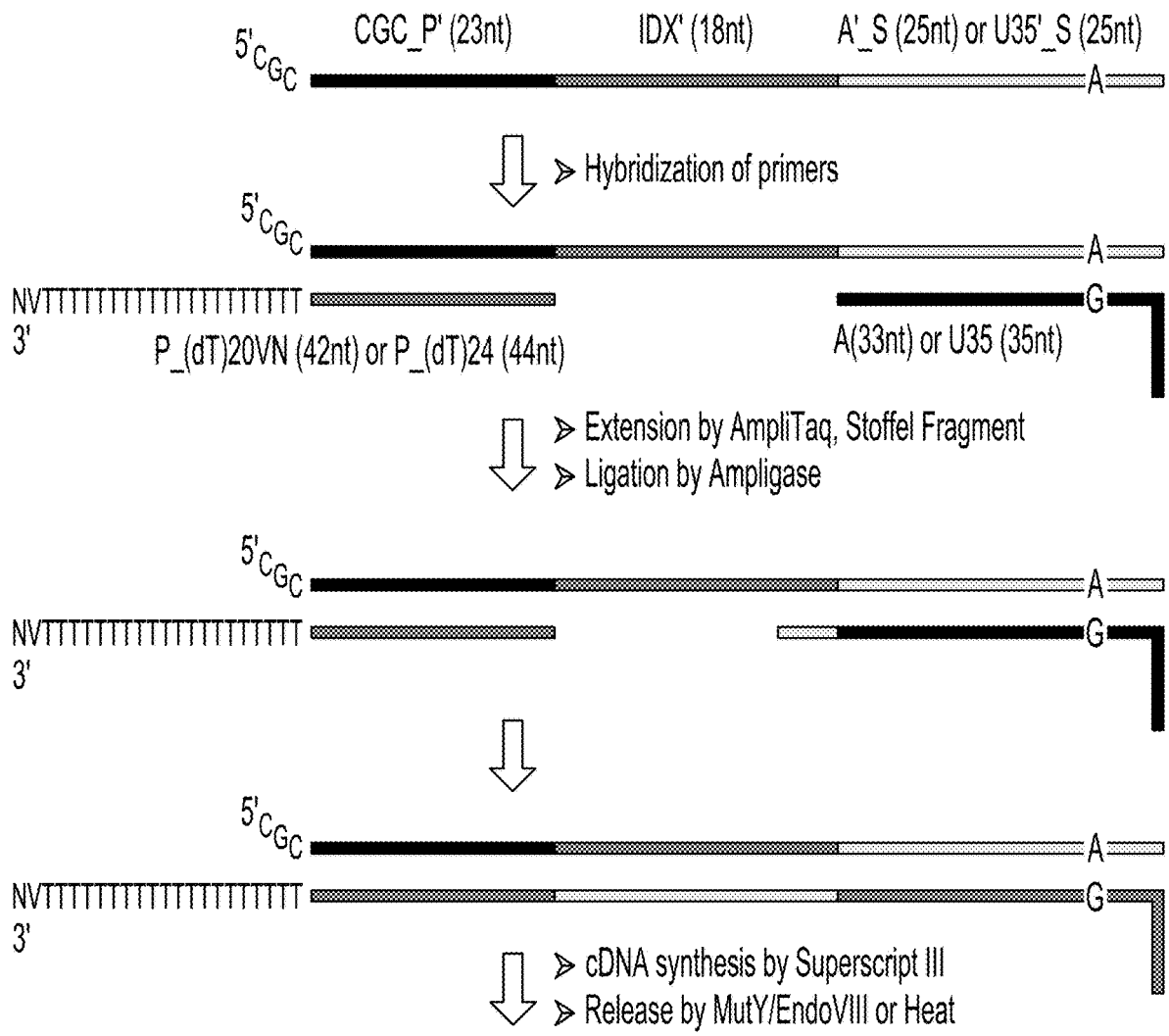
FIG. 3 shows 3' to 5' surface probe composition and synthesis of 5' to 3' oriented capture probes that are indirectly immobilized at the array surface.

The method is depicted in FIG. 3.

Tissue Preparation

The following experiments demonstrate how tissue sample sections may be prepared for use in the methods of the invention.

Preparation of Fresh Frozen Tissue and Sectioning onto Capture Probe Arrays

Fresh non-fixed mouse brain tissue was trimmed if necessary and frozen down in −40° C. cold isopentane and subsequently mounted for sectioning with a cryostat at 10 µm. A slice of tissue was applied onto each capture probe array to be used.

Preparation of Formalin-Fixed Paraffin-Embedded (FFPE) Tissue

Mouse brain tissue was fixed in 4% formalin at 4° C. for 24 h. After that it was incubated as follows: 3× incubation in 70% ethanol for 1 hour; 1× incubation in 80% ethanol for 1 hour; 1× incubation in 96% ethanol for 1 hour; 3× incubation in 100% ethanol for 1 hour; and 2× incubation in xylene at room temperature for 1 h.

The dehydrated samples were then incubated in liquid low melting paraffin 52-54° C. for up to 3 hours, during which the paraffin was changed once to wash out residual xylene. Finished tissue blocks were then stored at RT. Sections were then cut at 4 µm in paraffin with a microtome onto each capture probe array to be used.

The sections were dried at 37° C. on the array slides for 24 hours and stored at RT.

Deparaffinization of FFPE Tissue

Formalin fixed paraffinized mouse brain 10 µm sections attached to CodeLink slides were deparaffinised in xylene twice for: 10 min, 99.5% ethanol for 2 min; 96% ethanol for 2 min; 70% ethanol for 2 min; and were then air dried.

cDNA Synthesis

The following experiments demonstrate that mRNA captured on the array from the tissue sample sections may be used as template for cDNA synthesis.

cDNA Synthesis on Chip

A 16 well mask and Chip Clip slide holder from Whatman was attached to a CodeLink slide. The SuperScript™III One-step RT-PCR System with Platinum®Taq DNA Polymerase from Invitrogen was used when performing the cDNA synthesis. For each reaction 25 µl 2× reaction mix (SuperScript™III One-step RT-PCR System with Platinum®Taq DNA Polymerase, Invitrogen), 22.5 µl H₂O and 0.5 µl 100×BSA were mixed and heated to 50° C. SuperScript III/Platinum Taq enzyme mix was added to the reaction mix, 2 µl per reaction, and 50 µl of the reaction mix was added to each well on the chip. The chip was incubated at 50° C. for 30 min (Thermomixer Comfort, Eppendorf).

The reaction mix was removed from the wells and the slide was washed with: 2×SSC, 0.1% SDS at 50° C. for 10 min; 0.2×SSC at room temperature for 1 min; and 0.1×SSC at room temperature for 1 min. The chip was then spin dried.

In the case of FFPE tissue sections, the sections could now be stained and visualized before removal of the tissue, see below section on visualization.

Visualization

Hybridization of Fluorescent Marker Probes Prior to Staining

Prior to tissue application fluorescent marker probes were hybridized to features comprising marker oligonucleotides printed on the capture probe array. The fluorescent marker probes aid in the orientation of the resulting image after tissue visualization, making it possible to combine the image with the resulting expression profiles for individual capture probe "tag" (positional domain) sequences obtained after sequencing. To hybridize fluorescent probes a hybridization solution containing 4×SSC and 0.1% SDS, 2 µM detection probe (P) was incubated for 4 min at 50° C. Meanwhile the in-house array was attached to a ChipClip (Whatman). The array was subsequently incubated at 50° C. for 30 min at 300 rpm shake with 50 µL of hybridization solution per well.

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry.

General Histological Staining of FFPE Tissue Sections Prior to or Post cDNA Synthesis FFPE tissue sections immobilized on capture probe arrays were washed and rehydrated after deparaffinization prior to cDNA synthesis as described previously, or washed after cDNA synthesis as described previously. They are then treated as follows: incubate for 3 minutes in Hematoxylin; rinse with deionized water; incubate 5 minutes in tap water; rapidly dip 8 to 12 times in acid ethanol; rinse 2×1 minute in tap water; rinse 2 minutes in deionized water; incubate 30 seconds in Eosin; wash 3×5 minutes in 95% ethanol; wash 3×5 minutes in 100% ethanol; wash 3×10 minutes in xylene (can be done overnight); place coverslip on slides using DPX; dry slides in the hood overnight.

General Immunohistochemistry Staining of a Target Protein in FFPE Tissue Sections Prior to or Post cDNA Synthesis FFPE tissue sections immobilized on capture probe arrays were washed and rehydrated after deparaffinization prior to cDNA synthesis as described previously, or washed after cDNA synthesis as described previously. They were then treated as follows without being allowed to dry during the whole staining process: sections were incubated with primary antibody (dilute primary antibody in blocking solution comprising 1×Tris Buffered Saline (50 mM Tris, 150 mM NaCl, pH 7.6), 4% donkey serum and 0.1% triton-x) in a wet chamber overnight at RT; rinse three times with 1×TBS; incubate section with matching secondary antibody conjugated to a fluorochrome (FITC, Cy3 or Cy5) in a wet chamber at RT for 1 hour. Rinse 3× with 1×TBS, remove as much as possible of TBS and mount section with ProLong Gold+DAPI (Invitrogen) and analyze with fluorescence microscope and matching filter sets.

Removal of Residual Tissue

Frozen Tissue

For fresh frozen mouse brain tissue the washing step directly following cDNA synthesis was enough to remove the tissue completely.

FFPE Tissue

The slides with attached formalin fixed paraffinized mouse brain tissue sections were attached to ChipClip slide holders and 16 well masks (Whatman). For each 150 µl Proteinase K Digest Buffer from the RNeasy FFPE kit (Qiagen), 10 µl Proteinase K Solution (Qiagen) was added. 50 µl of the final mixture was added to each well and the slide was incubated at 56° C. for 30 min.

Capture Probe (cDNA) Release

Capture Probe Release with Uracil Cleaving USER Enzyme Mixture in PCR Buffer (Covalently Attached Probes)

A 16 well mask and CodeLink slide was attached to the ChipClip holder (Whatman). 50 µl of a mixture containing 1× FastStart High Fidelity Reaction Buffer with 1.8 mM MgCl2 (Roche), 200 µM dNTPs (New England Biolabs) and 0.1 U/1 µl USER Enzyme (New England Biolabs) was heated to 37° C. and was added to each well and incubated at 37° C. for 30 min with mixing (3 seconds at 300 rpm, 6 seconds at rest) (Thermomixer comfort; Eppendorf). The reaction mixture containing the released cDNA and probes was then recovered from the wells with a pipette.

Capture Probe Release with Uracil Cleaving USER Enzyme Mixture in TdT (Terminal Transferase) Buffer (Covalently Attached Probes)

50 µl of a mixture containing: 1×TdT buffer (20 mM Tris-acetate (pH 7.9), 50 mM Potassium Acetate and 10 mM Magnesium Acetate) (New England Biolabs, www.neb.com); 0.1 µg/µl BSA (New England Biolabs); and 0.1 U/µl USER Enzyme (New England Biolabs) was heated to 37° C. and was added to each well and incubated at 37° C. for 30 min with mixing (3 seconds at 300 rpm, 6 seconds at rest) (Thermomixer comfort; Eppendorf). The reaction mixture containing the released cDNA and probes was then recovered from the wells with a pipette.

Capture Probe Release with Boiling Hot Water (Covalently Attached Probes)

A 16 well mask and CodeLink slide was attached to the ChipClip holder (Whatman). 50 µl of 99° C. water was pipetted into each well. The 99° C. water was allowed to react for 30 minutes. The reaction mixture containing the released cDNA and probes was then recovered from the wells with a pipette.

Capture Probe Release with Heated PCR Buffer (Hybridized In Situ Synthesized Capture Probes, i.e. Capture Probes Hybridized to Surface Probes)

50 µl of a mixture containing: 1×TdT buffer (20 mM Tris-acetate (pH 7.9), 50 mM Potassium Acetate and 10 mM Magnesium Acetate) (New England Biolabs, www.neb.com); 0.1 µg/µl BSA (New England Biolabs); and 0.1 U/µl USER Enzyme (New England Biolabs) was preheated to 95° C. The mixture was then added to each well and incubated for 5 minutes at 95° C. with mixing (3 seconds at 300 rpm, 6 seconds at rest) (Thermomixer comfort; Eppendorf). The reaction mixture containing the released probes was then recovered from the wells.

Capture Probe Release with Heated TdT (Terminal Transferase) Buffer (Hybridized In Situ Synthesized Capture Probes, i.e. Capture Probes Hybridized to Surface Probes)

50 µl of a mixture containing: 1×TdT buffer (20 mM Tris-acetate (pH 7.9), 50 mM Potassium Acetate and 10 mM Magnesium Acetate) (New England Biolabs, www.neb.com); 0.1 µg/µl BSA (New England Biolabs); and 0.1 U/µl USER Enzyme (New England Biolabs) was preheated to 95° C. The mixture was then added to each well and incubated for 5 minutes at 95° C. with mixing (3 seconds at 300 rpm, 6 seconds at rest) (Thermomixer comfort; Eppendorf). The reaction mixture containing the released probes was then recovered from the wells.

Figure 4:
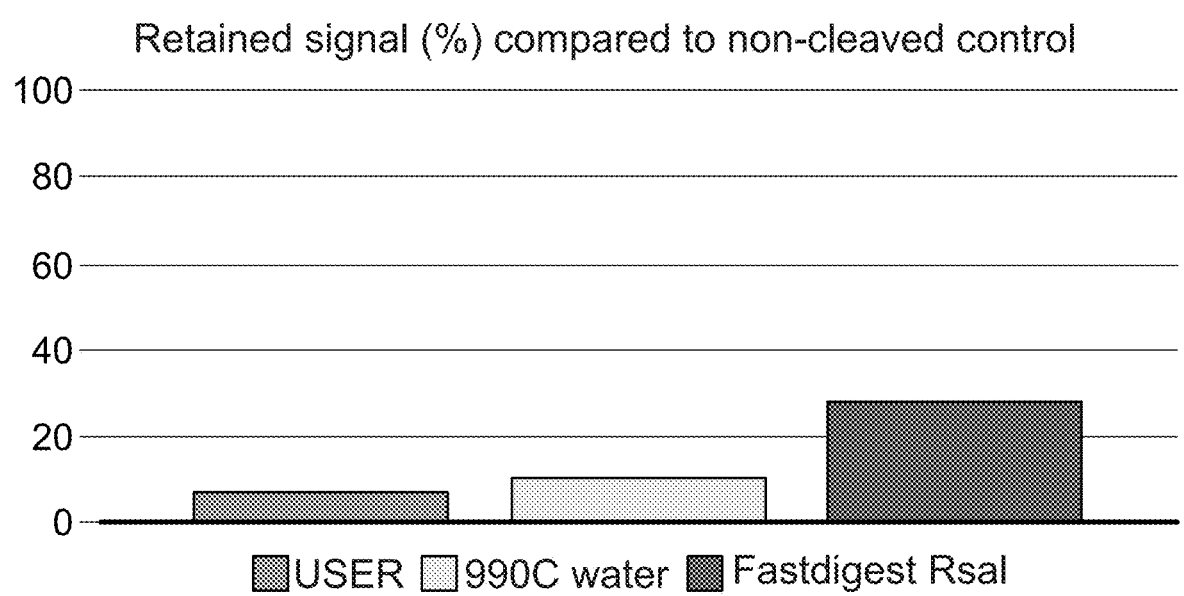
FIG. 4 shows a bar chart demonstrating the efficiency of enzymatic cleavage (USER or Rsal) from in-house manufactured arrays and by 99° C. water from Agilent manufactured arrays, as measured by hybridization of fluorescently labelled probes to the array surface after probe release.

The efficacy of treating the array with the USER enzyme and water heated to 99° C. can be seen in FIG. 3. Enzymatic cleavage using the USER enzyme and the Rsal enzyme was performed using the "in-house" arrays described above (FIG. 4). Hot water mediated release of DNA surface probes was performed using commercial arrays manufactured by Agilent (see FIG. 5).

Probe Collection and Linker Introduction

The experiments demonstrate that first strand cDNA released from the array surface may be modified to produce double stranded DNA and subsequently amplified.

Whole Transcriptome Amplification by the Picoplex Whole Genome Amplification Kit (Capture Probe Sequences Including Positional Domain (Tag) Sequences not Retained at the Edge of the Resulting dsDNA)

Capture probes were released with uracil cleaving USER enzyme mixture in PCR buffer (covalently attached capture probes) or with heated PCR buffer (hybridized in situ synthesized capture probes, i.e. capture probes hybridized to surface probes).

The released cDNA was amplified using the Picoplex (Rubicon Genomics) random primer whole genome amplification method, which was carried out according to manufacturers instructions.

Whole Transcriptome Amplification by dA Tailing with Terminal Transferase (TdT) (Capture Probe Sequences Including Positional Domain (Tag) Sequences Retained at the End of the Resulting dsDNA)

Capture probes were released with uracil cleaving USER enzyme mixture in TdT (terminal transferase) buffer (covalently attached capture probes) or with heated TdT (terminal transferase) buffer (hybridized in situ synthesized capture probes, i.e. capture probes hybridized to surface probes).

38 µl of cleavage mixture was placed in a clean 0.2 ml PCR tube. The mixture contained: 1×TdT buffer (20 mM Tris-acetate (pH 7.9), 50 mM Potassium Acetate and 10 mM Magnesium Acetate) (New England Biolabs, www.neb.com), 0.1 µg/µl BSA (New England Biolabs); 0.1 U/µl USER Enzyme (New England Biolabs) (not for heated release); released cDNA (extended from surface probes); and released surface probes. To the PCR tube, 0.5 µl RNase H (5 U/µl, final concentration of 0.06 U/µl), 1 µl TdT (20 U/µl, final concentration of 0.5 U/µl), and 0.5 µl dATPs (100 mM, final concentration of 1.25 mM), were added. For dA tailing, the tube was incubated in a thermocycler (Applied Biosystems) at 37° C. for 15 min followed by an inactivation of TdT at 70° C. for 10 min. After dA tailing, a PCR master mix was prepared. The mix contained: 1× Faststart HiFi PCR Buffer (pH 8.3) with 1.8 mM MgCl$_2$ (Roche); 0.2 mM of each dNTP (Fermentas); 0.2 µM of each primer, A (complementary to the amplification domain of the capture probe) and B_(dT)24 (Eurofins MWG Operon) (complementary to the poly-A tail to be added to the 3' end of the first cDNA strand); and 0.1 U/µl Faststart HiFi DNA polymerase (Roche). 23 µl of PCR Master mix was placed into nine clean 0.2 ml PCR tubes. 2 µl of dA tailing mixture were added to eight of the tubes, while 2 µl water (RNase/DNase free) was added to the last tube (negative control). PCR amplification was carried out with the following program: Hot start at 95° C. for 2 minutes, second strand synthesis at 50° C. for 2 minutes and 72° C. for 3 minutes, amplification with 30 PCR cycles at 95° C. for 30 seconds, 65° C. for 1 minutes, 72° C. for 3 minutes, and a final extension at 72° C. for 10 minutes.

Post-Reaction Cleanup and Analysis

Four amplification products were pooled together and were processed through a Qiaquick PCR purification column (Qiagen) and eluted into 30 µl EB (10 mM Tris-Cl, pH 8.5). The product was analyzed on a Bioanalyzer (Agilent). A DNA 1000 kit was used according to manufacturers instructions.

Sequencing

Illumina Sequencing dsDNA library for Illumina sequencing using sample indexing was carried out according to manufacturers instructions. Sequencing was carried out on an HiSeq2000 platform (Illumina).

Bioinformatics

Obtaining Digital Transcriptomic Information from Sequencing Data from Whole Transcriptome Libraries Amplified Using the dA Tailing Terminal Transferase Approach The sequencing data was sorted through the FastX toolkit FASTQ Barcode splitter tool into individual files for the respective capture probe positional domain (tag) sequences. Individually tagged sequencing data was then analyzed through mapping to the mouse genome with the Tophat mapping tool. The resulting SAM file was processed for transcript counts through the HTseq-count software.

Obtaining Digital Transcriptomic Information from Sequencing Data from Whole Transcriptome Libraries Amplified Using the Picoplex Whole Genome Amplification Kit Approach The sequencing data was converted from FASTQ format to FASTA format using the FastX toolkit FASTQ-to-FASTA converter. The sequencing reads was aligned to the capture probe positional domain (tag) sequences using Blastn and the reads with hits better than 1e$^{-6}$ to one of tag sequences were sorted out to individual files for each tag sequence respectively. The file of tag sequence reads was then aligned using Blastn to the mouse transcriptome, and hits were collected.

Combining Visualization Data and Expression Profiles

The expression profiles for individual capture probe positional domain (tag) sequences are combined with the spatial information obtained from the tissue sections through staining. Thereby the transcriptomic data from the cellular compartments of the tissue section can be analyzed in a directly comparative fashion, with the availability to distinguish distinct expression features for different cellular subtypes in a given structural context

EXAMPLE 2

FIGS. 8 to 12 show successful visualisation of stained FFPE mouse brain tissue (olfactory bulb) sections on top of a bar-coded transcriptome capture array, according to the general procedure described in Example 1. As compared with the experiment with fresh frozen tissue in Example 1, FIG. 8 shows better morphology with the FFPE tissue. FIGS. 9 and 10 show how tissue may be positioned on different types of probe density arrays.

EXAMPLE 3

Whole Transcriptome Amplification by Random Primer Second Strand Synthesis Followed by Universal Handle Amplification (Capture Probe Sequences Including Tag Sequences Retained at the End of the Resulting dsDNA)

Following capture probe release with uracil cleaving USER enzyme mixture in PCR buffer (covalently attached probes)

Or

Following capture probe release with heated PCR buffer (hybridized in situ synthesized capture probes)

1 µl RNase H (5 U/µl) was added to each of two tubes, final concentration of 0.12 U/µl, containing 40 µl 1× Faststart HiFi PCR Buffer (pH 8.3) with 1.8 mM MgCl$_2$ (Roche, www.roche-applied-science.com), 0.2 mM of each dNTP (Fermentas, www.fermentas.com), 0.1 µg/µl BSA (New England Biolabs, www.neb.com), 0.1 U/µl USER Enzyme (New England Biolabs), released cDNA (extended from surface probes) and released surface probes. The tubes were incubated at 37° C. for 30 min followed by 70° C. for 20 min in a thermo cycler (Applied Biosystems, www.appliedbiosystems.com). 1 µl Klenow Fragment (3' to 5' exo minus) (Illumina, www.illumina.com) and 1 µl handle coupled random primer (10 µM) (Eurofins MWG Operon, www.eurofinsdna.com) was added to the two tubes (B_R8 (octamer) to one of the tubes and B_R6 (hexamer) to the other tube), final concentration of 0.23 µM. The two tubes were incubated at 15° C. for 15 min, 25° C. for 15 min, 37° C. for 15 min and finally 75° C. for 20 min in a thermo cycler (Applied Biosystems). After the incubation, of each primer, A_P and B (10 µM) (Eurofins MWG Operon), was added to both tubes, final concentration of 0.22 µM each. 1 µl Faststart HiFi DNA polymerase (5 U/µl) (Roche) was also added to both tubes, final concentration of 0.11 U/µl. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes. After the amplification, 40 µl from each of the two tubes were purified with Qiaquick PCR purification columns (Qiagen, www.qiagen.com) and eluted into 30 µl EB (10 mM Tris-Cl, pH 8.5). The Purified products were analyzed with a Bioanalyzer (Agilent, www.home.agilent.com), DNA 7500 kit were used. The results are shown in FIGS. 13 and 14.

This Example demonstrates the use of random hexamer and random octamer second strand synthesis, followed by amplification to generate the population from the released cDNA molecules.

EXAMPLE 4

Amplification of ID-Specific and Gene Specific Products after cDNA Synthesis and Probe Collection Following capture probe release with uracil cleaving USER enzyme mixture in PCR buffer (covalently attached probes).

The cleaved cDNA was amplified in final reaction volumes of 10 µl. 7 µl cleaved template, 1 µl ID-specific forward primer (2 µM), 1 µl gene-specific reverse primer (2 µM) and 1 µl FastStart High Fidelity Enzyme Blend in 1.4×

FastStart High Fidelity Reaction Buffer with 1.8 mM MgCl$_2$ to give a final reaction of 10 µl with 1× FastStart High Fidelity Reaction Buffer with 1.8 mM MgCl$_2$ and 1 U FastStart High Fidelity Enzyme Blend. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes.

Primer sequences, resulting in a product of approximately 250 bp,

```
Beta-2 microglobulin (B2M) primer
5'-TGGGGGTGAGAATTGCTAAG-3'      (SEQ ID NO: 43)

ID-1 primer
5'-CCTTCTCCTTCTCCTTCACC-3'      (SEQ ID NO: 44)

ID-5 primer
5'-GTCCTCTATTCCGTCACCAT-3'      (SEQ ID NO: 45)

ID-20 primer
5'-CTGCTTCTTCCTGGAACTCA-3'      (SEQ ID NO: 46)
```

The results are shown in FIG. 15. This shows successful amplification of ID-specific and gene-specific products using two different ID primers (i.e. specific for ID tags positioned at different locations on the microarray and the same gene specific primer from a brain tissue covering all the probes. Accordingly this experiment establishes that products may be identified by an ID tag-specific or target nucleic acid specific amplification reaction. It is further established that different ID tags may be distinguished. A second experiment, with tissue covering only half of the ID probes (i.e. capture probes) on the array resulted in a positive result (PCR product) for spots that were covered with tissue.

EXAMPLE 5

Spatial Genomics

Background. The method has as its purpose to capture DNA molecules from a tissue sample with retained spatial resolution, making it possible to determine from what part of the tissue a particular DNA fragment stems.

Method. The principle of the method is to use microarrays with immobilized DNA oligos (capture probes) carrying spatial labeling tag sequences (positional domains). Each feature of oligos of the microarray carries a 1) a unique labeling tag (positional domain) and 2) a capture sequence (capture domain). Keeping track of where which labeling tag is geographically placed on the array surface makes it possible to extract positional information in two dimensions from each labeling tag. Fragmented genomic DNA is added to the microarray, for instance through the addition of a thin section of FFPE treated tissue. The genomic DNA in this tissue section is pre-fragmented due to the fixation treatment.

Once the tissue slice has been placed on the array, a universal tailing reaction is carried out through the use of a terminal transferase enzyme. The tailing reaction adds polydA tails to the protruding 3' ends of the genomic DNA fragments in the tissue. The oligos on the surface are blocked from tailing by terminal transferase through a hybridized and 3' blocked polydA probe.

Following the terminal transferase tailing, the genomic DNA fragments are able to hybridize to the spatially tagged oligos in their vicinity through the polydA tail meeting the polydT capture sequence on the surface oligos. After hybridization is completed a strand displacing polymerase such as Klenow exo-can use the oligo on the surface as a primer for creation of a new DNA strand complementary to the hybridized genomic DNA fragment. The new DNA strand will now also contain the positional information of the surface oligo's labeling tag.

As a last step the newly generated labeled DNA strands are cleaved from the surface through either enzymatic means, denaturation or physical means. The strands are then collected and can be subjected to downstream amplification of the entire set of strands through introduction of universal handles, amplification of specific amplicons, and/or sequencing.

FIG. 16 is a schematic illustration of this process.

Materials and Methods

Preparation of In-House Printed Microarray with 5' to 3' Oriented Probes

20 DNA-capture oligos with individual tag sequences (Table 1) were spotted on glass slides to function as capture probes. The probes were synthesized with a 5'-terminus amino linker with a C6 spacer. All probes where synthesized by Sigma-Aldrich (St. Louis, Mo., USA). The DNA-capture probes were suspended at a concentration of 20 µM in 150 mM sodium phosphate, pH 8.5 and were spotted using a Nanoplotter NP2.1/E (Gesim, Grosserkmannsdorf, Germany) onto CodeLink™ Activated microarray slides (7.5 cm×2.5 cm; Surmodics, Eden Prairie, Minn., USA). After printing, surface blocking was performed according to the manufacturers instructions. The probes were printed in 16 identical arrays on the slide, and each array contained a pre-defined printing pattern. The 16 sub-arrays were separated during hybridization by a 16-pad mask (ChipClip™ Schleicher & Schuell BioScience, Keene, N.H., USA).

Preparation of In-House Printed Microarray with 3' to 5' Oriented Probes and Synthesis of 5' to 3' Oriented Capture Probes Printing of oligos was performed as in the case with 5' to 3' oriented probes above.

To hybridize primers for capture probe synthesis hybridization solution containing 4×SSC and 0.1% SDS, 2 µM extension primer (A_primer) and 2 µM thread joining primer (p_poly_dT) was incubated for 4 min at 50° C. Meanwhile the in-house array was attached to a ChipClip (Whatman). The array was subsequently incubated at 50° C. for 30 min at 300 rpm shake with 50 µL of hybridization solution per well.

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry and placed back in the ChipClip.

For extension and ligation 50 µL of enzyme mix containing 10×Ampligase buffer, 2.5 U AmpliTaq DNA Polymerase Stoffel Fragment (Applied Biosystems), 10 U Ampligase (Epicentre Biotechnologies), dNTPs 2 mM each (Fermentas) and water, is pipetted to each well. The array is subsequently incubated at 55° C. for 30 min. After incubation the array is washed according to previously described array washing method but the first step has the duration of 10 min instead of 6 min.

Hybridization of polydA Probe for Protection of Surface Oligo Capture Sequences from dA Tailing To hybridize a 3'-biotin blocked polydA probe for protection of the surface oligo capture sequences a hybridization solution containing 4×SSC and 0.1% SDS, 2 µM 3'bio-polydA was incubated for 4 min at 50° C. Meanwhile the in-house array was attached to a ChipClip (Whatman). The array was subsequently incubated at 50° C. for 30 min at 300 rpm shake with 50 μL of hybridization solution per well.

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry and placed back in the ChipClip.

Preparation of Formalin-Fixed Paraffin-Embedded (FFPE) Tissue

Mouse brain tissue was fixed in 4% formalin at 4° C. for 24 h. After that it was incubated as follows: 3× incubation in 70% ethanol for 1 hour, 1× incubation in 80% ethanol for 1 hour, 1× incubation in 96% ethanol for 1 hour, 3× incubation in 100% ethanol for 1 hour, 2× incubation in xylene at room temperature for 1 h.

The dehydrated samples were then incubated in liquid low melting paraffin 52-54° C. for up to 3 hours, during which the paraffin in changed once to wash out residual xylene. Finished tissue blocks were then stored at RT. Sections were then cut at 4 μm in paraffin with a microtome onto each capture probe array to be used.

The sections are dried at 37° C. on the array slides for 24 hours and store at RT.

Deparaffinization of FFPE Tissue

Formalin fixed paraffinized mouse brain 10 μm sections attached to CodeLink slides were deparaffinised in xylene twice for 10 min, 99.5% ethanol for 2 min, 96% ethanol for 2 min, 70% ethanol for 2 min and were then air dried.

Universal Tailing of Genomic DNA

For dA tailing a 50 μl reaction mixture containing 1×TdT buffer (20 mM Tris-acetate (pH 7.9), 50 mM Potassium Acetate and 10 mM Magnesium Acetate) (New England Biolabs, www.neb.com), 0.1 μg/μl BSA (New England Biolabs), 1 μl TdT (20 U/μl) and 0.5 μl dATPs (100 mM) was prepared. The mixture was added to the array surface and the array was incubated in a thermo cycler (Applied Biosystems) at 37° C. for 15 min followed by an inactivation of TdT at 70° C. for 10 min. After this the temperature was lowered to 50° C. again to allow for hybridization of dA tailed genomic fragments to the surface oligo capture sequences.

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry.

Extension of Labeled DNA

A 50 μl reaction mixture containing 50 μl of a mixture containing 1× Klenow buffer, 200 μM dNTPs (New England Biolabs) and 1 μl Klenow Fragment (3' to 5' exo minus) and was heated to 37° C. and was added to each well and incubated at 37° C. for 30 min with mixing (3 s. 300 rpm, 6 s. rest) (Thermomixer comfort; Eppendorf).

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry.

Removal of Residual Tissue

The slides with attached formalin fixed paraffinized mouse brain tissue sections were attached to ChipClip slide holders and 16 well masks (Whatman). For each 150 μl Proteinase K Digest Buffer from the RNeasy FFPE kit (Qiagen) 10 μl Proteinase K Solution (Qiagen) was added. 50 μl of the final mixture was added to each well and the slide was incubated at 56° C. for 30 min.

Capture Probe Release with Uracil Cleaving USER Enzyme Mixture in PCR Buffer (Covalently Attached Probes)

A 16 well mask and CodeLink slide was attached to the ChipClip holder (Whatman). 50 μl of a mixture containing 1× FastStart High Fidelity Reaction Buffer with 1.8 mM $MgCl_2$ (Roche), 200 μM dNTPs (New England Biolabs) and 0.1 U/1 μl USER Enzyme (New England Biolabs) was heated to 37° C. and was added to each well and incubated at 37° C. for 30 min with mixing (3 s. 300 rpm, 6 s. rest) (Thermomixer comfort; Eppendorf). The reaction mixture containing the released cDNA and probes was then recovered from the wells with a pipette.

Amplification of ID-Specific and Gene Specific Products after Synthesis of Labelled DNA and Probe Collection Following capture probe release with uracil cleaving USER enzyme mixture in PCR buffer (covalently attached probes).

The cleaved DNA was amplified in final reaction volumes of 10 μl. 7 μl cleaved template, 1 μl ID-specific forward primer (2 μM), 1 μl gene-specific reverse primer (2 μM) and 1 μl FastStart High Fidelity Enzyme Blend in 1.4× FastStart High Fidelity Reaction Buffer with 1.8 mM $MgCl_2$ to give a final reaction of 10 μl with 1× FastStart High Fidelity Reaction Buffer with 1.8 mM $MgCl_2$ and 1 U FastStart High Fidelity Enzyme Blend. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes.

Whole Genome Amplification by Random Primer Second Strand Synthesis Followed by Universal Handle Amplification (Capture Probe Sequences Including Tag Sequences Retained at the End of the Resulting dsDNA)

Following capture probe release with uracil cleaving USER enzyme mixture in PCR buffer (covalently attached probes).

A reaction mixture containing 40 μl 1× Faststart HiFi PCR Buffer (pH 8.3) with 1.8 mM $MgCl_2$ (Roche, www.roche-applied-science.com), 0.2 mM of each dNTP (Fermentas, www.fermentas.com), 0.1 μg/μl BSA (New England Biolabs, www.neb.com), 0.1 U/μl USER Enzyme (New England Biolabs), released DNA (extended from surface probes) and released surface probes. The tubes were incubated at 37° C. for 30 min followed by 70° C. for 20 min in a thermo cycler (Applied Biosystems, www.appliedbiosystems.com). 1 μl Klenow Fragment (3' to 5' exo minus) (Illumina, www.illumina.com) and 1 μl handle coupled random primer (10 μM) (Eurofins MWG Operon, www.eurofinsdna.com) was added to the tube. The tube was incubated at 15° C. for 15 min, 25° C. for 15 min, 37° C. for 15 min and finally 75° C. for 20 min in a thermo cycler (Applied Biosystems). After the incubation, 1 μl of each primer, A_P and B (10 μM) (Eurofins MWG Operon), was added to the tube. 1 μl Faststart HiFi DNA polymerase (5 U/μ1) (Roche) was also added to the tube. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes. After the amplification, 40 μl from the tube was purified with Qiaquick PCR purification columns (Qiagen, www.qiagen-.com) and eluted into 30 μl EB (10 mM Tris-Cl, pH 8.5). The Purified product was analyzed with a Bioanalyzer (Agilent, www.home.agilent.com), DNA 7500 kit were used.

Visualization

Hybridization of Fluorescent Marker Probes Prior to Staining

Prior to tissue application fluorescent marker probes are hybridized to designated marker sequences printed on the capture probe array. The fluorescent marker probes aid in the orientation of the resulting image after tissue visualization, making it possible to combine the image with the resulting expression profiles for individual capture probe tag sequences obtained after sequencing. To hybridize fluorescent probes a hybridization solution containing 4×SSC and 0.1% SDS, 2 μM detection probe (P) was incubated for 4 min at 50° C. Meanwhile the in-house array was attached to a ChipClip (Whatman). The array was subsequently incubated at 50° C. for 30 min at 300 rpm shake with 50 μL of hybridization solution per well.

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry.

General Histological Staining of FFPE Tissue Sections Prior to or Post Synthesis of Labeled DNA FFPE tissue sections immobilized on capture probe arrays are washed and rehydrated after deparaffinization prior to synthesis of labeled as described previously, or washed after synthesis of labeled DNA as described previously. They are then treated as follows: incubate for 3 minutes in Hematoxylin, rinse with deionized water, incubate 5 minutes in tap water, rapidly dip 8 to 12 times in acid ethanol, rinse 2×1 minute in tap water, rinse 2 minutes in deionized water, incubate 30 seconds in Eosin, wash 3×5 minutes in 95% ethanol, wash 3×5 minutes in 100% ethanol, wash 3×10 minutes in xylene (can be done overnight), place coverslip on slides using DPX, dry slides in the hood overnight.

General Immunohistochemistry Staining of a Target Protein in FFPE Tissue Sections Prior to or Post Synthesis of Labeled DNA FFPE tissue sections immobilized on capture probe arrays are washed and rehydrated after deparaffinization prior to synthesis of labeled DNA as described previously, or washed after synthesis of labeled DNA as described previously. They are then treated as follows without being let to dry during the whole staining process: Dilute primary antibody in blocking solution (1×TBS (Tris Buffered Saline (50 mM Tris, 150 mM NaCl, pH 7.6), 4% donkey serum, 0.1% triton-x), incubate sections with primary antibody in a wet chamber overnight at RT, rinse 3× with 1×TBS, incubate section with matching secondary antibody conjugated to a fluorochrome (FITC, Cy3 or Cy5) in a wet chamber at RT for 1 h, Rinse 3× with 1×TBS, remove as much as possible of TBS and mount section with ProLong Gold+DAPI (Invitrogen) and analyze with fluorescence microscope and matching filter sets.

EXAMPLE 6

This experiment was conducted following the principles of Example 5, but using fragmented genomic DNA on the array rather than tissue. The genomic DNA was pre-fragmented to a mean size of 200 bp and 700 bp respectively. This experiment shows that the principle works. Fragmented genomic DNA is very similar to FFPE tissue.

Amplification of Internal Gene Specific Products after Synthesis of Labelled DNA and Probe Collection Following capture probe release with uracil cleaving USER enzyme mixture in PCR buffer (covalently attached probes) containing 1× FastStart High Fidelity Reaction Buffer with 1.8 mM MgCl$_2$ (Roche), 200 μM dNTPs (New England Biolabs) and 0.1 U/1 μl USER Enzyme (New England Biolabs).

The cleaved DNA was amplified in a final reaction volume of 50 μl. To 47 μl cleaved template was added 1 μl ID-specific forward primer (10 μM), 1 μl gene-specific reverse primer (10 μM) and 1 μl FastStart High Fidelity Enzyme Blend. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes.

Amplification of Label-Specific and Gene Specific Products after Synthesis of Labelled DNA and Probe Collection Following capture probe release with uracil cleaving USER enzyme mixture in PCR buffer (covalently attached probes) containing 1× FastStart High Fidelity Reaction Buffer with 1.8 mM MgCl$_2$ (Roche), 200 μM dNTPs (New England Biolabs) and 0.1 U/1 μl USER Enzyme (New England Biolabs).

The cleaved DNA was amplified in a final reaction volume of 50 μl. To 47 μl cleaved template was added 1 μl label-specific forward primer (10 μM), 1 μl gene-specific reverse primer (10 μM) and 1 μl FastStart High Fidelity Enzyme Blend. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes.

Forward—Genomic DNA Human Primer
5'-GACTGCTCTTTTCACCCATC-3' (SEQ ID NO: 47)
Reverse—Genomic DNA Human Primer
5'-GGAGCTGCTGGTGCAGGG-3' (SEQ ID NO: 48)
P—Label Specific Primer
5'-ATCTCGACTGCCACTCTGAA-3' (SEQ ID NO: 49)

The results are shown in FIGS. 17 to 20. The Figures show internal products amplified on the array—the detected peaks in FIGS. 17 and 18 are of the expected size. This thus demonstrates that genomic DNA may be captured and amplified. In FIGS. 19 and 20, the expected product is a smear given that the random fragmentation and terminal transferase labeling of genomic DNA will generate a very diverse sample pool.

EXAMPLE 7

Alternative Synthesis of 5' to 3' Oriented Capture Probes Using Polymerase Extension and Terminal Transferase Tailing To hybridize primers for capture probe synthesis hybridization solution containing 4×SSC and 0.1% SDS and 2 μM extension primer (A_primer) was incubated for 4 min at 50° C. Meanwhile the in-house array (see Example 1) was attached to a ChipClip (Whatman). The array was subsequently incubated at 50° C. for 30 min at 300 rpm shake with 50 μL of hybridization solution per well.

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry and placed back in the ChipClip.

1 μl Klenow Fragment (3' to 5' exo minus) (Illumina, www.illumina.com) together with 10× Klenow buffer, dNTPs 2 mM each (Fermentas) and water, was mixed into a 50 μl reaction and was pipetted into each well.

The array was incubated at 15° C. for 15 min, 25° C. for 15 min, 37° C. for 15 min and finally 75° C. for 20 min in an Eppendorf Thermomixer.

After incubation, the array was removed from the ChipClip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry and placed back in the ChipClip.

For dT tailing a 50 µl reaction mixture containing 1×TdT buffer (20 mM Tris-acetate (pH 7.9), 50 mM Potassium Acetate and 10 mM Magnesium Acetate) (New England Biolabs, www.neb.com), 0.1 µg/µl BSA (New England Biolabs), 0.5 µl RNase H (5 U/µ1), 1 µl TdT (20 U/µl) and 0.5 µl dTTPs (100 mM) was prepared. The mixture was added to the array surface and the array was incubated in a thermo cycler (Applied Biosystems) at 37° C. for 15 min followed by an inactivation of TdT at 70° C. for 10 min.

EXAMPLE 8

Spatial transcriptomics using 5' to 3' high probe density arrays and formalin-fixed frozen (FF-frozen) tissue with USER system cleavage and amplification via terminal transferase Array Preparation Pre-fabricated high-density microarrays chips were ordered from Roche-Nimblegen (Madison, Wis., USA). Each capture probe array contained 135,000 features of which 132,640 features carried a capture probe comprising a unique ID-tag sequence (positional domain) and a capture region (capture domain). Each feature was 13×13 µm in size. The capture probes were composed 5' to 3' of a universal domain containing five dUTP bases (a cleavage domain) and a general amplification domain, an ID tag (positional domain) and a capture region (capture domain) (FIG. 22 and Table 2). Each array was also fitted with a frame of marker probes (FIG. 23) carrying a generic 30 bp sequence (Table 2) to enable hybridization of fluorescent probes to help with orientation during array visualization.

Tissue Preparation—Preparation of Formalin-Fixed Frozen Tissue

The animal (mouse) was perfused with 50 ml PBS and 100 ml 4% formalin solution. After excision of the olfactory bulb, the tissue was put into a 4% formalin bath for post-fixation for 24 hrs. The tissue was then sucrose treated in 30% sucrose dissolved in PBS for 24 hrs to stabilize morphology and to remove excess formalin. The tissue was frozen at a controlled rate down to −40° C. and kept at −20° C. between experiments. Similar preparation of tissue post-fixed for 3 hrs or without post-fixation was carried out for a parallel specimen. Perfusion with 2% formalin without post-fixation was also used successfully. Similarly the sucrose treatment step could be omitted. The tissue was mounted into a cryostat for sectioning at 10 µm. A slice of tissue was applied onto each capture probe array to be used. Optionally for better tissue adherence, the array chip was placed at 50° C. for 15 minutes.

Optional Control—Total RNA Preparation from Sectioned Tissue

Total RNA was extracted from a single tissue section (10 µm) using the RNeasy FFPE kit (Qiagen) according to manufacturers instructions. The total RNA obtained from the tissue section was used in control experiments for a comparison with experiments in which the RNA was captured on the array directly from the tissue section. Accordingly, in the case where totalRNA was applied to the array the staining, visualization and degradation of tissue steps were omitted.

On-Chip Reactions

The hybridization of marker probe to the frame probes, reverse transcription, nuclear staining, tissue digestion and probe cleavage reactions were all performed in a 16 well silicone gasket (Arraylt, Sunnyvale, Calif., USA) with a reaction volume of 50 µl per well. To prevent evaporation, the cassettes were covered with plate sealers (In Vitro AB, Stockholm, Sweden).

Optional—Tissue Permeabilization Prior to cDNA Synthesis

For permeabilization using Proteinase K, proteinase K (Qiagen, Hilden, Germany) was diluted to 1 µg/ml in PBS. The solution was added to the wells and the slide incubated at room temperature for 5 minutes, followed by a gradual increase to 80° C. over 10 minutes. The slide was washed briefly in PBS before the reverse transcription reaction.

Alternatively for permeabilization using microwaves, after tissue attachment, the slide was placed at the bottom of a glass jar containing 50 ml 0.2×SSC (Sigma-Aldrich) and was heated in a microwave oven for 1 minute at 800 W. Directly after microwave treatment the slide was placed onto a paper tissue and was dried for 30 minutes in a chamber protected from unnecessary air exposure. After drying, the slide was briefly dipped in water (RNase/DNase free) and finally spin-dried by a centrifuge before cDNA synthesis was initiated.

cDNA Synthesis

For the reverse transcription reaction the SuperScript III One-Step RT-PCR System with Platinum Taq (Life Technologies/Invitrogen, Carlsbad, Calif., USA) was used. Reverse transcription reactions contained 1× reaction mix, 1×BSA (New England Biolabs, Ipswich, Mass., USA) and 2 µl SuperScript III RT/Platinum Taq mix in a final volume of 50 µl. This solution was heated to 50° C. before application to the tissue sections and the reaction was performed at 50° C. for 30 minutes. The reverse transcription solution was subsequently removed from the wells and the slide was allowed to air dry for 2 hours.

Tissue Visualization

After cDNA synthesis, nuclear staining and hybridization of the marker probe to the frame probes (probes attached to the array substrate to enable orientation of the tissue sample on the array) was done simultaneously. A solution with DAPI at a concentration of 300 nM and marker probe at a concentration of 170 nM in PBS was prepared. This solution was added to the wells and the slide was incubated at room temperature for 5 minutes, followed by brief washing in PBS and spin drying.

Alternatively the marker probe was hybridized to the frame probes prior to placing the tissue on the array. The marker probe was then diluted to 170 nM in hybridization buffer (4×SSC, 0.1% SDS). This solution was heated to 50° C. before application to the chip and the hybridization was performed at 50° C. for 30 minutes at 300 rpm. After hybridization, the slide was washed in 2×SSC, 0.1% SDS at 50° C. and 300 rpm for 10 minutes, 0.2×SSC at 300 rpm for 1 minute and 0.1×SSC at 300 rpm for 1 minute. In that case the staining solution after cDNA synthesis only contained the nuclear DAPI stain diluted to 300 nM in PBS. The solution was applied to the wells and the slide was incubated at room temperature for 5 minutes, followed by brief washing in PBS and spin drying.

The sections were microscopically examined with a Zeiss Axio Imager Z2 and processed with MetaSystems software.

Tissue Removal

The tissue sections were digested using Proteinase K diluted to 1.25 µg/µl in PKD buffer from the RNeasy FFPE Kit (both from Qiagen) at 56° C. for 30 minutes with an interval mix at 300 rpm for 3 seconds, then 6 seconds rest. The slide was subsequently washed in 2×SSC, 0.1% SDS at 50° C. and 300 rpm for 10 minutes, 0.2×SSC at 300 rpm for 1 minute and 0.1×SSC at 300 rpm for 1 minute.

Probe Release

The 16-well Hybridization Cassette with silicone gasket (Arraylt) was preheated to 37° C. and attached to the Nimblegen slide. A volume of 50 µl of cleavage mixture preheated to 37° C., consisting of Lysis buffer at an unknown concentration (Takara), 0.1 U/µl USER Enzyme (NEB) and 0.1 µg/µl BSA was added to each of wells containing surface immobilized cDNA. After removal of bubbles the slide was sealed and incubated at 37° C. for 30 minutes in a Thermomixer comfort with cycled shaking at 300 rpm for 3 seconds with 6 seconds rest in between. After the incubation 45 µl cleavage mixture was collected from each of the used wells and placed into 0.2 ml PCR tubes (FIG. 24).

Library Preparation

Exonuclease Treatment

After cooling the solutions on ice for 2 minutes, Exonuclease I (NEB) was added, to remove unextended cDNA probes, to a final volume of 46.2 µl and a final concentration of 0.52 U/µl. The tubes were incubated in a thermo cycler (Applied Biosystems) at 37° C. for 30 minutes followed by inactivation of the exonuclease at 80° C. for 25 minutes.

dA-Tailing by Terminal Transferase

After the exonuclease step, 45 µl polyA-tailing mixture, according to manufacturers instructions consisting of TdT Buffer (Takara), 3 mM dATP (Takara) and manufacturers TdT Enzyme mix (TdT and RNase H) (Takara), was added to each of the samples. The mixtures were incubated in a thermocycler at 37° C. for 15 minutes followed by inactivation of TdT at 70° C. for 10 minutes.

Second-Strand Synthesis and PCR-Amplification

After dA-tailing, 23 µl PCR master mix was placed into four new 0.2 ml PCR tubes per sample, to each tube 2 µl sample was added as a template. The final PCRs consisted of 1× Ex Taq buffer (Takara), 200 µM of each dNTP (Takara), 600 nM A_primer (MWG), 600 nM B_dT20VN_primer (MWG) and 0.025 U/µl Ex Taq polymerase (Takara)(Table 2). A second cDNA strand was created by running one cycle in a thermocycler at 95° C. for 3 minutes, 50° C. for 2 minutes and 72° C. for 3 minutes. Then the samples were amplified by running 20 cycles (for library preparation) or 30 cycles (to confirm the presence of cDNA) at 95° C. for 30 seconds, 67° C. for 1 minute and 72° C. for 3 minutes, followed by a final extension at 72° C. for 10 minutes.

Library Cleanup

After amplification, the four PCRs (100 µl) were mixed with 500 µl binding buffer (Qiagen) and placed in a Qiaquick PCR purification column (Qiagen) and spun for 1 minute at 17,900×g in order to bind the amplified cDNA to the membrane. The membrane was then washed with wash buffer (Qiagen) containing ethanol and finally eluted into 50 µl of 10 mM Tris-Cl, pH 8.5.

The purified and concentrated sample was further purified and concentrated by CA-purification (purification by superparamagnetic beads conjugated to carboxylic acid) with an MBS robot (Magnetic Biosolutions). A final PEG concentration of 10% was used in order to remove fragments below 150-200 bp. The amplified cDNA was allowed to bind to the CA-beads (Invitrogen) for 10 min and were then eluted into 15 µl of 10 mM Tris-Cl, pH 8.5.

Library Quality Analysis

Samples amplified for 30 cycles were analyzed with an Agilent Bioanalyzer (Agilent) in order to confirm the presence of an amplified cDNA library, the DNA High Sensitivity kit or DNA 1000 kit were used depending on the amount of material.

Sequencing Library Preparation

Library Indexing

Samples amplified for 20 cycles were used further to prepare sequencing libraries. An index PCR master mix was prepared for each sample and 23 µl was placed into six 0.2 ml tubes. 2 µl of the amplified and purified cDNA was added to each of the six PCRs as template making the PCRs containing 1× Phusion master mix (Fermentas), 500 nM InPE1.0 (Illumine), 500 nM Index 1-12 (Illumine), and 0.4 nM InPE2.0 (Illumine). The samples were amplified in a thermocycler for 18 cycles at 98° C. for 30 seconds, 65° C. for 30 seconds and 72° C. for 1 minute, followed by a final extension at 72° C. for 5 minutes.

Sequencing Library Cleanup

After amplification, the six PCRs (150 µl) were mixed with 750 µl binding buffer and placed in a Qiaquick PCR purification column and spun for 1 minute at 17,900×g in order to bind the amplified cDNA to the membrane (because of the large sample volume (900 µl), the sample was split in two (each 450 µl) and was bound in two separate steps). The membrane was then washed with wash buffer containing ethanol and finally eluted into 50 µl of 10 mM Tris-Cl, pH 8.5.

The purified and concentrated sample was further purified and concentrated by CA-purification with an MBS robot. A final PEG concentration of 7.8% was used in order to remove fragments below 300-350 bp. The amplified cDNA was allowed to bind to the CA-beads for 10 min and were then eluted into 15 µl of 10 mM Tris-Cl, pH 8.5. Samples were analyzed with an Agilent Bioanalyzer in order to confirm the presence and size of the finished libraries, the DNA High Sensitivity kit or DNA 1000 kit were used according to manufacturers instructions depending on the amount of material (FIG. 25).

Sequencing

The libraries were sequenced on the Illumine Hiseq2000 or Miseq depending on desired data throughput according to manufacturers instructions. Optionally for read 2, a custom sequencing primer B_r2 was used to avoid sequencing through the homopolymeric stretch of 20 T.

Data Analysis

Read 1 was trimmed 42 bases at 5' end. Read 2 was trimmed 25 bases at 5' end (optionally no bases were trimmed from read 2 if the custom primer was used). The reads were then mapped with bowtie to the repeat masked *Mus musculus* 9 genome assembly and the output was formatted in the SAM file format. Mapped reads were extracted and annotated with UCSC refGene gene annotations. Indexes were retrieved with 'indexFinder' (an inhouse software for index retrieval). A mongo DB database was then created containing information about all caught transcripts and their respective index position on the chip.

A matlab implementation was connected to the database and allowed for spatial visualization and analysis of the data (FIG. 26).

Optionally the data visualization was overlaid with the microscopic image using the fluorescently labelled frame probes for exact alignment and enabling spatial transcriptomic data extraction.

EXAMPLE 9

Spatial Transcriptomics Using 3' to 5' High Probe Density Arrays and FFPE Tissue with MutY System Cleavage and Amplification Via TdT Array Preparation Pre-fabricated high-density microarrays chips were ordered from Roche-Nimblegen (Madison, Wis., USA). Each used capture probe array contained 72k features out of which 66,022 contained a unique ID-tag complementary sequence. Each feature was 16×16 µm in size. The capture probes were composed 3' to 5' in the same way as the probes used for the in-house printed 3' to 5' arrays with the exception to 3 additional bases being added to the upper (P') general handle of the probe to make it a long version of P', LP' (Table 2). Each array was also fitted with a frame of probes carrying a generic 30 bp sequence to enable hybridization of fluorescent probes to help with orientation during array visualization.

Synthesis of 5' to 3' Oriented Capture Probes

The synthesis of 5' to 3' oriented capture probes on the high-density arrays was carried out as in the case with in-house printed arrays, with the exception that the extension and ligation steps were carried out at 55° C. for 15 mins followed by 72° C. for 15 mins. The A-handle probe (Table 2) included an A/G mismatch to allow for subsequent release of probes through the MutY enzymatic system described below. The P-probe was replaced by a longer LP version to match the longer probes on the surface.

Preparation of Formalin-Fixed Paraffin-Embedded Tissue and Deparaffinization

This was carried out as described above in the in-house protocol.

cDNA Synthesis and Staining cDNA synthesis and staining was carried out as in the protocol for 5' to 3' oriented high-density Nimblegen arrays with the exception that biotin labeled dCTPs and dATPs were added to the cDNA synthesis together with the four regular dNTPs (each was present at 25× times more than the biotin labeled ones).

Tissue Removal

Tissue removal was carried out in the same way as in the protocol for 5' to 3' oriented high-density Nimblegen arrays described in Example 8.

Probe Cleavage by MutY

A 16-well Incubation chamber with silicone gasket (ArrayIT) was preheated to 37° C. and attached to the Codelink slide. A volume of 50 µl of cleavage mixture preheated to 37° C., consisting of 1× Endonuclease VIII Buffer (NEB), 10 U/µl MutY (Trevigen), 10 U/µl Endonuclease VIII (NEB), 0.1 µg/µl BSA was added to each of wells containing surface immobilized cDNA. After removal of bubbles the slide was sealed and incubated at 37° C. for 30 minutes in a Thermomixer comfort with cycled shaking at 300 rpm for 3 seconds with 6 seconds rest in between. After the incubation, the plate sealer was removed and 40 µl cleavage mixture was collected from each of the used wells and placed into a PCR plate.

Library Preparation

Biotin-Streptavidin Mediated Library Cleanup

To remove unextended cDNA probes and to change buffer, the samples were purified by binding the biotin labeled cDNA to streptavidin coated C1-beads (Invitrogen) and washing the beads with 0.1M NaOH (made fresh). The purification was carried out with an MBS robot (Magnetic Biosolutions), the biotin labelled cDNA was allowed to bind to the C1-beads for 10 min and was then eluted into 20 µl of water by heating the bead-water solution to 80° C. to break the biotin-streptavidin binding.

dA-Tailing by Terminal Transferase

After the purification step, 18 µl of each sample was placed into new 0.2 ml PCR tubes and mixed with 22 µl of a polyA-tailing master mix leading to a 40 µl reaction mixture according to manufacturers instructions consisting of lysis buffer (Takara, Cellamp Whole Transcriptome Amplification kit), TdT Buffer (Takara), 1.5 mM dATP (Takara) and TdT Enzyme mix (TdT and RNase H) (Takara). The mixtures were incubated in a thermocycler at 37° C. for 15 minutes followed by inactivation of TdT at 70° C. for 10 minutes.

Second-Strand Synthesis and PCR-Amplification

After dA-tailing, 23 µl PCR master mix was placed into four new 0.2 ml PCR tubes per sample, to each tube 2 µl sample was added as a template. The final PCRs consisted of 1× Ex Taq buffer (Takara), 200 µM of each dNTP (Takara), 600 nM A_primer (MWG), 600 nM B_dT20VN_primer (MWG) and 0.025 U/µl Ex Taq polymerase (Takara). A second cDNA strand was created by running one cycle in a thermo cycler at 95° C. for 3 minutes, 50° C. for 2 minutes and 72° C. for 3 minutes. Then the samples were amplified by running 20 cycles (for library preparation) or 30 cycles (to confirm the presence of cDNA) at 95° C. for 30 seconds, 67° C. for 1 minute and 72° C. for 3 minutes, followed by a final extension at 72° C. for 10 minutes.

Library Cleanup

After amplification, the four PCRs (100 µl) were mixed with 500 µl binding buffer (Qiagen) and placed in a Qiaquick PCR purification column (Qiagen) and spun for 1 minute at 17,900×g in order to bind the amplified cDNA to the membrane. The membrane was then washed with wash buffer (Qiagen) containing ethanol and finally eluted into 50 µl of 10 mM Tris-HCl, pH 8.5.

The purified and concentrated sample was further purified and concentrated by CA-purification (purification by superparamagnetic beads conjugated to carboxylic acid) with an MBS robot (Magnetic Biosolutions). A final PEG concentration of 10% was used in order to remove fragments below 150-200 bp. The amplified cDNA was allowed to bind to the CA-beads (Invitrogen) for 10 min and were then eluted into 15 µl of 10 mM Tris-HCl, pH 8.5.

Second PCR-Amplification

The final PCRs consisted of 1× Ex Taq buffer (Takara), 200 µM of each dNTP (Takara), 600 nM A_primer (MWG), 600 nM B_primer (MWG) and 0.025 U/µl Ex Taq polymerase (Takara). The samples were heated to 95° C. for 3 minutes, and then amplified by running 10 cycles at 95° C. for 30 seconds, 65° C. for 1 minute and 72° C. for 3 minutes, followed by a final extension at 72° C. for 10 minutes.

Second Library Cleanup

After amplification, the four PCRs (100 µl) were mixed with 500 µl binding buffer (Qiagen) and placed in a Qiaquick PCR purification column (Qiagen) and spun for 1 minute at 17,900×g in order to bind the amplified cDNA to the membrane. The membrane was then washed with wash buffer (Qiagen) containing ethanol and finally eluted into 50 µl of 10 mM Tris-Cl, pH 8.5.

The purified and concentrated sample was further purified and concentrated by CA-purification (purification by superparamagnetic beads conjugated to carboxylic acid) with an MBS robot (Magnetic Biosolutions). A final PEG concentration of 10% was used in order to remove fragments below 150-200 bp. The amplified cDNA was allowed to bind to the CA-beads (Invitrogen) for 10 min and were then eluted into 15 µl of 10 mM Tris-HCl, pH 8.5.

Sequencing Library Preparation

Library Indexing

Samples amplified for 20 cycles were used further to prepare sequencing libraries. An index PCR master mix was prepared for each sample and 23 µl was placed into six 0.2 ml tubes. 2 µl of the amplified and purified cDNA was added to each of the six PCRs as template making the PCRs containing 1× Phusion master mix (Fermentas), 500 nM InPE1.0 (Illumine), 500 nM Index 1-12 (Illumine), and 0.4 nM InPE2.0 (Illumine). The samples were amplified in a thermo cycler for 18 cycles at 98° C. for 30 seconds, 65° C. for 30 seconds and 72° C. for 1 minute, followed by a final extension at 72° C. for 5 minutes.

Sequencing Library Cleanup

After amplification, the samples was purified and concentrated by CA-purification with an MBS robot. A final PEG concentration of 7.8% was used in order to remove fragments below 300-350 bp. The amplified cDNA was allowed to bind to the CA-beads for 10 min and were then eluted into 15 µl of 10 mM Tris-HCl, pH 8.5.

10 µl of the amplified and purified samples were placed on a Caliper XT chip and fragments between 480 bp and 720 bp were cut out with the Caliper XT (Caliper). Samples were analyzed with an Agilent Bioanalyzer in order to confirm the presence and size of the finished libraries, the DNA High Sensitivity kit was used.

Sequencing and Data Analysis

Sequencing and Bioinformatic was carried out in the same way as in the protocol for 5' to 3' oriented high-density Nimblegen arrays described in Example 8. However, in the data analysis, read 1 was not used in the mapping of transcripts. Specific Olfr transcripts could be sorted out using the Matlab visualization tool (FIG. 27).

EXAMPLE 10

Spatial Transcriptomics Using in House Printed 41-Tag Microarray with 5' to 3' Oriented Probes and Formalin-Fixed Frozen (FF-Frozen) Tissue with Permeabilization Through ProteinaseK or Microwaving with USER System Cleavage and Amplification Via TdT Array Preparation In-house arrays were printed as previously described but with a pattern of 41 unique ID-tag probes with the same composition as the probes in the 5' to 3' oriented high-density array in Example 8 (FIG. 28).

All other steps were carried out in the same way as in the protocol described in Example 8.

EXAMPLE 11

Alternative Method for Performing the cDNA Synthesis Step cDNA synthesis on chip as described above can also be combined with template switching to create a second strand by adding a template switching primer to the cDNA synthesis reaction (Table 2). The second amplification domain is introduced by coupling it to terminal bases added by the reverse transcriptase at the 3' end of the first cDNA strand, and primes the synthesis of the second strand. The library can be readily amplified directly after release of the double-stranded complex from the array surface.

EXAMPLE 12

Spatial Genomics Using in House Printed 41-Tag Microarray with 5' to 3' Oriented Probes and Fragmented Poly-A Tailed gDNA with USER System Cleavage and Amplification Via TdT-Tailing or Translocation Specific Primers Array Preparation In-house arrays were printed using Codelink slides (Surmodics) as previously described but with a pattern of 41 unique ID-tag probes with the same composition as the probes in the 5' to 3' oriented high-density in Example 8.

Total DNA Preparation from Cells

DNA Fragmentation

Genomic DNA (gDNA) was extracted by DNeasy kit (Qiagen) according to the manufacturers instructions from A431 and U2OS cell lines. The DNA was fragmented to 500 bp on a Covaris sonicator (Covaris) according to manufacturers instructions.

The sample was purified and concentrated by CA-purification (purification by super-paramagnetic beads conjugated to carboxylic acid) with an MBS robot (Magnetic Biosolutions). A final PEG concentration of 10% was used in order to remove fragments below 150-200 bp. The fragmented DNA was allowed to bind to the CA-beads (Invitrogen) for 10 min and were then eluted into 15 µl of 10 mM Tris-HCl, pH 8.5.

Optional Control—Spiking of Different Cell Lines

Through spiking of A431 DNA into U2OS DNA different levels of capture sensitivity can be measured, such as from spiking of 1%, 10% or 50% of A431 DNA.

dA-Tailing by Terminal Transferase

A 45 µl polyA-tailing mixture, according to manufacturers instructions consisting of TdT Buffer (Takara), 3 mM dATP (Takara) and TdT Enzyme mix (TdT and RNase H) (Takara), was added to 0.5 µg of fragmented DNA. The mixtures were incubated in a thermocycler at 37° C. for 30 minutes followed by inactivation of TdT at 80° C. for 20 minutes. The dA-tailed fragments were then cleaned through a Qiaquick (Qiagen) column according to manufacturers instructions and the concentration was measured using the Qubit system (Invitrogen) according to manufacturers instructions.

On-Chip Experiments

The hybridization, second strand synthesis and cleavage reactions were performed on chip in a 16 well silicone gasket (Arraylt, Sunnyvale, Calif., USA). To prevent evaporation, the cassettes were covered with plate sealers (In Vitro AB, Stockholm, Sweden).

Hybridization 117 ng of DNA was deposited onto a well on a prewarmed array (50° C.) in a total volume of 45 µl consisting of 1×NEB buffer (New England Biolabs) and 1×BSA. The mixture was incubated for 30 mins at 50° C. in a Thermomixer Comfort (Eppendorf) fitted with an MTP block at 300 rpm shake.

Second Strand Synthesis

Without removing the hybridization mixture, 15 µl of a Klenow extension reaction mixture consisting of 1×NEB buffer 1.5 µl Klenow polymerase, and 3.75 µl dNTPs (2 mM each) was added to the well. The reaction mixture was incubated in a Thermomixer Comport (Eppendorf) 37° C. for 30 mins without shaking.

The slide was subsequently washed in 2×SSC, 0.1% SDS at 50° C. and 300 rpm for 10 minutes, 0.2×SSC at 300 rpm for 1 minute and 0.1×SSC at 300 rpm for 1 minute.

Probe Release

A volume of 50 µl of a mixture containing 1× FastStart High Fidelity Reaction Buffer with 1.8 mM MgCl$_2$ (Roche), 200 µM dNTPs (New England Biolabs), 1×BSA and 0.1 U/1 µl USER Enzyme (New England Biolabs) was heated to 37° C. and was added to each well and incubated at 37° C. for 30 min with mixing (3 seconds at 300 rpm, 6 seconds at rest) (Thermomixer comfort; Eppendorf). The reaction mixture containing the released DNA which was then recovered from the wells with a pipette.

Library Preparation

Amplification Reaction

Amplification was carried out in 10 µl reactions consisting of 7.5 µl released sample, 1 µl of each primer and 0.5 µl enzyme (Roche, FastStart HiFi PCR system). The reaction was cycled as 94° C. for 2 mins, one cycle of 94° C. 15 sec, 55° C. for 2 mins, 72° C. for 2 mins, 30 cycles of 94° C. for 15 secs, 65° C. for 30 secs, 72° C. for 90 secs, and a final elongation at 72° C. for 5 mins.

In the preparation of a library for sequencing the two primers consisted of the surface probe A-handle and either of a specific translocation primer (for A431) or a specific SNP primer coupled to the B-handle (Table 2).

Library Cleanup

The purified and concentrated sample was further purified and concentrated by CA-purification (purification by superparamagnetic beads conjugated to carboxylic acid) with an MBS robot (Magnetic Biosolutions). A final PEG concentration of 10% was used in order to remove fragments below 150-200 bp. The amplified DNA was allowed to bind to the CA-beads (Invitrogen) for 10 min and was then eluted into 15 µl of 10 mM Tris-HCl, pH 8.5.

Library Quality Analysis

Samples were analyzed with an Agilent Bioanalyzer (Agilent) in order to confirm the presence of an amplified DNA library, the DNA High Sensitivity kit or DNA 1000 kit were used depending on the amount of material.

Library Indexing

Samples amplified for 20 cycles were used further to prepare sequencing libraries. An index PCR master mix was prepared for each sample and 23 µl was placed into six 0.2 ml tubes. 2 µl of the amplified and purified cDNA was added to each of the six PCRs as template making the PCRs containing 1× Phusion master mix (Fermentas), 500 nM InPE1.0 (Illumine), 500 nM Index 1-12 (Illumine), and 0.4 nM InPE2.0 (Illumine). The samples were amplified in a thermo cycler for 18 cycles at 98° C. for 30 seconds, 65° C. for 30 seconds and 72° C. for 1 minute, followed by a final extension at 72° C. for 5 minutes.

Sequencing Library Cleanup

The purified and concentrated sample was further purified and concentrated by CA-purification with an MBS robot. A final PEG concentration of 7.8% was used in order to remove fragments below 300-350 bp. The amplified DNA was allowed to bind to the CA-beads for 10 min and were then eluted into 15 µl of 10 mM Tris-Cl, pH 8.5. Samples were analyzed with an Agilent Bioanalyzer in order to confirm the presence and size of the finished libraries, the DNA High Sensitivity kit or DNA 1000 kit were used according to manufacturers instructions depending on the amount of material (FIG. 29).

Sequencing

Sequencing was carried out in the same way as in the protocol for 5' to 3' oriented high-density Nimblegen arrays described in Example 8.

Data Analysis

Data analysis was carried out to determine the sensitivity of capture of the arrayed ID-capture probes. Read 2 was sorted based on its content of either of the translocation or SNP primers. These reads were then sorted per their ID contained in Read 1.

Optional Control—Direct Amplification of Cell-Line Specific Translocations

This was used to measure the capture sensitivity of spiked cell lines directly by PCR. The forward and reverse primers (Table 2) for the A431 translocations were used to try and detect the presence of the translocation in the second strand copied and released material (FIG. 30).

TABLE 2

Oligos used for spatial transcriptomics and spatial genomics

Example 8
Nimblegen 5' to 3' arrays with free 3' end Array probes

5' to 3'

Probe1 (SEQ ID NO: 50)
UUUUUACACTCTTTCCCTACACGACGCTCTTCCGATCTGTCCGATATGATTGCCGCTTTTTTTTTTTTTTTTTTTVN Probe2 (SEQ ID NO: 51)
UUUUUACACTCTTTCCCTACACGACGCTCTTCCGATCTATGAGCCGGGTTCATCTTTTTTTTTTTTTTTTTTTTVN Probe3 (SEQ ID NO: 52)
UUUUUACACTCTTTCCCTACACGACGCTCTTCCGATCTTGAGGCACTCTGTTGGGATTTTTTTTTTTTTTTTTTTVN Probe4 (SEQ ID NO: 53)
UUUUUACACTCTTTCCCTACACGACGCTCTTCCGATCTATGATTAGTCGCCATTCGTTTTTTTTTTTTTTTTTTTVN Probe5 (SEQ ID NO: 54)
UUUUUACACTCTTTCCCTACACGACGCTCTTCCGATCTACTTGAGGGTAGATGTTTTTTTTTTTTTTTTTTTTTVN Probe6 (SEQ ID NO: 55)
UUUUUACACTCTTTCCCTACACGACGCTCTTCCGATCTATGGCCAATACTGTTATCTTTTTTTTTTTTTTTTTTTVN Probe7 (SEQ ID NO: 56)
UUUUUACACTCTTTCCCTACACGACGCTCTTCCGATCTCGCTACCCTGATTCGACCTTTTTTTTTTTTTTTTTTTVN Probe8 (SEQ ID NO: 57)
UUUUUACACTCTTTCCCTACACGACGCTCTTCCGATCTGCCCACTTTCGCCGTAGTTTTTTTTTTTTTTTTTTTTVN Probe9 (SEQ ID NO: 58)
UUUUUACACTCTTTCCCTACACGACGCTCTTCCGATCTAGCAACTTTGAGCAAGATTTTTTTTTTTTTTTTTTTTVN TABLE 2-continued Oligos used for spatial transcriptomics and spatial genomics

| Probe10 (SEQ ID NO: 59) | UUUUUACACTCTTTCCCTACACGACGCTCTTCCGATCTGCCAATTCGGAATTCCGGTTTTTTTTTTTTTTTTTTTVN |
| Probe11 (SEQ ID NO: 60) | UUUUUACACTCTTTCCCTACACGACGCTCTTCCGATCTTCGCCCAAGGTAATACATTTTTTTTTTTTTTTTTTTVN |
| Probe12 (SEQ ID NO: 61) | UUUUUACACTCTTTCCCTACACGACGCTCTTCCGATCTTCGCATTTCCTATTCGAGTTTTTTTTTTTTTTTTTTTVN |
| Probe13 (SEQ ID NO: 62) | UUUUUACACTCTTTCCCTACACGACGCTCTTCCGATCTTTGCTAAATCTAACCGCCTTTTTTTTTTTTTTTTTTTVN |
| Probe14 (SEQ ID NO: 63) | UUUUUACACTCTTTCCCTACACGACGCTCTTCCGATCTGGAATTAAATTCTGATGGTTTTTTTTTTTTTTTTTTTVN |
| Probe15 (SEQ ID NO: 64) | UUUUUACACTCTTTCCCTACACGACGCTCTTCCGATCTCATTACATAGGTGCTAAGTTTTTTTTTTTTTTTTTTTVN |
| Probe16 (SEQ ID NO: 65) | UUUUUACACTCTTTCCCTACACGACGCTCTTCCGATCTATTGACTTGCGCTCGCACTTTTTTTTTTTTTTTTTTTVN |
| Probe17 (SEQ ID NO: 66) | UUUUUACACTCTTTCCCTACACGACGCTCTTCCGATCTATAGTATCTCCCAAGTTCTTTTTTTTTTTTTTTTTTTVN |
| Probe18 (SEQ ID NO: 67) | UUUUUACACTCTTTCCCTACACGACGCTCTTCCGATCTGTGCGCCTGTAATCCGCATTTTTTTTTTTTTTTTTTTVN |
| Probe19 (SEQ ID NO: 68) | UUUUUACACTCTTTCCCTACACGACGCTCTTCCGATCTGCGCCACTCTTTAGGTAGTTTTTTTTTTTTTTTTTTTVN |
| Probe20 (SEQ ID NO: 69) | UUUUUACACTCTTTCCCTACACGACGCTCTTCCGATCTTATGCAAGTGATTGGCTTTTTTTTTTTTTTTTTTTVN |
| Probe21 (SEQ ID NO: 70) | UUUUUACACTCTTTCCCTACACGACGCTCTTCCGATCTCCAAGCCACGTTTATACGTTTTTTTTTTTTTTTTTTTVN |
| Probe22 (SEQ ID NO: 71) | UUUUUACACTCTTTCCCTACACGACGCTCTTCCGATCTACCTGATTGCTGTATAACTTTTTTTTTTTTTTTTTTTVN |
| Probe23 (SEQ ID NO: 72) | UUUUUACACTCTTTCCCTACACGACGCTCTTCCGATCTCAGCGCATCTATCCTCTATTTTTTTTTTTTTTTTTTTVN |
| Probe24 (SEQ ID NO: 73) | UUUUUACACTCTTTCCCTACACGACGCTCTTCCGATCTTCCACGCGTAGGACTAGTTTTTTTTTTTTTTTTTTTVN |
| Probe25 (SEQ ID NO: 74) | UUUUUACACTCTTTCCCTACACGACGCTCTTCCGATCTCGACTAAGTATGTAGCGCTTTTTTTTTTTTTTTTTTTVN |

Frame probe

| Layout1 (SEQ ID NO: 75) | AAATTTCGTCTGCTATCGCGCTTCTGTACC |

Fluorescent marker probe

| PS_1 (SEQ ID NO: 76) | GGTACAGAAGCGCGATAGCAG - Cy3 |

Second strand synthesis and first PCR Amplification handles

| A_primer (SEQ ID NO: 77) | ACACTCTTTCCCTACACGACGCTCTTCCGATCT |
| B_dt20VN_primer (SEQ ID NO: 78) | AGACGTGTGCTCTTCCGATCTTTTTTTTTTTTTTTTTTTTVN |

TABLE 2-continued

Oligos used for spatial transcriptomics and spatial genomics

Custom sequencing primer

B_r2 (SEQ ID NO: 79)　TCA GAC GTG TGC TCT TCC GAT CTT TTT TTT TTT TTT TTT TTT T

Example 9
Nimblegen 3' to 5' arrays with free 5' end Array probes

5' to 3'

Probe1 (SEQ ID NO: 80)　GCGTTCAGAGTGGCAGTCGAGATCACGCGGCAATCATATCGGACAGATCGGAAGAGCGTAGTGTAG Probe2 (SEQ ID NO: 81)　GCGTTCAGAGTGGCAGTCGAGATCACAAGATGAACCCGGCTCATAGATCGGAAGAGCGTAGTGTAG Probe3 (SEQ ID NO: 82)　GCGTTCAGAGTGGCAGTCGAGATCACTCCCAACAGAGTGCCTCAAGATCGGAAGAGCGTAGTGTAG Probe4 (SEQ ID NO: 83)　GCGTTCAGAGTGGCAGTCGAGATCACCGAATGGCGACTAATCATAGATCGGAAGAGCGTAGTGTAG Probe5 (SEQ ID NO: 84)　GCGTTCAGAGTGGCAGTCGAGATCACAAACATCTACCCTCAAGTAGATCGGAAGAGCGTAGTGTAG Probe6 (SEQ ID NO: 85)　GCGTTCAGAGTGGCAGTCGAGATCACGATAACAGTATTGGCCATAGATCGGAAGAGCGTAGTGTAG Probe7 (SEQ ID NO: 86)　GCGTTCAGAGTGGCAGTCGAGATCACGGTCGAATCAGGGTAGCGAGATCGGAAGAGCGTAGTGTAG Probe8 (SEQ ID NO: 87)　GCGTTCAGAGTGGCAGTCGAGATCACACTACGGCGAAAGTGGGCAGATCGGAAGAGCGTAGTGTAG Probe9 (SEQ ID NO: 88)　GCGTTCAGAGTGGCAGTCGAGATCACATCTTGCTCAAAGTTGCTAGATCGGAAGAGCGTAGTGTAG Probe10 (SEQ ID NO: 89)　GCGTTCAGAGTGGCAGTCGAGATCACCCGGAATTCCGAATTGGCAGATCGGAAGAGCGTAGTGTAG Probe11 (SEQ ID NO: 90)　GCGTTCAGAGTGGCAGTCGAGATCACATGTATTACCTTGGGCGAAGATCGGAAGAGCGTAGTGTAG Probe12 (SEQ ID NO: 91)　GCGTTCAGAGTGGCAGTCGAGATCACCTCGAATAGGAAATGCGAAGATCGGAAGAGCGTAGTGTAG Probe13 (SEQ ID NO: 92)　GCGTTCAGAGTGGCAGTCGAGATCACGGCGGTTAGATTTAGCAAAGATCGGAAGAGCGTAGTGTAG Probe14 (SEQ ID NO: 93)　GCGTTCAGAGTGGCAGTCGAGATCACCCATCAGAATTTAATTCCAGATCGGAAGAGCGTAGTGTAG Probe15 (SEQ ID NO: 94)　GCGTTCAGAGTGGCAGTCGAGATCACCTTAGCACCTATGTAATGAGATCGGAAGAGCGTAGTGTAG Probe16 (SEQ ID NO: 95)　GCGTTCAGAGTGGCAGTCGAGATCACGTGCGAGCGCAAGTCAATAGATCGGAAGAGCGTAGTGTAG Probe17 (SEQ ID NO: 96)　GCGTTCAGAGTGGCAGTCGAGATCACGAACTTGGGAGATACTATAGATCGGAAGAGCGTAGTGTAG Probe18 (SEQ ID NO: 97)　GCGTTCAGAGTGGCAGTCGAGATCACTGCGGATTACAGGCGCACAGATCGGAAGAGCGTAGTGTAG Probe19 (SEQ ID NO: 98)　GCGTTCAGAGTGGCAGTCGAGATCACCTACCTAAAGAGTGGCGCAGATCGGAAGAGCGTAGTGTAG Probe20 (SEQ ID NO: 99)　GCGTTCAGAGTGGCAGTCGAGATCACAAGCCAATCACTTGCATAAGATCGGAAGAGCGTAGTGTAG Probe21 (SEQ ID NO: 100)　GCGTTCAGAGTGGCAGTCGAGATCACCGTATAAACGTGGCTTGGAGATCGGAAGAGCGTAGTGTAG Probe22 (SEQ ID NO: 101)　GCGTTCAGAGTGGCAGTCGAGATCACGTTATACAGCAATCAGGTAGATCGGAAGAGCGTAGTGTAG Probe23 (SEQ ID NO: 102)　GCGTTCAGAGTGGCAGTCGAGATCACTAGAGGATAGATGCGCTGAGATCGGAAGAGCGTAGTGTAG TABLE 2-continued Oligos used for spatial transcriptomics and spatial genomics

| | |
|---|---|
| Probe24 (SEQ ID NO: 103) | GCGTTCAGAGTGGCAGTCGAGATCACACTAGTCCTACGCGTGGAAGATCGGAAGAGCGTAGTGTAG |
| Probe25 (SEQ ID NO: 104) | GCGTTCAGAGTGGCAGTCGAGATCACGCGCTACATACTTAGTCGAGATCGGAAGAGCGTAGTGTAG |

Frame probe

| | |
|---|---|
| Layout1 (SEQ ID NO: 105) | AAATTTCGTCTGCTATCGCGCTTCTGTACC |

Capture probe

| | |
|---|---|
| LP_Poly-dTVN (SEQ ID NO: 106) | GTGATCTCGACTGCCACTCTGAATTTTTTTTTTTTTTTTTTTVN |

Amplification handle probe

| | |
|---|---|
| A-handle (SEQ ID NO: 107) | ACACTCTTTCCCTACACGACGCTCTTCCGATCT |

Second strand synthesis and first PCR amplification handles

| | |
|---|---|
| A_primer (SEQ ID NO: 108) | ACACTCTTTCCCTACACGACGCTCTTCCGATCT |
| B_dt20VN_primer (SEQ ID NO: 109) | AGACGTGTGCTCTTCCGATCTTTTTTTTTTTTTTTTTTTTVN |

Second PCR

| | |
|---|---|
| A_primer (SEQ ID NO: 110) | ACACTCTTTCCCTACACGACGCTCTTCCGATCT |
| B_primer (SEQ ID NO: 111) | GTGACTGGAGTTCAGACGTGTGCTCTTCCGATCT |

Example 11
Template switching

| | |
|---|---|
| Templateswitch_longB (SEQ ID NO: 112) | GTGACTGGAGTTCAGACGTGTGCTCTTCCGATCTATrGrGrG |

Example 12
Spatial genomics

| | |
|---|---|
| A_primer (SEQ ID NO: 113) | ACACTCTTTCCCTACACGACGCTCTTCCGATCT |
| B_A431_Chr2+ 2_FW_A (SEQ ID NO: 114) | AGACGTGTGCTCTTCCGATCTTGGCTGCCTGAGGCAATG |
| B_A431_Chr2+ 2_RE_A (SEQ ID NO: 115) | AGACGTGTGCTCTTCCGATCTCTCGCTAACAAGCAGAGAGAAC |
| B_A431_Chr3+ 7_FW_B (SEQ ID NO: 116) | AGACGTGTGCTCTTCCGATCTTGAGAACAAGGGGGAAGAG |
| B_A431_Chr3+ 7_RE_B (SEQ ID NO: 117) | AGACGTGTGCTCTTCCGATCTCGGTGAAACAAGCAGGTAAC |
| B_NT_1_FW (SEQ ID NO: 118) | AGACGTGTGCTCTTCCGATCTCATTCCCACACTCATCACAC |
| B_NT_1_RE (SEQ ID NO: 119) | AGACGTGTGCTCTTCCGATCTTCACACTGGAGAAAGACCC |
| B_NT_2_FW (SEQ ID NO: 120) | AGACGTGTGCTCTTCCGATCTGGGGTTCAGAGTGATTTTTCAG |
| B_NT_2_RE (SEQ ID NO: 121) | AGACGTGTGCTCTTCCGATCTTCCGTTTTCTTTCAGTGCC |

What is claimed is:

1. A method for determining the location of a nucleic acid in a tissue section comprising:
   a) providing a substrate comprising a plurality of capture probes, wherein a capture probe of the plurality of capture probes comprises:
      (i) a capture domain that binds the nucleic acid, and
      (ii) a positional domain comprising a nucleotide sequence, wherein the nucleotide sequence of each of the positional domains is unique to a distinct position in the substrate;
   b) contacting the tissue section with the substrate;
   c) releasing the capture probe from the substrate;
   d) extending a 3' end of the capture probe using the nucleic acid of the tissue section bound to the capture domain as a template to generate an extended nucleic acid product; and
   e) determining (i) all or a part of the nucleotide sequence of the nucleic acid of the tissue section bound to the capture domain, or a complement thereof, and (ii) the nucleotide sequence of the positional domain, or a complement thereof, wherein the nucleotide sequences of (i) and (ii) indicate the nucleic acid was obtained from the tissue section at a distinct position on the substrate by the capture probe, thereby determining the location of the nucleic acid in the tissue section.

2. The method of claim 1, wherein the substrate comprises a polymer.

3. The method of claim 1, wherein the nucleic acid is DNA.

4. The method of claim 1, wherein the nucleic acid is RNA.

5. The method of claim 1, wherein the capture domain comprises a nucleotide sequence for the capture of mRNA, wherein in the capture domain comprises a poly-T sequence.

6. The method of claim 2, wherein the polymer is affixed to a solid support.

7. The method of claim 6, wherein the solid support comprises one of glass, silicon, poly-lysine coated material, nitrocellulose, polystyrene, cyclic olefin copolymers (COCs), cyclic olefin polymers (COPs), polypropylene, polyethylene, and polycarbonate.

8. The method of claim 1, wherein the extending in step (d) comprises performing a reverse transcription reaction and wherein the generated extended nucleic acid product is a cDNA.

9. The method of claim 1, wherein the determining in step (e) comprises amplifying all or a portion of the extended nucleic acid product, or the complement thereof, to generate one or more amplified nucleic acid products.

10. The method of claim 9, wherein the method further comprises releasing the one or more amplified nucleic acid products from the substrate.

11. The method of claim 1, wherein the determining in step (e) comprises sequencing.

12. The method of claim 1, wherein the method further comprises imaging the tissue section, and the method further comprises correlating the nucleotide sequence of the positional domain to the location in the imaged tissue section.

13. The method of claim 12, wherein the imaging comprises one or more of: light field, bright field, dark field, phase contrast, fluorescence microscopy, reflection, interference, and confocal microscopy.

14. The method of claim 1, wherein the capture probe comprises the following domains oriented 5' to 3':
   (i) a cleavage domain,
   (ii) the positional domain, and
   (iii) the capture domain;
   wherein the step of releasing the capture probe from the substrate comprises cleaving the cleavage domain.

15. The method of claim 1, wherein the releasing in step (c) comprises enzymatic cleavage, chemical cleavage, or applying heat.

16. A method for determining the location of a nucleic acid in a tissue section comprising:
   a) providing a substrate comprising a plurality capture probes, wherein a capture probe of the plurality of capture probe comprises:
      (i) a capture domain that binds a nucleic acid, and
      (ii) a positional domain comprising a nucleotide sequence, wherein the nucleotide sequence of each of the positional domains is unique to a distinct position in the substrate;
   b) contacting a tissue section with the substrate;
   c) imaging one or more fluorescent marker probes;
   d) releasing the capture probe from the substrate;
   e) extending a 3' end of the capture probe using the nucleic acid of the tissue section bound to the capture domain as a template to generate an extended nucleic acid product; and
   f) determining (i) all or a part of the nucleotide sequence of the nucleic acid of the tissue section bound to the capture domain, or a complement thereof, and (ii) the nucleotide sequence of the positional domain, or a complement thereof, wherein the nucleotide sequences of (i) and (ii) indicate the nucleic acid was obtained from the tissue section at a distinct position on the substrate by the capture probe, thereby determining the location of the nucleic acid in the tissue section.

17. The method of claim 16, wherein the substrate comprises a polymer and the polymer is affixed to a solid support.

18. The method of claim 17, wherein the solid support comprises one of glass, silicon, poly-lysine coated material, nitrocellulose, polystyrene, cyclic olefin copolymers (COCs), cyclic olefin polymers (COPs), polypropylene, polyethylene, and polycarbonate.

19. The method of claim 16, wherein the nucleic acid is DNA.

20. The method of claim 16, wherein the nucleic acid is RNA.

21. The method of claim 16, wherein the capture domain comprises a nucleotide sequence for the capture of mRNA.

22. The method of claim 21, wherein the capture domain comprises a poly-T sequence.

23. The method of claim 16, wherein the extending in step (e) comprises performing a reverse transcription reaction and wherein the generated extended nucleic acid product is a cDNA.

24. The method of claim 16, wherein the determining in (e) comprises amplifying all or a portion of the extended nucleic acid product, or the complement thereof, to generate one or more amplified nucleic acid products.

25. The method of claim 16, wherein the method further comprises releasing the one or more amplified nucleic acid products from the substrate.

26. The method of claim 16, wherein the further comprises correlating the nucleotide sequence of the positional domain to the location in the imaged tissue section.

27. The method of claim 16, wherein the capture probe comprises the following domains oriented 5' to 3':
  (i) a cleavage domain
  (ii) the positional domain, and
  (iii) the capture domain;
  wherein the step of releasing the capture probe from the substrate comprises cleaving the cleavage domain.

28. The method of claim 16, wherein the releasing in step (c) comprises enzymatic cleavage, chemical cleavage, or applying heat.

29. The method of claim 16, wherein the determining in step (e) comprises sequencing.

30. The method of claim 16, wherein the imaging comprise one or more of: light field, bright field, dark field, phase contrast, fluorescence microscopy, reflection, interference, and confocal microscopy.

* * * * *

UNITED STATES PATENT AND TRADEMARK OFFICE
CERTIFICATE OF CORRECTION

| | |
|---|---|
| PATENT NO. | : 11,352,659 B2 |
| APPLICATION NO. | : 17/474922 |
| DATED | : June 7, 2022 |
| INVENTOR(S) | : Jonas Frisen, Patrik Stahl and Joakim Lundeberg |

It is certified that error appears in the above-identified patent and that said Letters Patent is hereby corrected as shown below:

On the Title Page

Column 1 item (56) under Related U.S. Application Data, Line 6, Below "10,030,261." insert -- (30) Foreign Application Priority Data Apr. 13, 2011 (GB) .............................. 1106254.4 --, as a new field.

Column 2 item (56) under Other Publications, Line 2, delete "anitsense" and insert -- antisense --.

Signed and Sealed this
Second Day of August, 2022

Katherine Kelly Vidal
*Director of the United States Patent and Trademark Office*